US011832508B2

(12) United States Patent
Takizawa et al.

(10) Patent No.: US 11,832,508 B2
(45) Date of Patent: *Nov. 28, 2023

(54) ORGANIC ELECTROLUMINESCENCE DEVICE

(71) Applicant: UDC IRELAND LIMITED, Dublin (IE)

(72) Inventors: Hiroo Takizawa, Shizuoka (JP); Saki Takada, Kanagawa (JP); Eiji Fukuzaki, Kanagawa (JP)

(73) Assignee: UDC IRELAND LIMITED, Dublin (IE)

(*) Notice: Subject to any disclaimer, the term of this patent is extended or adjusted under 35 U.S.C. 154(b) by 448 days.

This patent is subject to a terminal disclaimer.

(21) Appl. No.: 16/535,491

(22) Filed: Aug. 8, 2019

(65) Prior Publication Data

US 2019/0372030 A1 Dec. 5, 2019

Related U.S. Application Data

(63) Continuation of application No. 14/613,073, filed on Feb. 3, 2015, now Pat. No. 10,403,832, which is a (Continued)

(30) Foreign Application Priority Data

Aug. 31, 2009 (JP) ................................ 2009-201150

(51) Int. Cl.
*H01L 51/00* (2006.01)
*H10K 85/30* (2023.01)
(Continued)

(52) U.S. Cl.
CPC ......... *H10K 85/346* (2023.02); *C07D 213/16* (2013.01); *C07D 213/26* (2013.01);
(Continued)

(58) Field of Classification Search
CPC ............ H01L 51/0087; H01L 51/0085; H01L 51/009; H01L 51/0072; H01L 51/5016;
(Continued)

(56) References Cited

U.S. PATENT DOCUMENTS

| | | | | |
|---|---|---|---|---|
| 6,391,482 | B1 | 5/2002 | Matsuo | |
| 8,945,725 | B2 * | 2/2015 | Takizawa ............ | C07D 263/62 428/690 |

(Continued)

FOREIGN PATENT DOCUMENTS

| | | |
|---|---|---|
| CN | 1517427 | 8/2004 |
| JP | 2001043973 A | 2/2001 |

(Continued)

OTHER PUBLICATIONS

English language translation of WO 2007/029533, pp. 1-49, Nov. 8, 2021.*

(Continued)

*Primary Examiner* — Alexander C Kollias
(74) *Attorney, Agent, or Firm* — Riverside Law LLP

(57) ABSTRACT

The present invention relates to an electroluminescence device having high luminous efficiency (for example, external quantum efficiency) and high durability and causing little chromaticity shift after device deterioration. The present invention also relates to an organic electroluminescence device material comprising a substrate having thereon a pair of electrode and at least one organic layer between the electrodes, the organic layer containing a light emitting layer, wherein the light emitting layer contains a metal complex having a group represented by formula (I).

(Continued)

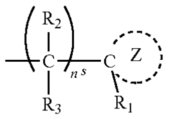

(I)

19 Claims, 1 Drawing Sheet

Related U.S. Application Data continuation of application No. 13/393,272, filed as application No. PCT/JP2010/064664 on Aug. 24, 2010, now Pat. No. 8,945,725.

(51) Int. Cl.

| | |
|---|---|
| ***C07D 213/16*** | (2006.01) |
| ***C07D 213/26*** | (2006.01) |
| ***C07D 213/57*** | (2006.01) |
| ***C07D 213/61*** | (2006.01) |
| ***C07D 213/79*** | (2006.01) |
| ***C07D 215/04*** | (2006.01) |
| ***C07D 217/06*** | (2006.01) |
| ***C07D 221/06*** | (2006.01) |
| ***C07D 233/60*** | (2006.01) |
| ***C07D 263/62*** | (2006.01) |
| ***C07D 401/04*** | (2006.01) |
| ***C07D 401/06*** | (2006.01) |
| ***C07D 401/14*** | (2006.01) |
| ***C07D 405/14*** | (2006.01) |
| ***C07D 409/04*** | (2006.01) |
| ***C09K 11/06*** | (2006.01) |
| ***H05B 33/10*** | (2006.01) |
| ***C09B 57/10*** | (2006.01) |
| ***C09B 57/00*** | (2006.01) |
| ***C07F 15/00*** | (2006.01) |
| *H10K 50/11* | (2023.01) |
| *H10K 85/60* | (2023.01) |
| *H10K 101/10* | (2023.01) |

(52) U.S. Cl.

CPC ......... *C07D 213/57* (2013.01); *C07D 213/61* (2013.01); *C07D 213/79* (2013.01); *C07D 215/04* (2013.01); *C07D 217/06* (2013.01); *C07D 221/06* (2013.01); *C07D 233/60* (2013.01); *C07D 263/62* (2013.01); *C07D 401/04* (2013.01); *C07D 401/06* (2013.01); *C07D 401/14* (2013.01); *C07D 405/14* (2013.01); *C07D 409/04* (2013.01); *C07F 15/0033* (2013.01); *C07F 15/0086* (2013.01); *C09B 57/00* (2013.01); *C09B 57/10* (2013.01); *C09K 11/06* (2013.01); *H05B 33/10* (2013.01); *H10K 85/342* (2023.02); *H10K 85/361* (2023.02); *C09K 2211/1007* (2013.01); *C09K 2211/1011* (2013.01); *C09K 2211/1029* (2013.01); *C09K 2211/1033* (2013.01); *C09K 2211/1037* (2013.01); *C09K 2211/1044* (2013.01); *C09K 2211/1051* (2013.01); *C09K 2211/1059* (2013.01); *C09K 2211/1088* (2013.01); *C09K 2211/1092* (2013.01); *C09K 2211/185* (2013.01); *C09K 2211/187* (2013.01); *C09K 2211/188* (2013.01); *H10K 50/11* (2023.02); *H10K 85/6572* (2023.02); *H10K 2101/10* (2023.02); *Y10S 428/917* (2013.01)

(58) Field of Classification Search

CPC .. C07D 213/16; C07D 213/26; C07D 213/57; C07D 213/61; C07D 213/79; C07D 215/04; C07D 217/06; C07D 221/06; C07D 233/60; C07D 263/62; C07D 401/04; C07D 401/06; C07D 401/14; C07D 405/14; C07D 409/04; C07F 15/0033; C07F 15/0086; C09B 57/00; C09B 57/10; C09K 11/06; C09K 2211/1007; C09K 2211/1011; C09K 2211/1029; C09K 2211/1033; C09K 2211/1037; C09K 2211/1044; C09K 2211/1051; C09K 2211/1059; C09K 2211/1088; C09K 2211/1092; C09K 2211/185; C09K 2211/187; C09K 2211/188; H05B 33/10; Y10S 428/917; H10K 85/346; H10K 85/342

See application file for complete search history.

(56) References Cited

U.S. PATENT DOCUMENTS

| | | | | |
|---|---|---|---|---|
| 10,403,832 | B2 * | 9/2019 | Takizawa | C09K 11/06 |
| 2001/0019782 | A1 | 9/2001 | Igarashi | |
| 2003/0072964 | A1 * | 4/2003 | Kwong | C09K 11/06 428/690 |
| 2006/0073359 | A1 * | 4/2006 | Ise | C07F 15/0086 428/690 |
| 2007/0190359 | A1 * | 8/2007 | Knowles | C09B 57/00 428/690 |
| 2007/0249834 | A1 | 10/2007 | Stossel | |
| 2008/0038586 | A1 | 2/2008 | Nishizeki | |
| 2008/0286604 | A1 | 11/2008 | Inoue | |
| 2008/0297033 | A1 | 12/2008 | Knowles | |
| 2010/0141125 | A1 | 6/2010 | Otsu | |
| 2010/0141126 | A1 | 6/2010 | Otsu | |
| 2011/0073849 | A1 | 3/2011 | Knowles | |
| 2011/0204348 | A1 | 8/2011 | Nishizeki | |
| 2013/0082209 | A1 | 4/2013 | Stoessel | |
| 2013/0112920 | A1 | 5/2013 | Stoessel | |
| 2015/0263297 | A1 | 9/2015 | Stoessel | |
| 2015/0270500 | A1 | 9/2015 | Stoessel | |
| 2016/0233443 | A1 | 8/2016 | Stoessel | |

FOREIGN PATENT DOCUMENTS

| | | | |
|---|---|---|---|
| JP | 2008016827 | A | 1/2008 |
| JP | 2008021687 | A | 1/2008 |
| JP | 2008500377 | A | 1/2008 |
| JP | 2008210941 | A | 9/2008 |
| JP | 2008311608 | A | 12/2008 |
| JP | 2009001546 | A | 1/2009 |
| JP | 2009102533 | A | 5/2009 |
| JP | 2009526071 | A | 7/2009 |
| KR | 101903793 | | 10/2018 |
| KR | 102028130 | | 10/2019 |
| WO | 02060910 | A1 | 8/2002 |
| WO | 2006008976 | A1 | 1/2006 |
| WO | 2007029461 | A1 | 3/2007 |
| WO | 2007029533 | | 3/2007 |
| WO | 2008117889 | A1 | 10/2008 |
| WO | 2008140069 | A1 | 11/2008 |
| WO | 2008140114 | A1 | 11/2008 |
| WO | 2008140115 | A1 | 11/2008 |
| WO | 2008143059 | A1 | 11/2008 |

OTHER PUBLICATIONS

English language translation of JP 2008-016827, pp. 1-89, Nov. 8, 2021.*

(56) References Cited

OTHER PUBLICATIONS

Richard J. Lewis, Sr. "Hawley's Condensed Chemical Dictionary, 12th Edition", John Wiley & Sons, Inc., New York p. 858 (1993).*

* cited by examiner

ORGANIC ELECTROLUMINESCENCE DEVICE

The present application is a continuation of U.S. patent application Ser. No. 14/613,073, filed Feb. 3, 2015, now allowed, which is a continuation of U.S. patent application Ser. No. 13/393,272, filed Feb. 29, 2012, now U.S. Pat. No. 8,945,725, issued Feb. 3, 2015, which is a 35 U.S.C. § 371 national phase application from, and claiming priority to, International Application No. PCT/JP2010/064664, filed Aug. 24, 2010, which claims priority to Japanese Patent Application No. 2009-201150, filed Aug. 31, 2009, all of which applications are incorporated by reference herein in their entireties.

TECHNICAL FIELD

The present invention relates to a luminescence device capable of converting an electric energy into light and thereby producing luminescence. More specifically, the present invention relates to an organic electroluminescence device (luminescence device or EL device).

BACKGROUND ART

An organic electroluminescence (EL) device is attracting as a promising display device because high-luminance intensity luminescence can be obtained with a low voltage. An important characteristic value of this organic electroluminescence device is a power consumption. The power consumption is represented by a product of a voltage and a current, and as the voltage value necessary for obtaining desired brightness is lower and the current value is smaller, the power consumption of the device can be more reduced.

In the production of an organic electroluminescence device, as for the method to form a thin film that is an organic layer provided between a pair of electrodes, a vapor deposition process such as vacuum deposition and a wet process such as spin coating method, printing method and an inkjet method are being performed.

Among these, when a wet process is used, an organic compound polymer whose deposition is difficult by a dry process such as vapor deposition can be used, and in the case of use for a flexible display or the like, the wet process is suitable in view of durability such as flexibility and film strength and is preferred particularly when fabricating a large-area device.

However, an organic electroluminescence device obtained by the wet process has a problem that the luminous efficiency or device durability is poor.

In recent years, the device efficiency is progressively increased by using a phosphorescent material. As for the phosphorescent material, an iridium complex, a platinum complex and the like are known (see, for example, JP-A-2001-247859 and JP-A-2007-19462), but a device satisfying both high efficiency and high durability has not yet been developed.

Also, an organic EL device where a specific phosphorescence material substituted with a specific kind of an alkyl group at a specific position with an attempt to obtain a material capable of realizing high efficiency and low voltage of a device is used as a light emitting material has been reported (see, for example, JP-A-2008-210941 and US 2008-0297033). In JP-A-2008-210941, an organic EL device containing a compound having a cyclopropyl group as the substituent is described, but this is insufficient in view of luminescence quantum efficiency, drive voltage and durability, and more improvements are being demanded.

Furthermore, conventional devices sometimes cause a chromaticity shift after device deterioration, and also in this respect, improvements are being demanded.

SUMMARY OF INVENTION

An object of the present invention is to provide an organic electroluminescence device having high efficiency and high durability and causing little chromaticity shift after device deterioration. Another object of the present invention is to provide a phosphorescence material having a specific alkyl group, which is suitable for use in the device.

These objects have been attained by the following techniques.

[1]

An organic electroluminescence device including a substrate having thereon a pair of electrodes and at least one organic layer between said electrodes, the organic layer containing a light emitting layer, wherein any one layer of the organic layer contains a metal complex having a group represented by the following formula (I).

(I)

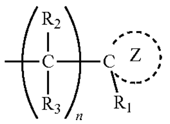

(In formula (I), $R_1$ represents an alkyl group, each of $R_2$ and $R_3$ independently represents a hydrogen atom or an alkyl group, n represents an integer of 0 to 6, and Z represents a saturated 5- to 8-membered ring.)

[2]

The organic electroluminescence device according to [1], wherein in formula (I), n represents an integer of 1 to 3.

[3]

The organic electroluminescence device according to [1] or [2], wherein in formula (I), n is 1.

[4]

The organic electroluminescence device according to any one of [1] to [3], wherein in formula (I), each of $R_2$ and $R_3$ represents a hydrogen atom.

[5]

The organic electroluminescence device according to any one of [1] to [4], wherein in formula (I), Z represents a cyclopentyl group or a cyclohexyl group.

[6]

The organic electroluminescence device according to any one of [1] to [5], wherein the metal complex having a group represented by formula (I) is a metal complex represented by the following formula (1).

(1)

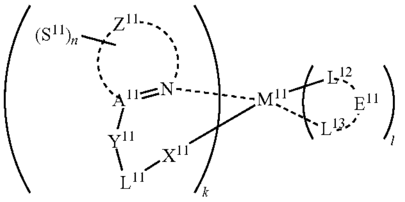

(In formula (1), $M^{11}$ represents a metal belong to Groups 8 to 11 in the periodic table of elements, $A^{11}$ represents a nitrogen atom or a carbon atom, $X^{11}$ represents an oxygen atom, a sulfur atom, a substituted or unsubstituted nitrogen atom or a single bond, $Y^{11}$ represents a linking group or a single bond, $L^{11}$ represents a partial structure having an atom bonded to $X^{11}$, $Z^{11}$ represents an aromatic nitrogen-containing heterocyclic ring, each of $L^{12}$ and $L^{13}$ represents a carbon atom, a nitrogen atom, an oxygen atom or a phosphorus atom, $E^{11}$ represents an atomic group for forming a bidentate ligand together with $L^{12}$ and $L^{13}$, k represents an integer of 1 to 3, l represents an integer of 0 to 2, k+l is 2 or 3, $S^{11}$ represents a group represented by formula (I), n represents an integer of 1 to 4, and each $S^{11}$ may be the same as or different from every other $S^{11}$.)

[7]

The organic electroluminescence device according to [6], wherein the metal complex represented by formula (1) is a metal complex represented by the following formula (2).

(2)

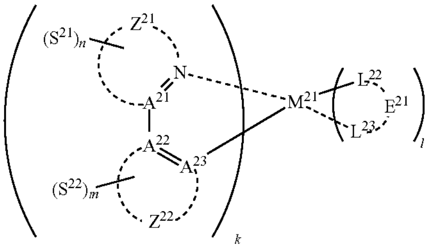

(In formula (2), $M^{21}$ represents a metal belong to Groups 8 to 11 in the periodic table of elements, each of $A^{21}$ to $A^{23}$ independently represents a nitrogen atom or a carbon atom, $Z^{21}$ represents an aromatic nitrogen-containing heterocyclic ring, $Z^{22}$ represents an aromatic heterocyclic ring or an aromatic hydrocarbon ring, each of $L^{22}$ and $L^{23}$ represents a carbon atom, a nitrogen atom, an oxygen atom or a phosphorus atom, $E^{21}$ represents an atomic group for forming a bidentate ligand together with $L^{22}$ and $L^{23}$, k represents an integer of 1 to 3, l represents an integer of 0 to 2, k+l is 2 or 3, each of $S^{21}$ and $S^{22}$ independently represents a group represented by formula (I), each of n and m represents an integer of 0 to 4, n+m is an integer of 1 to 4, and each $S^{21}$ or $S^{22}$ may be the same as or different from every other $S^{21}$ or $S^{22}$.)

[8]

The organic electroluminescence device according to [7], wherein the metal complex represented by formula (2) is represented by the following formula (4).

(4)

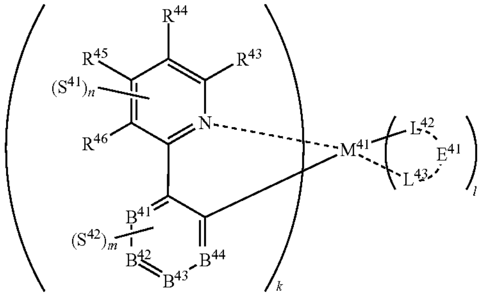

(In formula (4), $M^{41}$ represents a metal belong to Groups 8 to 11 in the periodic table of elements, each of $R^{43}$ to $R^{46}$ independently represents a hydrogen atom or a substituent, each of $B^{41}$ to $B^{44}$ independently represents a nitrogen atom or C—$R^{47}$, $R^{47}$ represents a hydrogen atom or a substituent, each $R^{47}$ may be the same as or different from every other $R^{47}$, each of $L^{42}$ and $L^{43}$ represents a carbon atom, a nitrogen atom, an oxygen atom or a phosphorus atom, $E^{41}$ represents an atomic group for forming a bidentate ligand together with $L^{42}$ and $L^{43}$, k represents an integer of 1 to 3, l represents an integer of 0 to 2, k+l is 2 or 3, each of $S^{41}$ and $S^{42}$ independently represents a group represented by formula (I), each of n and m represents an integer of 0 to 4, n+m is an integer of 1 to 4, and each $S^{41}$ or $S^{42}$ may be the same as or different from every other $S^{41}$ or $S^{42}$.)

[9]

The organic electroluminescence device according to [8], wherein the metal complex represented by formula (4) is represented by the following formula (5).

(5)

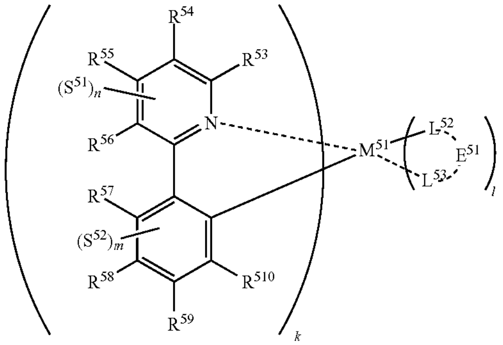

(In formula (5), $M^{51}$ represents a metal belong to Groups 8 to 11 in the periodic table of elements, each of $R^{53}$ to $R^{59}$ and $R^{510}$ independently represents a hydrogen atom or a substituent, each of $L^{52}$ and $L^{53}$ represents a carbon atom, a nitrogen atom, an oxygen atom or a phosphorus atom, $E^{51}$ represents an atomic group for forming a bidentate ligand together with $L^{52}$ and $L^{53}$, k represents an integer of 1 to 3, l represents an integer of 0 to 2, k+l is 2 or 3, each of $S^{51}$ and $S^{52}$ independently represents a group represented by formula (I), each of n and m represents an integer of 0 to 4, n+m is an integer of 1 to 4, and each $S^{51}$ or $S^{52}$ may be the same as or different from every other $S^{51}$ or $S^{52}$.)

[10]

The organic electroluminescence device according to [7], wherein the metal complex represented by formula (2) is represented by the following formula (7).

(7)

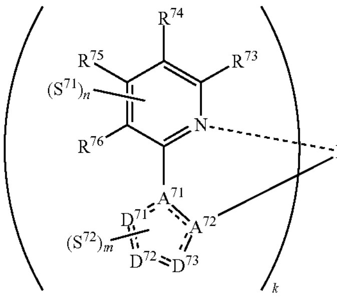

(In formula (7), $M^{71}$ represents a metal belong to Groups 8 to 11 in the periodic table of elements, each of $R^{73}$ to $R^{76}$ independently represents a hydrogen atom or a substituent, each of $A^{71}$ and $A^{72}$ independently represents a nitrogen atom or a carbon atom, each of $D^{71}$ to $D^{73}$ independently represents an atom selected from carbon, nitrogen, oxygen, sulfur and silicon, the bond between atoms in the 5-membered ring formed by $D^{71}$ to $D^{73}$, $A^{71}$ and $A^{72}$ represents a single bond or a double bond, each of $D^{71}$ to $D^{73}$ when these can be further substituted may have a substituent, each of $L^{72}$ and $L^{73}$ represents a carbon atom, a nitrogen atom, an oxygen atom or a phosphorus atom, $E^{71}$ represents an atomic group for forming a bidentate ligand together with $L^{72}$ and $L^{73}$, k represents an integer of 1 to 3, l represents an integer of 0 to 2, k+l is 2 or 3, each of $S^{71}$ and $S^{72}$ independently represents a group represented by formula (I), each of n and m represents an integer of 0 to 4, n+m is an integer of 1 to 4, and each $S^{71}$ or $S^{72}$ may be the same as or different from every other $S^{71}$ or $S^{72}$.)

[11]

The organic electroluminescence device according to [7], wherein the metal complex represented by formula (2) is represented by the following formula (9).

(9)

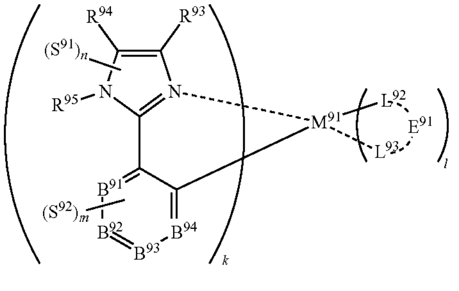

(In formula (9), $M^{91}$ represents a metal belong to Groups 8 to 11 in the periodic table of elements, each of $R^{93}$ and $R^{94}$ independently represents a hydrogen atom or a substituent, $R^{95}$ represents a hydrogen atom or a substituent, each of $B^{91}$ to $B^{94}$ independently represents a nitrogen atom or C—$R^{96}$, $R^{96}$ represents a hydrogen atom or a substituent, each $R^{96}$ may be the same as or different from every other $R^{96}$, each of $L^{92}$ and $L^{93}$ represents a carbon atom, a nitrogen atom, an oxygen atom or a phosphorus atom, $E^{91}$ represents an atomic group for forming a bidentate ligand together with $L^{92}$ and $L^{93}$, k represents an integer of 1 to 3, l represents an integer of 0 to 2, k+l is 2 or 3, each of $S^{91}$ and $S^{92}$ independently represents a group represented by formula (I), each of n and m represents an integer of 0 to 4, n+m is an integer of 1 to 4, and each $S^{91}$ or $S^{92}$ may be the same as or different from every other $S^{91}$ or $S^{92}$.)

[12]

The organic electroluminescence device according to [7], wherein the metal complex represented by formula (2) is represented by the following formula (12).

(12)

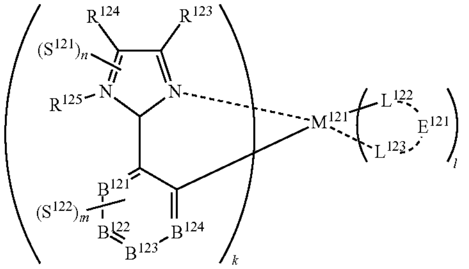

(In formula (12), $M^{121}$ represents a metal belong to Groups 8 to 11 in the periodic table of elements, each of $R^{123}$ to $R^{125}$ independently represents a hydrogen atom or a substituent, each of $B^{121}$ to $B^{124}$ independently represents a nitrogen atom or C—$R^{126}$, $R^{126}$ represents a hydrogen atom or a substituent, each $R^{126}$ may be the same as or different from every other $R^{126}$, each of $L^{122}$ and $L^{123}$ represents a carbon atom, a nitrogen atom, an oxygen atom or a phosphorus atom, $E^{121}$ represents an atomic group for forming a bidentate ligand together with $L^{122}$ and $L^{123}$, k represents an integer of 1 to 3, l represents an integer of 0 to 2, k+l is 2 or 3, each of $S^{121}$ and $S^{122}$ independently represents a group represented by formula (I), each of n and m represents an integer of 0 to 4, n+m is an integer of 1 to 4, and each $S^{121}$ or $S^{122}$ may be the same as or different from every other $S^{121}$ or $S^{122}$.)

[13]

The organic electroluminescence device according to [6], wherein the metal complex represented by formula (1) is a metal complex represented by the following formula (13).

(13)

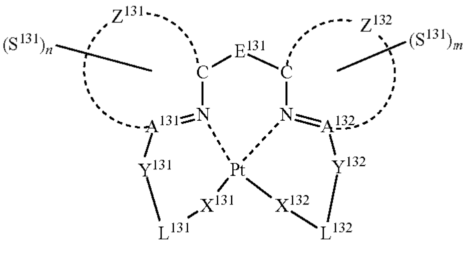

(In formula (13), each of $A^{131}$ and $A^{132}$ represents a nitrogen atom or a carbon atom, each of $Y^{131}$ and $Y^{132}$ represents a linking group or a single bond, each of $L^{131}$ and $L^{132}$ represents a partial structure having an atom bonded to Pt, each of $Z^{131}$ and $Z^{132}$ represents an aromatic nitrogen-containing heterocyclic ring, each of $X^{131}$ and $X^{132}$ represents an oxygen atom, a sulfur atom, a substituted or unsubstituted nitrogen atom or a single bond, $E^{131}$ represents a divalent linking group, each of $S^{131}$ and $S^{132}$ independently represents a group represented by formula (I), each of n and m represents an integer of 0 to 4, n+m is an integer of 1 to 4, and each $S^{131}$ or $S^{132}$ may be the same as or different from every other $S^{131}$ or $S^{132}$.)

[14]

The organic electroluminescence device according to [13], wherein the metal complex represented by formula (13) is represented by the following formula (14).

(14)

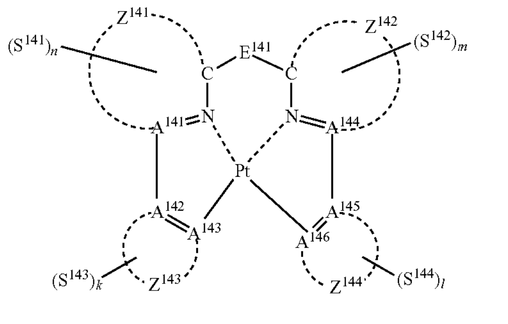

(In formula (14), wherein each of $A^{141}$ to $A^{146}$ independently represents a nitrogen atom or a carbon atom, each of $Z^{141}$ and $Z^{142}$ independently represents an aromatic nitrogen-containing heterocyclic ring, each of $Z^{143}$ and $Z^{144}$ independently represents an aromatic heterocyclic ring or an aromatic hydrocarbon ring, $E^{141}$ represents a divalent linking group, each of $S^{141}$ to $S^{144}$ independently represents a group represented by formula (I), each of n, m, k and l represents an integer of 0 to 4, n+m+k+l is an integer of 1 to 4, and each $S^{141}$, $S^{142}$, $S^{143}$ or $S^{144}$ may be the same as or different from every other $S^{141}$, $S^{142}$, $S^{143}$ or $S^{144}$.)

[15]

The organic electroluminescence device according to [14], wherein the metal complex represented by formula (14) is represented by the following formula (15).

(15)

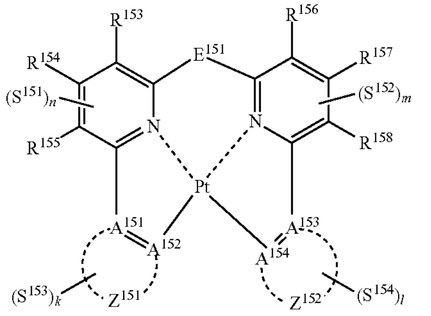

(In formula (15), each of $A^{151}$ to $A^{154}$ independently represents a nitrogen atom or a carbon atom, each of $R^{153}$ to $R^{158}$ independently represents a hydrogen atom or a substituent, each of $Z^{151}$ and $Z^{152}$ independently represents an aromatic heterocyclic ring or an aromatic hydrocarbon ring, $E^{151}$ represents a divalent linking group, each of $S^{151}$ to $S^{154}$ independently represents a group represented by formula (I), each of n, m, k and l represents an integer of 0 to 4, n+m+k+l is an integer of 1 to 4, and each $S^{151}$, $S^{152}$, $S^{153}$ or $S^{154}$ may be the same as or different from every other $S^{151}$, $S^{152}$, $S^{153}$ or $S^{154}$.)

[16]

The organic electroluminescence device according to [14], wherein the metal complex represented by formula (14) is represented by the following formula (18).

(18)

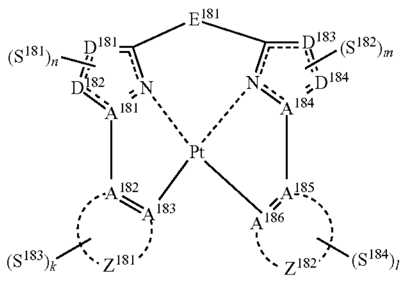

(In formula (18), each of $A^{181}$ to $A^{186}$ independently represents a nitrogen atom or a carbon atom, each of $D^{181}$ to $D^{184}$ independently represents an atom selected from carbon, nitrogen, oxygen, sulfur and silicon, the bond between atoms in the 5-membered ring formed by $D^{181}$, $D^{182}$, $A^{181}$, the nitrogen atom and the carbon atom or by $D^{183}$, $D^{184}$, $A^{184}$, the nitrogen atom and the carbon atom represents a single bond or a double bond, each of $D^{181}$ to $D^{184}$ when these can be further substituted may have a substituent, each of $Z^{181}$ and $Z^{182}$ independently represents an aromatic heterocyclic ring or an aromatic hydrocarbon ring, $E^{181}$ represents a divalent linking group, each of $S^{181}$ to $S^{184}$ independently represents a group represented by formula (I), each of n, m, k and l represents an integer of 0 to 4, n+m+k+l is an integer of 1 to 4, and each $S^{181}$, $S^{182}$, $S^{183}$ or $S^{184}$ may be the same as or different from every other $S^{181}$, $S^{182}$, $S^{183}$ or $S^{184}$.)

[17]

The organic electroluminescence device according to any one of [1] to [5], wherein the metal complex having a group represented by formula (I) is a phosphorescent metal complex containing a monoanionic bidentate ligand represented by the following formulae (A1) to (A4) and a metal having an atomic weight of 40 or more.

(A1)

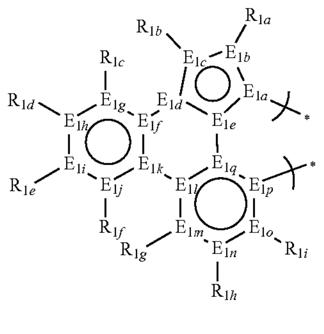

-continued (A2)

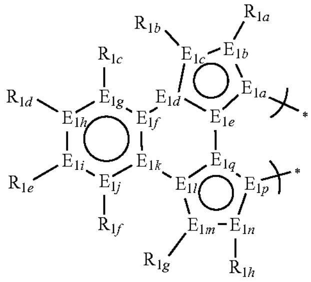

(A3)

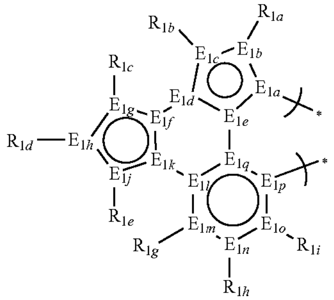

(A4)

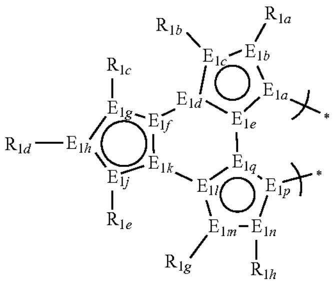

(In formulae (A1) to (A4), each of $E_{1a}$ $E_{1q}$ independently represents a carbon atom or a heteroatom, each of $R_{1a}$ to $R_{1i}$ independently represents a hydrogen atom or a substituent, provided that at least one of $R_{1a}$ to $R_{1i}$ represents a group represented by formula (I), and each of the structures represented by formulae (A1) to (A4) has a structure with 18 π-electrons in total.)

[18]

The organic electroluminescence device according to [17], wherein said phosphorescent metal complex contains a monoanionic bidentate ligand represented by the following formula (A1-3) or (A3-3) and a metal having an atomic weight of 40 or more.

(A1-3)

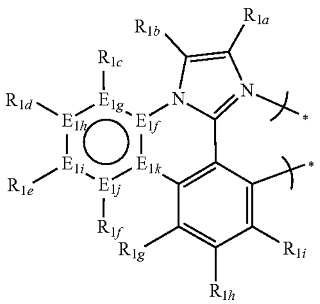

-continued (A3-3)

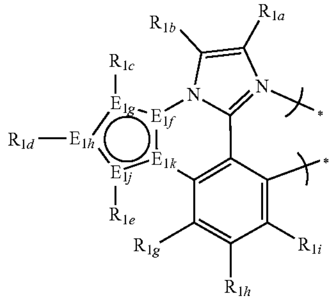

(In formulae (A1-3) to (A3-3), each of $E_{1f}$ to $E_{1k}$ independently represents a carbon atom or a heteroatom, each of $R_{1a}$ to $R_{1i}$ independently represents a hydrogen atom or a substituent, provided that at least one of $R_{1a}$ to $R_{1i}$ represents a group represented by formula (I), and each of the structures represented by formulae (A1-3) and (A3-3) has a structure with 18 π-electrons in total.)

[19]

The organic electroluminescence device according to [18], wherein said phosphorescent metal complex is an iridium complex represented by the following formula (A9).

(A9)

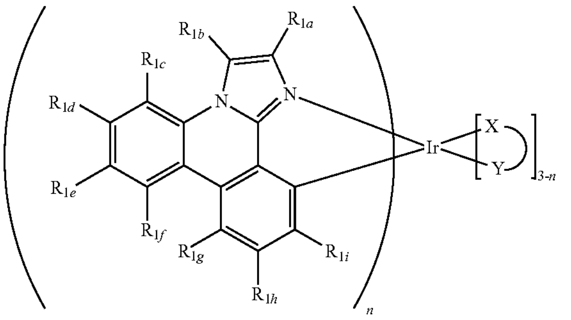

(In formula (9), each of $R_{1a}$ to $R_{1i}$ independently represents a hydrogen atom or a substituent, provided that at least one of $R_{1a}$ to $R_{1i}$ represents a group represented by formula (I), X—Y represents a monoanionic bidentate ligand, and n represents an integer of 1 to 3.)

[20]

The organic electroluminescence device according to any one of [1] to [19], wherein the metal complex having a group represented by formula (I) is contained in the light emitting layer.

[21]

The organic electroluminescence device according to any one of [1] to [20], wherein a carbazole or indole structure-containing material is further contained in any one of the organic layer.

[22]

The organic electroluminescence device according to any one of [1] to [21], wherein a carbazole or indole structure-containing material is further contained in the light emitting layer.

[23]

A composition containing a metal complex having a group represented by formula (I) in [1].

[24]

A light emitting layer containing a metal complex having a group represented by formula (I) in [1].

[25]

A light emission apparatus using the organic electroluminescence device according to any one of [1] to [22].

[26]

A display apparatus using the organic electroluminescence device according to any one of [1] to [22].

[27]

An illumination apparatus using the organic electroluminescence device according to any one of [1] to [22].

The organic electroluminescence device of the present invention contains a metal complex having a group represented by formula (I). By this configuration, an organic electroluminescence device (in the context of the present invention, this term is used with the same meaning as "the device of the present invention") having high luminous efficiency (for example, external quantum efficiency) and high durability and causing little chromaticity shift after device deterioration can be provided. Also, a long life of the device can be realized.

DESCRIPTION OF EMBODIMENTS

Figure 1:
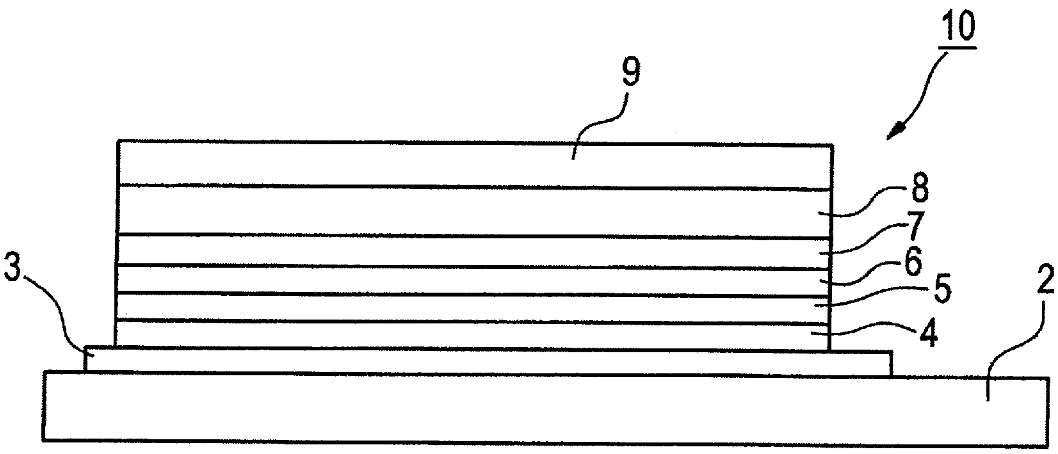
FIG. 1 is a schematic view showing one example of the configuration of the organic electroluminescence device according to the present invention.

The organic electroluminescence device of the present invention is an organic electroluminescence device including a substrate having thereon a pair of electrodes and at least one organic layer between said electrodes, the organic layer containing a light emitting layer, wherein any one layer of the organic layer contains a metal complex having a group represented by the following formula (I):

(I)

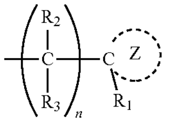

(wherein $R_1$ represents an alkyl group, each of $R_2$ and $R_3$ independently represents a hydrogen atom or an alkyl group, n represents an integer of 0 to 6, and Z represents a saturated 5- to 8-membered ring).

The metal complex having a group represented by formula (I) includes its tautomers and is a metal complex having a group containing a specific saturated ring group. It has been considered that usually, when a secondary or tertiary carbon is substituted on an aromatic heterocyclic ring or an aromatic hydrocarbon ring, a hydrogen elimination reaction or a dimerization reaction from the excited state occurs, giving rise to decrease in the device life. However, introduction of a sterically bulky group is expected to bring about spatial separation of reactive sites of the light emitting material, whereby a hydrogen elimination reaction or dimerization reaction of the metal complex is suppressed and the device life is prolonged.

Particularly, in an organic electroluminescence device using, as the light emitting material, a metal complex of the present invention where a group containing a saturated ring group having quaternary carbon in a saturated 5- to 8-membered ring group is substituted on a ligand, that is, an aromatic heterocyclic ring or an aromatic hydrocarbon ring, the saturated ring group is sterically bulky but is more compactly and rigidly organized as compared with a chain group having the same number of atoms as the structure. Accordingly, the film state is considered to change by any form while keeping an appropriate intermolecular distance, whereby the degree of order in the molecular arrangement is increased, as a result, a charge career mobility in the device using the metal complex is increased, and an effect such as enhancement of the device efficiency and reduction of the drive voltage is obtained.

Also, by the stable film structure at driving, it is presumed that the metal complex can contribute also to the enhancement of durability.

Furthermore, in the embodiment where a saturated ring group as the group represented by formula (I) is combined to the ligand through a substituted or unsubstituted methylene group, the flexibility of the group represented by formula (I) is increased and the dispersibility of the light emitting material to the organic layer is enhanced as compared with the conventional alkyl group-substituted phosphorescent material, as a result, interaction of light emitting material molecules with each other is suppressed. These improved dispersibility and reduced interaction are presumed to enable more enhancing the device efficiency and easily obtaining an effect of reducing the chromaticity shift at the device deterioration.

According to the embodiment where a group represented by formula (I) having high flexibility is introduced, the solubility of the phosphorescent material in an organic solvent can be increased, and a high-concentration solution can be prepared. The coating step using a high-concentration solution is advantageous for improvement of the film homogeneity and reduction in impurities (dissolved oxygen, water), and an enhanced efficiency and a long life of a device fabricated by a wet process can be realized.

$R_1$ represents an alkyl group. Here, $R_1$ represents an alkyl group which may be substituted or may be linear or branched, and preferably represents an alkyl group having a carbon number of 1 to 12, more preferably from 1 to 6. $R_1$ is preferably an unsubstituted alkyl group, more preferably an unsubstituted linear alkyl group, still more preferably a methyl group or an ethyl group, and most preferably a methyl group.

Each of $R_2$ and $R_3$ independently represents a hydrogen atom or an alkyl group. Here, each of $R_2$ and $R_3$ independently represents a hydrogen atom or an alkyl group which may be substituted or may be linear or branched, and preferably represents an alkyl group having a carbon number of 1 to 12, more preferably from 1 to 6. Each of $R_2$ and $R_3$ is preferably a hydrogen atom or an unsubstituted alkyl group, more preferably a hydrogen atom or an unsubstituted linear alkyl group, still more preferably a hydrogen atom or a methyl group, yet still more preferably a hydrogen atom.

n represents an integer of 0 to 6, and n is preferably an integer of 1 to 6, more preferably an integer of 1 to 3, yet still more preferably 1.

When n is 1 or more, the flexibility of the group represented by formula (I) is increased and the dispersibility of the light emitting material to the organic layer is enhanced, as a result, interaction of light emitting material molecules with each other is suppressed. These improved dispersibility and reduced interaction are considered to enable enhancing the device efficiency and easily obtaining an effect of reducing the chromaticity shift at the device deterioration.

Z represents a saturated 5- to 8-membered ring, more preferably a 5- or 6-membered ring, together with C. The saturated 5- to 8-membered ring represented by Z is preferably formed of a carbon atom, a hydrogen atom, an oxygen atom, a nitrogen atom and a sulfur atom, more preferably formed of a carbon atom, a hydrogen atom and an oxygen atom, still more preferably formed of a carbon atom and a hydrogen atom.

Preferred examples of the saturated 5- to 8-membered ring represented by Z include a cyclopentane ring, a cyclohexane ring, a cycloheptane ring, a cyclooctane ring, a tetrahydrofuran ring, a tetrahydropyran ring, a tetrahydrothiophene ring, a dioxane ring, a pyrrolidine ring, a piperidine ring, a piperazine ring and a morpholine ring. Among these, a cyclopentane ring, a cyclohexane ring, a cycloheptane ring and a cyclooctane ring are more preferred, and a cyclopentane ring and a cyclohexane ring are still more preferred.

The saturated 5- to 8-membered ring is generally excellent in the chemical stability as compared with a saturated 3- or 4-membered ring and therefore, the device of the present invention using a light emitting material having a group represented by formula (I) is considered to be excellent in the drive durability as compared with a device using a light emitting layer having a substituent containing a saturated 3- or 4-membered ring. Also, thanks to the bulky and rigid structure, the effect by the enhanced degree of order in the arrangement is considered to be great.

Furthermore, the group represented by formula (I) has a quaternary carbon atom in the saturated ring group and therefore, is bulky as well as rigid, and this is presumed to make larger the effect by the enhanced degree of order and enable obtaining an effect in terms of enhancement of the device efficiency, reduction of the drive voltage and improvement of the durability.

The saturated 5- to 8-membered ring represented by Z may further have a substituent thereon. Preferred examples of this substituent include an alkyl group, a cycloalkyl group and an aryl group.

Substituents a1 to a31 are illustrated below as preferred examples of the group represented by formula (1), but the present invention is not limited thereto.

a1

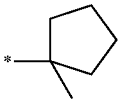

a2

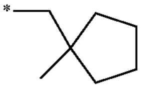

a3

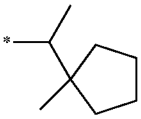

-continued a4

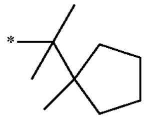

a5

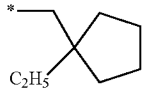

a6

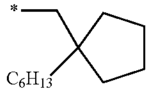

a7

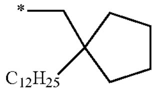

a8

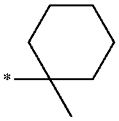

a9

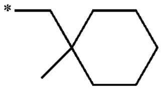

a10

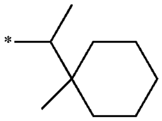

a11

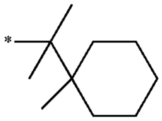

a12

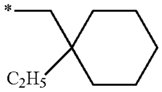

a13

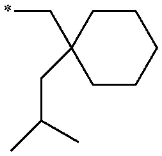

a14

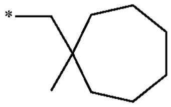

a15

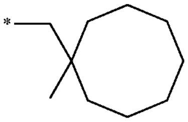

-continued a16

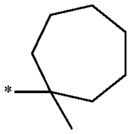

a17

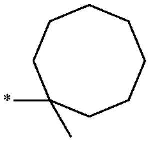

a18

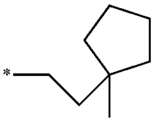

a19

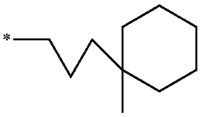

a20

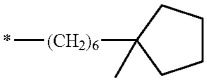

a21

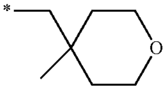

a22

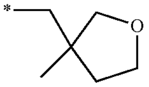

a23

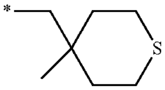

a24

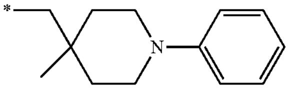

a25

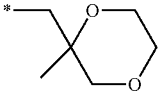

a26

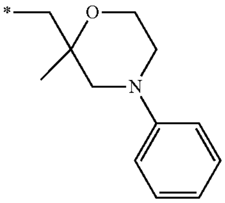

a27

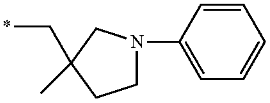

a28

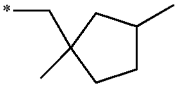

-continued a29

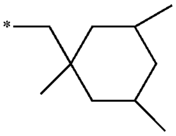

a30

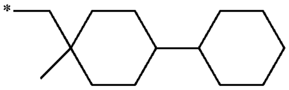

a31

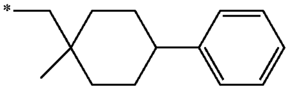

Among these, a1, a2, a3, a5, a8, a9, a10, a12, a14, a15, a18, a19, a28, a29, a30 and a31 are preferred, a2, a5, a9, a12, a18, a19, a28 and a29 are more preferred, and a2, a5, a9 and a12 are still more preferred.

[Compound Represented by Formula (1)]

The compound represented by formula (1) is described in detail.

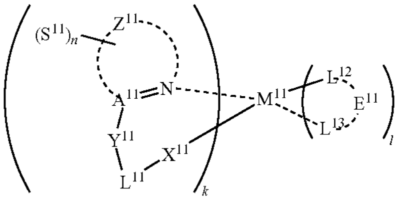

(1)

(In formula (1), $M^{11}$ represents a metal belong to Groups 8 to 11 in the periodic table of elements, $A^{11}$ represents a nitrogen atom or a carbon atom, $X^{11}$ represents an oxygen atom, a sulfur atom, a substituted or unsubstituted nitrogen atom or a single bond, $Y^{11}$ represents a linking group or a single bond, $L^{11}$ represents a partial structure having an atom bonded to $X^{11}$, $Z^{11}$ represents an aromatic nitrogen-containing heterocyclic ring, each of $L^{12}$ and $L^{13}$ represents a carbon atom, a nitrogen atom, an oxygen atom or a phosphorus atom, $E^{11}$ represents an atomic group for forming a bidentate ligand together with $L^{12}$ and $L^{13}$, k represents an integer of 1 to 3, l represents an integer of 0 to 2, k+l is 2 or 3, each $S^{11}$ independently represents a group represented by formula (I), n represents an integer of 1 to 4, and each $S^{11}$ may be the same as or different from every other $S^{11}$).

$M^{11}$ represents a metal (may be a metal atom or ion) belonging to Groups 8 to 11 in the periodic table of elements and is preferably gold, copper, platinum, palladium, nickel, iridium rhodium, osmium or ruthenium, more preferably gold, platinum, palladium iridium or ruthenium, still more preferably gold, platinum, palladium or iridium, and most preferably platinum or iridium.

$A^{11}$ represents a nitrogen atom or a carbon atom and forms an aromatic nitrogen-containing heterocyclic ring together with the N atom and $Z^{11}$.

Examples of the aromatic nitrogen-containing heterocyclic ring represented by $Z^{11}$ in formula (1) include a pyridine ring, a pyridazine ring, a pyrimidine ring, a pyrazine ring, a triazine ring, a benzimidazole ring, an oxadiazole ring, a triazole ring, an imidazole ring, a pyrazole ring, a thiazole ring, an oxazole ring, a benzimidazole ring, a benzothiazole ring, a benzoxazole ring, an isoquinoline ring, a quinoxaline ring, a quinazoline ring, a phthalazine ring, a carboline ring, and a ring where a carbon atom of a hydrocarbon ring constituting a carboline ring is further substituted with a nitrogen atom.

$Z^{11}$ is preferably a pyridine ring, a pyrimidine ring, a pyrazine ring, a benzimidazole ring, an oxadiazole ring, a triazole ring, an imidazole ring, a pyrazole ring, a thiazole ring, an oxazole ring, a benzimidazole ring, a benzothiazole ring, a benzoxazole ring, an isoquinoline ring or a quinoxaline ring, more preferably a pyridine ring, a pyrimidine ring, a pyrazine ring, an imidazole ring, a pyrazole ring, an isoquinoline ring or a quinoxaline ring, still more preferably an isoquinoline ring, a benzoxazole ring, a pyridine ring, an imidazole ring or a pyrazole ring.

The aromatic nitrogen-containing heterocyclic ring may have a substituent, and those described below as Substituent Group A can be applied to the substituent.

(Substituent Group A)

An alkyl group (preferably having a carbon number of 1 to 30, more preferably from 1 to 20, still more preferably from 1 to 10, e.g., methyl, ethyl, isopropyl, tert-butyl, n-octyl, n-decyl, n-hexadecyl, trifluoromethyl, pentafluoroethyl), a cycloalkyl group (preferably having a carbon number of 3 to 30, more preferably from 3 to 20, still more preferably from 3 to 10, e.g., cyclopropyl, cyclopentyl, cyclohexyl), an alkenyl group (preferably having a carbon number of 2 to 30, more preferably from 2 to 20, still more preferably from 2 to 10, e.g., vinyl, allyl, 2-butenyl, 3-pentenyl), an alkynyl group (preferably having a carbon number of 2 to 30, more preferably from 2 to 20, still more preferably from 2 to 10, e.g., propargyl, 3-pentynyl), an aryl group (preferably having a carbon number of 6 to 30, more preferably from 6 to 20, still more preferably from 6 to 12, e.g., phenyl, p-methylphenyl, naphthyl, anthranyl), an amino group (preferably having a carbon number of 0 to 30, more preferably from 0 to 20, still more preferably from 0 to 10, e.g., amino, methylamino, dimethylamino, diethylamino, dibenzylamino, diphenylamino, ditolylamino), an alkoxy group (preferably having a carbon number of 1 to 30, more preferably from 1 to 20, still more preferably from 1 to 10, e.g., methoxy, ethoxy, butoxy, 2-ethylhexyloxy), an aryloxy group (preferably having a carbon number of 6 to 30, more preferably from 6 to 20, still more preferably from 6 to 12, e.g., phenyloxy, 1-naphthyloxy, 2-naphthyloxy), a heterocyclic oxy group (preferably having a carbon number of 1 to 30, more preferably from 1 to 20, still more preferably from 1 to 12, e.g., pyridyloxy, pyrazyloxy, pyrimidyloxy, quinolyloxy), an acyl group (preferably having a carbon number of 1 to 30, more preferably from 1 to 20, still more preferably from 1 to 12, e.g., acetyl, benzoyl, formyl, pivaloyl), an alkoxycarbonyl group (preferably having a carbon number of 2 to 30, more preferably from 2 to 20, still more preferably from 2 to 12, e.g., methoxycarbonyl, ethoxycarbonyl), an aryloxycarbonyl group (preferably having a carbon number of 7 to 30, more preferably from 7 to 20, still more preferably from 7 to 12, e.g., phenyloxycarbonyl), an acyloxy group (preferably having a carbon number of 2 to 30, more preferably from 2 to 20, still more preferably from 2 to 10, e.g., acetoxy, benzoyloxy), an acylamino group (preferably having a carbon number of 2 to 30, more preferably from 2 to 20, still more preferably from 2 to 10, e.g., acetylamino, benzoylamino), an alkoxycarbonylamino group (preferably having a carbon number of 2 to 30, more preferably from 2 to 20, still more preferably from 2 to 12, e.g., methoxycarbonylamino), an aryloxycarbonylamino group (preferably having a carbon number of 7 to 30, more preferably from 7 to 20, still more preferably from 7 to 12, e.g., phenyloxycarbonylamino), a sulfonylamino group (preferably having a carbon number of 1 to 30, more preferably from 1 to 20, still more preferably from 1 to 12, e.g., methanesulfonylamino, benzenesulfonylamino), a sulfamoyl group (preferably having a carbon number of 0 to 30, more preferably from 0 to 20, still more preferably from 0 to 12, e.g., sulfamoyl, methylsulfamoyl, dimethylsulfamoyl, phenylsulfamoyl), a carbamoyl group (preferably having a carbon number of 1 to 30, more preferably from 1 to 20, still more preferably from 1 to 12, e.g., carbamoyl, methylcarbamoyl, diethylcarbamoyl, phenylcarbamoyl), an alkylthio group (preferably having a carbon number of 1 to 30, more preferably from 1 to 20, still more preferably from 1 to 12, e.g., methylthio, ethylthio), an arylthio group (preferably having a carbon number of 6 to 30, more preferably from 6 to 20, still more preferably from 6 to 12, e.g., phenylthio), a heterocyclic thio group (preferably having a carbon number of 1 to 30, more preferably from 1 to 20, still more preferably from 1 to 12, e.g., pyridylthio, 2-benzimizolylthio, 2-benzoxazolylthio, 2-benzothiazolylthio), a sulfonyl group (preferably having a carbon number of 1 to 30, more preferably from 1 to 20, still more preferably from 1 to 12, e.g., mesyl, tosyl), a sulfonyl group (preferably having a carbon number of 1 to 30, more preferably from 1 to 20, still more preferably from 1 to 12, e.g., methanesulfinyl, benzenesulfinyl), a ureido group (preferably having a carbon number of 1 to 30, more preferably from 1 to 20, still more preferably from 1 to 12, e.g., ureido, methylureido, phenylureido), a phosphoric acid amido group (preferably having a carbon number of 1 to 30, more preferably from 1 to 20, still more preferably from 1 to 12, e.g., diethylphosphoric acid amido, phenylphosphoric acid amido), a hydroxy group, a mercapto group, a halogen atom (for example, a fluorine atom, a chlorine atom, a bromine atom and an iodine atom, preferably a fluorine atom), a cyano group, a sulfo group, a carboxyl group, a nitro group, a hydroxamic acid group, a sulfino group, a hydrazino group, an imino group, a heterocyclic group (preferably having a carbon number of 1 to 30, more preferably from 1 to 12; examples of the heteroatom include a nitrogen atom, an oxygen atom and a sulfur atom; specifically an imidazolyl group, a pyridyl group, a quinolyl group, a furyl group, a thienyl group, a piperidyl group, a morpholino group, a benzoxazolyl group, a benzimidazolyl group, a benzothiazolyl group, a carbazolyl group, an azepinyl group and the like), a silyl group (preferably having a carbon number of 3 to 40, more preferably from 3 to 30, still more preferably from 3 to 24, e.g., trimethylsilyl, triphenylsilyl), and a silyloxy group (preferably having a carbon number of 3 to 40, more preferably from 3 to 30, still more preferably from 3 to 24, e.g., trimethylsilyloxy, triphenylsilyloxy). These substituents may be further substituted.

Also, a plurality of these substituents may combine with each other to form a ring.

The substituent of the aromatic nitrogen-containing heterocyclic ring is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

$X^{11}$ represents an oxygen atom, a sulfur atom, a substituted or unsubstituted nitrogen atom or a single bond and is preferably an oxygen atom, a sulfur atom or a single bond, more preferably an oxygen atom or a single bond, still more preferably a single bond. In the case where $X^{11}$ represents a substituted nitrogen atom, the substituent is, for example, preferably a substituent selected from Substituent Group A, more preferably an alkyl group, a cycloalkyl group or an aryl group, still more preferably an alkyl group having a carbon number of 1 to 7 or an aryl group having a carbon number of 6 to 12 (number of ring members: from 1 to 2).

$Y^{11}$ represents a linking group or a single bond. The linking group is not particularly limited but is preferably a single bond or a divalent linking group containing a carbon atom, a nitrogen atom, an oxygen atom, a sulfur atom, a silicon atom, a germanium atom or a phosphorus atom, more preferably a single bond or a group selected from Linking Group A shown below.

Linking Group A:

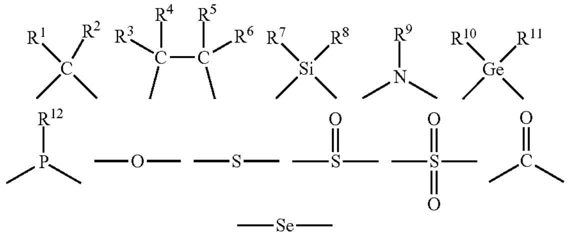

In Liking Group A, each of $R^1$, $R^2$, $R^3$, $R^4$, $R^5$, $R^6$, $R^7$, $R^8$, $R^9$, $R^{10}$, $R^{11}$ and $R^{12}$ ($R^1$ to $R^{12}$) independently represents a hydrogen atom or a substituent selected from substituents including Substituent Group A. In the case where each of $R^1$ to $R^{12}$ represents a substituent, the substituent is preferably a substituent selected from Substituent Group A. Each of $R^1$ to $R^{12}$ when these can be substituted may further have a substituent, and $R^1$ and $R^2$, $R^3$ and $R^4$, $R^5$ and $R^6$, $R^3$ and $R^5$, $R^3$ and $R^6$, $R^4$ and $R^6$, or $R^{10}$ and $R^{11}$ may combine with each other to form a ring.

$Y^{11}$ is more preferably a single bond or a substituent selected from Linking Group A. Among these, a single bond, $—C(R^1)(R^2)—$, $—C(R^3)(R^4)C(R^5)(R^6)—$, $—Si(R^7)(R^8)—$, $—N(R^9)—$, —O—, —S—, —SO—, $—SO_2—$ and —CO— are preferred, a single bond, $—C(R^1)(R^2)—$, $—C(R^3)(R^4)C(R^5)(R^6)—$, $—Si(R^7)(R^8)—$, —O— and —S— are more preferred, a single bond $—C(R^1)(R^2)—$ and $—C(R^3)(R^4)C(R^5)(R^6)—$ are still more preferred, and a single bond is yet still more preferred.

In $—C(R^1)(R^2)—$, each of $R^1$ and $R^2$ is preferably a hydrogen atom or a substituent selected from Substituent Group B below.

(Substituent Group B)

The substituent includes an alkyl group, a cycloalkyl group, an aryl group, a halogen atom, an amino group, an alkylthio group, an arylthio group, an alkyloxy group, an aryloxy group, a hydroxy group, a mercapto group and a halogen atom. Among these, an alkyl group, a cycloalkyl group, an aryl group, a halogen atom, an alkylthio group, an arylthio group, an alkyloxy group, an aryloxy group and a halogen atom are preferred, and an alkyl group and an aryl group are more preferred.)

In $—C(R^3)(R^4)C(R^5)(R^6)—$, each of $R^3$, $R^4$, $R^5$ and $R^6$ is preferably a hydrogen atom or a substituent selected from Substituent Group B.

In $—Si(R^7)(R^8)—$, each of $R^7$ and $R^8$ is preferably a hydrogen atom or a substituent selected from Substituent Group B.

In $—Ge(R^{10})(R^{11})—$, each of $R^{10}$ and $R^{11}$ is preferably a hydrogen atom or a substituent selected from Substituent Group B.

In $—N(R^9)—$, $R^9$ is preferably a hydrogen atom, an alkyl group, a cycloalkyl group or an aryl group, more preferably an alkyl group or an aryl group, still more preferably an aryl group.

In $—P(R^{12})—$, $R^{12}$ has the same meaning as the preferred range of $R^9$.

In formula (1), $L^{11}$ represents a partial structure having an atom bonded to $X^{11}$. The partial structure of $L^{11}$ is preferably a group bonded through a carbon atom, a group bonded through a nitrogen atom, a group bonded through a silicon atom, a group bonded through a phosphorus atom, a group bonded through an oxygen atom, or a group bonded through a sulfur atom, more preferably a group bonded through a carbon atom, a nitrogen atom, an oxygen atom or a sulfur atom, still more preferably a group bonded through a carbon atom or an oxygen atom.

The group bonded through a carbon atom is preferably a substituted or unsubstituted aryl group bonded through a carbon atom, a substituted or unsubstituted 5-membered heteroaryl group bonded through a carbon atom, or a substituted or unsubstituted 6-membered heteroaryl group bonded through a carbon atom, more preferably a substituted or unsubstituted aryl group bonded through a carbon atom, a substituted or unsubstituted nitrogen-containing 5-membered heteroaryl group bonded through a carbon atom, or a nitrogen-containing 6-membered heteroaryl group bonded through a carbon atom, still more preferably a substituted aryl group bonded through a carbon atom.

The group bonded through an oxygen atom is preferably a substituted or unsubstituted hydroxyl group or a substituted or unsubstituted carboxyl group, more preferably a substituted or unsubstituted carboxyl group.

The group bonded through a nitrogen atom is preferably a substituted amino group or a nitrogen-containing 5-membered heteroaryl group bonded through a nitrogen atom, more preferably a nitrogen-containing 5-membered heteroaryl group bonded through a nitrogen atom, still more preferably a substituted carbazole group, a substituted pyrrole group or a substituted indole group.

The group bonded through a phosphorus atom is preferably a substituted phosphino group. The group bonded through a silicon atom is preferably a substituted silyl group. The group bonded through a sulfur atom is preferably a thiol group or a substituted thiol group.

Each of $L^{12}$ and $L^{13}$ represents a carbon atom, a nitrogen atom, an oxygen atom or a phosphorus atom, and $E^{11}$ represents an atomic group for forming a bidentate ligand together with $L^{12}$ and $L^{13}$. The combination of $L^{12}$ and $L^{13}$ is not particularly limited but is preferably nitrogen atom-carbon atom, nitrogen atom-oxygen atom, or oxygen atom-oxygen atom. The bidentate ligand represented by $L^{12}$-$E^{11}$-$L^{13}$ is not particularly limited, but specific examples thereof include substituted or unsubstituted phenylpyridine, phenylpyrazole, phenylimidazole, phenyltriazole, phenyltetrazole, pyridylpyridine, imidazolylpyridine, pyrazolylpyridine, triazolylpyridine, pyrazabole, diphenylphosphinoethylene, picolinic acid and acetylacetone. Among these, phenylpyridine, phenylpyrazole, phenylimidazole, pyridylpyridine, pyrazabole, picolinic acid and acetylacetone are preferred, and phenylpyridine, pyridylpyridine, picolinic acid and acetylacetone are more preferred. These groups may be further substituted with the above-described substituent.

k represents an integer of 1 to 3, l represents an integer of 0 to 2, and k+l is 2 or 3. l is preferably 1 or 0, more preferably 0.

$S^{11}$ represents a group represented by formula (I).

As the group represented by formula (I), substituents a1 to a31 are preferred, a1, a2, a3, a5, a8, a9, a10, a12, a14, a15, a18, a19, a28, a29, a30 and a31 are more preferred, a2, a5, a9, a12, a18, a19, a28 and a29 are still more preferred, and a2, a5, a9 and a12 are most preferred. This is presumed because all of bulkiness, rigidity and compactness are satisfied.

The group represented by formula (I) contains a quaternary carbon-containing saturated ring group in a saturated 5- to 8-membered ring and therefore, is sterically bulky but is more compactly and rigidly organized as compared with a chain group having the same number of atoms as the framework. Accordingly, the film state is considered to change by any form while keeping an appropriate intermolecular distance, whereby the degree of order in the molecular arrangement is increased, as a result, the device using, as the light emitting material, the metal complex having a group represented by formula (I) allows easy flow of a current, and an effect such as enhancement of the device efficiency and reduction of the drive voltage is obtained. Furthermore, thanks to the stable film structure at driving, it is presumed that the metal complex can contribute also to the enhancement of durability.

In addition, the saturated 5- to 8-membered ring is generally excellent in the chemical stability as compared with a saturated 3- or 4-membered ring and therefore, the device of the present invention using a light emitting material having a group represented by formula (I) is considered to be excellent in the drive durability as compared with a device using a light emitting layer having a substituent containing a saturated 3- or 4-membered ring. Also, thanks to the bulky and rigid structure, the effect by the enhanced degree of order in the arrangement is considered to be great.

n represents an integer of 1 to 4. n is preferably 1 or 2.

The compound represented by formula (1) is preferably represented by the following formula (2):

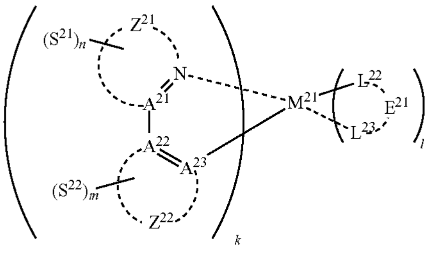

(2)

(In formula (2), $M^{21}$ represents a metal belong to Groups 8 to 11 in the periodic table of elements, each of $A^{21}$ to $A^{23}$ independently represents a nitrogen atom or a carbon atom, $Z^{21}$ represents an aromatic nitrogen-containing heterocyclic ring, $Z^{22}$ represents an aromatic heterocyclic ring or an aromatic hydrocarbon ring, each of $L^{22}$ and $L^{23}$ represents a carbon atom, a nitrogen atom, an oxygen atom or a phosphorus atom, $E^{21}$ represents an atomic group for forming a bidentate ligand together with $L^{22}$ and $L^{23}$, k represents an integer of 1 to 3, l represents an integer of 0 to 2, k+l is 2 or 3, each of $S^{21}$ and $S^{22}$ independently represents a group represented by formula (I), each of n and m represents an integer of 0 to 4, n+m is an integer of 1 to 4, and each $S^{21}$ or $S^{22}$ may be the same as or different from every other $S^{21}$ or $S^{22}$).

In formula (2), $M^{21}$, $A^{21}$, $Z^{21}$, $L^{22}$, $L^{23}$, $E^{21}$, $S^{21}$, $S^{22}$, k and l have the same meanings as $M^{11}$, $A^{11}$, $Z^{11}$, $L^{12}$, $L^{13}$, $E^{11}$, $S^{11}$, k and l in formula (1), and the preferred ranges are also the same.

Each of $A^{22}$ and $A^{23}$ represents a nitrogen atom or a carbon atom, and these form an aromatic heterocyclic ring or an aromatic hydrocarbon ring together with $Z^{22}$.

Examples of the aromatic heterocyclic ring or aromatic hydrocarbon ring represented by $Z^{22}$ include a benzene ring, a naphthalene ring, an anthracene ring, a pyrene ring, a phenanthrene ring, a perylene ring, a pyridine ring, a quinoline ring, an isoquinoline ring, a phenanthridine ring, a pyrimidine ring, a pyrazine ring, a pyridazine ring, a triazine ring, a cinnoline ring, an acridine ring, a phthalazine ring, a quinazoline ring, a quinoxaline ring, a naphthyridine ring, a pteridine ring, a pyrrole ring, a pyrazole ring, a triazole ring, an indole ring, a carbazole ring, an indazole ring, a benzimidazole ring, an oxazole ring, a thiazole ring, an oxadiazole ring, a thiadiazole ring, a benzoxazole ring, a benzothiazole ring, an imidazopyridine ring, a thiophene ring, a benzothiophene ring, a furan ring, a benzofuran ring, a phosphole ring, a phosphinine ring and a silole ring.

$Z^{22}$ is preferably a benzene ring, a naphthalene ring, a benzoxazole ring, a pyrazole ring, an imidazole ring, a triazole ring, a pyridine ring, an indole ring or a thiophene ring, more preferably a benzene ring, a pyrazole ring, a pyridine ring, a benzoxazole ring or a thiophene ring.

$Z^{22}$ may have a substituent, and those described above as Substituent Group A can be applied to the substituent. Furthermore, $Z^{22}$ may form a condensed ring with other rings.

This substituent is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfonyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

Each of n and m represents an integer of 0 to 4, and n+m is an integer of 1 to 4. n+m is preferably 1 or 2.

The compound represented by formula (2) is preferably represented by the following formula (3):

(3)

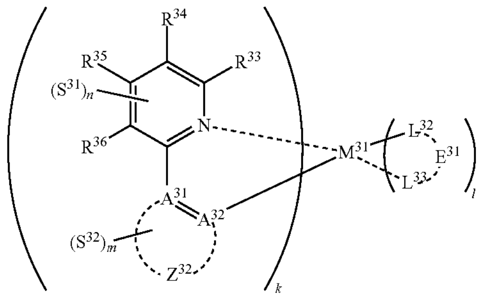

(In formula (3), $M^{31}$ represents a metal belong to Groups 8 to 11 in the periodic table of elements, each of $A^{31}$ and $A^{32}$ independently represents a nitrogen atom or a carbon atom, each of $R^{33}$ to $R^{36}$ independently represents a hydrogen atom or a substituent, $Z^{32}$ represents an aromatic heterocyclic ring or an aromatic hydrocarbon ring, each of $L^{32}$ and $L^{33}$ independently represents a carbon atom, a nitrogen atom, an oxygen atom or a phosphorus atom, $E^{31}$ represents an atomic group for forming a bidentate ligand together with $L^{32}$ and $L^{33}$, k represents an integer of 1 to 3, l represents an integer of 0 to 2, k+l is 2 or 3, each of $S^{31}$ and $S^{32}$ independently represents a group represented by formula (I), each of n and m represents an integer of 0 to 4, n+m is an integer of 1 to 4, and each $S^{31}$ or $S^{32}$ may be the same as or different from every other $S^{31}$ or $S^{32}$).

In formula (3), $M^{31}$, $A^{31}$, $A^{32}$, $Z^{32}$, $L^{32}$, $L^{33}$, $E^{31}$, $S^{31}$, $S^{32}$, n, m, k and l have the same meanings as $M^{21}$, $A^{22}$, $A^{23}$, $Z^{22}$, $L^{22}$, $L^{23}$, $E^{21}$, $S^{21}$, $S^{22}$, n, m, k and l in formula (2), and the preferred ranges are also the same.

Each of $R^{33}$ to $R^{36}$ independently represents a hydrogen atom or a substituent selected from substituents including Substituent Group A. The substituent is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

The compound represented by formula (3) is preferably represented by the following formula (4):

(4)

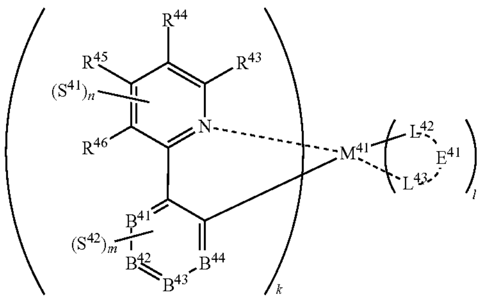

(In formula (4), $M^{41}$ represents a metal belong to Groups 8 to 11 in the periodic table of elements, each of $R^{43}$ to $R^{46}$ independently represents a hydrogen atom or a substituent, each of $B^{41}$ to $B^{44}$ independently represents a nitrogen atom or C—$R^{47}$, $R^{47}$ represents a hydrogen atom or a substituent, each $R^{47}$ may be the same as or different from every other $R^{47}$, each of $L^{42}$ and $L^{43}$ represents a carbon atom, a nitrogen atom, an oxygen atom or a phosphorus atom, $E^{41}$ represents an atomic group for forming a bidentate ligand together with $L^{42}$ and $L^{43}$, k represents an integer of 1 to 3, l represents an integer of 0 to 2, k+l is 2 or 3, each of $S^{41}$ and $S^{42}$ independently represents a group represented by formula (I), each of n and m represents an integer of 0 to 4, n+m is an integer of 1 to 4, and each $S^{41}$ or $S^{42}$ may be the same as or different from every other $S^{41}$ or $S^{42}$).

In formula (4), $M^{41}$, $R^{43}$ to $R^{46}$, $L^{42}$, $L^{43}$, $E^{41}$, $S^{41}$, $S^{42}$, n, m, k and l have the same meanings as $M^{31}$, $R^{33}$ to $R^{36}$, $L^{32}$, $L^{33}$, $E^{31}$, $S^{31}$, $S^{32}$, n, m, k and l in formula (3), and the preferred ranges are also the same.

Each of $B^{41}$ to $B^{44}$ independently represents a nitrogen atom or C—$R^{47}$, and $R^{47}$ represents a hydrogen atom or a substituent. The combination of $B^{41}$ to $B^{44}$ is not particularly limited but out of $B^{41}$ to $B^{44}$, the number of nitrogen atoms is preferably from 0 to 2, more preferably from 0 to 1.

As for the substituent represented by $R^{47}$, those described above as Substituent Group A can be applied.

Each $R^{47}$ may be the same as or different from every other $R^{47}$. $R^{47}$ may further have a substituent, and those described above as Substituent Group A can be applied to the substituent. Also, $R^{47}$'s may combine with each other to form a condensed ring, and examples of the ring formed include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring.

$R^{47}$ is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

The compound represented by formula (4) is preferably represented by the following formula (5):

(5)

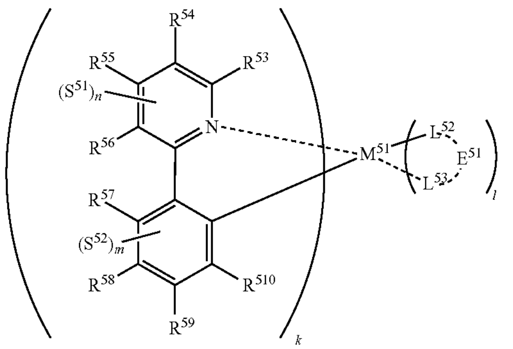

(In formula (5), $M^{51}$ represents a metal belong to Groups 8 to 11 in the periodic table of elements, each of $R^{53}$ to $R^{59}$ and $R^{510}$ independently represents a hydrogen atom or a substituent, each of $L^{52}$ and $L^{53}$ represents a carbon atom, a nitrogen atom, an oxygen atom or a phosphorus atom, $E^{51}$ represents an atomic group for forming a bidentate ligand together with $L^{52}$ and $L^{53}$, k represents an integer of 1 to 3, l represents an integer of 0 to 2, k+l is 2 or 3, each of $S^{51}$ and $S^{52}$ independently represents a group represented by formula (I), each of n and m represents an integer of 0 to 4, n+m is an integer of 1 to 4, and each $S^{51}$ or $S^{52}$ may be the same as or different from every other $S^{51}$ or $S^{52}$).

In formula (5), $M^{51}$, $L^{52}$, $L^{53}$, $E^{51}$, $S^{51}$, $S^{52}$, k and l have the same meanings as $M^{41}$, $L^{42}$, $L^{43}$, $E^{41}$, $S^{41}$, $S^{42}$, k and l in formula (4), and the preferred ranges are also the same.

Each of $R^{53}$ to $R^{59}$ and $R^{510}$ independently represents a hydrogen atom or a substituent selected from substituents including Substituent Group A. The substituent is preferably an alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

Each of n and m represents an integer of 0 to 4, and n+m is an integer of 1 to 4. n+m is preferably 1 or 2.

One preferred embodiment of formula (5) is represented by formula (5-1):

(5-1)

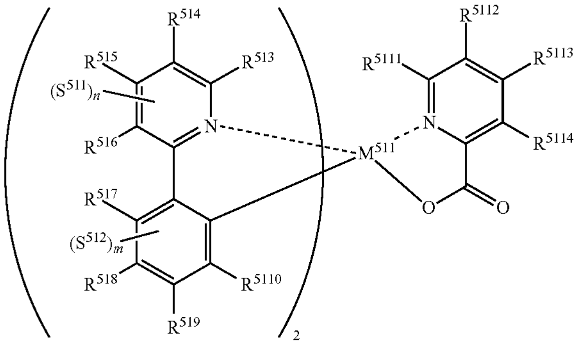

(In formula (5-1), $M^{511}$ represents a metal belong to Groups 8 to 11 in the periodic table of elements, each of $R^{513}$ to $R^{5114}$ independently represents a hydrogen atom or a substituent, each of $S^{511}$ and $S^{512}$ independently represents a group represented by formula (I), each of n and m represents an integer of 0 to 4, n+m is an integer of 1 to 4, and each $S^{511}$ or $S^{512}$ may be the same as or different from every other $S^{511}$ or $S^{512}$).

In formula (5-1), $M^{511}$, $R^{513}$ to $R^{516}$, $R^{517}$ to $R^{5110}$, $S^{511}$, $S^{512}$, n and m have the same meanings as $M^{51}$, $R^{53}$ to $R^{56}$, $R^{57}$ to $R^{510}$, $S^{51}$, $S^{52}$, n and m in formula (5), and the preferred ranges are also the same.

Each of $R^{5111}$ to $R^{5114}$ independently represents a hydrogen atom or a substituent selected from substituents including Substituent Group A. The substituent is preferably an alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

Each of $R^{5111}$ to $R^{5114}$ is preferably a hydrogen atom.

One preferred embodiment of formula (5) is represented by formula (5-2):

(5-2)

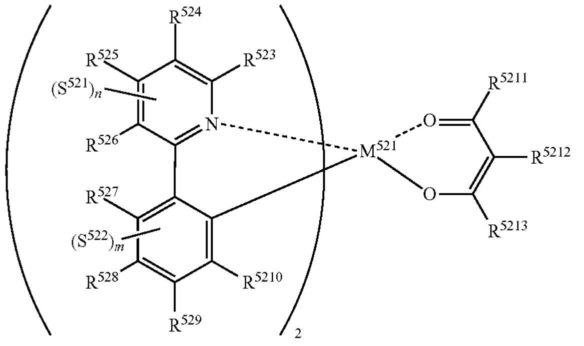

(In formula (5-2), $M^{521}$ represents a metal belong to Groups 8 to 11 in the periodic table of elements, each of $R^{523}$ to $R^{5213}$ independently represents a hydrogen atom or a substituent, each of $S^{521}$ and $S^{522}$ independently represents a group represented by formula (I), each of n and m represents an integer of 0 to 4, n+m is an integer of 1 to 4, and each $S^{521}$ or $S^{522}$ may be the same as or different from every other $S^{521}$ or $S^{522}$).

In formula (5-2), $M^{521}$, $R^{523}$ to $R^{526}$, $R^{527}$ to $R^{5210}$, $S^{521}$, $S^{522}$, n and m have the same meanings as $M^{51}$, $R^{53}$ to $R^{56}$, $R^{57}$ to $R^{510}$, $S^{51}$, $S^{52}$, n and m in formula (5), and the preferred ranges are also the same.

Each of $R^{5211}$ to $R^{5213}$ independently represents a hydrogen atom or may have a substituent selected from substituents including Substituent Group A. The substituent is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

Each of $R^{5211}$ to $R^{5213}$ is preferably a hydrogen atom, a methyl group or a tert-butyl group.

One preferred embodiment of formula (5) is represented by formula (5-3):

(5-3)

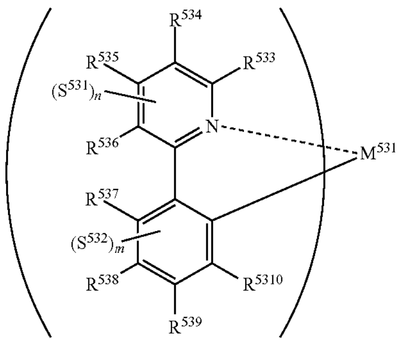

(In formula (5-3), $M^{531}$ represents a metal belong to Groups 8 to 11 in the periodic table of elements, each of $R^{533}$ to $R^{5310}$ independently represents a hydrogen atom or a substituent, each of $S^{531}$ and $S^{532}$ independently represents a group represented by formula (I), each of n and m represents an integer of 0 to 4, n+m is an integer of 1 to 4, and each $S^{531}$ or $S^{532}$ may be the same as or different from every other $S^{531}$ or $S^{532}$).

In formula (5-3), $M^{531}$, $R^{533}$ to $R^{5310}$, $S^{531}$, $S^{532}$, n and m have the same meanings as $M^{51}$, $R^{53}$ to $R^{510}$, $S^{51}$, $S^{52}$, n and m in formula (5), and the preferred ranges are also the same.

The compound represented by formula (4) is preferably represented by the following formula (6):

(6)

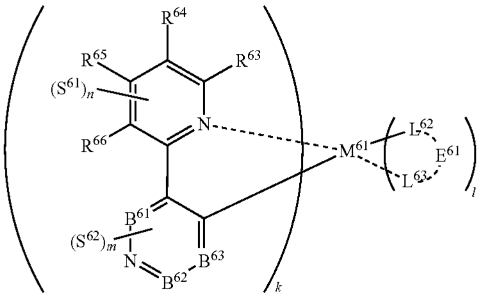

(In formula (6), $M^{61}$ represents a metal belong to Groups 8 to 11 in the periodic table of elements, each of $R^{63}$ to $R^{66}$ independently represents a hydrogen atom or a substituent, each of $B^{61}$ to $B^{63}$ independently represents a nitrogen atom or C—$R^{67}$, $R^{67}$ represents a hydrogen atom or a substituent, each $R^{67}$ may be the same as or different from every other $R^{67}$, each of $L^{62}$ and $L^{63}$ represents a carbon atom, a nitrogen atom, an oxygen atom or a phosphorus atom, $E^{61}$ represents an atomic group for forming a bidentate ligand together with $L^{62}$ and $L^{63}$, k represents an integer of 1 to 3, l represents an integer of 0 to 2, k+l is 2 or 3, each of $S^{61}$ and $S^{62}$ independently represents a group represented by formula (I), each of n and m represents an integer of 0 to 4, n+m is an integer of 1 to 4, and each $S^{61}$ or $S^{62}$ may be the same as or different from every other $S^{61}$ or $S^{62}$).

In formula (6), $M^{61}$, $L^{62}$, $L^{63}$, $E^{61}$, $S^{61}$, $S^{62}$, k and l have the same meaning as $M^{41}$, $L^{42}$, $L^{43}$, $E^{41}$, $S^{41}$, $S^{42}$, k and l in formula (4), and the preferred ranges are also the same.

$R^{63}$ to $R^{66}$ and $B^{61}$ to $B^{63}$ have the same meanings as $R^{43}$ to $R^{46}$ and $B^{41}$ to $B^{44}$ in formula (4), and the preferred ranges are also the same.

Each of n and m represents an integer of 0 to 4, and n+m is an integer of 1 to 4. n+m is preferably 1 or 2.

One preferred embodiment of formula (6) is represented by formula (6-1):

(6-1)

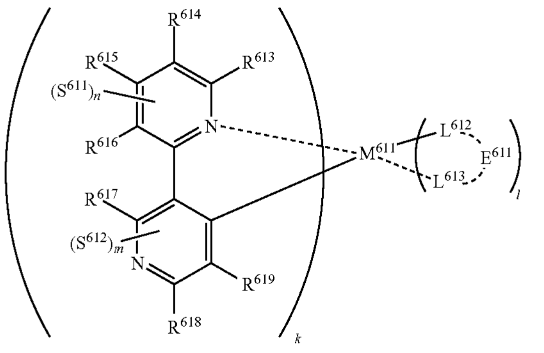

(In formula (6-1), $M^{611}$ a metal belong to Groups 8 to 11 in the periodic table of elements, each of $R^{613}$ to $R^{619}$ independently represents a hydrogen atom or a substituent, each of $L^{612}$ and $L^{613}$ represents a carbon atom, a nitrogen atom, an oxygen atom or a phosphorus atom, $E^{611}$ represents an atomic group for forming a bidentate ligand together with $L^{612}$ and $L^{613}$, k represents an integer of 1 to 3, l represents an integer of 0 to 2, k+l is 2 or 3, each of $S^{611}$ and $S^{612}$ independently represents a group represented by formula (I), and each $S^{611}$ or $S^{612}$ may be the same as or different from every other $S^{611}$ or $S^{612}$).

In formula (6-1), $M^{611}$, $R^{613}$ to $R^{619}$, $L^{612}$, $L^{613}$, $E^{611}$, $S^{611}$, $S^{612}$, n, m, k and l have the same meanings as $M^{61}$, $R^{63}$ to $R^{66}$, $L^{62}$, $L^{63}$, $E^{61}$, $S^{61}$, $S^{62}$, n, m, k and l in formula (6), and the preferred ranges are also the same.

Each of $R^{617}$ to $R^{619}$ independently represents a hydrogen atom or a substituent selected from substituents including Substituent Group A. The substituent is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

One preferred embodiment of formula (6-1) is represented by formula (6-2):

(6-2)

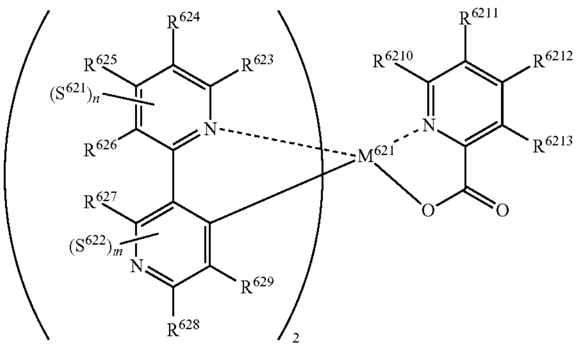

(In formula (6-2), $M^{621}$ represents a metal belong to Groups 8 to 11 in the periodic table of elements, each of $R^{623}$ to $R^{629}$ independently represents a hydrogen atom or a substituent, each of $S^{621}$ and $S^{622}$ independently represents a group represented by formula (I), each of n and m represents an integer of 0 to 4, n+m is an integer of 1 to 4, and each $S^{621}$ or $S^{622}$ may be the same as or different from every other $S^{621}$ or $S^{622}$).

In formula (6-2), $M^{621}$, $R^{623}$ to $R^{626}$, $R^{627}$ to $R^{629}$, $S^{621}$, $S^{622}$, n and m have the same meanings as $M^{611}$, $R^{613}$ to $R^{616}$, $R^{617}$ to $R^{619}$, $S^{611}$, $S^{612}$, n and m in formula (6-1), and the preferred ranges are also the same.

Each of $R^{623}$ to $R^{626}$ independently represents a hydrogen atom or a substituent selected from substituents including Substituent Group A. The substituent is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfonyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

One preferred embodiment of formula (6-1) is represented by formula (6-3):

(6-3)

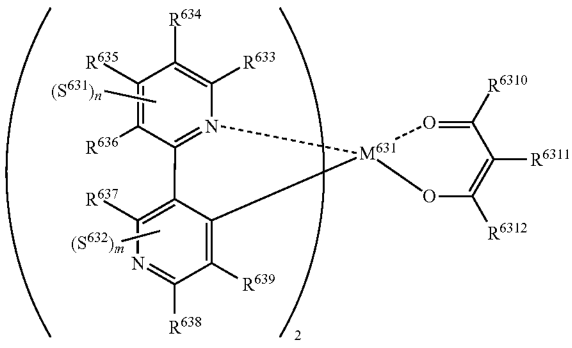

(In formula (6-3), $M^{631}$ represents a metal belong to Groups 8 to 11 in the periodic table of elements, each of $R^{633}$ to $R^{6312}$ independently represents a hydrogen atom or a substituent, each of $S^{631}$ and $S^{632}$ independently represents a group represented by formula (I), and each $S^{631}$ or $S^{632}$ may be the same as or different from every other $S^{631}$ or $S^{632}$).

In formula (6-3), $M^{631}$, $R^{633}$ to $R^{636}$, $R^{637}$ to $R^{639}$, $S^{631}$, $S^{632}$, n and m have the same meanings as $M^{611}$, $R^{613}$ to $R^{616}$, $R^{617}$ to $R^{619}$, $S^{611}$, $S^{612}$, n and m in formula (6-1), and the preferred ranges are also the same.

Each of $R^{6310}$ to $R^{6312}$ independently represents a hydrogen atom or a substituent selected from substituents including Substituent Group A. The substituent is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

Each of $R^{6310}$ to $R^{6312}$ is preferably a hydrogen atom, a methyl group or a tert-butyl group.

One preferred embodiment of formula (6-1) is represented by formula (6-4):

(6-4)

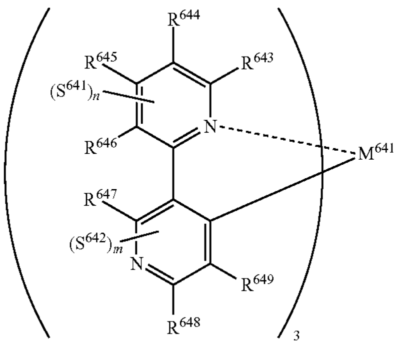

(In formula (6-4), $M^{641}$ represents a metal belong to Groups 8 to 11 in the periodic table of elements, each of $R^{643}$ to $R^{649}$ independently represents a hydrogen atom or a substituent, each of $S^{641}$ and $S^{642}$ independently represents a group represented by formula (I), each of n and m represents an integer of 0 to 4, n+m is an integer of 1 to 4, and each $S^{641}$ or $S^{642}$ may be the same as or different from every other $S^{641}$ or $S^{642}$).

In formula (6-4), $M^{641}$, $R^{643}$ to $R^{646}$, $R^{647}$ to $R^{649}$, $S^{641}$, $S^{642}$, n and m have the same meanings as $M^{611}$, $R^{613}$ to $R^{616}$, $R^{617}$ to $R^{619}$, $S^{611}$, $S^{612}$, n and m in formula (6-1), and the preferred ranges are also the same.

The compound represented by formula (3) is preferably represented by the following formula (7):

(7)

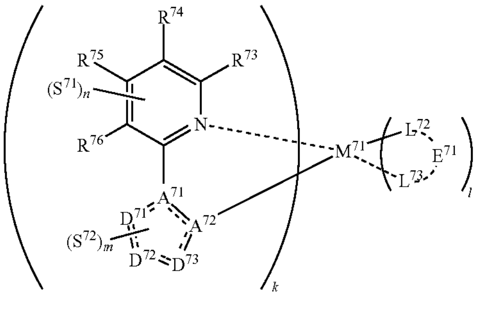

(In formula (7), $M^{71}$ represents a metal belong to Groups 8 to 11 in the periodic table of elements, each of $R^{73}$ to $R^{76}$ independently represents a hydrogen atom or a substituent, each of $A^{71}$ and $A^{72}$ independently represents a nitrogen atom or a carbon atom, each of $D^{71}$ to $D^{73}$ independently represents an atom selected from carbon, nitrogen, oxygen, sulfur and silicon, the bond between atoms in the 5-membered ring formed by $D^{71}$ to $D^{73}$, $A^{71}$ and $A^{72}$ represents a single bond or a double bond, each of $D^{71}$ to $D^{73}$ may have a substituent when these can be further substituted, each of $L^{72}$ and $L^{73}$ represents a carbon atom, a nitrogen atom, an oxygen atom or a phosphorus atom, $E^{71}$ represents an atomic group for forming a bidentate ligand together with $L^{72}$ and $L^{73}$, k represents an integer of 1 to 3, l represents an integer of 0 to 2, k+l is 2 or 3, each of $S^{71}$ and $S^{72}$ independently represents a group represented by formula (I), each of n and m represents an integer of 0 to 4, n+m is an integer of 1 to 4, and each $S^{71}$ or $S^{72}$ may be the same as or different from every other $S^{71}$ or $S^{72}$).

In formula (7), $M^{71}$, $R^{73}$ to $R^{76}$. $L^{72}$, $L^{73}$, $E^{71}$, $S^{71}$, $S^{72}$, n, m, k and l have the same meanings as $M^{31}$, $R^{33}$ to $R^{36}$, $L^{32}$, $L^{33}$, $E^{31}$, $S^{31}$, $S^{32}$, n, m, k and l in formula (3), and the preferred ranges are also the same.

Each of $A^{71}$ and $A^{72}$ represents a nitrogen atom or a carbon atom, and these form an aromatic heterocyclic ring or aromatic hydrocarbon ring together with $D^{71}$ to $D^{73}$.

Each of $D^{71}$ to $D^{73}$ independently represents an atom selected from carbon, nitrogen, oxygen, sulfur and silicon, and the bond between atoms in the 5-membered ring formed by $D^{71}$ to $D^{73}$, $A^{71}$ and $A^{72}$ is not particularly limited but may be any combination of a single bond and a double bond. Each of $D^{71}$ to $D^{73}$ is preferably a carbon atom or a nitrogen atom.

In the 5-membered ring formed by $D^{71}$ to $D^{73}$, $A^{71}$ and $A^{72}$, the number of nitrogen atoms is preferably from 1 to 3, more preferably from 1 to 2.

Each of $D^{71}$ to $D^{73}$ may have a substituent selected from Substituent Group A when these can be further substituted. The substituents may combine with each other to form a condensed ring, and examples of the ring formed include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring.

The substituent is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

One preferred embodiment of formula (7) is represented by formula (7-1):

(7-1)

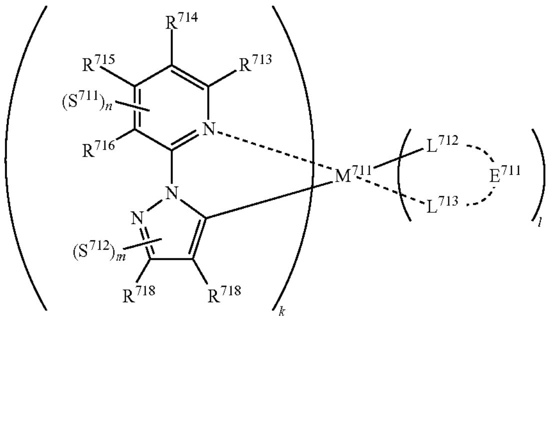

(In formula (7-1), $M^{711}$ represents a metal belong to Groups 8 to 11 in the periodic table of elements, each of $R^{713}$ to $R^{718}$ independently represents a hydrogen atom or a substituent, each of $L^{712}$ and $L^{713}$ represents a carbon atom, a nitrogen atom, an oxygen atom or a phosphorus atom, $E^{711}$ represents an atomic group for forming a bidentate ligand together with $L^{712}$ and $L^{713}$, k represents an integer of 1 to 3, l represents an integer of 0 to 2, k+l is 2 or 3, each of $S^{711}$ and $S^{712}$ independently represents a group represented by formula (I), each of n and m represents an integer of 0 to 4, n+m is an integer of 1 to 4, and each $S^{711}$ or $S^{712}$ may be the same as or different from every other $S^{711}$ or $S^{712}$).

In formula (7-1), $M^{711}$, $R^{713}$ to $R^{718}$, $L^{712}$, $L^{713}$, $E^{711}$, $S^{711}$, $S^{712}$, n, m, k and l have the same meanings as $M^{71}$, $R^{73}$ to $R^{76}$, $L^{72}$, $L^{73}$, $E^{71}$, $S^{71}$, $S^{72}$, n, m, k and l in formula (7), and the preferred ranges are also the same.

The compound represented by formula (2) is preferably represented by the following formula (8):

(8)

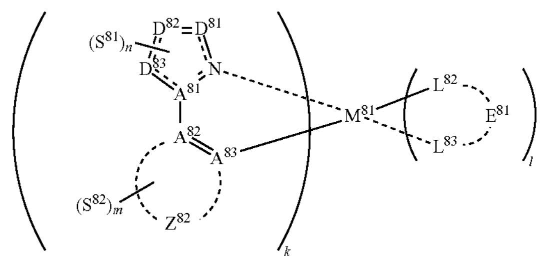

(In formula (8), $M^{81}$ represents a metal belong to Groups 8 to 11 in the periodic table of elements, each of $A^{81}$ to $A^{83}$ independently represents a nitrogen atom or a carbon atom, each of $D^{81}$ to $D^{83}$ independently represents an atom selected from carbon, nitrogen, oxygen, sulfur and silicon, the bond between atoms in the 5-membered ring formed by $D^{81}$ to $D^{83}$, $A^{81}$ and the N atom represents a single bond or a double bond, each of $D^{81}$ to $D^{83}$ when these can be further substituted may have a substituent, $Z^{82}$ represents an aromatic heterocyclic ring or an aromatic hydrocarbon ring, each of $L^{82}$ and $L^{83}$ represents a carbon atom, a nitrogen atom, an oxygen atom or a phosphorus atom, $E^{81}$ represents an atomic group for forming a bidentate ligand together with $L^{82}$ and $L^{83}$, k represents an integer of 1 to 3, l represents an integer of 0 to 2, k+l is 2 or 3, each of $S^{81}$ and $S^{82}$ independently represents a group represented by formula (I), each of n and m represents an integer of 0 to 4, n+m is an integer of 1 to 4, and each $S^{81}$ or $S^{82}$ may be the same as or different from every other $S^{81}$ or $S^{82}$).

In formula (8), $M^{81}$, $A^{82}$, $A^{83}$, $Z^{82}$, $L^{82}$, $L^{83}$, $E^{81}$, $S^{81}$, $S^{82}$, n, m, k and l have the same meanings as $M^{21}$, $A^{21}$, $A^{22}$, $Z^{22}$, $L^{22}$, $L^{23}$, $E^{21}$, $S^{21}$, $S^{22}$, n, m, k and l in formula (2), and the preferred ranges are also the same.

Each of $D^{81}$ to $D^{83}$ independently represents an atom selected from carbon, nitrogen, oxygen, sulfur and silicon, and the bond between atoms in the 5-membered ring formed by $D^{81}$ to $D^{83}$, $A^{81}$ and the nitrogen atom is not particularly limited but may be any combination of a single bond and a double bond. Each of $D^{81}$ to $D^{83}$ is preferably a carbon atom or a nitrogen atom.

In the 5-membered ring formed by $D^{81}$ to $D^{83}$, $A^{81}$ and the nitrogen atom, the number of nitrogen atoms is preferably from 1 to 3, more preferably from 1 to 2.

Each of $D^{81}$ to $D^{83}$ may have a substituent selected from Substituent Group A when these can be further substituted. The substituents may combine with each other to form a condensed ring, and examples of the ring formed include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring.

The substituent is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

The compound represented by formula (8) is preferably represented by the following formula (9):

(9)

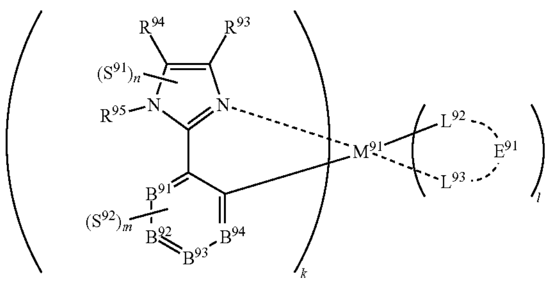

(In formula (9), $M^{91}$ represents a metal belong to Groups 8 to 11 in the periodic table of elements, each of $R^{93}$ and $R^{94}$ independently represents a hydrogen atom or a substituent, $R^{95}$ represents a hydrogen atom or a substituent, each of $B^{91}$ to $B^{94}$ independently represents a nitrogen atom or C—$R^{96}$, $R^{96}$ represents a hydrogen atom or a substituent, each $R^{96}$ may be the same as or different from every other $R^{96}$, each of $L^{92}$ and $L^{93}$ represents a carbon atom, a nitrogen atom, an oxygen atom or a phosphorus atom, $E^{91}$ represents an atomic group for forming a bidentate ligand together with $L^{92}$ and $L^{93}$, k represents an integer of 1 to 3, l represents an integer of 0 to 2, k+l is 2 or 3, each of $S^{91}$ and $S^{92}$ independently represents a group represented by formula (I), each of n and m represents an integer of 0 to 4, n+m is an integer of 1 to 4, and each $S^{91}$ or $S^{92}$ may be the same as or different from every other $S^{91}$ or $S^{92}$).

In formula (9), $M^{91}$, $L^{92}$, $L^{93}$, $E^{91}$, $S^{91}$, $S^{92}$, n, m, k and l have the same meanings as $M^{81}$, $L^{82}$, $L^{83}$, $E^{81}$, $S^{81}$, $S^{82}$, n, m, k and l in formula (8), and the preferred ranges are also the same.

Each of $B^{91}$ to $B^{94}$ independently represents a nitrogen atom or C—$R^{96}$, and $R^{96}$ represents a hydrogen atom or a substituent. The combination of $B^{91}$ to $B^{94}$ is not particularly limited but out of $B^{91}$ to $B^{94}$, the number of nitrogen atoms is preferably from 0 to 2, more preferably from 0 to 1.

Each of $R^{93}$ and $R^{94}$ independently represents a hydrogen atom or a substituent selected from substituents including Substituent Group A. The substituent is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

$R^{95}$ represents a hydrogen atom or a substituent selected from substituents including Substituent Group A. The substituent is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an alkoxy group, an aryloxy group, a cyano group, a fluorine atom or a heterocyclic group, still more preferably a substituted or unsubstituted alkyl group, a cycloalkyl group, a trifluoromethyl group or an aryl group.

As for the substituent represented by $R^{96}$, those described above as Substituent Group A can be applied.

Each $R^{96}$ may be the same as or different from every other $R^{96}$. $R^{96}$ may further have a substituent, and those described above as Substituent Group A can be applied to the substituent. Also, $R^{96}$'s may combine with each other to form a condensed ring, and examples of the ring formed include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring.

$R^{96}$ is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

The compound represented by formula (9) is preferably represented by the following formula (10):

(10)

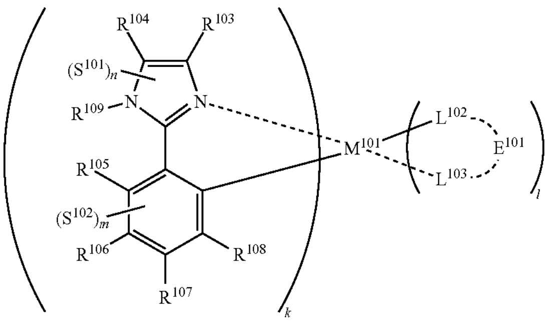

(In formula (10), $M^{101}$ represents a metal belong to Groups 8 to 11 in the periodic table of elements, each of $R^{103}$ to $R^{108}$ independently represents a hydrogen atom or a substituent, $R^{109}$ represents a hydrogen atom or a substituent, each of $L^{102}$ and $L^{103}$ represents a carbon atom, a nitrogen atom, an oxygen atom or a phosphorus atom, $E^{101}$ represents an atomic group for forming a bidentate ligand together with $L^{102}$ and $L^{103}$, k represents an integer of 1 to 3, l represents an integer of 0 to 2, k+l is 2 or 3, each of $S^{101}$ and $S^{102}$ independently represents a group represented by formula (I), each of n and m represents an integer of 0 to 4, n+m is an integer of 1 to 4, and each $S^{101}$ or $S^{102}$ may be the same as or different from every other $S^{101}$ or $S^{102}$).

In formula (10), $M^{101}$, $L^{102}$, $L^{103}$, $E^{101}$, $S^{101}$, $S^{102}$, k and l have the same meanings as $M^{91}$, $L^{92}$, $L^{93}$, $E^{91}$, $S^{91}$, $S^{92}$, k and l in formula (9), and the preferred ranges are also the same.

$R^{103}$ to $R^{108}$ have the same meanings as $R^{93}$ and $R^{94}$, and the preferred ranges are also the same.

$R^{109}$ has the same meaning as $R^{95}$, and the preferred range is also the same.

Each of n and m represents an integer of 0 to 4, and n+m is an integer of 1 to 4. n+m is preferably 1 or 2.

The compound represented by formula (9) is preferably represented by the following formula (11):

(11)

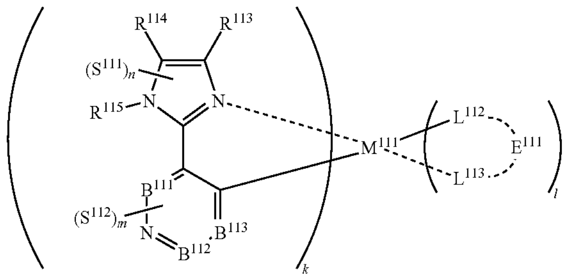

(In formula (11), $M^{111}$ represents a metal belong to Groups 8 to 11 in the periodic table of elements, each of $R^{113}$ and $R^{114}$ independently represents a hydrogen atom or a substituent, $R^{115}$ represents a hydrogen atom or a substituent, each of $B^{111}$ to $B^{113}$ independently represents a nitrogen atom or C—$R^{116}$, $R^{116}$ represents a hydrogen atom or a substituent, each $R^{116}$ may be the same as or different from every other $R^{116}$, each of $L^{112}$ and $L^{113}$ represents a carbon atom, a nitrogen atom, an oxygen atom or a phosphorus atom, $E^{111}$ represents an atomic group for forming a bidentate ligand together with $L^{112}$ and $L^{113}$, k represents an integer of 1 to 3, l represents an integer of 0 to 2, k+l is 2 or 3, each of $S^{111}$ and $S^{112}$ independently represents a group represented by formula (I), each of n and m represents an integer of 0 to 4, n+m is an integer of 1 to 4, and each $S^{111}$ or $S^{112}$ may be the same as or different from every other $S^{111}$ or $S^{112}$).

In formula (11), $M^{111}$, $S^{111}$, $S^{112}$, k and l have the same meanings as $M^{91}$, $S^{91}$, $S^{92}$, k and l in formula (9), and the preferred ranges are also the same.

$R^{113}$ and $R^{114}$ have the same meanings as $R^{93}$ and $R^{94}$, and the preferred ranges are also the same.

$R^{116}$ has the same meaning as $R^{95}$, and the preferred range is also the same.

$B^{111}$ to $B^{114}$ have the same meanings as $B^{91}$ to $B^{94}$, and the preferred ranges are also the same.

Each of n and m represents an integer of 0 to 4, and n+m is an integer of 1 to 4. n+m is preferably 1 or 2.

One preferred embodiment of formula (11) is represented by formula (11-1):

(11-1)

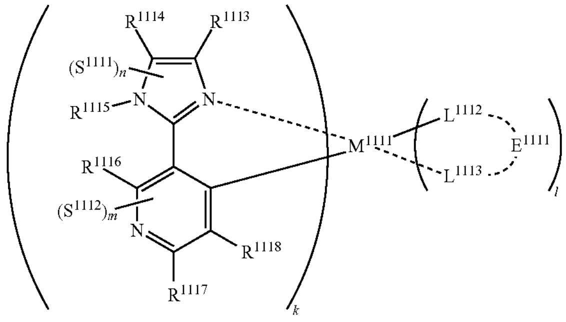

(In formula (11-1), $M^{1111}$ represents a metal belong to Groups 8 to 11 in the periodic table of elements, each of $R^{1113}$ and $R^{1114}$ independently represents a hydrogen atom or a substituent, $R^{1115}$ represents a hydrogen atom or a substituent, each of $R^{1116}$ to $R^{1118}$ independently represents a hydrogen atom or a substituent, each of $L^{1112}$ and $L^{1113}$ represents a carbon atom, a nitrogen atom, an oxygen atom or a phosphorus atom, $E^{1111}$ represents an atomic group for forming a bidentate ligand together with $L^{1112}$ and $L^{1113}$, k represents an integer of 1 to 3, l represents an integer of 0 to 2, k+l is 2 or 3, each of $S^{1111}$ and $S^{1112}$ independently represents a group represented by formula (I), each of n and m represents an integer of 0 to 4, n+m is an integer of 1 to 4, and each $S^{1111}$ or $S^{1112}$ may be the same as or different from every other $S^{1111}$ or $S^{1112}$).

In formula (11-1), $M^{1111}$, $R^{1113}$, $R^{1114}$, $R^{1115}$, $L^{1112}$, $L^{1113}$, $E^{1111}$, $S^{1111}$, $S^{1112}$, n, m, k and l have the same meanings as $M^{91}$, $R^{93}$, $R^{94}$, $R^{95}$, $L^{92}$, $L^{93}$, $E^{91}$, $S^{91}$, $S^{92}$, n, m, k and l in formula (9), and the preferred ranges are also the same.

Each of $R^{1116}$ to $R^{1118}$ independently represents a hydrogen atom or a substituent selected from substituents including Substituent Group A. The substituent is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

One preferred embodiment of formula (11-1) is represented by formula (11-2):

(11-2)

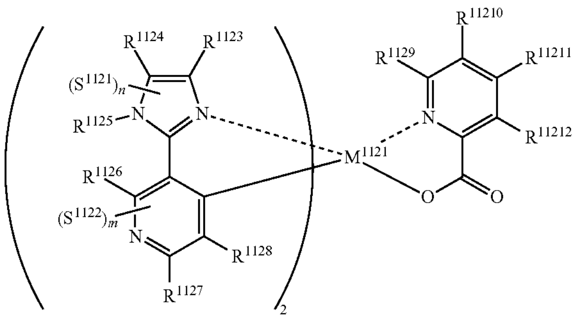

(In formula (11-2), $M^{1121}$ represents a metal belong to Groups 8 to 11 in the periodic table of elements, each of $R^{1123}$ and $R^{1124}$ independently represents a hydrogen atom or a substituent, $R^{1125}$ represents a hydrogen atom or a substituent, each of $R^{1126}$ to $R^{1128}$ and $R^{1129}$ to $R^{11212}$ independently represents a hydrogen atom or a substituent, each of $S^{1121}$ and $S^{1122}$ independently represents a group represented by formula (I), each of n and m represents an integer of 0 to 4, n+m is an integer of 1 to 4, and each $S^{1121}$ or $S^{1122}$ may be the same as or different from every other $S^{1121}$ or $S^{1122}$).

In formula (11-2), $M^{1121}$, $R^{1123}$, $R^{1124}$, $R^{1125}$, $R^{1126}$ to $R^{1128}$, $S^{1121}$, $S^{1122}$, n and m have the same meanings as $M^{1111}$, $R^{1113}$, $R^{1114}$, $R^{1115}$, $R^{1116}$ to $R^{1118}$, $S^{1111}$, $S^{1112}$, n and m in formula (11-1), and the preferred ranges are also the same.

Each of $R^{1129}$ to $R^{11212}$ independently represents a hydrogen atom or a substituent selected from substituents including Substituent Group A. The substituent is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

Each of $R^{1129}$ to $R^{11212}$ is preferably a hydrogen atom.

One preferred embodiment of formula (11-1) is represented by formula (11-3):

(11-3)

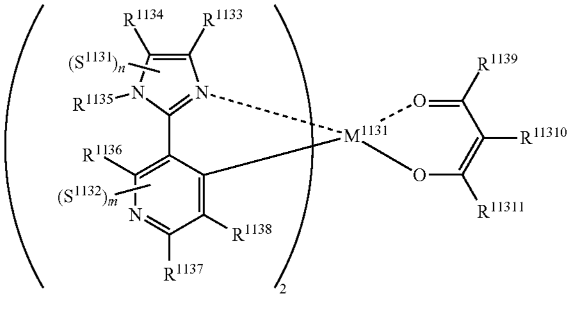

(In formula (11-3), $M^{1131}$ represents a metal belong to Groups 8 to 11 in the periodic table of elements, each of $R^{1133}$ and $R^{1134}$ independently represents a hydrogen atom or a substituent, $R^{1135}$ represents a hydrogen atom or a substituent, each of $R^{1136}$ to $R^{1138}$ and $R^{1139}$ to $R^{11311}$ independently represents a hydrogen atom or a substituent, each of $S^{1131}$ and $S^{1132}$ independently represents a group represented by formula (I), each of n and m represents an integer of 0 to 4, and n+m is an integer of 1 to 4).

In formula (11-3), $M^{1131}$, $R^{1133}$, $R^{1134}$, $R^{1135}$, $R^{1136}$ to $R^{1138}$, $S^{1131}$, $S^{1132}$, n and m have the same meanings as $M^{1111}$, $R^{1113}$, $R^{1114}$, $R^{1115}$, $R^{1116}$ to $R^{1118}$, $S^{1111}$, $S^{1112}$, n and m in formula (11-1), and the preferred ranges are also the same.

Each of $R^{1139}$ to $R^{11311}$ independently represents a hydrogen atom or a substituent selected from substituents including Substituent Group A. The substituent is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

Each of $R^{1139}$ to $R^{11311}$ is preferably a hydrogen atom or a methyl group.

One preferred embodiment of formula (11-1) is represented by formula (11-4):

(11-4)

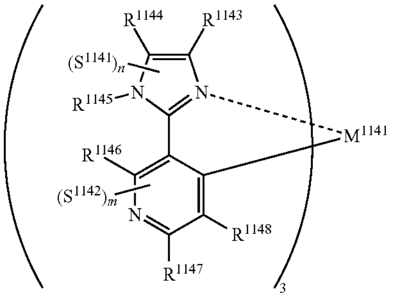

(In formula (11-4), $M^{1141}$ represents a metal belong to Groups 8 to 11 in the periodic table of elements, each of $R^{1143}$ and $R^{1144}$ independently represents a hydrogen atom or a substituent, $R^{1145}$ represents a hydrogen atom or a substituent, each of $R^{1146}$ to $R^{1148}$ independently represents a hydrogen atom or a substituent, each of $S^{1141}$ and $S^{1142}$ independently represents a group represented by formula (I), each of n and m represents an integer of 0 to 4, n+m is an integer of 1 to 4, and each $S^{1141}$ or $S^{1142}$ may be the same as or different from every other $S^{1141}$ or $S^{1142}$).

In formula (11-4), $M^{1141}$, $R^{1143}$, $R^{1144}$, $R^{1145}$, $R^{1146}$ to $R^{1148}$, $S^{1141}$, $S^{1142}$, n and m have the same meanings as $M^{1111}$, $R^{1113}$, $R^{1114}$, $R^{1115}$, $R^{1116}$ to $R^{1118}$, $S^{1111}$, $S^{1112}$, n and m in formula (11-1), and the preferred ranges are also the same.

The compound represented by formula (8) is preferably represented by the following formula (12):

(12)

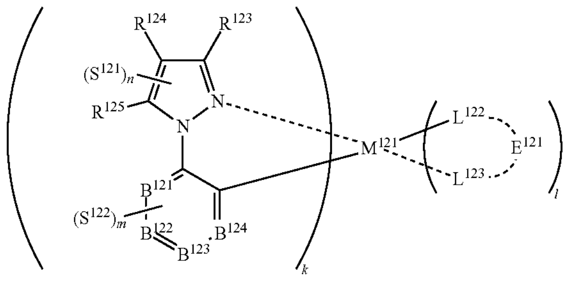

(In formula (12), $M^{121}$ represents a metal belong to Groups 8 to 11 in the periodic table of elements, each of $R^{123}$ to $R^{125}$ independently represents a hydrogen atom or a substituent, each of $B^{121}$ to $B^{124}$ independently represents a nitrogen atom or C—$R^{126}$, $R^{126}$ represents a hydrogen atom or a substituent, each $R^{126}$ may be the same as or different from every other $R^{126}$, each of $L^{122}$ and $L^{123}$ represents a carbon atom, a nitrogen atom, an oxygen atom or a phosphorus atom, $E^{121}$ represents an atomic group for forming a bidentate ligand together with $L^{122}$ and $L^{123}$, k represents an integer of 1 to 3, l represents an integer of 0 to 2, k+l is 2 or 3, each of $S^{121}$ and $S^{122}$ independently represents a group represented by formula (I), each of n and m represents an integer of 0 to 4, n+m is an integer of 1 to 4, and each $S^{121}$ or $S^{122}$ may be the same as or different from every other $S^{121}$ or $S^{122}$).

In formula (12), $M^{121}$, $L^{122}$, $L^{123}$, $E^{121}$, $S^{121}$, $S^{122}$, n, m, k and l have the same meanings as $M^{81}$, $L^{82}$, $L^{83}$, $E^{81}$, $S^{81}$, $S^{82}$, n, m, k and l in formula (8), and the preferred ranges are also the same.

Each of $R^{123}$ to $R^{125}$ independently represents a hydrogen atom or a substituent selected from substituents including Substituent Group A. The substituent is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

Each of $B^{121}$ to $B^{124}$ independently represents a nitrogen atom or C—$R^{126}$, and $R^{126}$ represents a hydrogen atom or a substituent. The combination of $B^{121}$ to $B^{124}$ is not particularly limited but out of $B^{121}$ to $B^{124}$, the number of nitrogen atoms is preferably from 0 to 2, more preferably from 0 to 1.

As for the substituent represented by $R^{126}$, those described above as Substituent Group A can be applied.

Each $R^{126}$ may be the same as or different from every other $R^{126}$. $R^{126}$ may further have a substituent, and those described above as Substituent Group A can be applied to the substituent. Also, $R^{126}$'s may combine with each other to form a condensed ring, and examples of the ring formed include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring.

$R^{126}$ is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

One preferred embodiment of formula (12) is represented by formula (12-1):

(12-1)

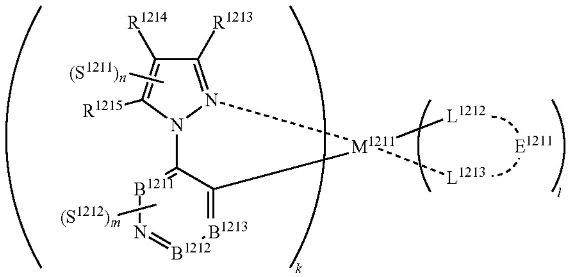

(In formula (12-1), $M^{1211}$ represents a metal belong to Groups 8 to 11 in the periodic table of elements, each of $R^{1213}$ to $R^{1215}$ independently represents a hydrogen atom or a substituent, each of $B^{1211}$ to $B^{1213}$ independently represents a nitrogen atom or C—$R^{1216}$, $R^{1216}$ represents a hydrogen atom or a substituent, each $R^{1216}$ may be the same as or different from every other $R^{1216}$, each of $L^{1212}$ and $L^{1213}$ represents an atomic group nitrogen atom, an oxygen atom or a phosphorus atom, $E^{1211}$ represents an atomic group for forming a bidentate ligand together with $L^{1212}$ and $L^{1213}$, k represents an integer of 1 to 3, l represents an integer of 0 to 2, k+l is 2 or 3, each of $S^{1211}$ and $S^{1212}$ independently represents a group represented by formula (I), each of n and m represents an integer of 0 to 4, n+m is an integer of 1 to 4, and each $S^{1211}$ or $S^{1212}$ may be the same as or different from every other $S^{1211}$ or $S^{1212}$).

In formula (12-1), $M^{1211}$, $R^{1213}$ to $R^{1215}$, $B^{1211}$ to $B^{1213}$, $L^{1212}$, $L^{1213}$, $E^{1211}$, $S^{1211}$, $S^{1212}$, n, m, k and l have the same meanings as $M^{121}$, $R^{123}$ to $R^{125}$, $B^{121}$ to $B^{124}$, $L^{122}$, $L^{123}$, $E^{121}$, $S^{121}$, $S^{122}$, n, m, k and l in formula (12), and the preferred ranges are also the same.

Formula (12) is preferably represented by formula (12-2).

(12-2)

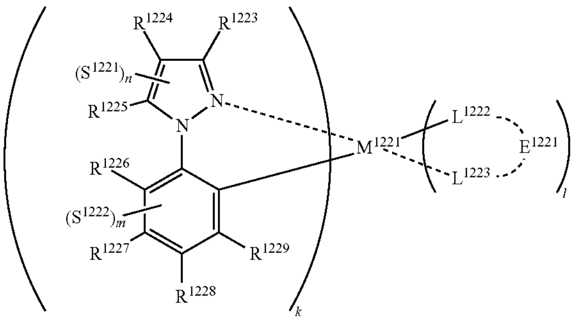

(In formula (12-2), $M^{1221}$ represents a metal belong to Groups 8 to 11 in the periodic table of elements, each of $R^{1223}$ to $R^{1229}$ independently represents a hydrogen atom or a substituent, each of $L^{1222}$ and $L^{1223}$ represents a carbon atom, a nitrogen atom, an oxygen atom or a phosphorus atom, $E^{1221}$ represents an atomic group for forming a bidentate ligand together with $L^{1222}$ and $L^{1223}$, k represents an integer of 1 to 3, l represents an integer of 0 to 2, k+l is 2 or 3, each of $S^{1221}$ and $S^{1222}$ independently represents a group represented by formula (I), each of n and m represents an integer of 0 to 4, n+m is an integer of 1 to 4, and each $S^{1221}$ or $S^{1222}$ may be the same as or different from every other $S^{1221}$ or $S^{1222}$).

In formula (12-2), $M^{1221}$, $R^{1223}$ to $R^{1225}$, $L^{1222}$, $L^{1223}$, $E^{1221}$, $S^{1221}$, $S^{1222}$, n, m, k and l have the same meanings as $M^{121}$, $R^{123}$ to $R^{125}$, $L^{122}$, $L^{123}$, $E^{121}$, $S^{121}$, $S^{122}$, n, m, k and l in formula (12), and the preferred ranges are also the same.

Each of $R^{1226}$ to $R^{1229}$ independently represents a hydrogen atom or may have a substituent selected from substituents including Substituent Group A, and the preferred ranges are the same as that of $R^{126}$ in formula (12).

The compound represented by formula (1) is preferably represented by the following formula (13):

(13)

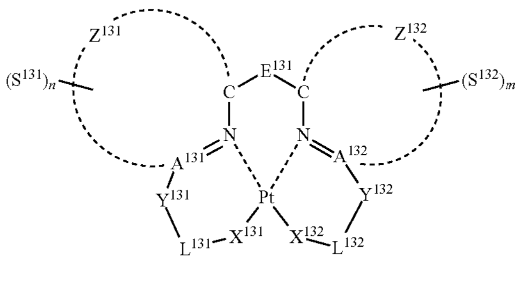

(In formula (13), each of $A^{131}$ and $A^{132}$ represents a nitrogen atom or a carbon atom, each of $Y^{131}$ and $Y^{132}$ represents a linking group or a single bond, each of $L^{131}$ and $L^{132}$ represents a partial structure having an atom bonded to Pt, each of $Z^{131}$ and $Z^{132}$ represents an aromatic nitrogen-containing heterocyclic ring, each of $X^{131}$ and $X^{132}$ represents an oxygen atom, a sulfur atom, a substituted or unsubstituted nitrogen atom or a single bond, $E^{131}$ represents a divalent linking group, each of $S^{131}$ and $S^{132}$ independently represents a group represented by formula (I), each of n and m represents an integer of 0 to 4, n+m is an integer of 1 to 4, and each $S^{131}$ or $S^{132}$ may be the same as or different from every other $S^{131}$ or $S^{132}$).

In formula (13), $A^{131}$ to $A^{136}$, $Z^{131}$ to $Z^{134}$, $S^{131}$ to $S^{134}$, $L^{131}$, $L^{132}$, $X^{131}$, $X^{132}$, $Y^{131}$, $Y^{132}$, n, m, k and l have the same meanings as $A^{11}$ to $A^{13}$, $Z^{11}$, $Z^{12}$, $S^{11}$, $S^{12}$, $L^{11}$, $X^{11}$, $Y^{11}$, n, m, k and l in formula (1), and the preferred rangers are also the same.

$E^{131}$ represents a divalent linking group. The linking group is not particularly limited but is preferably a divalent linking group composed of a single bond, a carbon atom, a nitrogen atom, an oxygen atom, a sulfur atom, a silicon atom or a germanium atom, more preferably a group selected from Linking Group A.

$E^{131}$ is preferably a substituent selected from Linking Group A, and among these, —C(R$^1$)(R$^2$)—, —C(R$^3$)(R$^4$)C(R$^5$)(R$^6$)—, —Si(R$^7$)(R$^8$)—, —N(R$^9$), —O—, —S—, —SO—, —$SO_2$— and —CO— are preferred, —C(R$^1$)(R$^2$)—, —C(R$^3$)(R$^4$)C(R$^5$)(R$^6$)—, —Si(R$^7$)(R$^8$)—, —O— and —S— are more preferred, —C(R$^1$)(R$^2$)— and —C(R$^3$)(R$^4$)C(R$^5$)(R$^6$)— are still more preferred.

In —C(R$^1$)(R$^2$)—, each of $R^1$ and $R^2$ is preferably a hydrogen atom or a substituent selected from Substituent Group B.

In —C(R$^3$)(R$^4$)C(R$^5$)(R$^6$)—, each of $R^3$, $R^4$, $R^5$ and $R^6$ is preferably a hydrogen atom or a substituent selected from Substituent Group B.

In —Si(R$^7$)(R$^8$)—, each of $R^7$ and $R^8$ is preferably a hydrogen atom or a substituent selected from Substituent Group B.

In —Ge(R$^{10}$)(R$^{11}$)—, each of $R^{10}$ and $R^{11}$ is preferably a hydrogen atom or a substituent selected from Substituent Group B.

In —N(R$^9$)—, $R^9$ is preferably a hydrogen atom, an alkyl group, a cycloalkyl group or an aryl group, more preferably an alkyl group or an aryl group, still more preferably an aryl group.

In —P(R$^{12}$)—, $R^{12}$ has the same meaning as the preferred range of $R^9$.

In formula (13), examples of the aromatic nitrogen-containing heterocyclic ring represented by $Z^{131}$ and $Z^{132}$ include a pyridine ring, a pyridazine ring, a pyrimidine ring, a pyrazine ring, a triazine ring, a benzimidazole ring, an oxadiazole ring, a triazole ring, an imidazole ring, a pyrazole ring, a thiazole ring, an oxazole ring, a benzimidazole ring, a benzothiazole ring, a benzoxazole ring, an isoquinoline ring, a quinoxaline ring, a quinazoline ring, a phthalazine ring, a carboline ring, and a ring where a carbon atom of a hydrocarbon ring constituting a carboline ring is further substituted with a nitrogen atom.

Each of $Z^{131}$ and $Z^{132}$ is preferably a pyridine ring, a pyrimidine ring, a pyrazine ring, a benzimidazole ring, an oxadiazole ring, a triazole ring, an imidazole ring, a pyrazole ring, a thiazole ring, an oxazole ring, a benzimidazole ring, a benzothiazole ring, a benzoxazole ring, an isoquinoline ring or a quinoxaline ring, more preferably a pyridine ring, a pyrimidine ring, a pyrazine ring, an imidazole ring, a pyrazole ring, an isoquinoline ring or a quinoxaline ring, still more preferably an isoquinoline ring, a benzoxazole ring, a pyridine ring, an imidazole ring or a pyrazole ring.

The aromatic nitrogen-containing heterocyclic ring may have a substituent, and those described as Substituent Group A can be applied to the substituent.

The substituent is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, stil, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

The compound represented by formula (13) is preferably represented by the following formula (14):

(14)

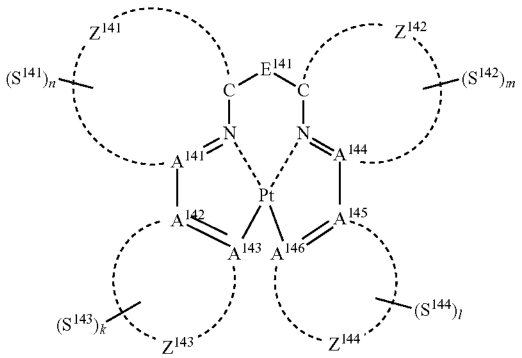

(In formula (14), each of $A^{141}$ to $A^{146}$ independently represents a nitrogen atom or a carbon atom, each of $Z^{141}$ and $Z^{142}$ independently represents an aromatic nitrogen-containing heterocyclic ring, each of $Z^{143}$ and $Z^{144}$ independently represents an aromatic heterocyclic ring or an aromatic hydrocarbon ring, $E^{141}$ represents a divalent linking group, each of $S^{141}$ to $S^{144}$ independently represents a group represented by formula (I), each of n, m, k and l represents an integer of 0 to 4, n+m+k+l is an integer of 1 to 4, and each $S^{141}$, $S^{142}$, $S^{143}$ or $S^{144}$ may be the same as or different from every other $S^{141}$, $S^{142}$, $S^{143}$ or $S^{144}$).

In formula (14), $A^{141}$ to $A^{146}$, $Z^{141}$ to $Z^{144}$, $S^{141}$ to $S^{144}$, $E^{141}$, n, m, k and l have the same meanings as $A^{131}$ to $A^{133}$, $Z^{131}$, $Z^{132}$, $S^{131}$, $S^{132}$, $E^{131}$, n, m, k and l in formula (13), and the preferred ranges are also the same.

Each of n and m represents an integer of 0 to 4, and n+m is an integer of 1 to 4. n+m is preferably 1 or 2.

The compound represented by formula (14) is preferably represented by the following formula (15):

(15)

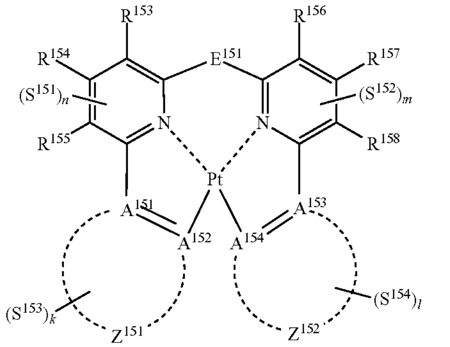

(In formula (15), each of $A^{151}$ to $A^{154}$ independently represents a nitrogen atom or a carbon atom, each of $R^{153}$ to $R^{158}$ independently represents a hydrogen atom or a substituent, each of $Z^{151}$ and $Z^{152}$ independently represents an aromatic heterocyclic ring or an aromatic hydrocarbon ring, $E^{151}$ represents a divalent linking group, each of $S^{151}$ to $S^{154}$ independently represents a group represented by formula (I), each of n, m, k and l represents an integer of 0 to 4, n+m+k+l is an integer of 1 to 4, and each $S^{151}$, $S^{152}$, $S^{153}$ or $S^{154}$ may be the same as or different from every other $S^{151}$, $S^{152}$, $S^{153}$ or $S^{154}$).

In formula (15), $A^{151}$, $A^{152}$, $A^{153}$, $A^{154}$, $Z^{151}$, $Z^{152}$, $E^{151}$, $S^{151}$ to $S^{154}$, n, m, k and 1 have the same meanings as $A^{142}$, $A^{143}$, $A^{145}$, $A^{146}$, $Z^{143}$, $Z^{144}$, $E^{141}$, $S^{141}$ to $S^{144}$, n, m, k and 1 in formula (14), and the preferred ranges are also the same.

Each of $R^{153}$ to $R^{158}$ independently represents a hydrogen atom or may have a substituent selected from substituents including Substituent Group A. The substituent is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

The compound represented by formula (15) is preferably represented by the following formula (16):

(16)

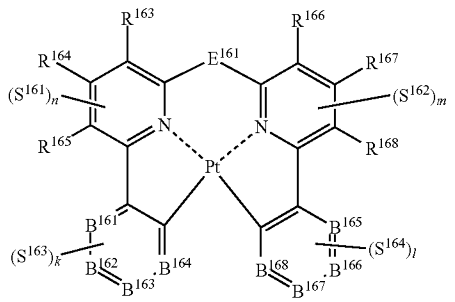

(In formula (16), each of $R^{163}$ to $R^{168}$ independently represents a hydrogen atom or a substituent, each of $B^{161}$ to $B^{168}$ independently represents a nitrogen atom or C—$R^{169}$, $R^{169}$ represents a hydrogen atom or a substituent, each $R^{169}$ may be the same as or different from every other $R^{169}$, $E^{161}$ represents a divalent linking group, each of $S^{161}$ to $S^{164}$ independently represents a group represented by formula (I), each of n, m, k and l represents an integer of 0 to 4, n+m+k+l is an integer of 1 to 4, and each $S^{161}$, $S^{162}$, $S^{163}$ or $S^{164}$ may be the same as or different from every other $S^{161}$, $S^{162}$, $S^{163}$ or $S^{164}$).

In formula (16), $R^{163}$ to $R^{168}$, $E^{161}$, $S^{161}$ to $S^{164}$, n, m, k and l have the same meanings as $R^{153}$ to $R^{158}$, $E^{151}$, $S^{151}$ to $S^{154}$, n, m, k and l in formula (15), and the preferred ranges are also the same.

Each of $B^{161}$ to $B^{168}$ independently represents a nitrogen atom or C—$R^{169}$, and $R^{169}$ represents a hydrogen atom or a substituent. The combination of $B^{161}$ to $B^{164}$ is not particularly limited but out of $B^{161}$ to $B^{164}$, the number of nitrogen atoms is preferably from 0 to 2, more preferably from 0 to 1, and out of $B^{165}$ to $B^{168}$, the number of nitrogen atoms is preferably from 0 to 2, more preferably from 0 to 1.

As for the substituent represented by $R^{169}$, those described as Substituent Group A can be applied.

Each $R^{169}$ may be the same as or different from every other $R^{169}$. $R^{169}$ may further have a substituent, and those described above as Substituent Group A can be applied to the substituent. Also, $R^{169}$'s may combine with each other to form a condensed ring, and examples of the ring formed include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring.

$R^{169}$ is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

The compound represented by formula (15) is preferably represented by the following formula (17):

(17)

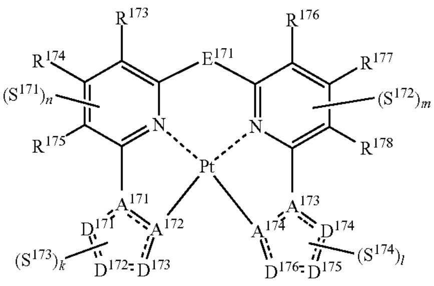

(In formula (17), each of $R^{173}$ to $R^{178}$ independently represents a hydrogen atom or a substituent, each of $A^{171}$ to $A^{174}$ independently represents a nitrogen atom or a carbon atom, each of $D^{171}$ to $D^{176}$ independently represents an atom selected from carbon, nitrogen, oxygen, sulfur and silicon, the bond between atoms in the 5-membered ring formed by $D^{171}$ to $D^{173}$, $A^{171}$ and $A^{172}$ or by $D^{174}$ to $D^{176}$, $A^{173}$ and $A^{174}$ represents a single bond or a double bond, each of $D^{171}$ to $D^{176}$ when these can be further substituted may have a substituent, $E^{171}$ represents a divalent linking group, each of $S^{171}$ to $S^{174}$ independently represents a group represented by formula (I), each of n, m, k and l represents an integer of 0 to 4, n+m+k+l is an integer of 1 to 4, and each $S^{171}$, $S^{172}$, $S^{173}$ or $S^{174}$ may be the same as or different from every other $S^{171}$, $S^{172}$, $S^{173}$ or $S^{174}$).

In formula (17), $R^{173}$ to $R^{178}$, $E^{171}$, $S^{171}$ to $S^{174}$, n, m, k and l have the same meanings as $R^{153}$ to $R^{158}$, $E^{151}$, $S^{151}$ to $S^{154}$, n, m, k and l in formula (15), and the preferred ranges are also the same.

Each of $A^{171}$, $A^{172}$, $A^{173}$ and $A^{174}$ independently represents a nitrogen atom or a carbon atom. $A^{171}$ and $A^{172}$ form an aromatic heterocyclic ring or an aromatic hydrocarbon ring together with $D^{171}$ to $D^{173}$, and $A^{173}$ and $A^{174}$ form an aromatic heterocyclic ring or an aromatic hydrocarbon ring together with $D^{174}$ to $D^{176}$.

Each of $D^{171}$ to $D^{173}$ and $D^{174}$ to $D^{176}$ independently represents an atom selected from carbon, nitrogen, oxygen, sulfur and silicon. The bond between atoms in the 5-membered ring formed by $A^{171}$, $A^{172}$ and $D^{173}$ or by $A^{173}$, $A^{174}$ and $D^{174}$ to $D^{176}$ is not particularly limited but may be any combination of a single bond and a double bond. Each of $D^{171}$ to $D^{173}$ and $D^{174}$ to $D^{176}$ is preferably a carbon atom or a nitrogen atom.

In the 5-membered ring formed by $A^{171}$, $A^{172}$ and $D^{171}$ to $D^{173}$ or by $A^{173}$, $A^{174}$ and $D^{174}$ to $D^{176}$, the number of nitrogen atoms is preferably from 1 to 3, more preferably from 1 to 2.

Each of $D^{171}$ to $D^{173}$ and $D^{174}$ to $D^{176}$ when these can be further substituted may have a substituent selected from Substituent Group A. The substituents may combine with each other to form a condensed ring, and examples of the ring formed include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring.

The substituent thereof is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

The compound represented by formula (14) is preferably represented by the following formula (18):

(18)

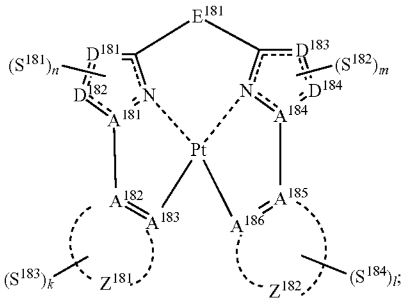

(In formula (18), each of $A^{181}$ to $A^{186}$ independently represents a nitrogen atom or a carbon atom, each of $D^{181}$ to $D^{184}$ independently represents an atom selected from carbon, nitrogen, oxygen, sulfur and silicon, the bond between atoms in the 5-membered ring formed by $D^{181}$, $D^{182}$, $A^{181}$, the nitrogen atom and the carbon atom or by $D^{183}$, $D^{184}$, $A^{184}$, the nitrogen atom and the carbon atom represents a single bond or a double bond, each of $D^{181}$ to $D^{184}$ when these can be further substituted may have a substituent, each of $Z^{181}$ and $Z^{182}$ independently represents an aromatic heterocyclic ring or an aromatic hydrocarbon ring, $E^{181}$ represents a divalent linking group, each of $S^{181}$ to $S^{184}$ independently represents a group represented by formula (I), each of n, m, k and l represents an integer of 0 to 4, n+m+k+l is an integer of 1 to 4, and each $S^{181}$, $S^{182}$, $S^{183}$ or $S^{184}$ may be the same as or different from every other $S^{181}$, $S^{182}$, $S^{183}$ or $S^{184}$).

In formula (18), $A^{182}$, $A^{183}$, $A^{185}$, $A^{186}$, $Z^{181}$, $Z^{182}$, $E^{181}$, $S^{181}$ to $S^{184}$, n, m, k and l have the same meanings as $A^{142}$, $A^{143}$, $A^{145}$, $A^{146}$, $Z^{143}$, $Z^{144}$, $E^{141}$, $S^{141}$ to $S^{144}$, n, m, k and 1 in formula (14), and the preferred ranges are also the same.

Each of $D^{181}$, $D^{182}$, $D^{183}$ and $D^{184}$ independently represents an atom selected from carbon, nitrogen, oxygen, sulfur and silicon. The bond between atoms in the 5-membered ring formed by $D^{181}$, $D^{182}$, $A^{181}$, the nitrogen atom and the carbon atom or by $D^{183}$, $D^{184}$, $A^{184}$, the nitrogen atom and the carbon atom is not particularly limited but may be any combination of a single bond and a double bond. Each of $D^{181}$, $D^{182}$, $D^{183}$ and $D^{184}$ is preferably a carbon atom or a nitrogen atom.

In the 5-membered ring formed by $D^{181}$, $D^{182}$, $A^{181}$, the nitrogen atom and the carbon atom or by $D^{183}$, $D^{184}$, $A^{184}$, the nitrogen atom and the carbon atom, the number of nitrogen atoms is preferably from 1 to 3, more preferably from 1 to 2.

Each of $D^{181}$, $D^{182}$, $D^{183}$ and $D^{184}$ when these can be further substituted may have a substituent selected from Substituent Group A. The substituents may combine with each other to form a condensed ring, and examples of the ring formed include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring.

The substituent is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

The compound represented by formula (18) is preferably represented by the following formula (19):

(19)

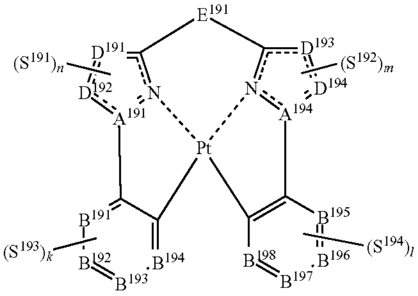

(In formula (19), each of $A^{191}$ and $A^{192}$ independently represents a nitrogen atom or a carbon atom, each of $D^{191}$ to $D^{194}$ independently represents an atom selected from carbon, nitrogen, oxygen, sulfur and silicon, the bond between atoms in the 5-membered ring formed by $D^{191}$, $D^{192}$, $A^{191}$, the nitrogen atom and the carbon atom or by $D^{193}$, $D^{194}$, $A^{194}$, the nitrogen atom and the carbon atom represents a single bond or a double bond, each of $D^{191}$ to $D^{194}$ when these can be further substituted may have a substituent, each of $B^{191}$ to $B^{198}$ independently represents a nitrogen atom or C—$R^{199}$, $R^{199}$ represents a hydrogen atom or a substituent, each $R^{199}$ may be the same as or different from every other $R^{199}$, $E^{191}$ represents a divalent linking group, each of $S^{191}$ to $S^{194}$ independently represents a group represented by formula (I), each of n, m, k and l represents an integer of 0 to 4, n+m+k+l is an integer of 1 to 4, and each $S^{191}$, $S^{192}$, $S^{193}$ or $S^{194}$ may be the same as or different from every other $S^{191}$, $S^{192}$, $S^{193}$ or $S^{194}$).

In formula (19), $E^{191}$, $S^{191}$ to $S^{194}$, n, m, k and l have the same meanings as $E^{181}$, $S^{181}$ to $S^{184}$, n, m, k and l in formula (18), and the preferred ranges are also the same.

Each of $B^{191}$ to $B^{198}$ independently represents a nitrogen atom or C—$R^{197}$, and $R^{197}$ represents a hydrogen atom or a substituent. The combination of $B^{191}$ to $B^{198}$ is not particularly limited but out of $B^{191}$ to $B^{194}$, the number of nitrogen atoms is preferably from 0 to 2, more preferably from 0 to 1, and out of $B^{195}$ to $B^{198}$, the number of nitrogen atoms is preferably from 0 to 2, more preferably from 0 to 1.

As for the substituent represented by $R^{197}$, those described as Substituent Group A can be applied.

Each $R^{197}$ may be the same as or different from every other $R^{197}$. $R^{197}$ may further have a substituent, and those described above as Substituent Group A can be applied to the substituent. Also, $R^{197}$'s may combine with each other to form a condensed ring, and examples of the ring formed include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring.

$R^{197}$ is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

The compound represented by formula (19) is preferably represented by the following formula (20):

(20)

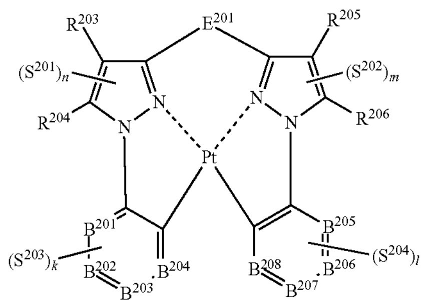

(In formula (20), each of $R^{203}$ to $R^{206}$ independently represents a hydrogen atom or a substituent, each of $B^{201}$ to $B^{208}$ independently represents a nitrogen atom or C—$R^{207}$, $R^{207}$ represents a hydrogen atom or a substituent, each $R^{207}$ may be the same as or different from every other $R^{207}$, $E^{201}$ represents a divalent linking group, each of $S^{201}$ to $S^{204}$ independently represents a group represented by formula (I), and each $S^{201}$, $S^{202}$, $S^{203}$ or $S^{204}$ may be the same as or different from every other $S^{201}$, $S^{202}$, $S^{203}$ or $S^{204}$).

In formula (20), $E^{201}$, $S^{201}$ to $S^{204}$, $B^{201}$ to $B^{208}$, $R^{203}$ to $R^{207}$, n, m, k and l have the same meanings as $E^{191}$, $S^{191}$ to $S^{194}$, $B^{191}$ to $B^{198}$, $R^{191}$ to $R^{197}$, n, m, k and l in formula (19), and the preferred ranges are also the same.

The compound represented by formula (19) is preferably represented by the following formula (21):

(21)

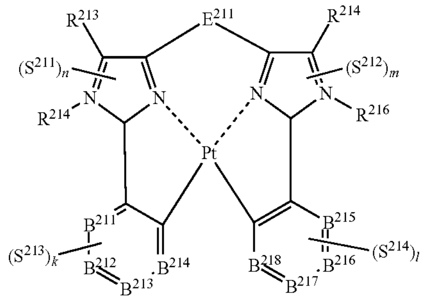

(In formula (21), each of $R^{213}$ and $R^{214}$ independently represents a hydrogen atom or a substituent, each of $R^{215}$ and $R^{216}$ independently represents a hydrogen atom or a substituent, each of $B^{211}$ to $B^{218}$ independently represents a nitrogen atom or C—$R^{217}$, $R^{217}$ represents a hydrogen atom or a substituent, each $R^{217}$ may be the same as or different from every other $R^{217}$, $E^{211}$ represents a divalent linking group, each of $S^{211}$ to $S^{214}$ independently represents a group represented by formula (I), each of n, m, k and l represents an integer of 0 to 4, n+m+k+l is an integer of 1 to 4, and each $S^{211}$, $S^{212}$, $S^{213}$ or $S^{214}$ may be the same as or different from every other $S^{211}$, $S^{212}$, $S^{231}$ or $S^{214}$).

In formula (21), $E^{211}$, $S^{211}$ to $S^{214}$, n, m, k and l have the same meanings as $E^{171}$, $S^{171}$ to $S^{174}$, n, m, k and l in formula (17), and the preferred ranges are also the same.

Each of $B^{211}$ to $B^{218}$ independently represents a nitrogen atom or C—$R^{217}$, and $R^{217}$ represents a hydrogen atom or a substituent. The combination of $B^{211}$ to $B^{218}$ is not particularly limited but out of $B^{211}$ to $B^{214}$, the number of nitrogen atoms is preferably from 0 to 2, more preferably from 0 to 1, and out of $B^{215}$ to $B^{218}$, the number of nitrogen atoms is preferably from 0 to 2, more preferably from 0 to 1.

Each of $R^{213}$ to $R^{216}$ independently represents a hydrogen atom or may have a substituent selected from substituents including Substituent Group A. The substituent is preferably a substituted or unsubstituted alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amido group, a hydroxy group, a mercapto group, a halogen atom, a sulfo group, a carboxyl group, a nitro group, a sulfino group, a heterocyclic group or a silyl group, more preferably a substituted or unsubstituted alkyl group, a cycloalkyl group, an aryl group, an amino group, an alkoxy group, an aryloxy group, a cyano group, a fluorine atom or a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

Each of the compounds represented by formulae (1) to (21) may be a polymer compound having the compound in the main or side chain.

The polymer compound may be a homopolymer compound or a copolymer, and the copolymer may be any of a random copolymer, an alternating copolymer and a block copolymer. In the case of a copolymer, the other monomer is preferably a monomer having a charge transport function moiety. Examples of the monomer having a charge transport function include a material having in its partial structure a compound described later as the host material, the material contained in the hole transporting layer, or the material contained in the electron transporting material. A monomer having in its partial structure a compound described as the host material is preferred.

In the case of a polymer compound, the molecular weight is preferably from 2,000 to less than 1,000,000, more preferably from 10,000 to less than 500,000, still more preferably from 10,000 to less than 100,000.

Specific examples of the compound represented by formula (1) for use in the present invention are illustrated below, but the present invention is not limited thereto.

1

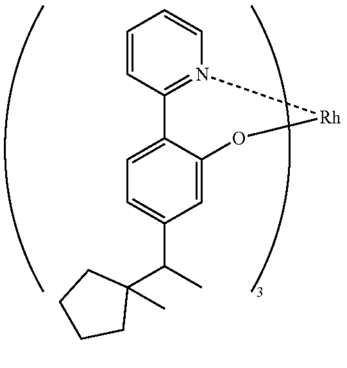

-continued
2
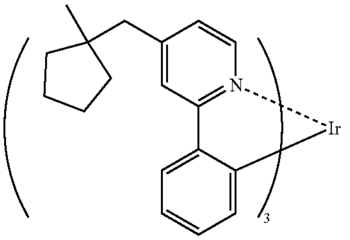
3
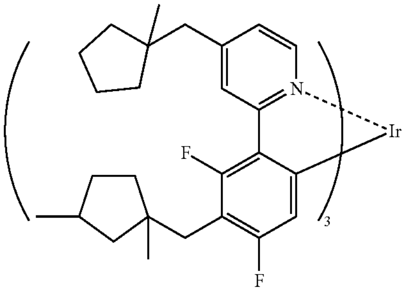
4
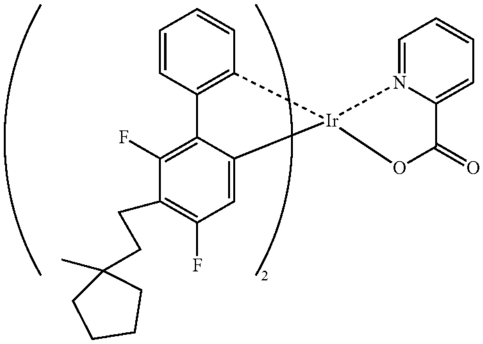
5
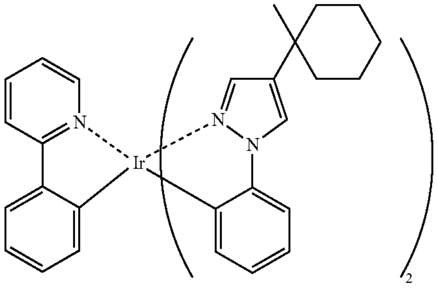
6
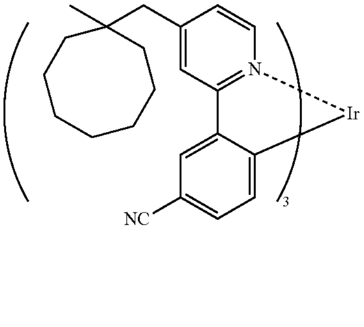
-continued
7
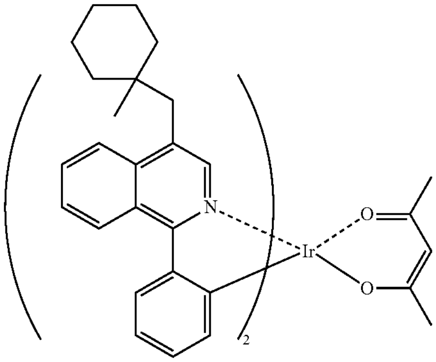
8
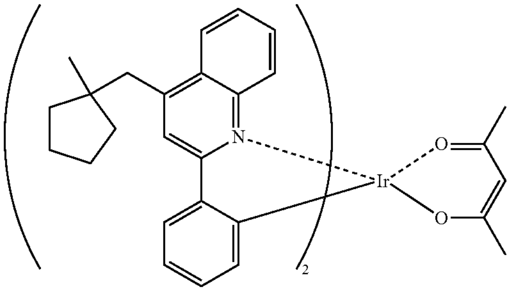
9
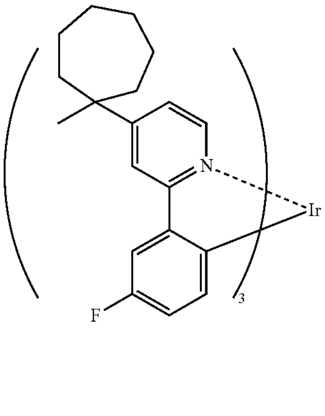
10
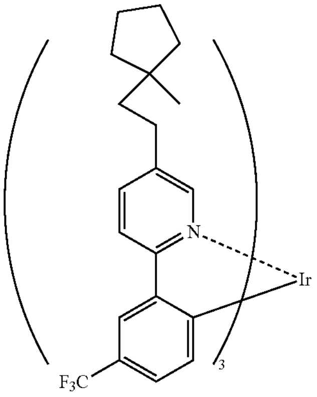

-continued
11
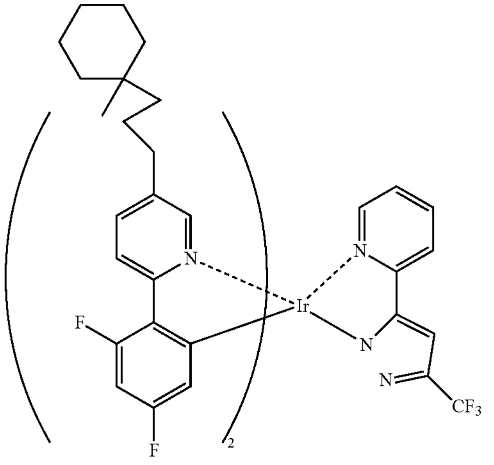
12
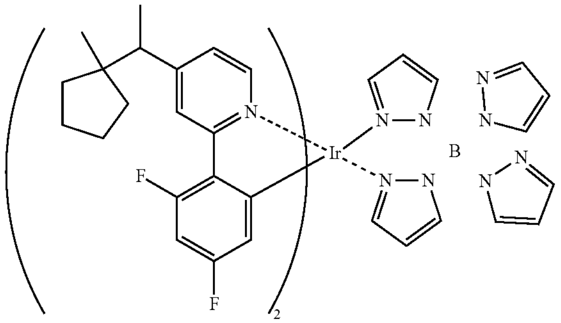
13
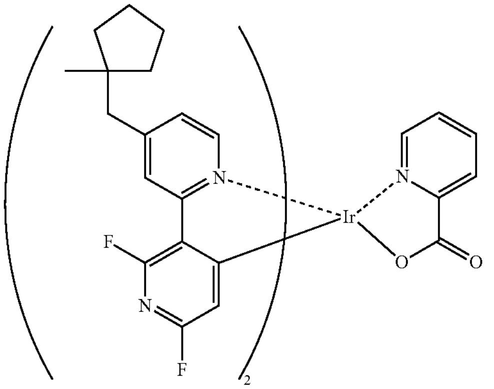
14
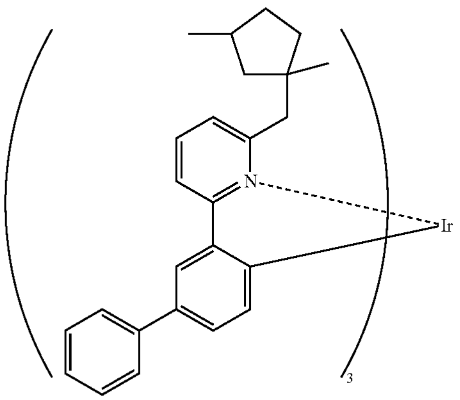
-continued
15
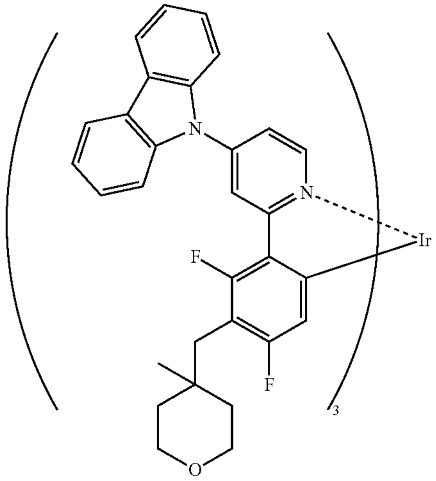
16
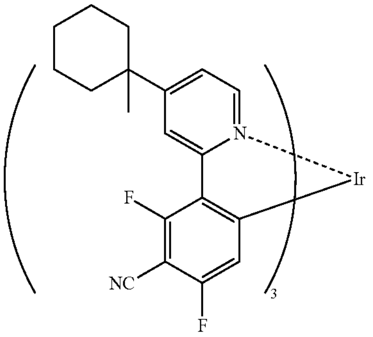
17
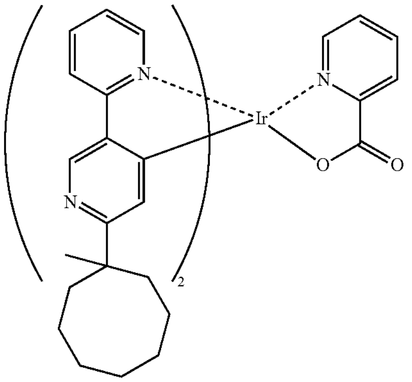
18
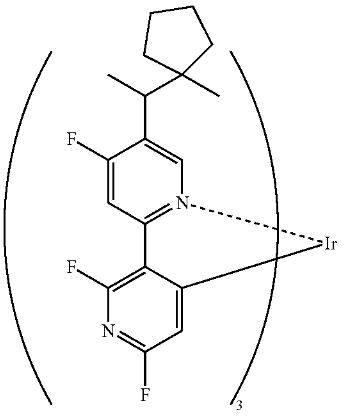

19
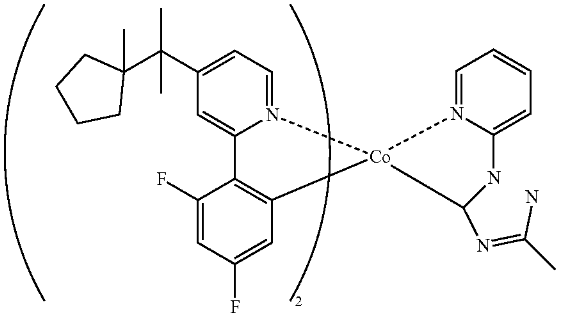
20
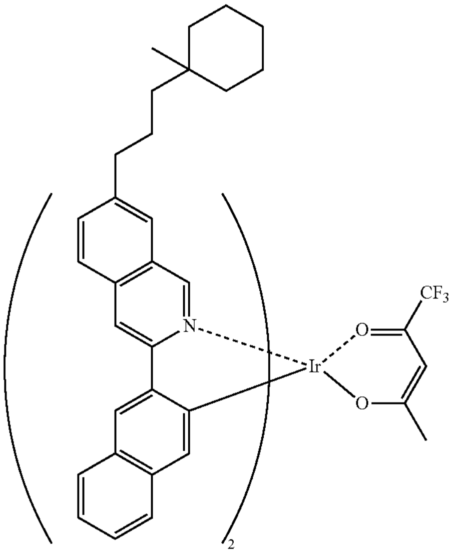
21
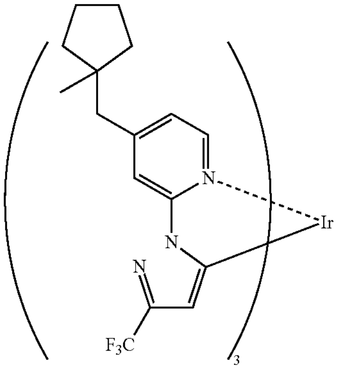
22
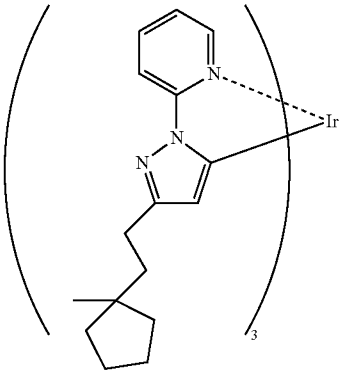
23
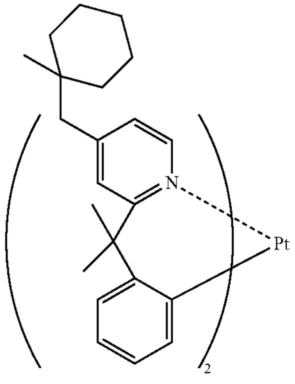
24
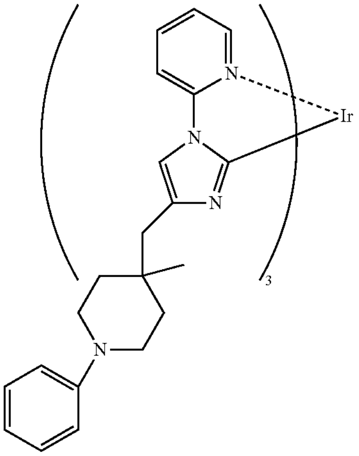
25
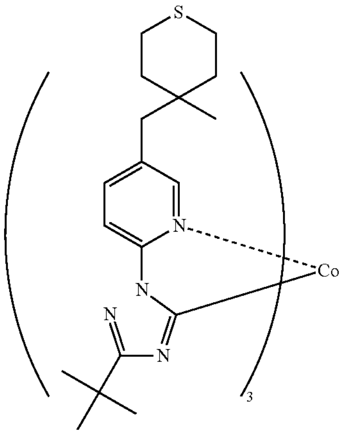
26
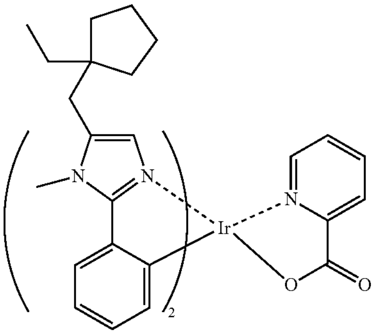

-continued
27
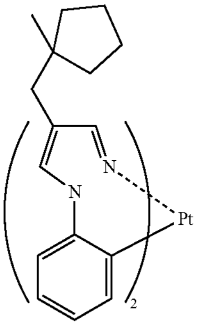
28
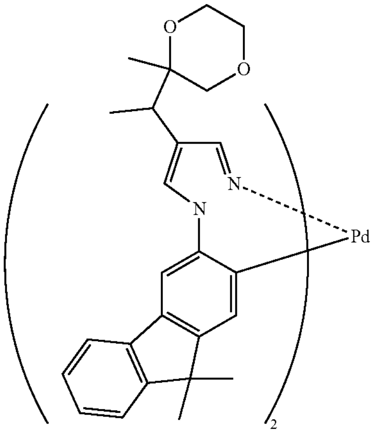
29
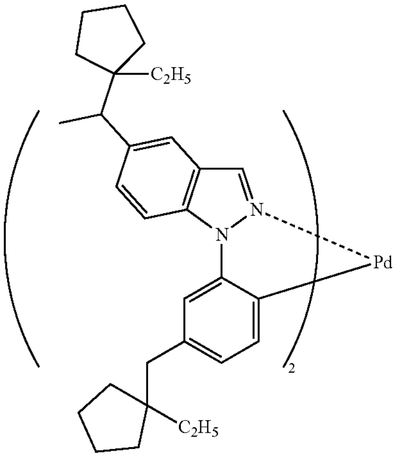
30
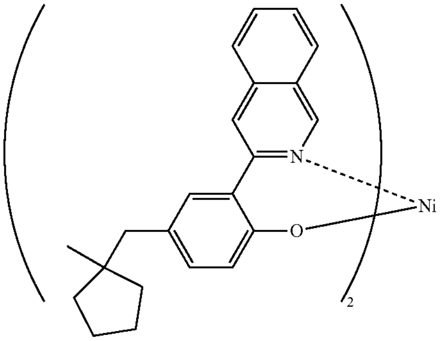
-continued
31
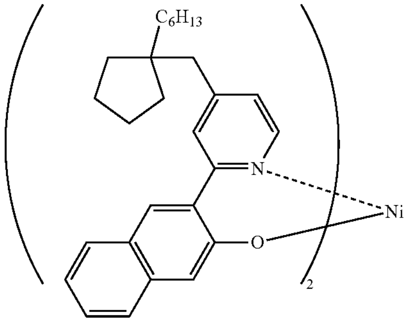
32
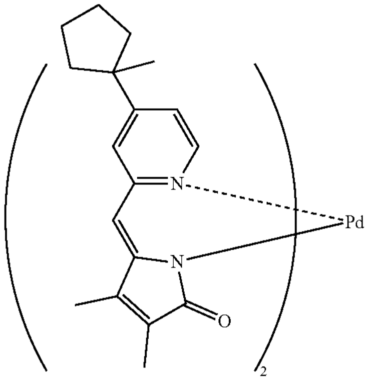
33
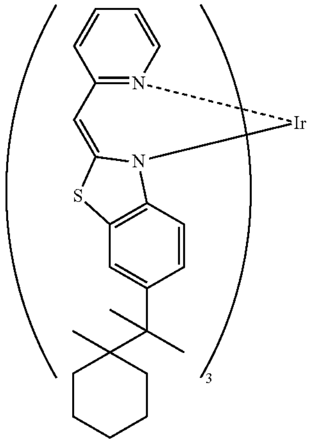
34
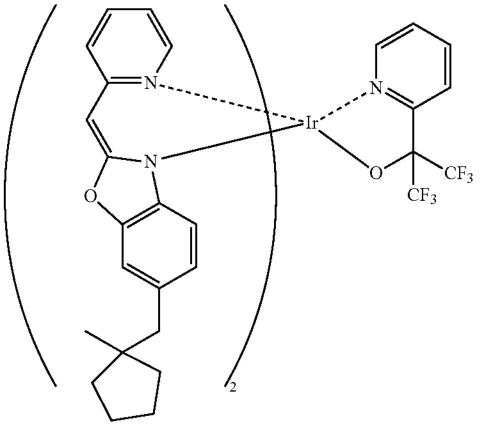

-continued
35
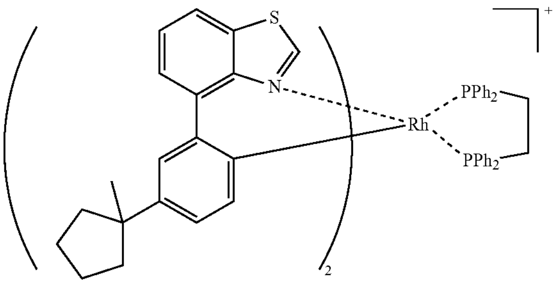
36
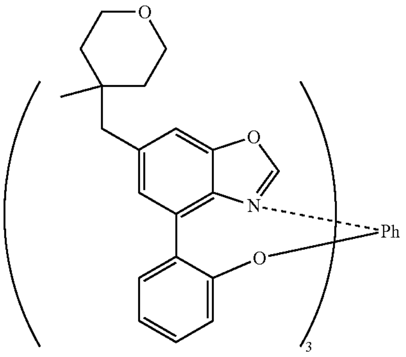
37
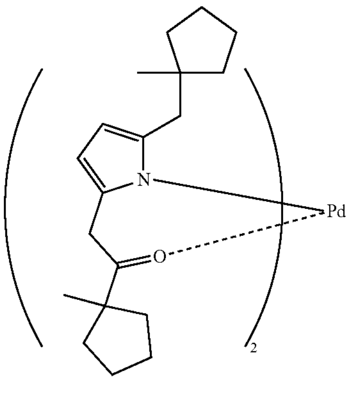
38
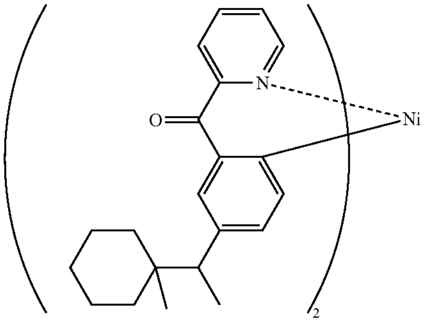
-continued
39
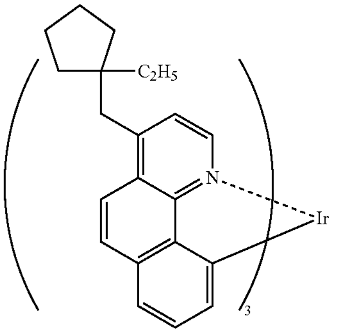
40
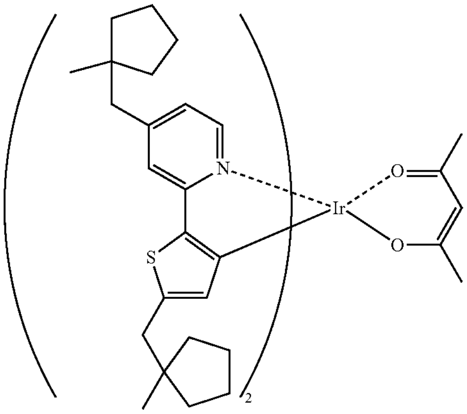
41
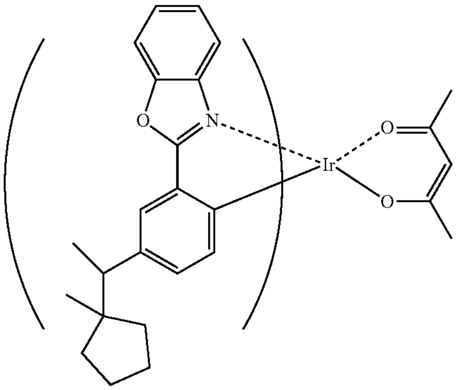
42
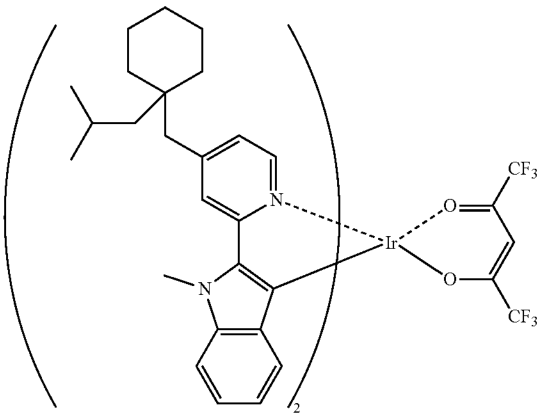

-continued
43
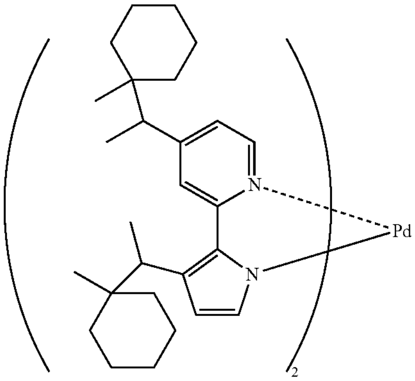
44
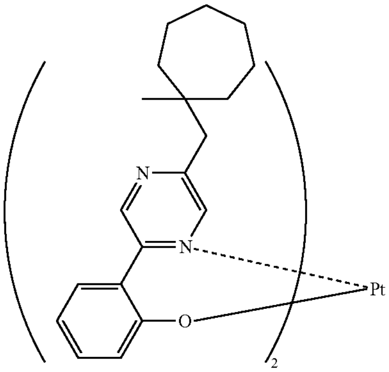
45
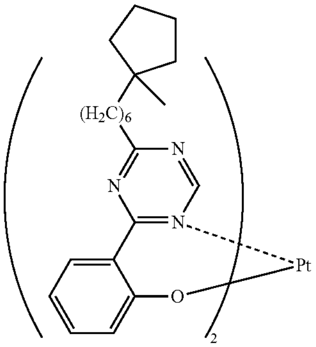
46
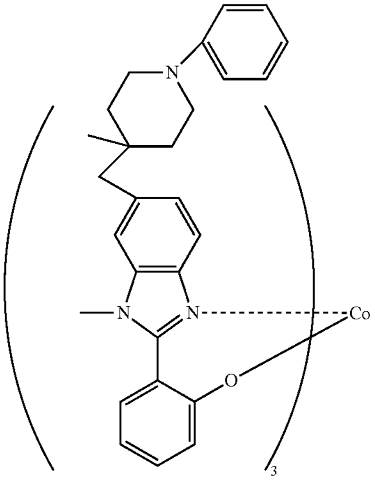
-continued
47
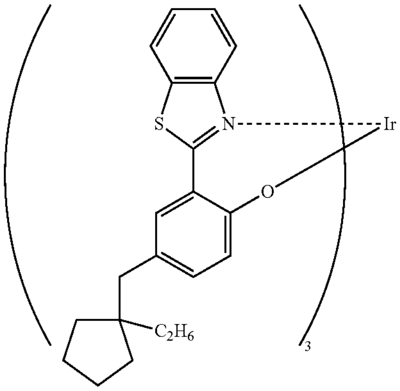
48
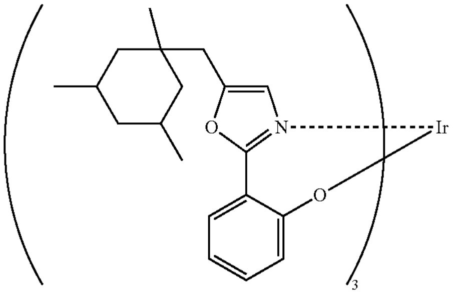
49
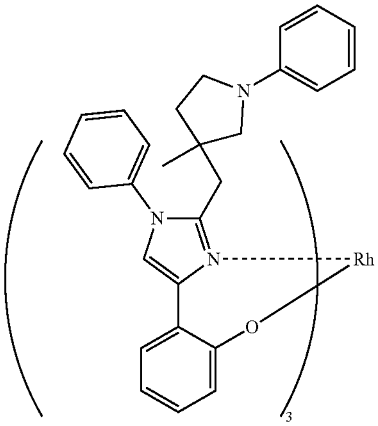
50
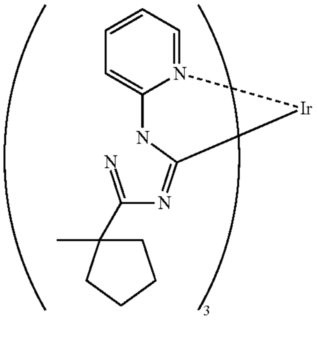

-continued
51
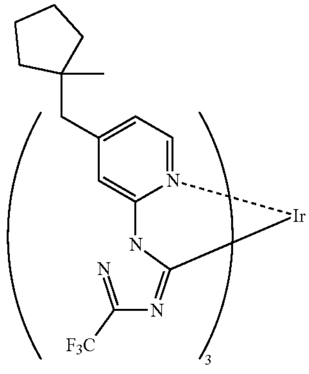
52
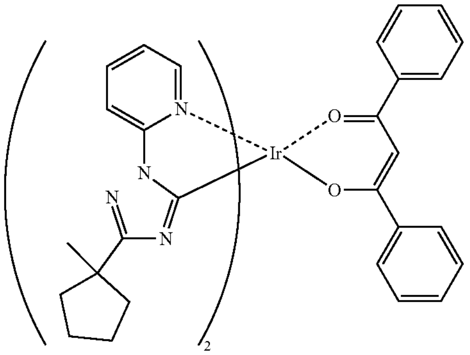
53
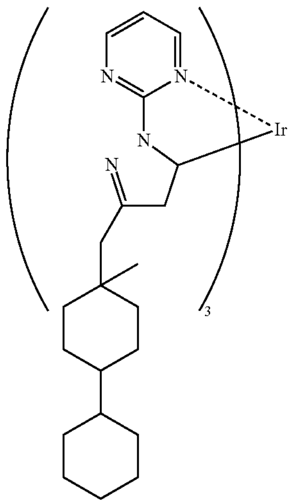
54
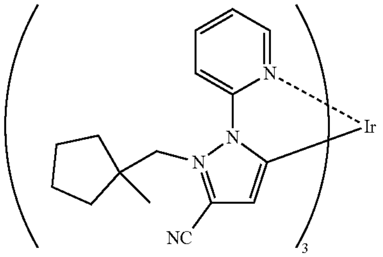
-continued
55
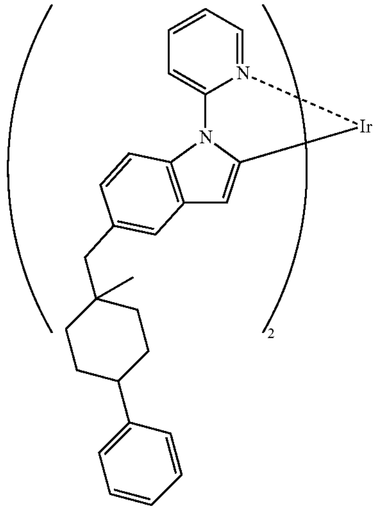
56
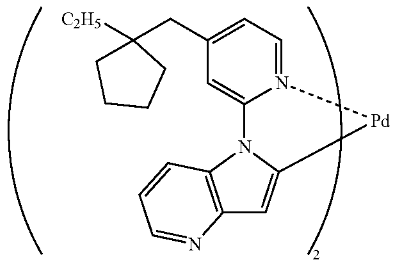
57
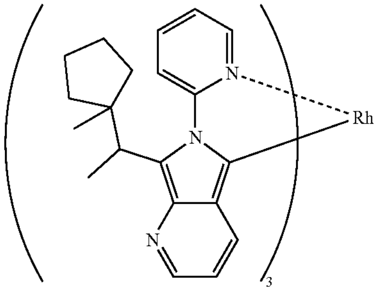
58
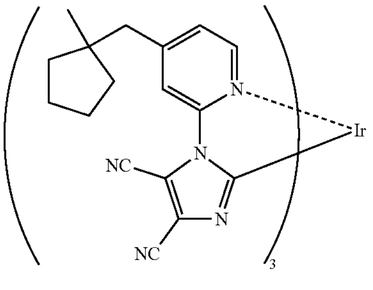
59
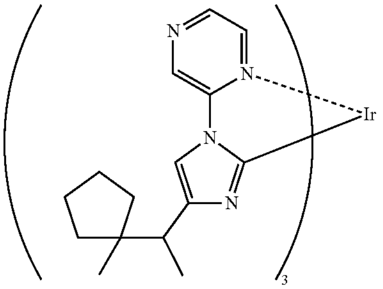

-continued
60
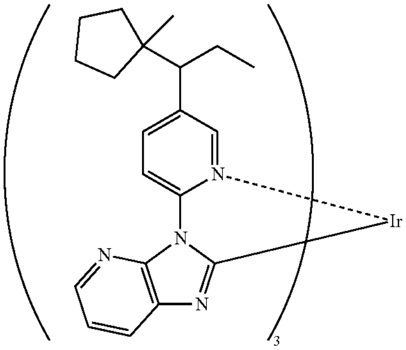
61
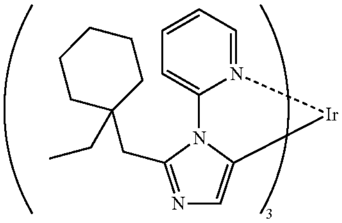
62
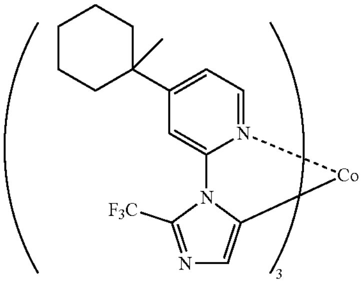
63
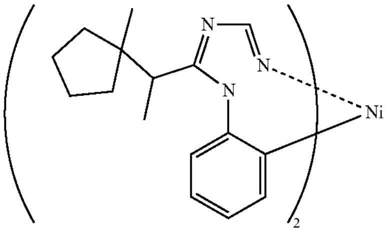
64
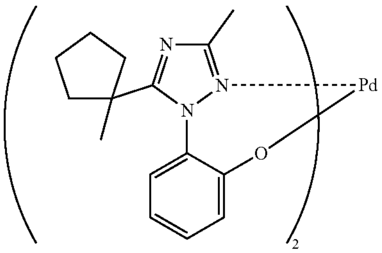
-continued
65
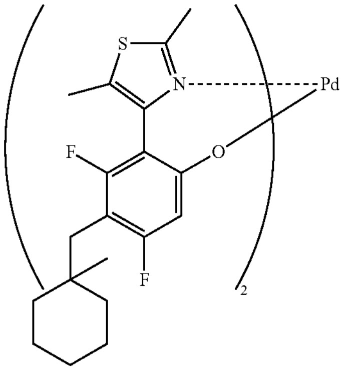
66
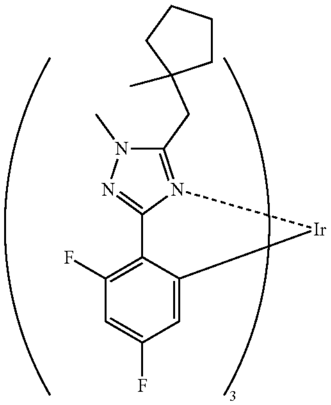
67
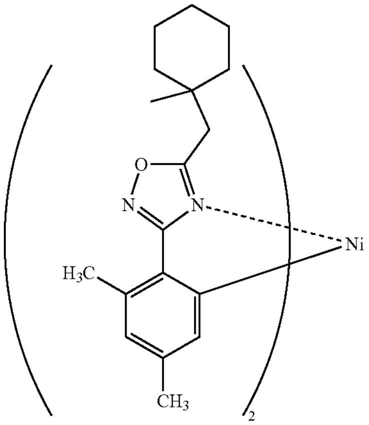

-continued
68
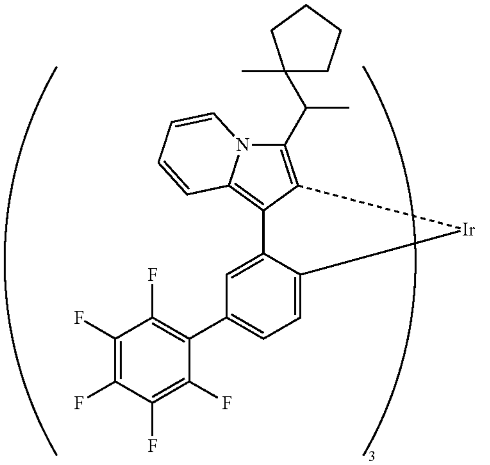
69
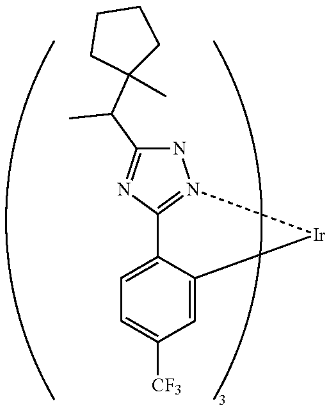
70
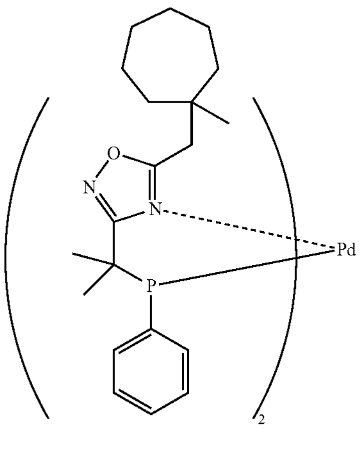
-continued
71
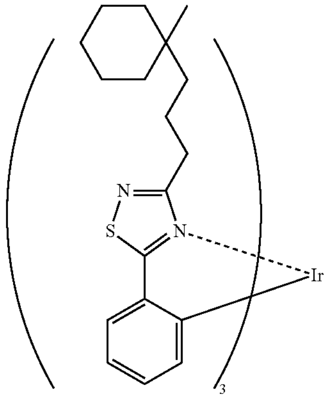
72
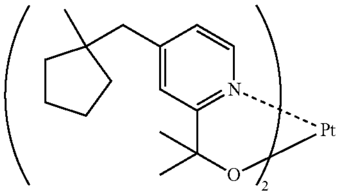
73
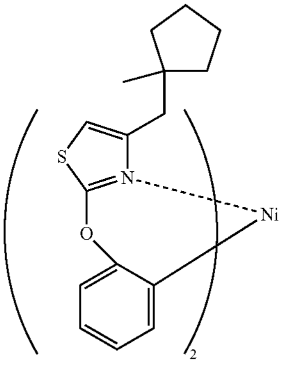
74
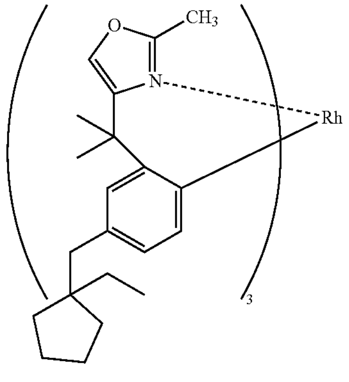
75
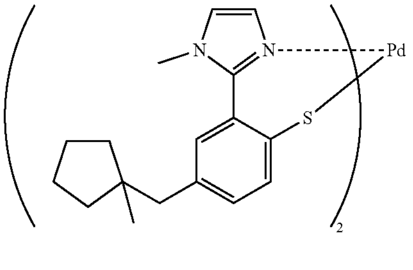

-continued
76
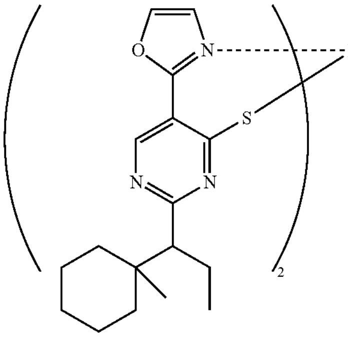
77
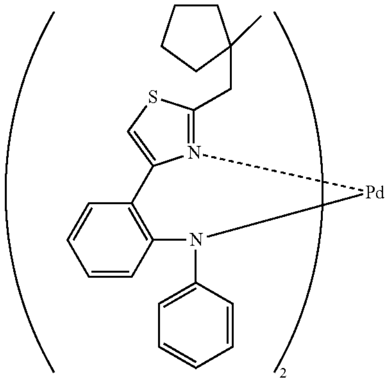
78
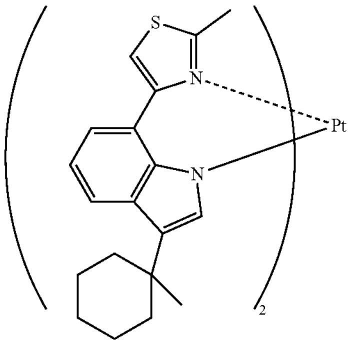
79
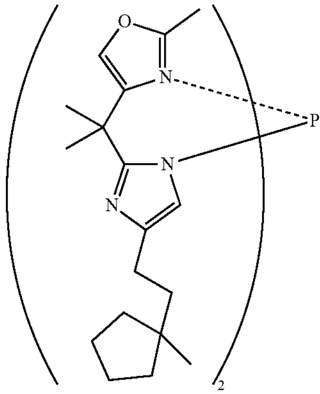
-continued
80
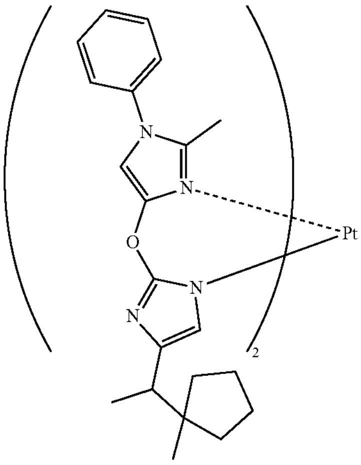
81
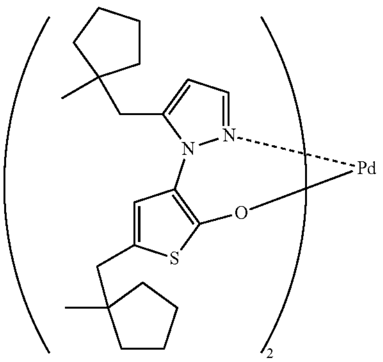
82
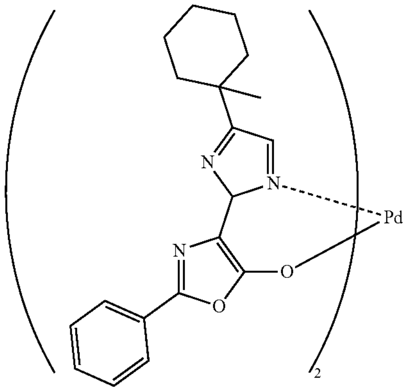
83
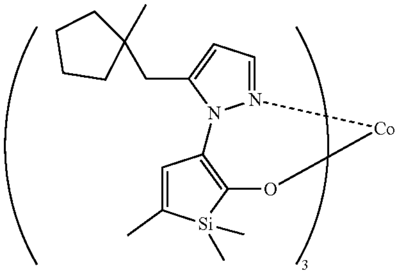

-continued
84
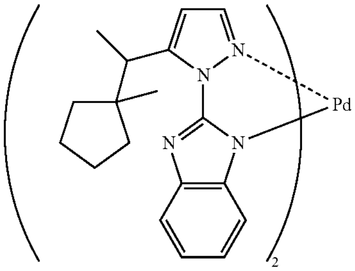
85
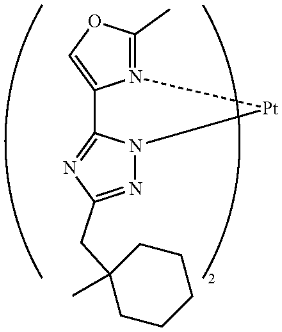
86
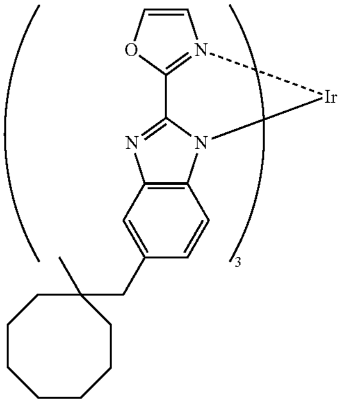
87
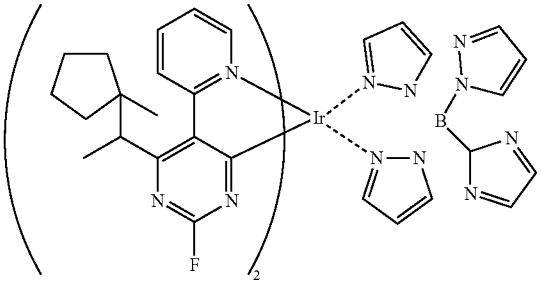
-continued
88
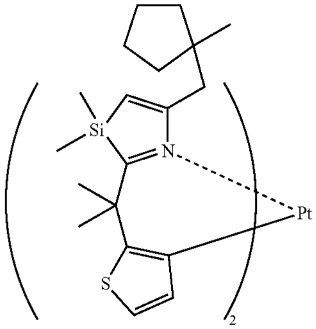
89
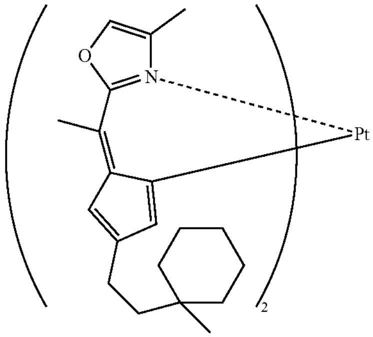
90
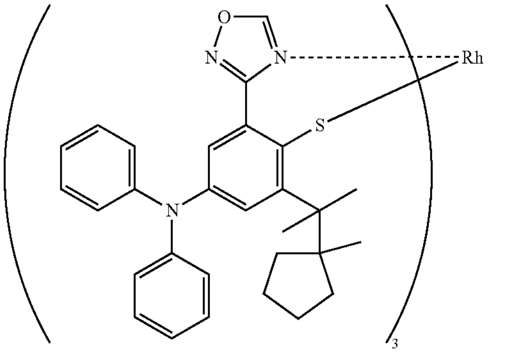
91
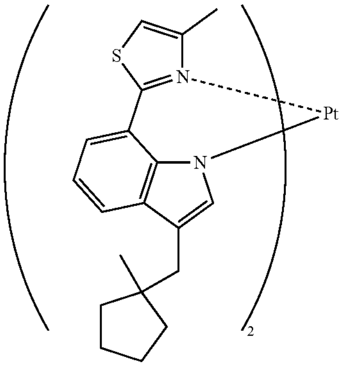

-continued
92
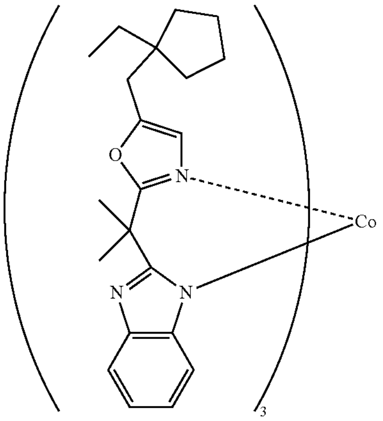
93
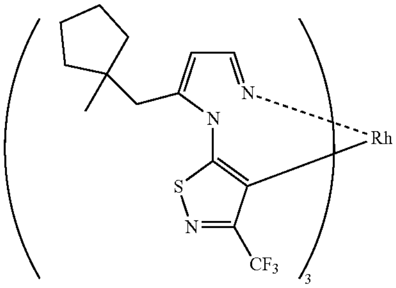
94
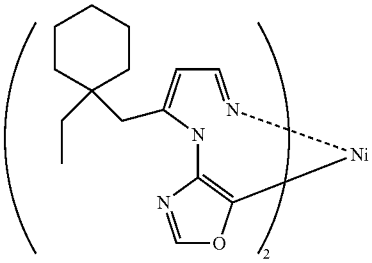
95
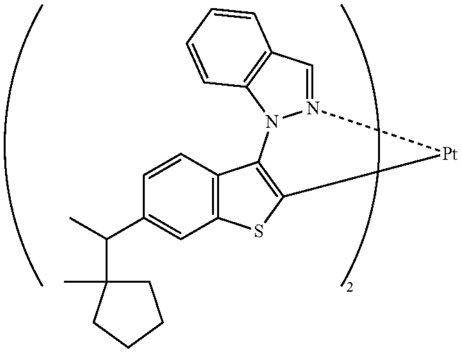
-continued
96
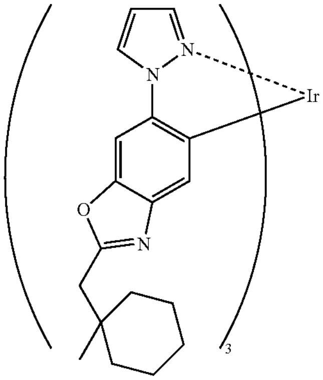
97
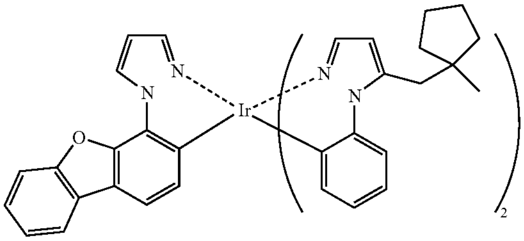
98
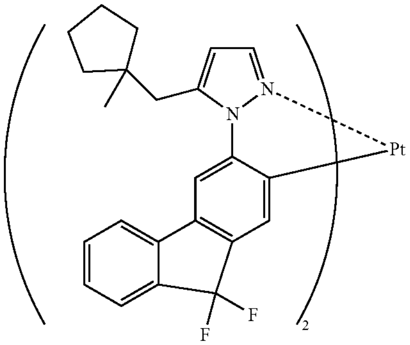
99
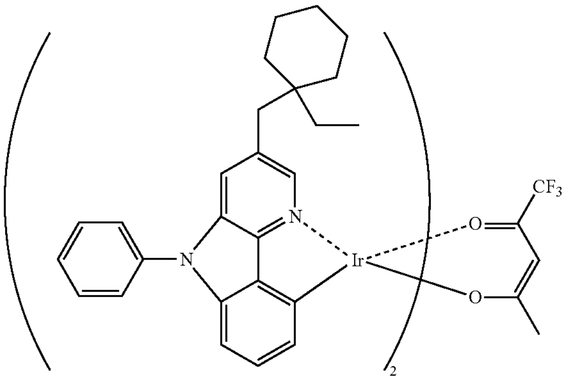

-continued
100
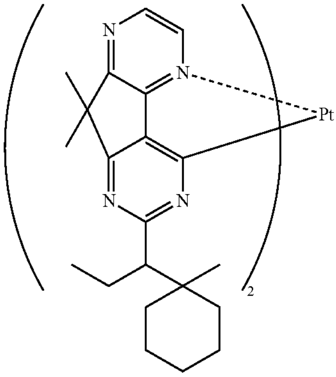
101
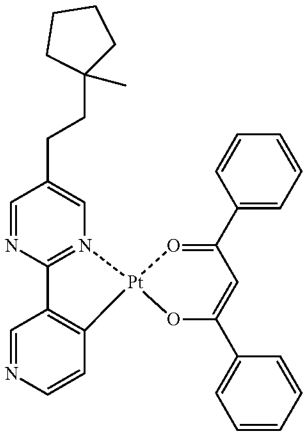
102
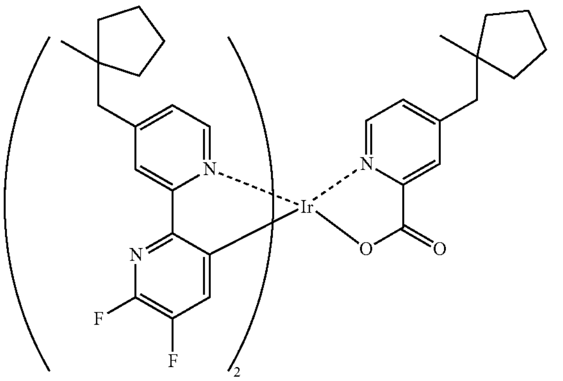
103
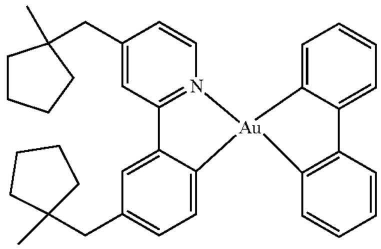
-continued
104
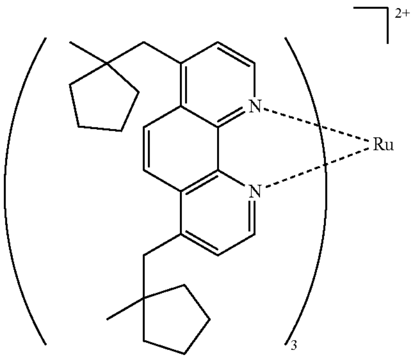
105
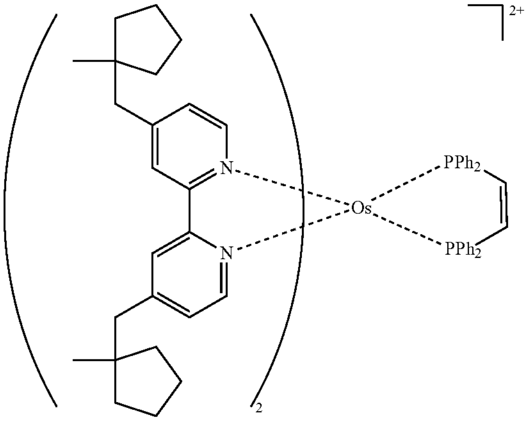
106
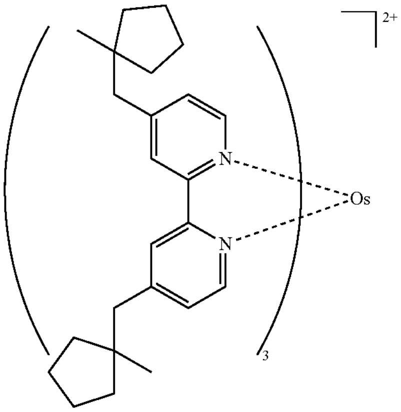
107
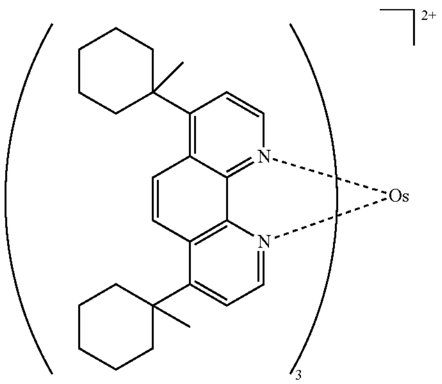

-continued
108
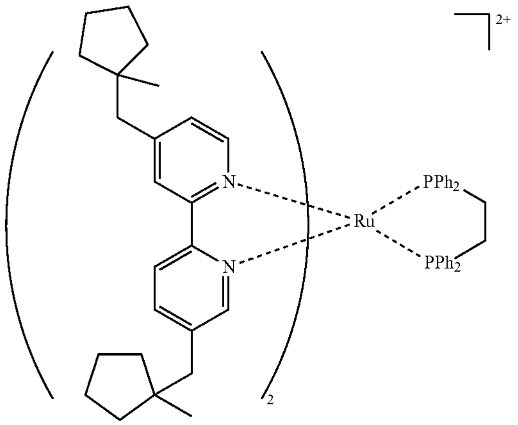
109
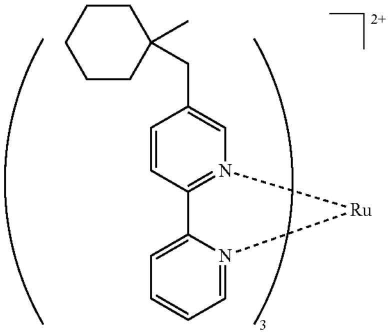
110
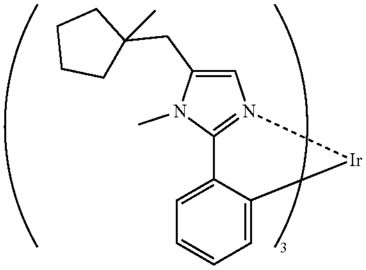
111
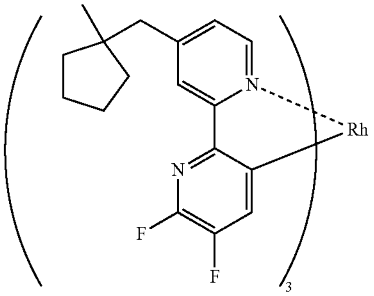
-continued
112
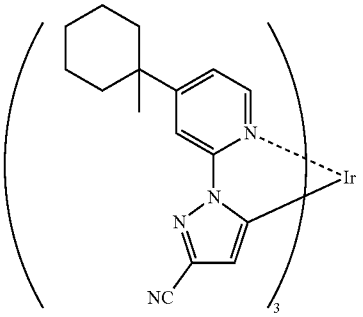
113
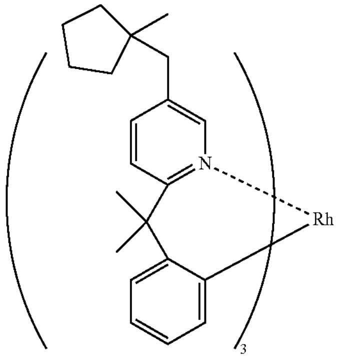
114
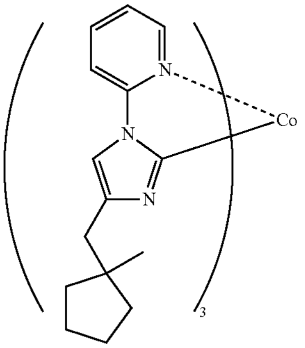
115
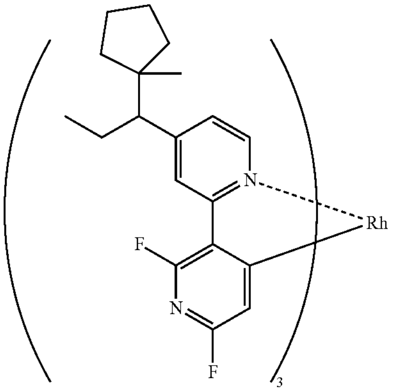

116
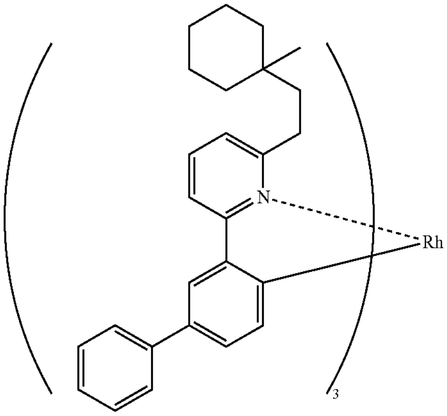
117
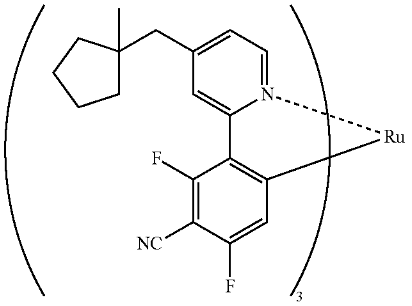
118
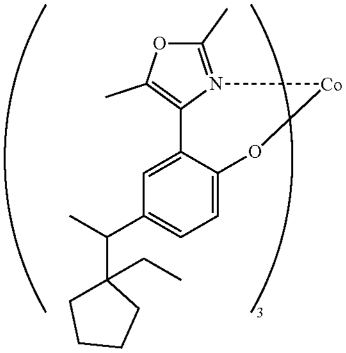
119
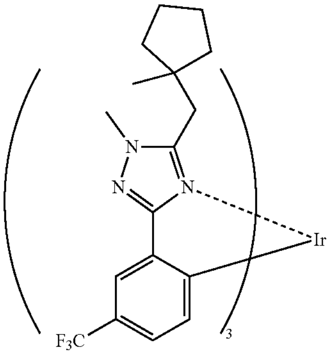
120
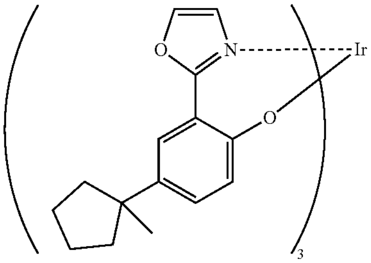
121
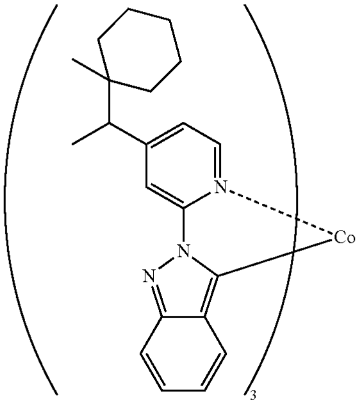
122
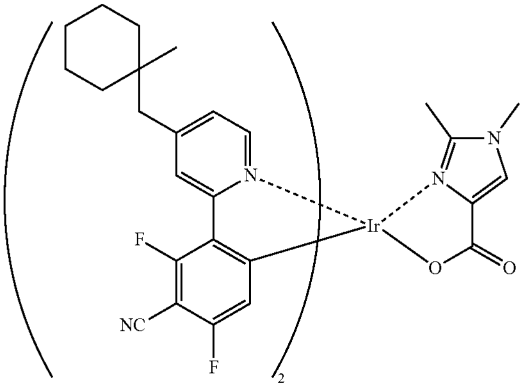
123
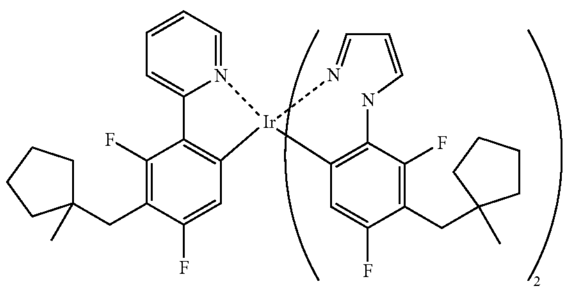

-continued
124
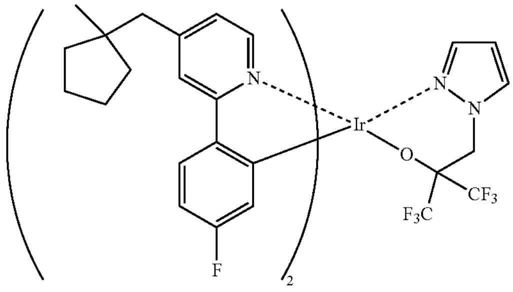
125
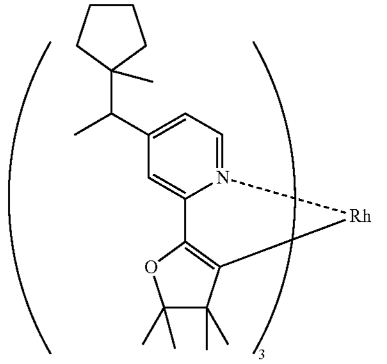
126
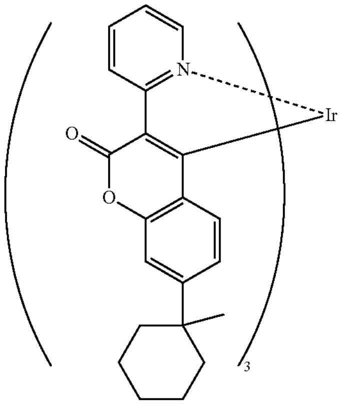
127
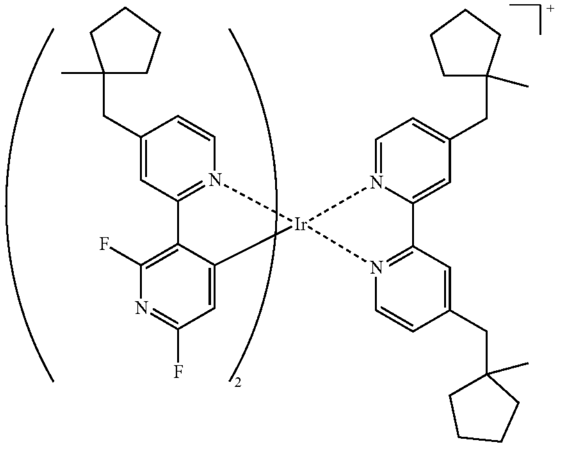
-continued
128
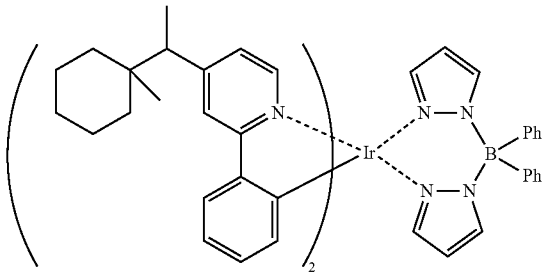
129
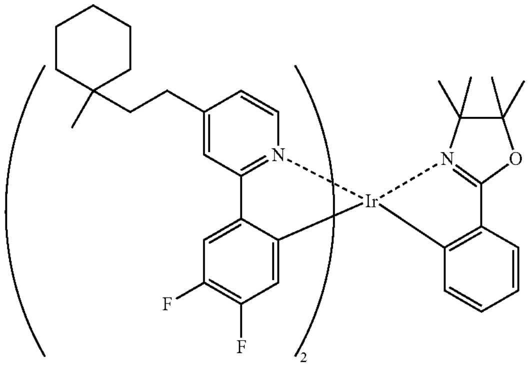
130
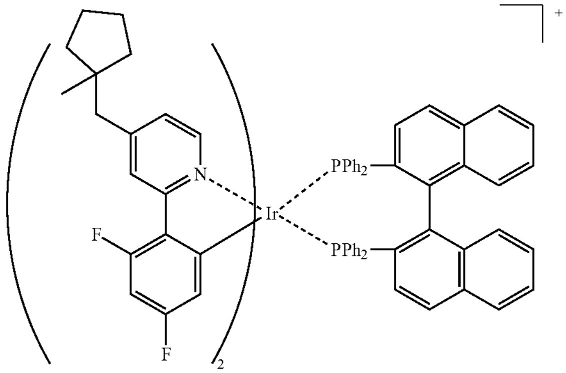
131
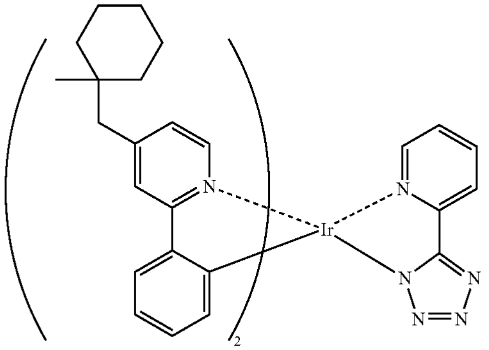

-continued
132
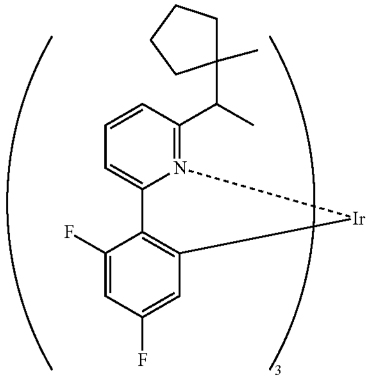
133
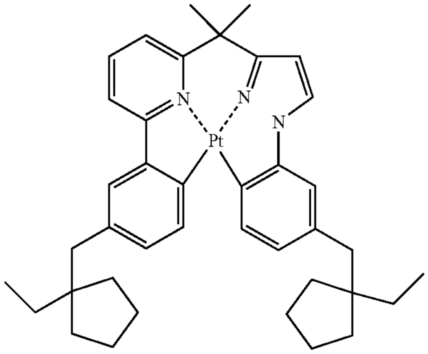
134
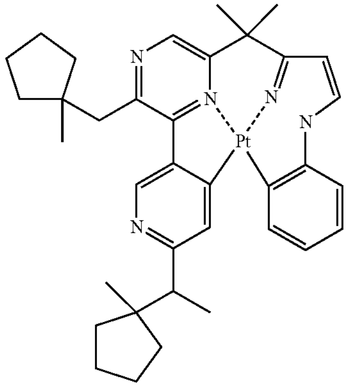
135
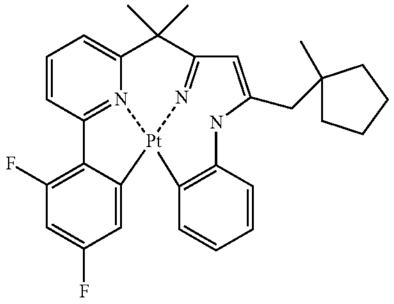
-continued
136
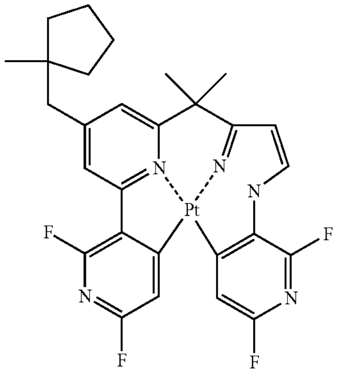
137
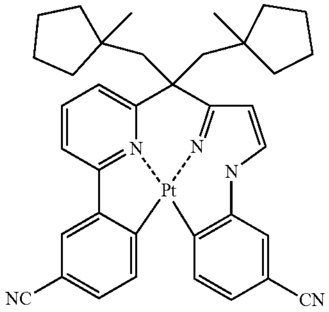
138
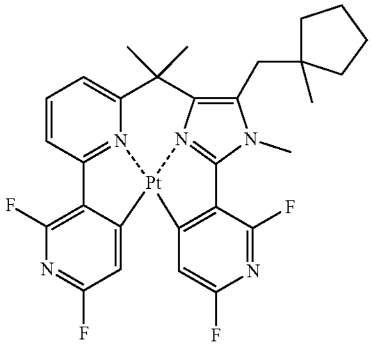
139
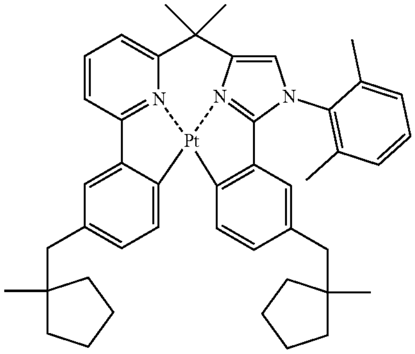

-continued
140
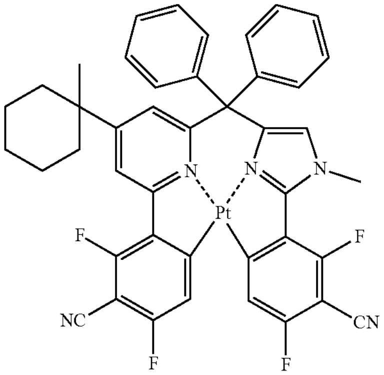
141
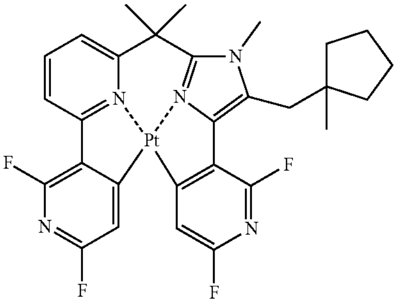
142
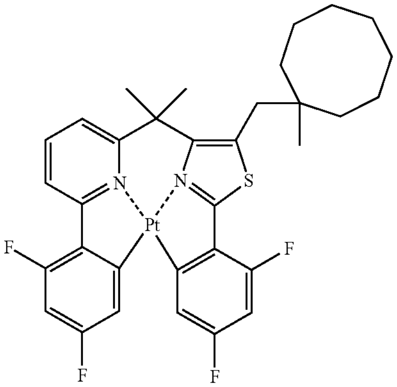
143
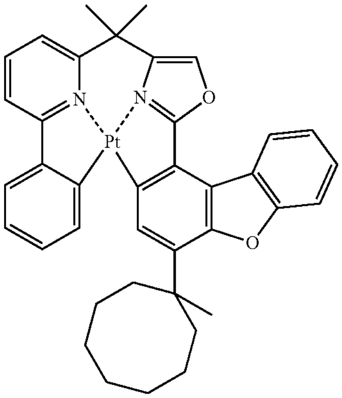
-continued
144
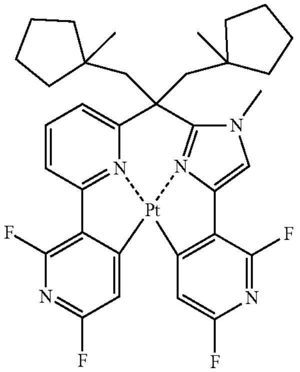
145
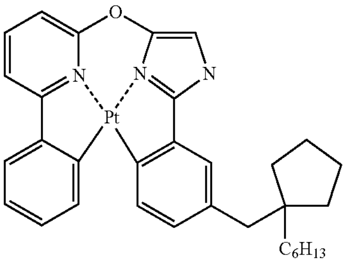
146
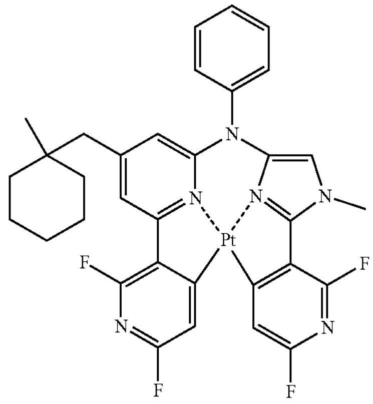
147
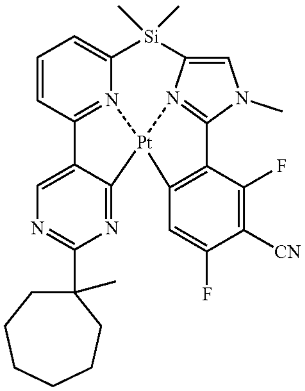

-continued
148
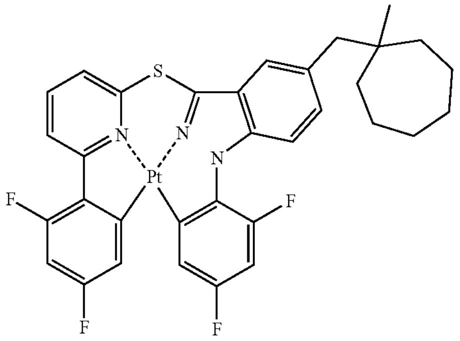
149
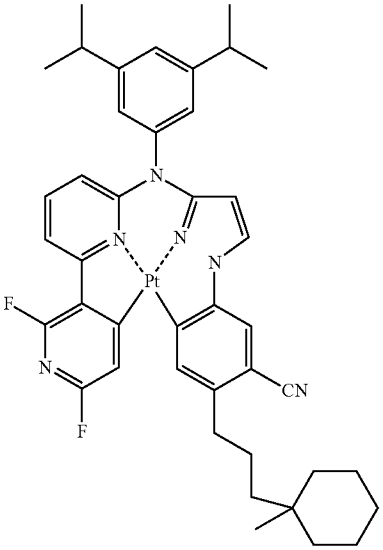
150
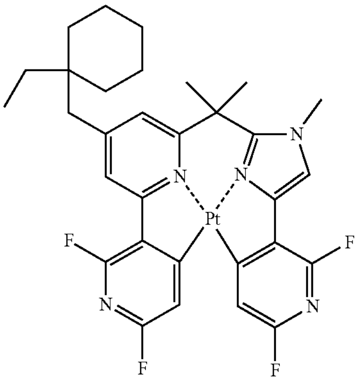
-continued
151
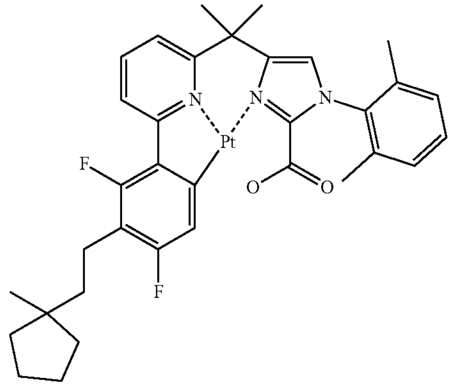
152
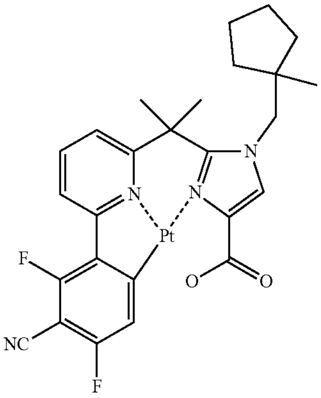
153
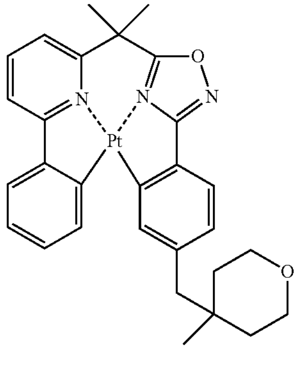
154
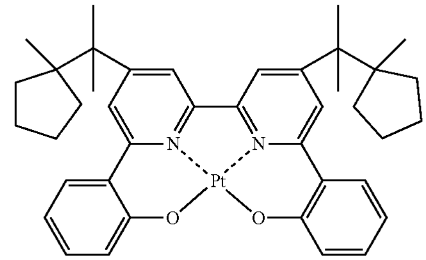

-continued
155
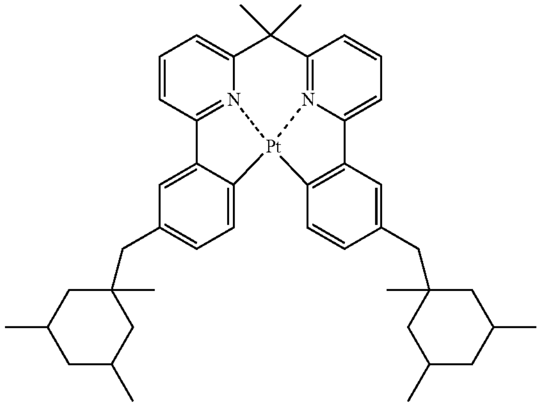
156
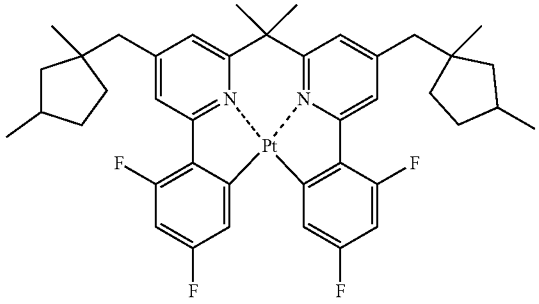
157
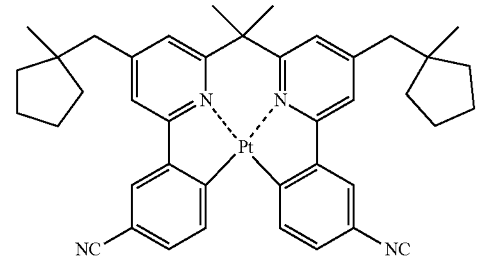
158
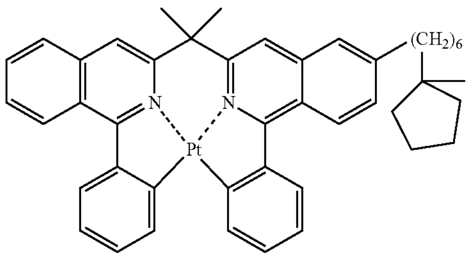
-continued
159
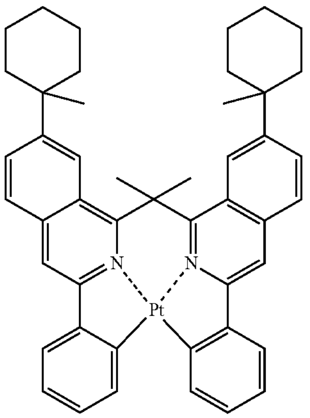
160
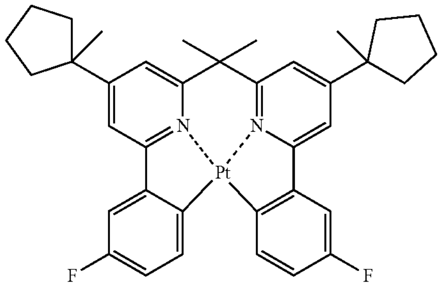
161
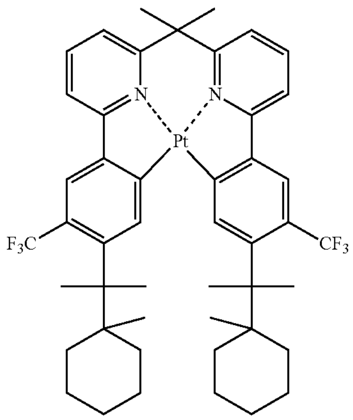
162
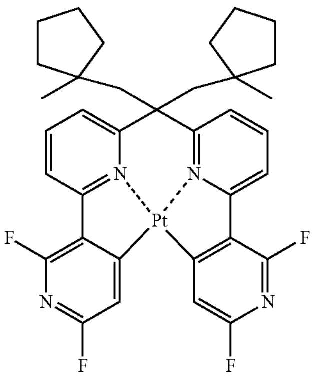

-continued
163
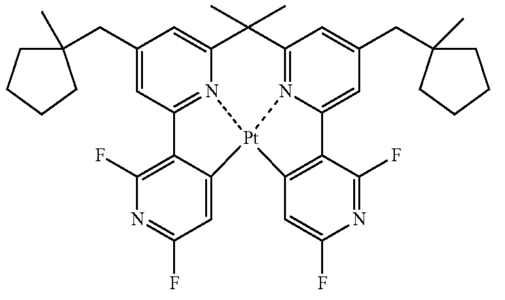
164
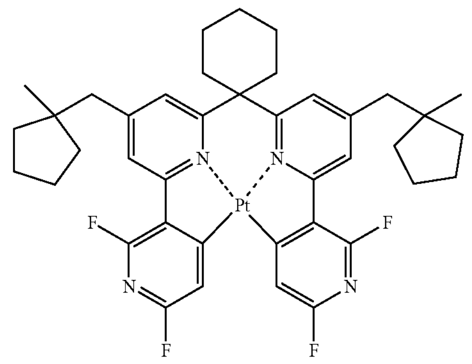
165
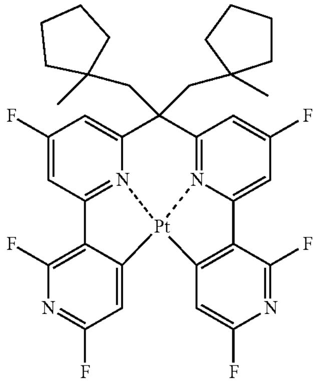
166
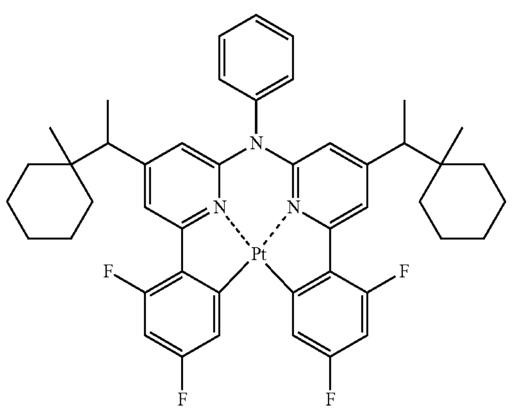
-continued
167
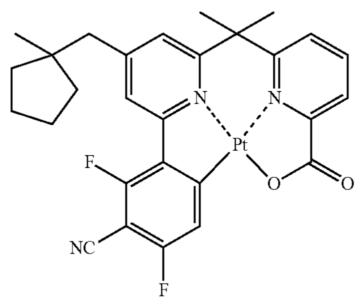
168
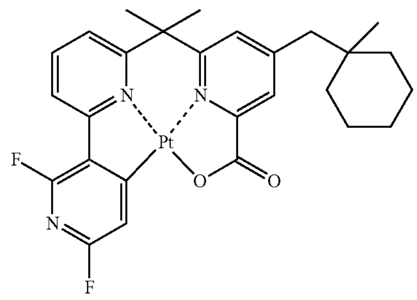
169
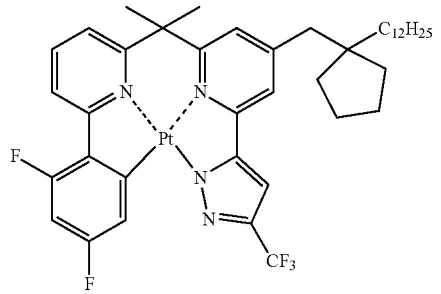
170
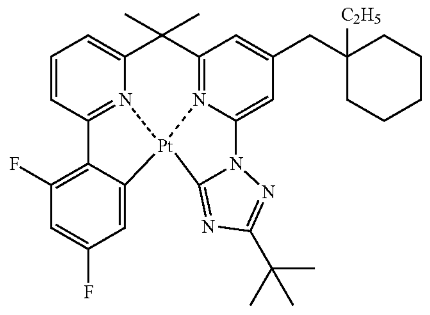
171
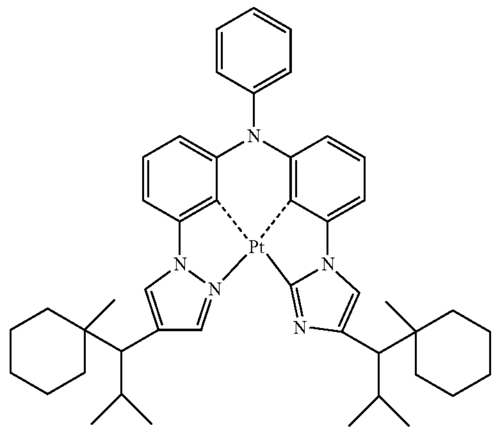

-continued
172
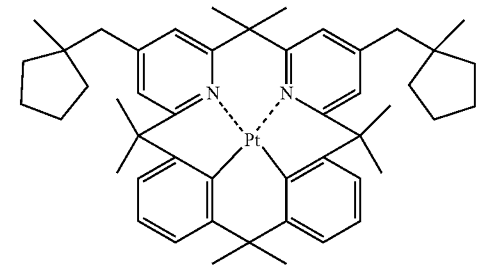
173
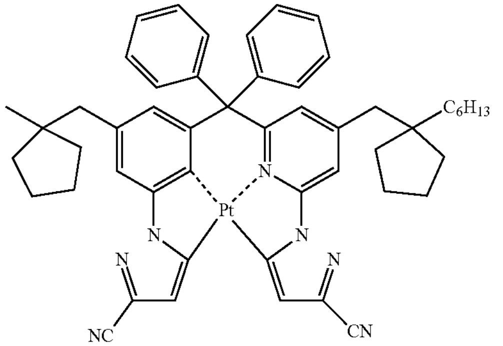
174
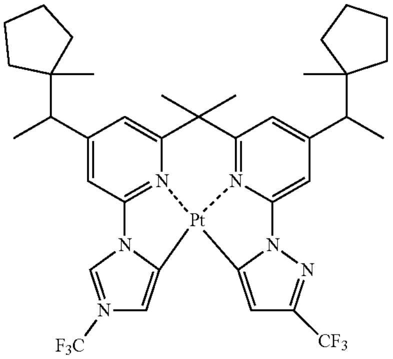
175
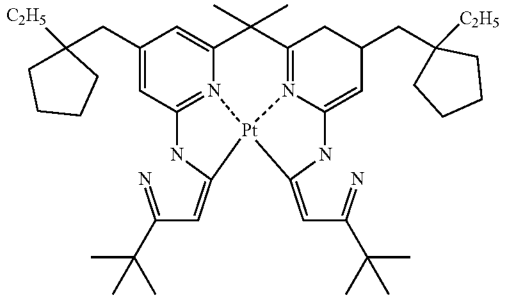
176
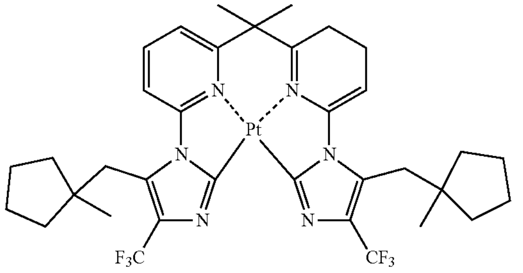
-continued
177
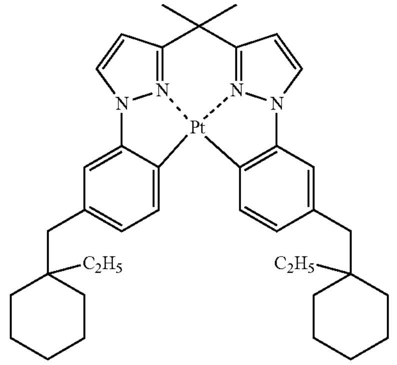
178
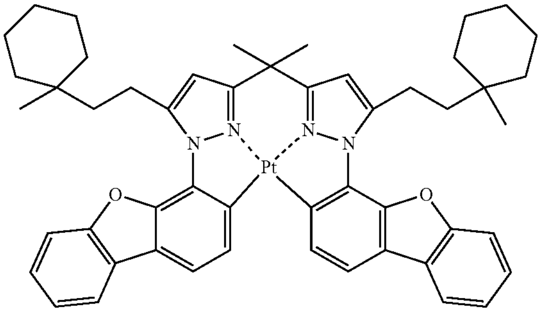
179
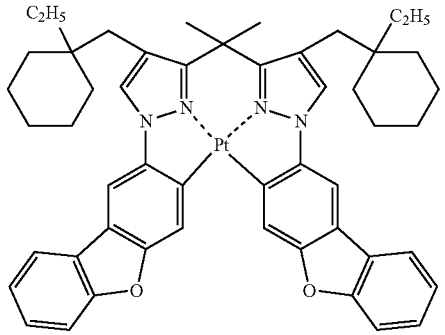
180
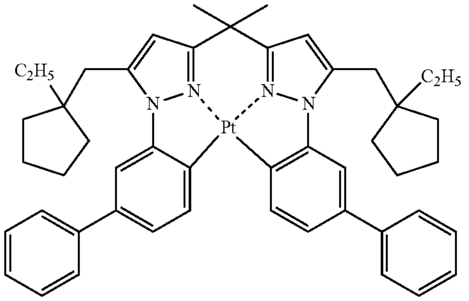
181
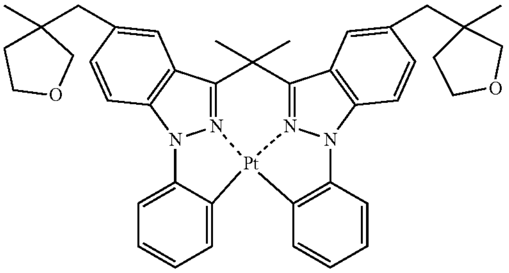

-continued
182
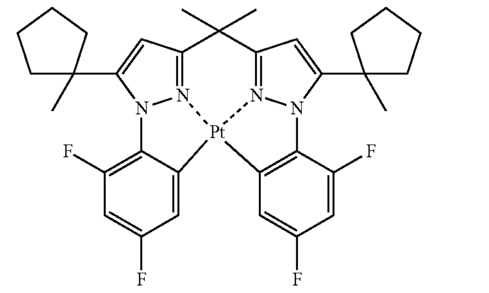
183
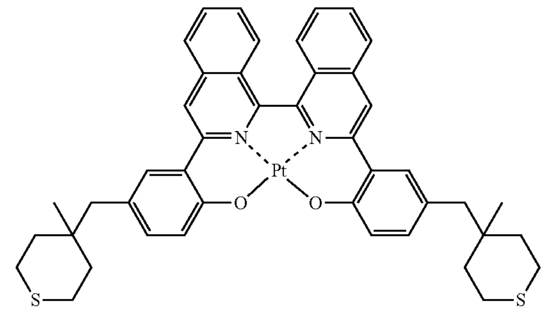
184
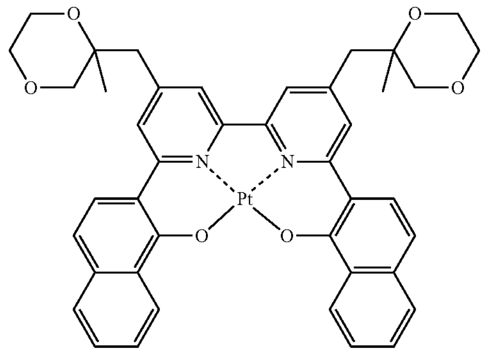
185
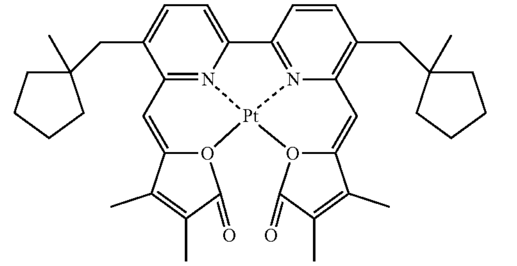
186
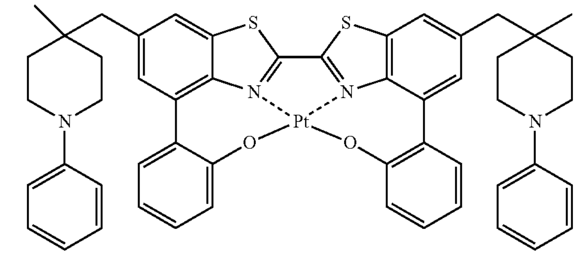
-continued
187
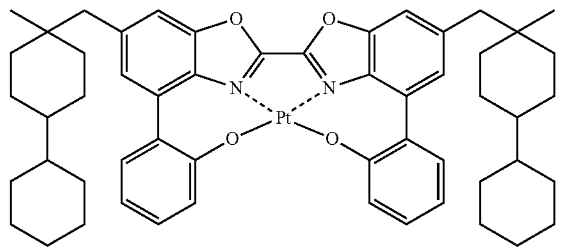
188
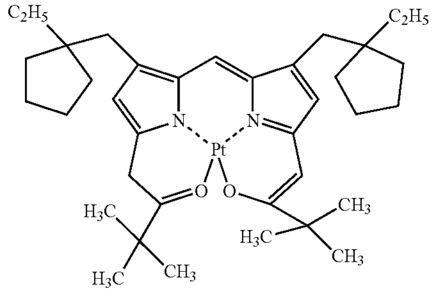
189
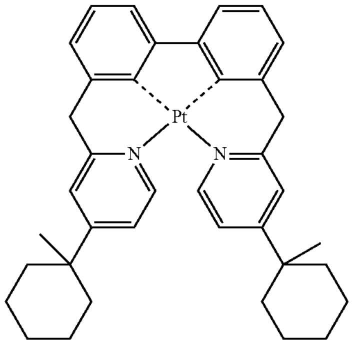
190
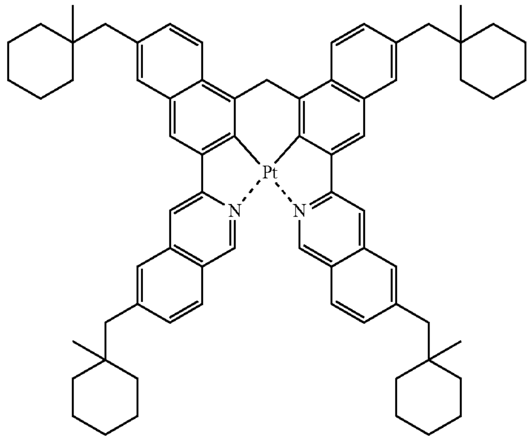

-continued
191
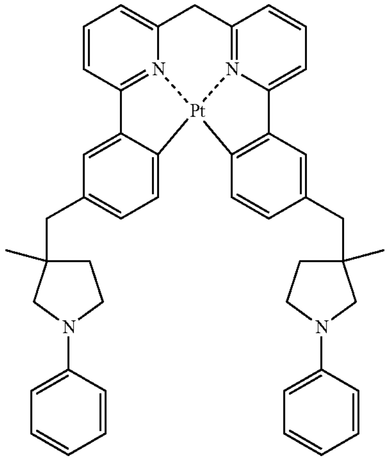
192
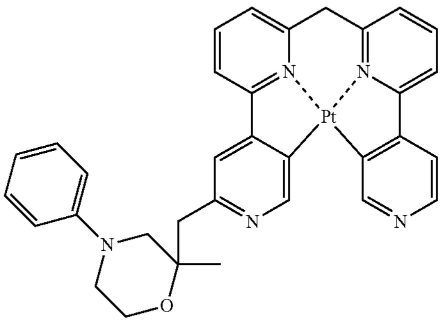
193
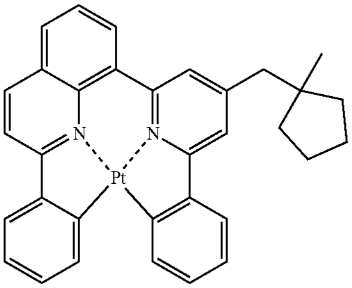
194
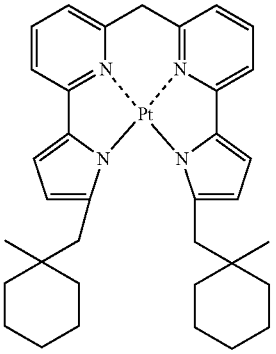
-continued
195
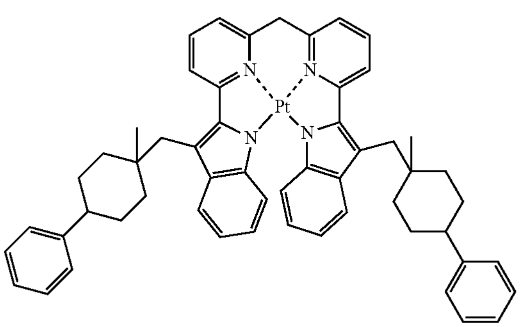
196
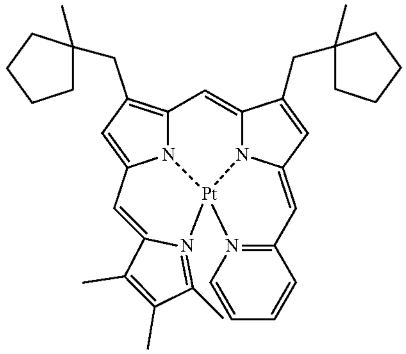
197
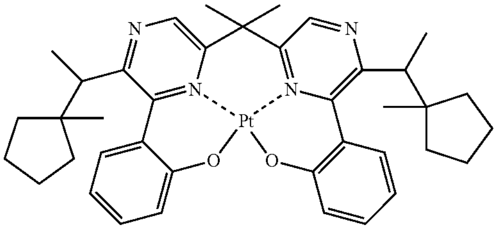
198
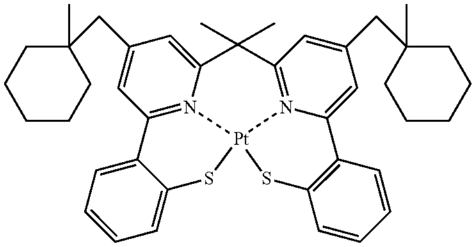
199
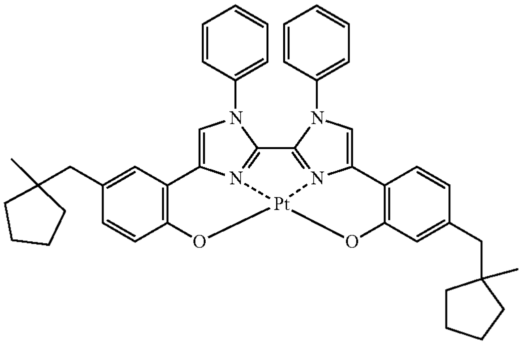

-continued
200
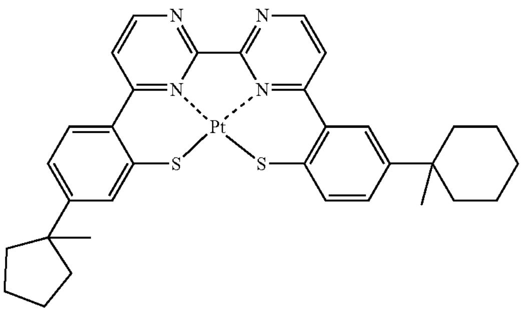
201
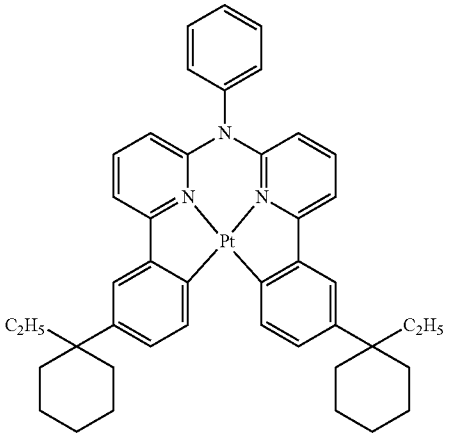
202
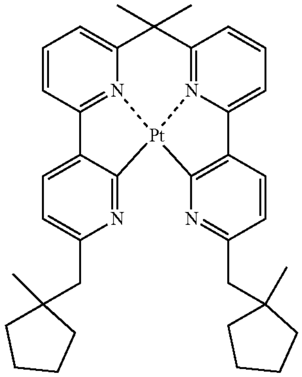
203
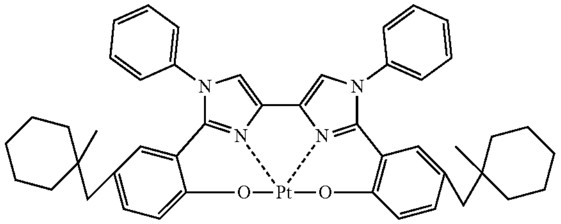
-continued
204
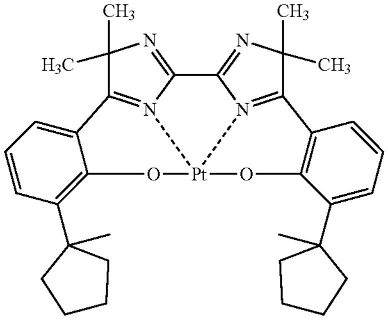
205
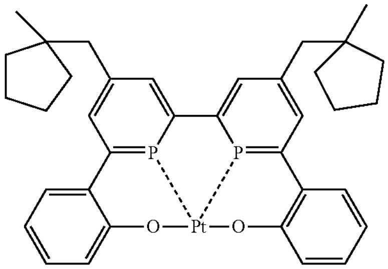
206
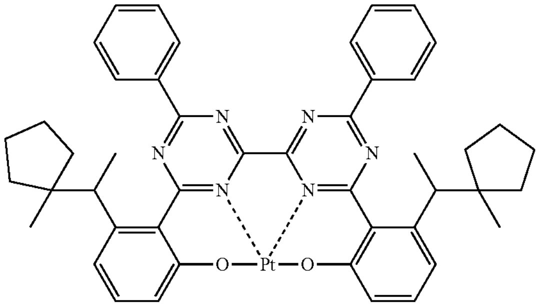
207
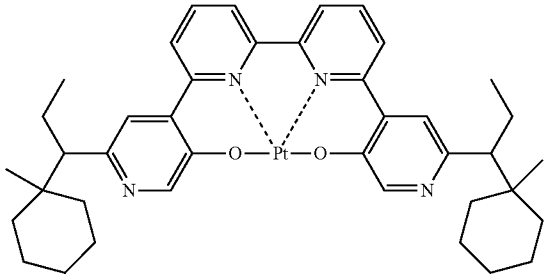
208
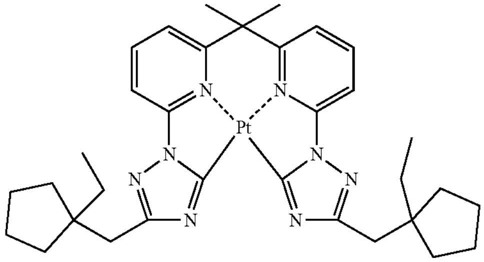

-continued
209
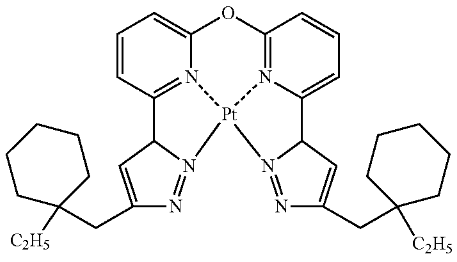
210
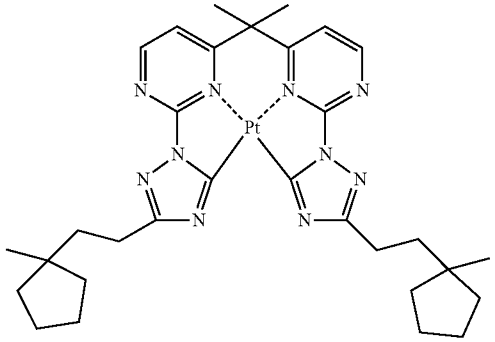
211
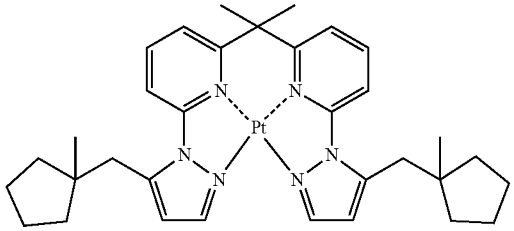
212
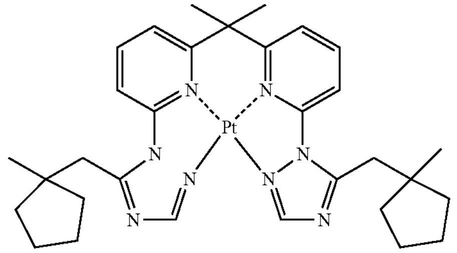
213
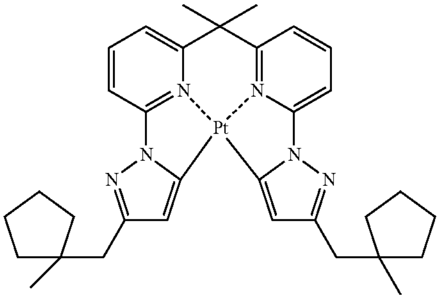
-continued
214
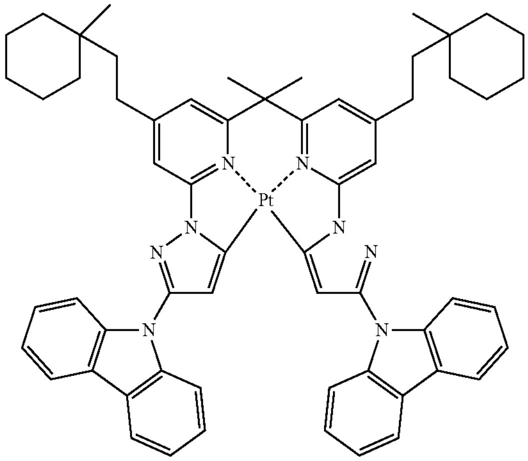
215
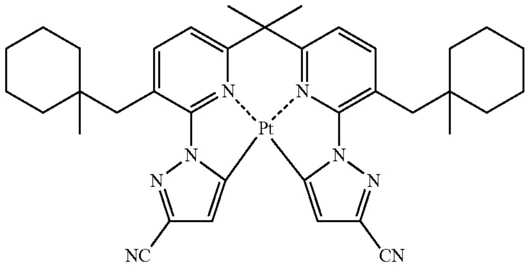
216
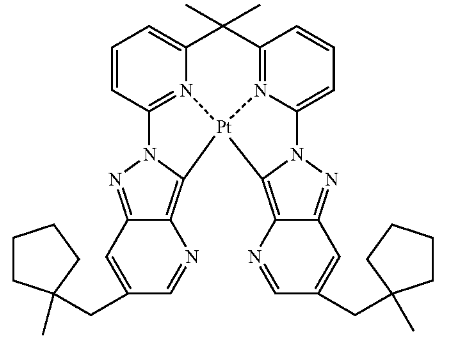
217
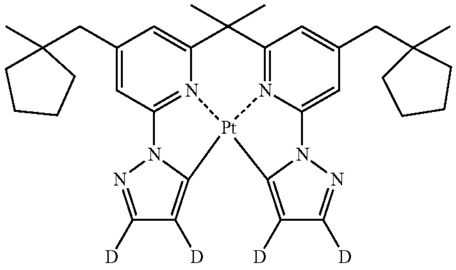

217
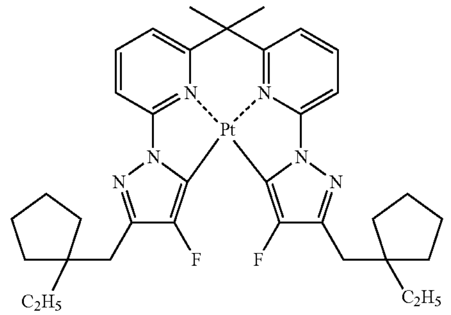
218
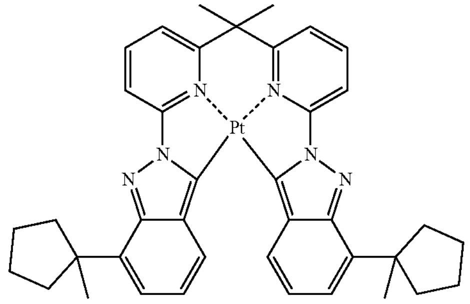
219
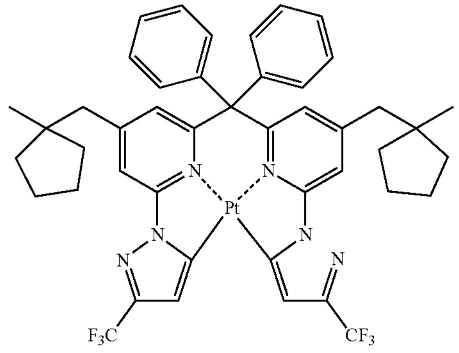
220
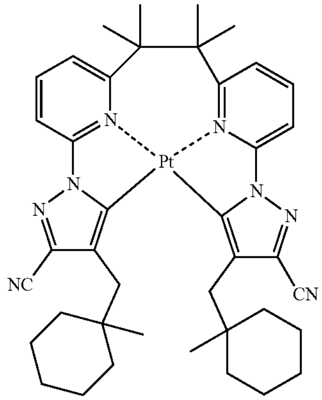
221
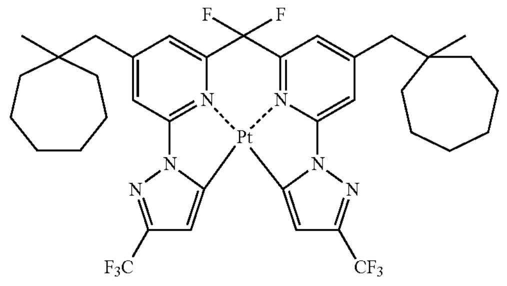
222
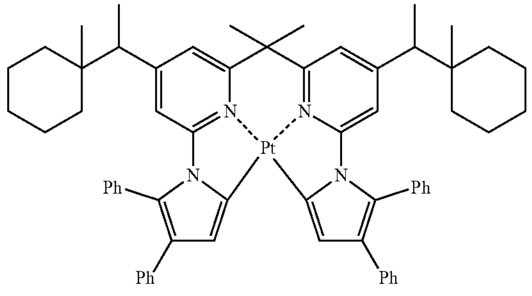
223
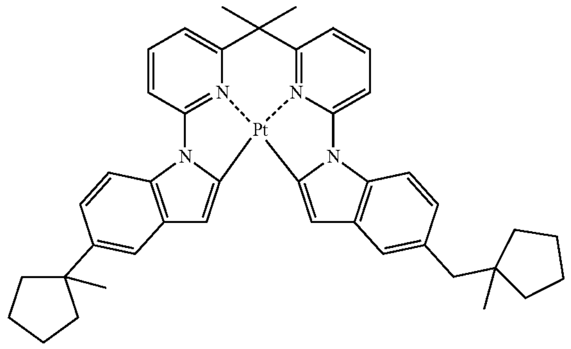
224
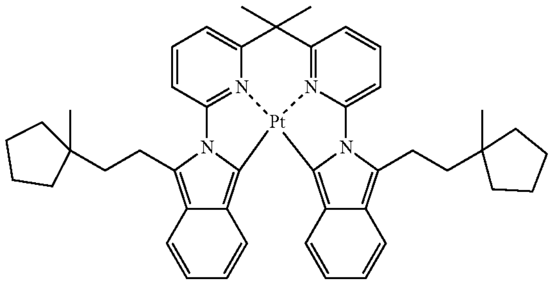
225
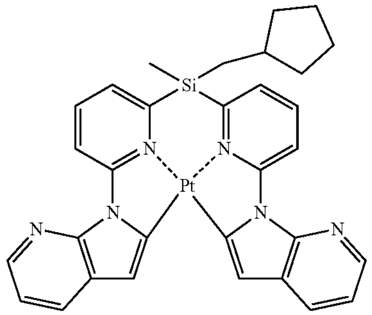

-continued
226
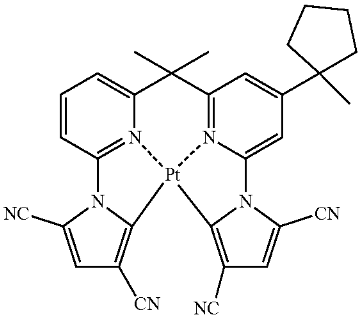
227
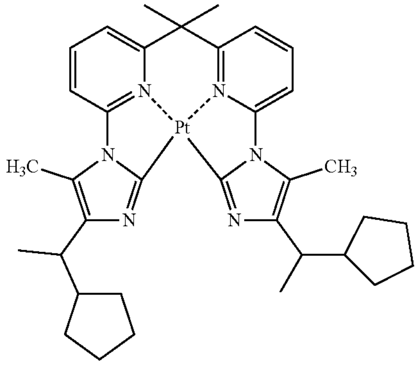
228
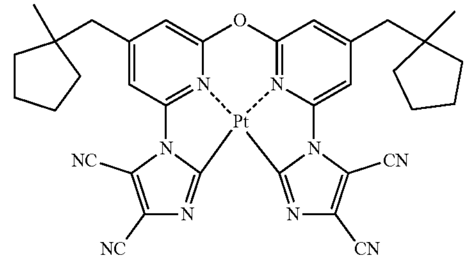
229
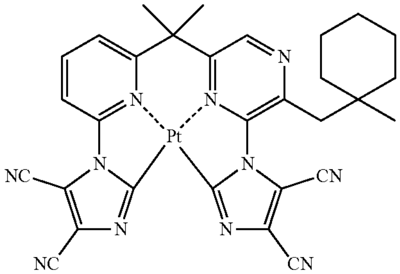
230
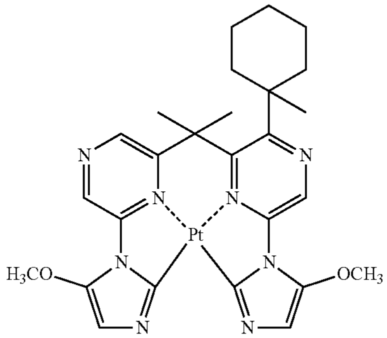
-continued
231
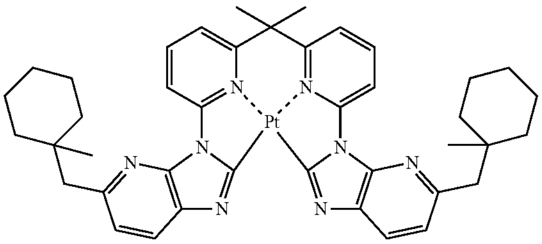
232
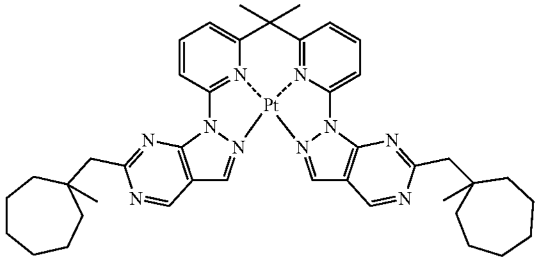
233
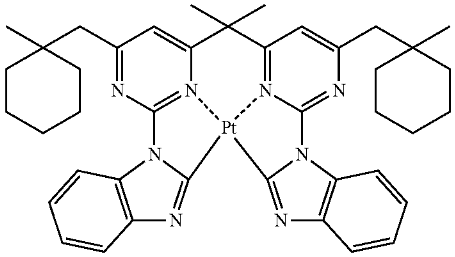
234
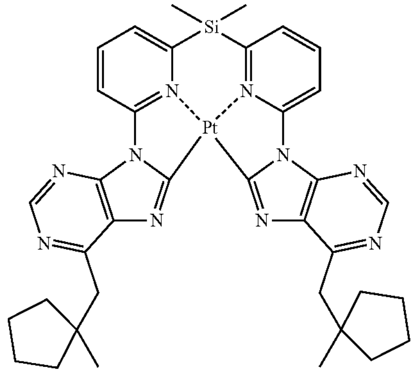
235
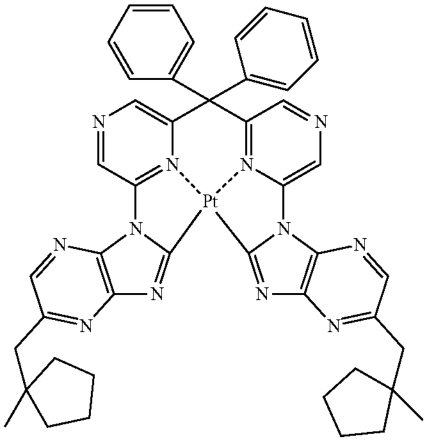

-continued
236
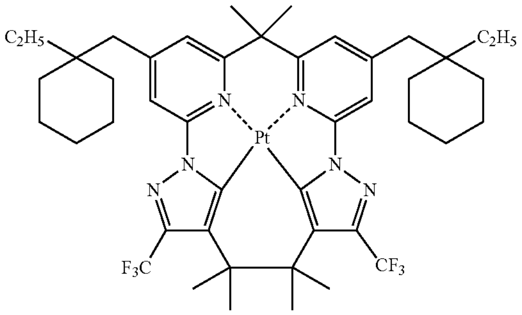
237
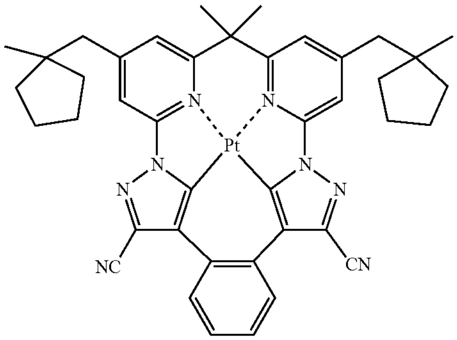
238
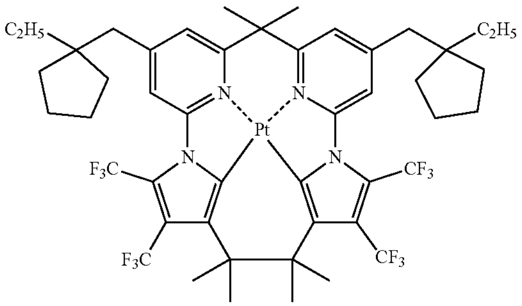
239
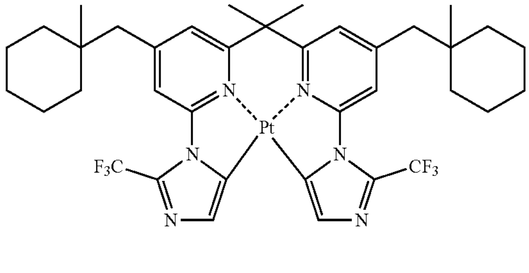
240
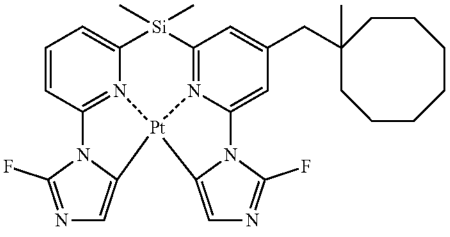
-continued
241
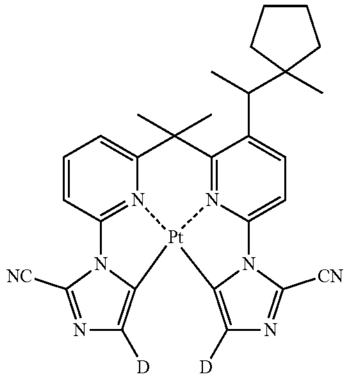
242
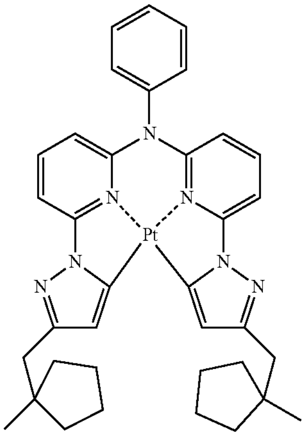
243
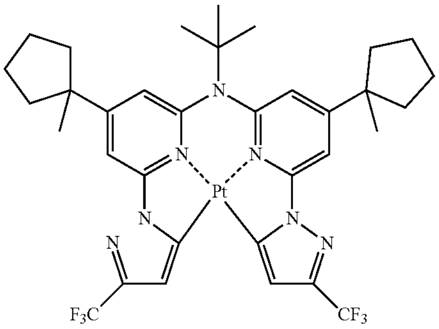
245
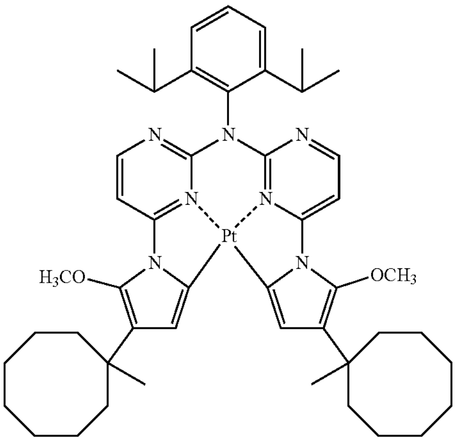

-continued
246
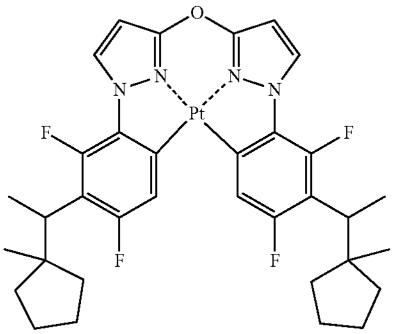
247
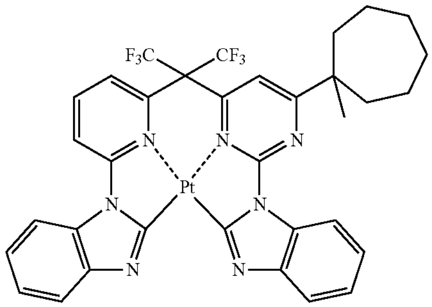
248
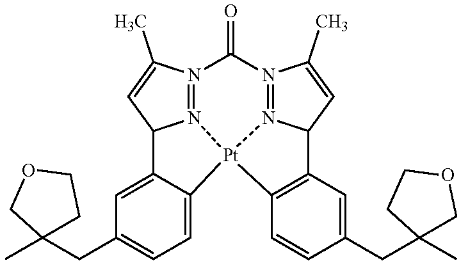
249
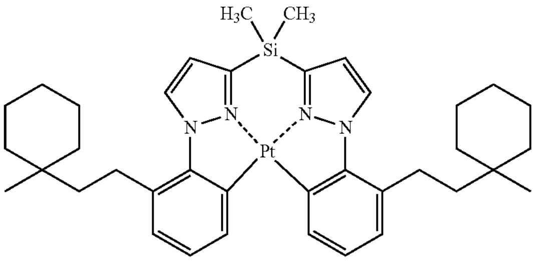
250
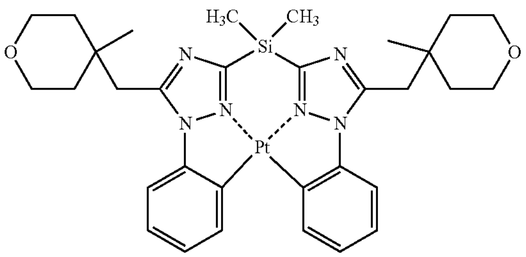
-continued
251
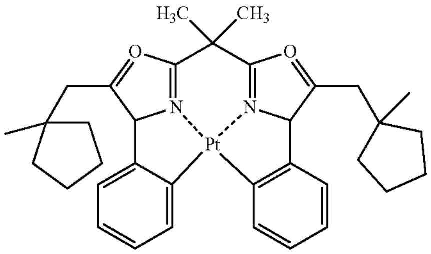
252
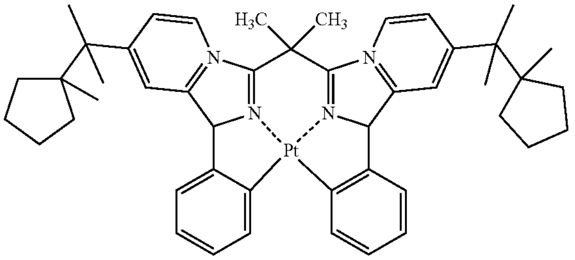
253
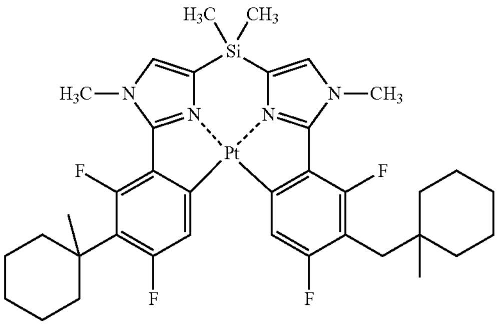
254
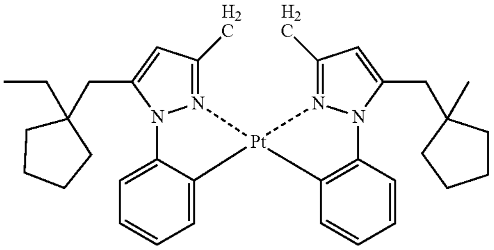
255
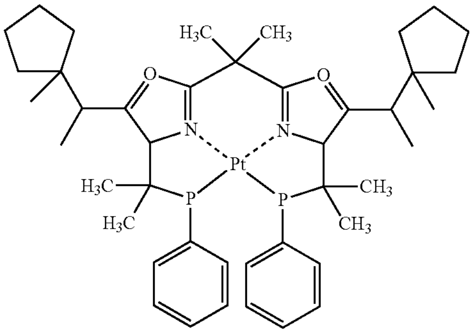

256
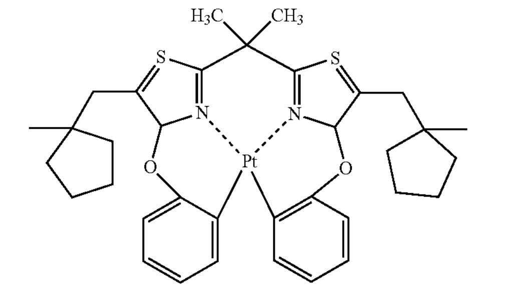
257
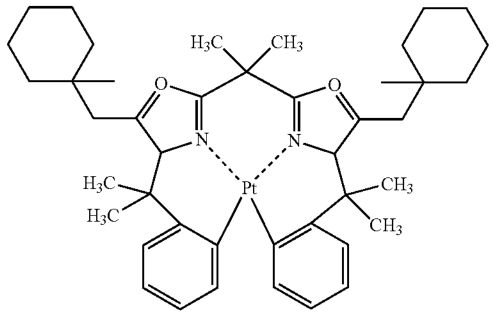
258
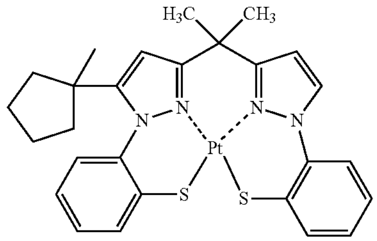
259
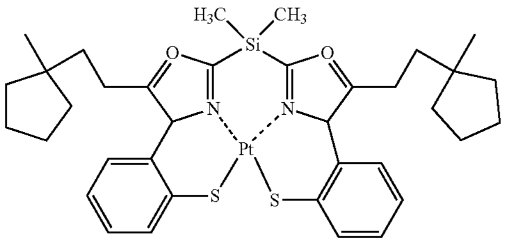
260
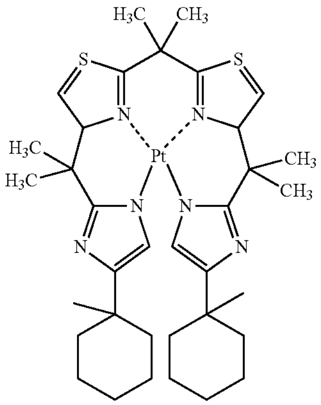
261
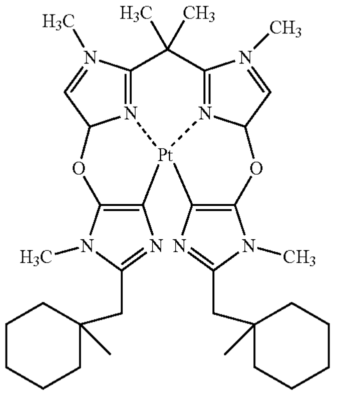
262
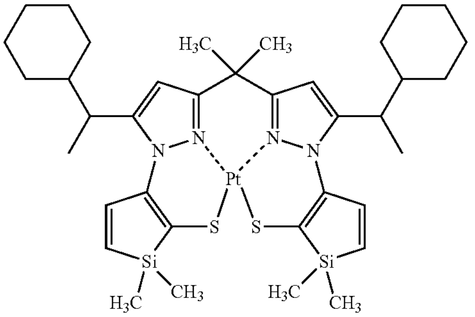
263
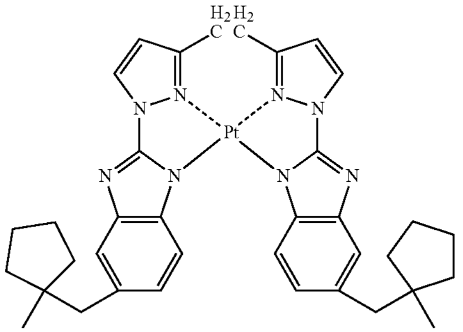
264
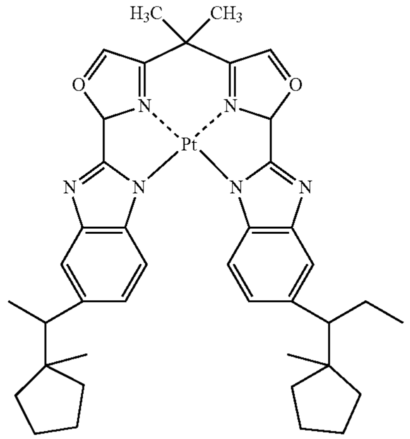

-continued
265
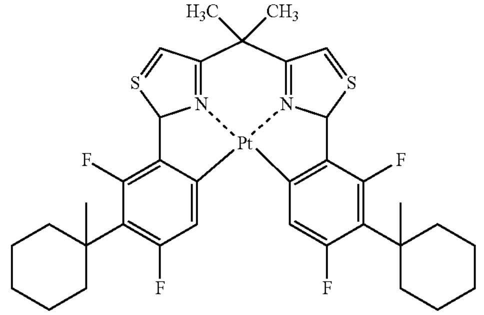
266
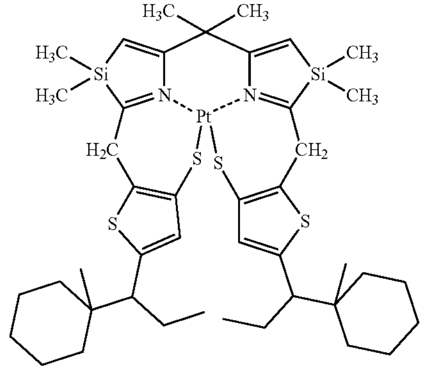
267
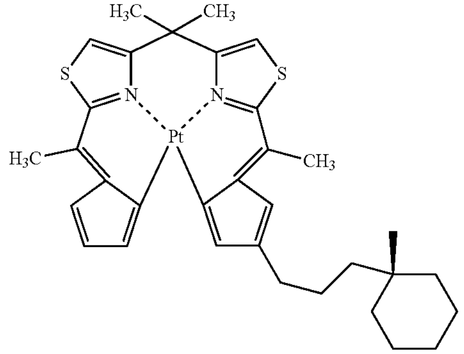
268
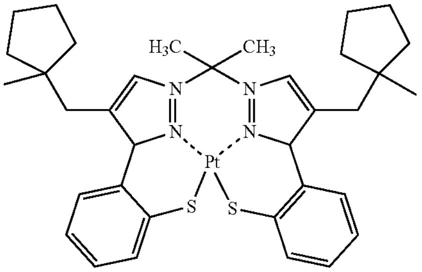
269
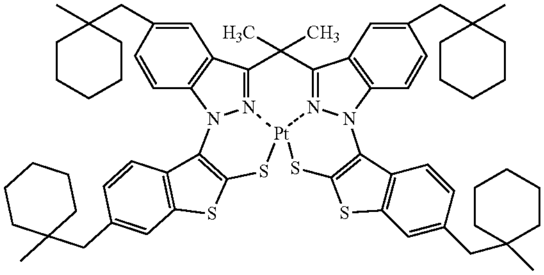
-continued
270
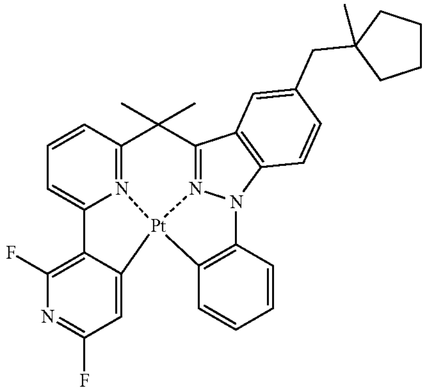
271
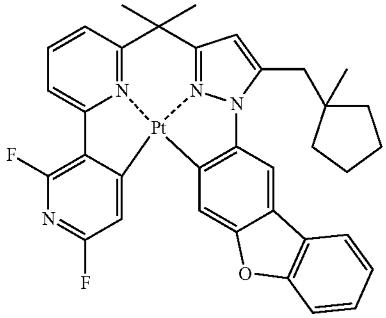
272
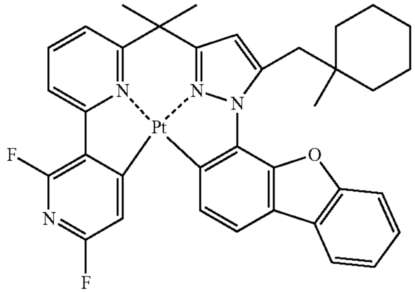
273
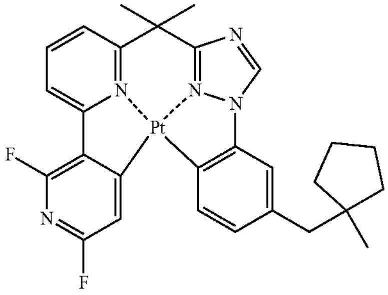

-continued
274
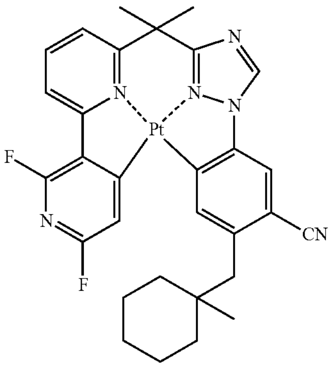
275
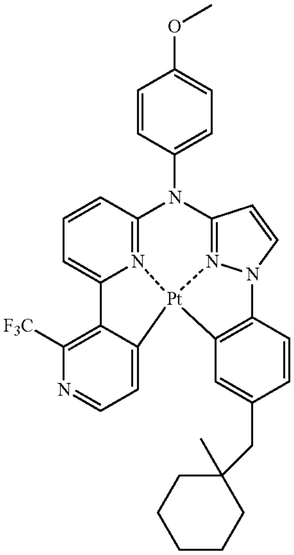
276
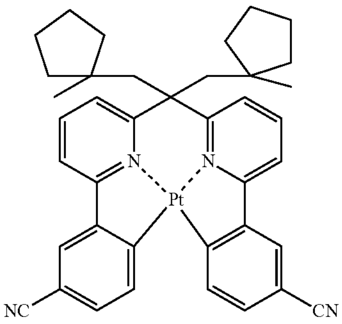
Other specific examples are illustrated below.
A-1
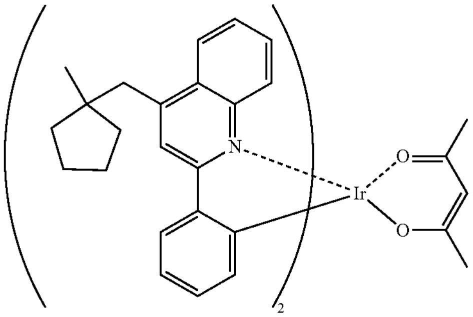
A-4
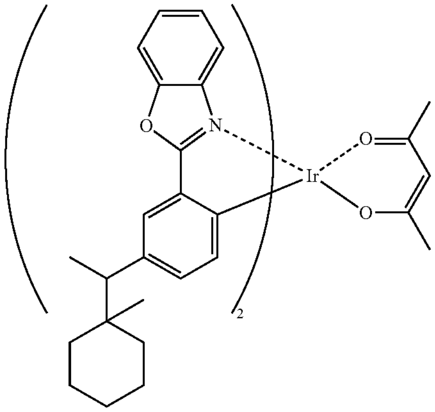
A-5
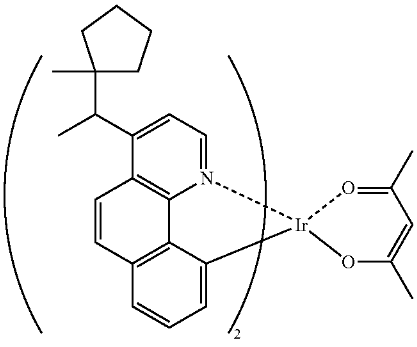
A-7
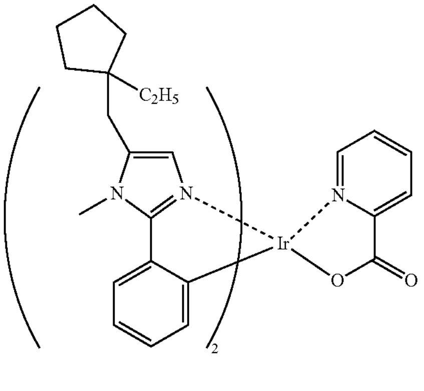

-continued
A-9
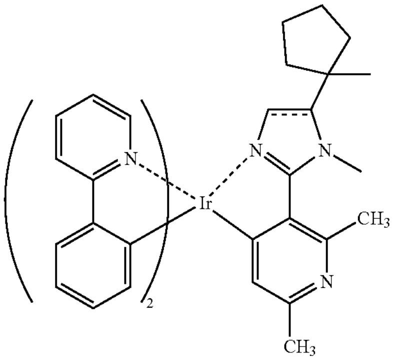
A-10
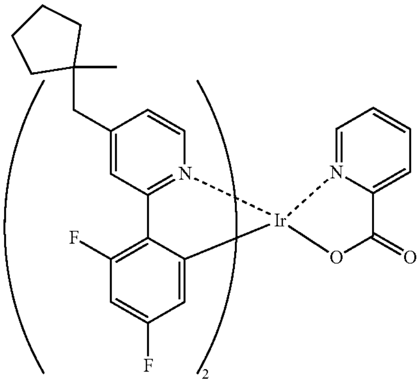
A-12
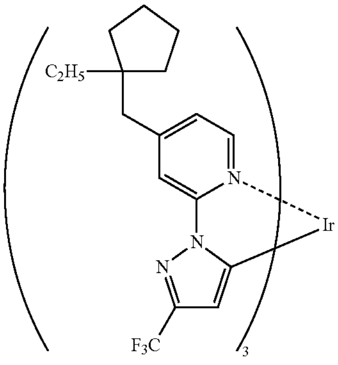
A-13
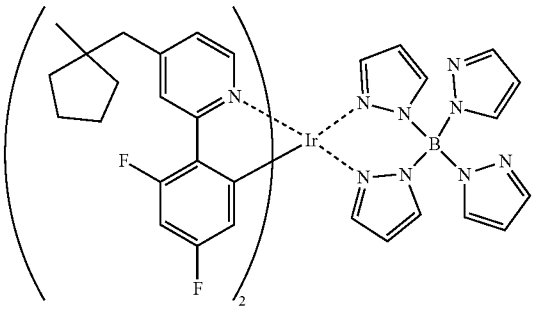
-continued
A-15
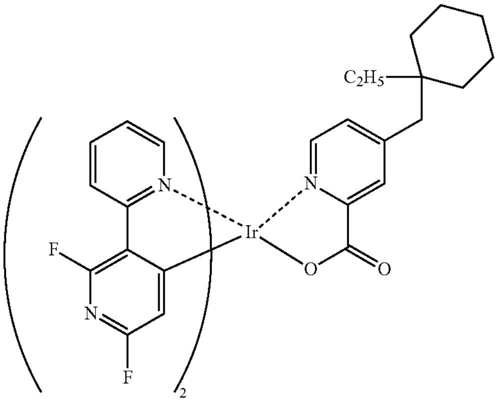
A-17
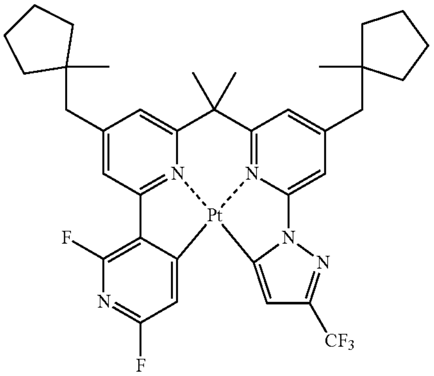
A-18
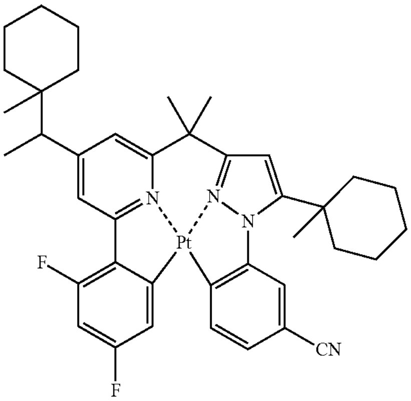
A-20
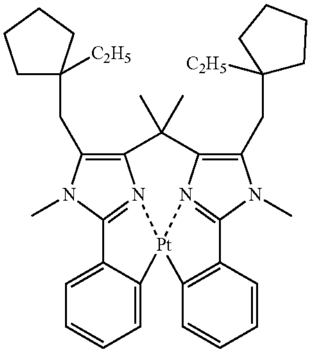

-continued
A-21
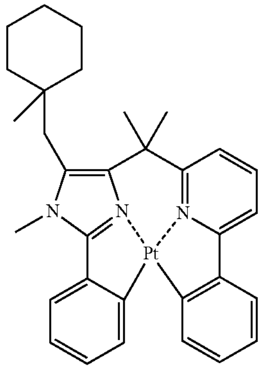
A-24
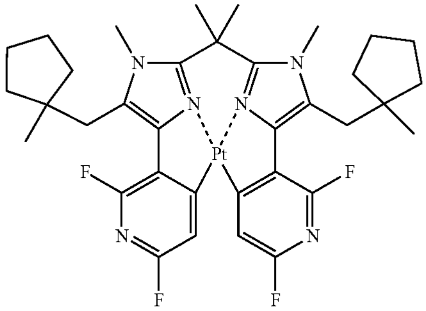
A-25
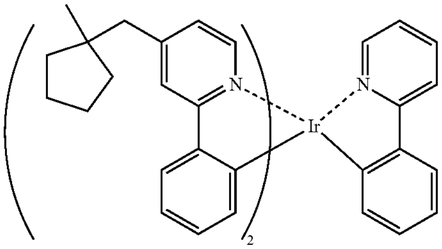
A-26
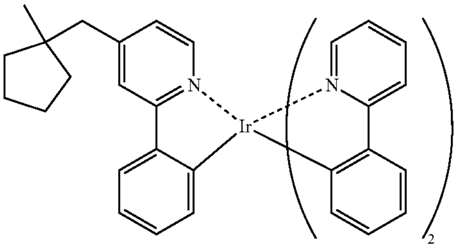
A-27
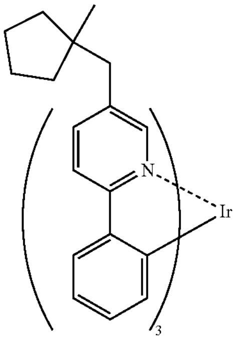
-continued
A-28
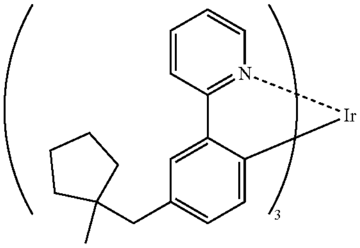
A-29
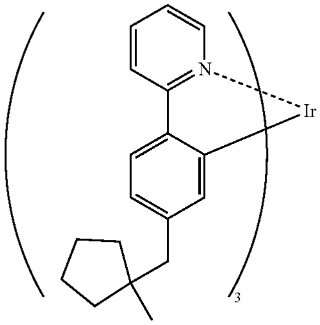
A-30
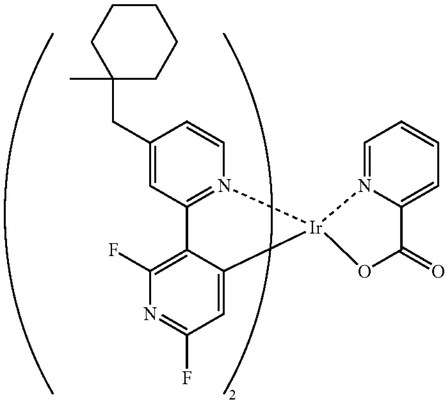
A-31
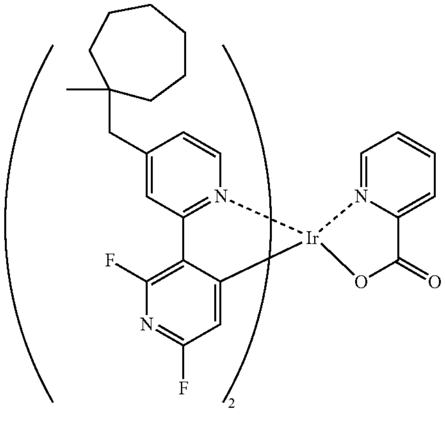

-continued

A-32

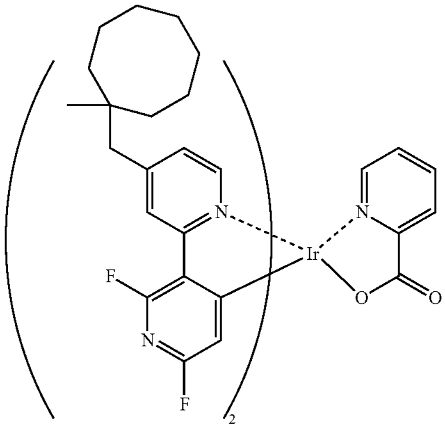

A-33

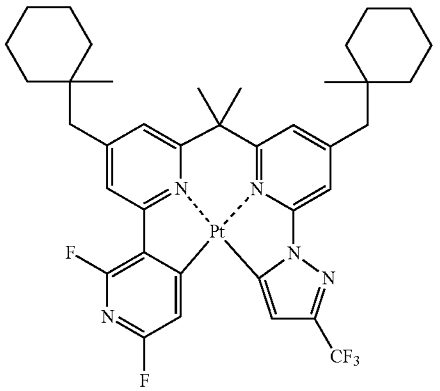

A-34

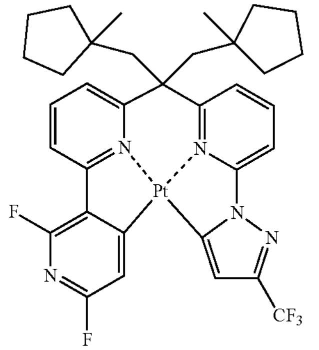

A-35

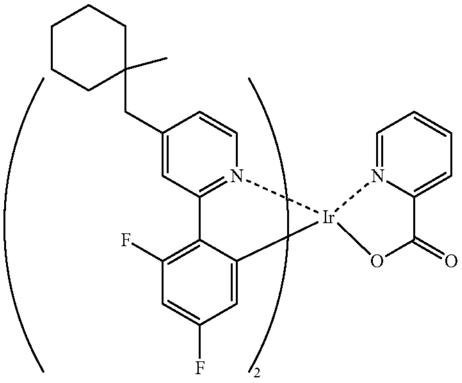

-continued

A-36

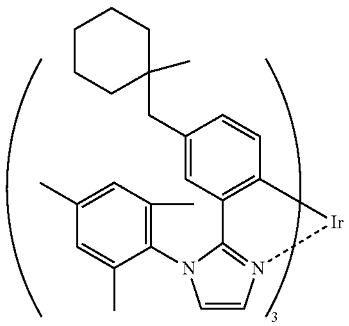

A-37

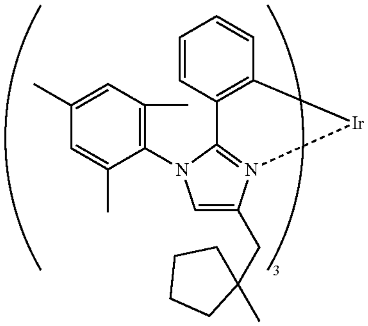

These compounds can be synthesized by various known synthesis methods described, for example, in *Org. Lett.,* 3, 2579-2581 (2001), *Inorg. Chem.,* 30, 1685-1687 (1991), *J. Am. Chem. Soc., Vol.* 123, 4304 (2001), *Inorg. Chem., Vol.* 40, 1704-1711 (2001), *Inorg. Chem.,* 41, 3055-3066 (2002), and *Eur. J. Org. Chem.,* 4, 695-709 (2004).

Furthermore, the above-described metal complex compounds can be synthesized by various techniques such as the method described in *Journal of Organic Chemistry,* 53, 786 (1988), G. R. Newkome et al., at page 789, from left column, line 53 to right column, line 7, the method described at page 790, left column, lines 18 to 38, the method described at page 790, right column, lines 19 to 30, a combination thereof, and the method described in *Chemische Berichte,* 113, 2749 (1980), H. Lexy et al., at page 2752, liens 26 to 35.

For example, a ligand or a dissociation product thereof and a metal compound are reacted with or without a solvent (for example, a halogen-based solvent, an alcohol-based solvent, an ether-based solvent, an ester-based solvent, a ketone-based solvent, a nitrile-based solvent, an amide-based solvent, a sulfone-based solvent, a sulfoxide-based solvent or water) in the presence or absence of a base (various inorganic or organic bases, for example, sodium methoxide, tert-butoxy potassium, triethylamine or potassium carbonate) at not higher than room temperature or under heating (in addition to normal heating, microwave heating is also effective), whereby the compound can be obtained.

In another embodiment of the present invention, the metal complex having a group represented by formula (I) is preferably a phosphorescent metal complex containing a monoanionic bidentate ligand represented by the following formulae (A1) to (A4) and a metal having an atomic weight of 40 or more.

Incidentally, in the formulae of ligands for use in the present invention, * is a coordination site to a metal, and each of the bond between $E_{1a}$ and the metal and the bond between $E_{1p}$ and the metal may be individually either a covalent bond or a coordinate bond.

The bidentate ligand represented by the following formulae (A1) to (A4) is described below.

[Bidentate Ligand Represented by Formulae (A1) to (A4)]

(A1)

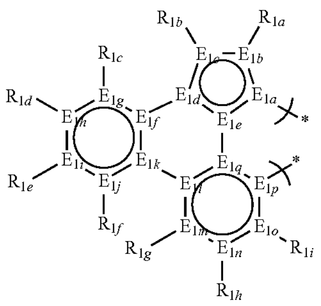

(A2)

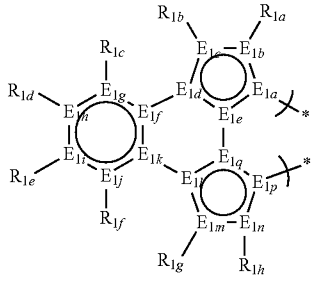

(A3)

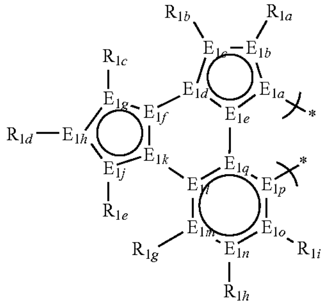

(A4)

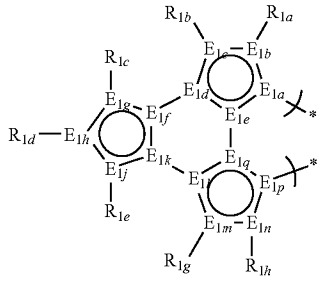

(In formulae (1) to (4), each of $E_{1a}$ $E_{1q}$ independently represents a carbon atom or a heteroatom, each of $R_{1a}$ to $R_{1i}$ independently represents a hydrogen atom or a substituent, provided that at least one of $R_{1a}$ to $R_{1i}$ represents a group represented by formula (I), and each of the frameworks represented by formulae (A1) to (A4) has a structure with 18 π-electrons in total).

At least one of $R_{1a}$ to $R_{1i}$ represents a group represented by formula (I).

As the group represented by formula (I) in $R_{1a}$ to $R_{1i}$, substituents a1 to a31 are preferred, a1, a2, a3, a5, a8, a9, a10, a12, a14, a15, a18, a19, a28, a29, a30 and a31 are more preferred, a2, a5, a9, a12, a18, a19, a28 and a29 are still more preferred, and a2, a5, a9 and a12 are most preferred. This is presumed because all of bulkiness, rigidity and compactness are satisfied.

Preferably, at least one of $R_{1a}$, $R_{1b}$, $R_{1d}$, $R_{1e}$, $R_{1g}$ and $R_{1h}$ is a group represented by formula (I), and more preferably, at least one of $R_{1a}$, $R_{1b}$, $R_{1d}$ and $R_{1e}$ is a group represented by formula (I). In formulae A1 and A2, still more preferably, at least one of $R_{1a}$, $R_{1b}$ and $R_{1d}$ is a group represented by formula (I), and yet still more preferably, at least one of $R_{1a}$ and $R_{1d}$ is a group represented by formula (I). In formulae A3 and A4, still more preferably, at least one of $R_{1a}$, $R_{1b}$ and $R_{1d}$ is a group represented by formula (I), and yet still more preferably, at least one of $R_{1a}$, $R_{1c}$ and $R_{1d}$ is a group represented by formula (I).

The bidentate ligand may combine with other ligands to form a tridentate, tetradentate, a pentadentate or hexadentate ligand.

Each of $E_{1a}$ to $E_{1q}$ is selected from a carbon atom and a hetero atom, preferably selected from a carbon atom and a nitrogen atom. $E_{1a}$ and $E_{1p}$ are preferably different atoms. The metal complex has a structure with 18 π-electrons.

The ring composed of $E_{1a}$ to $E_{1q}$ represents a 5-membered heterocycle, more specifically, oxazole, thiazole, isoxazole, isothiazole, pyrrole, imidazole, pyrazole, triazole, or tetrazole, preferably imidazole or pyrazole, more preferably imidazole. This 5-membered ring may form a condensed ring with other rings.

At least one of $E_{1a}$ to $E_{1e}$ preferably represents a nitrogen atom; more preferably, two or three of $E_{1a}$ to $E_{1e}$ represent a nitrogen atom; and still more preferably, two of $E_{1a}$ to $E_{1e}$ represent a nitrogen atom. In the case where two of $E_{1a}$ to $E_{1e}$ represent a nitrogen atom, preferably, two of $E_{1a}$, $E_{1d}$ and $E_{1e}$ represent a nitrogen atom; more preferably $E_{1a}$ and $E_{1d}$, or $E_{1a}$ and $E_{1e}$ represent a nitrogen atom; and still more preferably, $E_{1a}$ and $E_{1d}$ represent a nitrogen atom.

The ring formed by $E_{1f}$ to $E_{1k}$ is a 5- or 6-membered aromatic hydrocarbon ring or heterocyclic ring, preferably a 6-membered ring, more preferably a 6-membered aromatic hydrocarbon ring. Specific examples of the ring formed by $E_{1f}$ to $E_{1k}$ include benzene, oxazole, thiazole, isoxazole, isothiazole, oxadiazole, thiadiazole, furan, thiophene, pyrrole, imidazole, pyrazole, triazole, pyridine, pyrazine, pyrimidine, pyridazine and triazine. Among these, pyridine and benzene are preferred, and benzene is more preferred.

The ring formed by $E_{1l}$ to $E_{1q}$ is a 5- or 6-membered aromatic hydrocarbon ring or heterocyclic ring, preferably a 6-membered ring, still more preferably a 6-membered aromatic hydrocarbon ring. Specific examples of the ring formed by $E_{1l}$ to $E_{1q}$ include benzene, oxazole, thiazole, isoxazole, isothiazole, oxadiazole, thiadiazole, furan, thiophene, pyrrole, imidazole, pyrazole, triazole, pyridine, pyrazine, pyrimidine, pyridazine and triazine. Among these, pyridine and benzene are preferred, and benzene is more preferred.

Each of $R_{1a}$ to $R_{1i}$ independently represents a hydrogen atom or a substituent. The substituent is preferably a group selected from Substituent Group Z.

Specific examples of Substituent Group Z include an alkyl group, an alkenyl group, an alkynyl group, an aryl group, a heteroaryl group, an amino group, an alkoxy group, an aryloxy group, a heterocyclic oxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a heteroarylthio group, a sulfonyl group, a sulfinyl group, a ureido group, a phosphoric acid amido group, a hydroxy group, a mercapto group, a halogen atom, a cyano group, a sulfo group, a carboxyl group, a nitro group, a hydroxamic acid group, a sulfino group, a hydrazino group, an imino group, a heterocyclic group except for heteroaryl group, a silyl group, a silyloxy group and a deuterium atom. These substituents may further be substituted with other substituents.

Here, the alkyl group is preferably an alkyl group having a carbon number of 1 to 30, more preferably from 1 to 20, still more preferably from 1 to 10, and examples thereof include methyl, ethyl, n-propyl, isopropyl, n-butyl, tert-butyl, n-octyl, n-nonyl, n-decyl, n-dodecyl, n-octadecyl, n-hexadecyl, cyclopropyl, cyclobutyl, cyclopentyl, cyclohexyl, cyclooctyl, 1-adamantyl and trifluoromethyl.

The alkenyl group is preferably an alkenyl group having a carbon number of 2 to 30, more preferably from 2 to 20, still more preferably from 2 to 10, and examples thereof include vinyl, allyl, 1-propenyl, 1-isopropenyl, 1-butenyl, 2-butenyl and 3-pentenyl.

The alkynyl group is preferably an alkynyl group having a carbon number of 2 to 30, more preferably from 2 to 20, still more preferably from 2 to 10, and examples thereof include ethynyl, propargyl, 1-propynyl and 3-pentynyl.

The aryl group indicates an aromatic hydrocarbon monoradical. In the case where the aryl group is substituted, preferred examples of the substituent include a fluoro group, a hydrocarbon substituent, a heteroatom-substituted hydrocarbon substituent and a cyano group. The aryl group is preferably an aryl group having a carbon number of 6 to 30, more preferably from 6 to 20, still more preferably from 6 to 12, and examples thereof include phenyl, o-methylphenyl, m-methylphenyl, p-methylphenyl, 2,6-xylyl, p-cumenyl, mesityl, naphthyl and anthranyl.

The heteroaryl group indicates an aromatic heterocyclic monoradical. In the case where the heteroaryl group is substituted, preferred examples of the substituent include a fluoro group, a hydrocarbon substituent, a heteroelement-substituted hydrocarbon substituent and a cyano group. Examples of the heterocyclic group include imidazolyl, pyrazolyl, pyridyl, pyrazyl, pyrimidyl, triazinyl, quinolyl, isoquinolinyl, pyrrolyl, indolyl, furyl, thienyl, benzoxazolyl, benzimidazolyl, benzothiazolyl, carbazolyl and azepinyl.

The amino group is preferably an amino group having a carbon number of 0 to 30, more preferably from 0 to 20, still more preferably from 0 to 10, and examples thereof include amino, methylamino, dimethylamino, diethylamino, dibenzylamino, diphenylamino and ditolylamino.

The alkoxy group is preferably an alkoxy group having a carbon number of 1 to 30, more preferably from 1 to 20, still more preferably from 1 to 10, and examples thereof include methoxy, ethoxy, butoxy and 2-ethylhexyloxy.

The aryloxy group is preferably an aryloxy group having a carbon number of 6 to 30, more preferably from 6 to 20, still more preferably from 6 to 12, and examples thereof include phenyloxy, 1-naphthyloxy and 2-naphthyloxy.

The heterocyclic oxy group is preferably a heterocyclic oxy having a carbon number of 1 to 30, more preferably from 1 to 20, still more preferably from 1 to 12, and examples thereof include pyridyloxy, pyrazyloxy, pyrimidyloxy and quinolyloxy.

The acyl group is preferably an acyl group having a carbon number of 2 to 30, more preferably from 2 to 20, still more preferably from 2 to 12, and examples thereof include acetyl, benzoyl, formyl and pivaloyl.

The alkoxycarbonyl group is preferably an alkoxycarbonyl group having a carbon number of 2 to 30, more preferably from 2 to 20, still more preferably from 2 to 12, and examples thereof include methoxycarbonyl and ethoxycarbonyl.

The aryloxycarbonyl group is preferably an aryloxycarbonyl group having a carbon number of 7 to 30, more preferably from 7 to 20, still more preferably from 7 to 12, and examples thereof include phenyloxycarbonyl.

The acyloxy group is preferably an acyloxy group having a carbon number of 2 to 30, more preferably from 2 to 20, still more preferably from 2 to 10, and examples thereof include acetoxy and benzoyloxy.

The acylamino group is preferably an acylamino group having a carbon number of 2 to 30, more preferably from 2 to 20, still more preferably from 2 to 10, and examples thereof include acetylamino and benzoylamino.

The alkoxycarbonylamino group is preferably an alkoxycarbonylamino group having a carbon number of 2 to 30, more preferably from 2 to 20, still more preferably from 2 to 12, and examples thereof include methoxycarbonylamino.

The aryloxycarbonylamino group is preferably an aryloxycarbonylamino group having a carbon number of 7 to 30, more preferably from 7 to 20, still more preferably from 7 to 12, and examples thereof include phenyloxycarbonylamino.

The sulfonylamino group is preferably a sulfonylamino group having a carbon number of 1 to 30, more preferably from 1 to 20, still more preferably from 1 to 12, and examples thereof include methanesulfonylamino and benzenesulfonylamino.

The sulfamoyl group is preferably a sulfamoyl group having a carbon number of 0 to 30, more preferably from 0 to 20, still more preferably from 0 to 12, and examples thereof include sulfamoyl, methylsulfamoyl, dimethylsulfamoyl and phenylsulfamoyl.

The carbamoyl group is preferably a carbamoyl group having a carbon number of 1 to 30, more preferably from 1 to 20, still more preferably from 1 to 12, and examples thereof include carbamoyl, methylcarbamoyl, diethylcarbamoyl and phenylcarbamoyl.

The alkylthio group is preferably an alkylthio group having a carbon number of 1 to 30, more preferably from 1 to 20, still more preferably from 1 to 12, and examples thereof include methylthio and ethylthio.

The arylthio group is preferably an arylthio group having a carbon number of 6 to 30, more preferably from 6 to 20, still more preferably from 6 to 12, and examples thereof include phenylthio.

The heteroarylthio group is preferably a heteroarylthio group having a carbon number of 1 to 30, more preferably from 1 to 20, still more preferably from 1 to 12, and examples thereof include pyridylthio, 2-benzimidazolylthio, 2-benzoxazolylthio and 2-benzothiazolylthio.

The sulfonyl group is preferably a sulfonyl group having a carbon number of 1 to 30, more preferably from 1 to 20, still more preferably from 1 to 12, and examples thereof include mesyl, tosyl and trifluoromethanesulfonyl.

The sulfinyl group is preferably a sulfinyl group having a carbon number of 1 to 30, more preferably from 1 to 20, still more preferably from 1 to 12, and examples thereof include methanesulfinyl and benzenesulfinyl.

The ureido group is preferably a ureido group having a carbon number of 1 to 30, more preferably from 1 to 20, still more preferably from 1 to 12, and examples thereof include ureido, methylureido and phenylureido.

The phosphoric acid amido group is preferably a phosphoric acid amido group having a carbon number of 1 to 30, more preferably from 1 to 20, still more preferably from 1 to 12, and examples thereof include diethylphosphoric acid amido and phenylphosphoric acid amido.

Examples of the halogen atom include fluorine atom, chlorine atom, bromine atom and iodine atom.

The heterocyclic group except for heteroaryl group is preferably a heterocyclic group having a carbon number of 1 to 30, more preferably from 1 to 12. The heteroatom is, for example, nitrogen atom, oxygen atom or sulfur atom. Specific examples of the heterocyclic group include piperidyl, morpholino and pyrrolidyl.

The silyl group is preferably a silyl group having a carbon number of 3 to 40, more preferably from 3 to 30, still more preferably from 3 to 24, and examples thereof include trimethylsilyl, triethylsilyl, triisopropylsilyl, dimethyl-tert-butylsilyl, dimethylphenylsilyl, diphenyl-tert-butylsilyl, triphenylsilyl, tri-1-naphthylsilyl and tri-2-naphthylsilyl.

The silyloxy group is preferably a silyloxy group having a carbon number of 3 to 40, more preferably from 3 to 30, still more preferably from 3 to 24, and examples thereof include trimethylsilyloxy and triphenylsilyloxy.

Each of $R_{1a}$ to $R_{1i}$ is preferably a hydrogen atom, a hydrocarbon substituent (preferably an alkyl group, a cycloalkyl group or an aryl group), a cyano group, a fluoro group, $OR_{2a}$, $SR_{2a}$, $NR_{2a}R_{2b}$, $BR_{2a}R_{2b}$ or $SiR_{2a}R_{2b}R_{2c}$. Each of $R_{2a}$ to $R_{2c}$ is independently a hydrocarbon substituent or a hydrocarbon substituent substituted with a heteroatom. Two of $R_{1a}$ to $R_{1i}$ and $R_{2a}$ to $R_{2c}$ may combine with each other to form a saturated or unsaturated, aromatic or non-aromatic ring.

At least one of $R_{1a}$ to $R_{1i}$ is preferably an aryl group having a dihedral angle of 70° or more with respect to the mother structure, more preferably a substituent represented by the following formula ss-1, still more preferably a 2,6-disubstituted aryl group, and it is most preferred that $R_{1b}$ is a 2,6-disubstituted aryl group.

ss-1

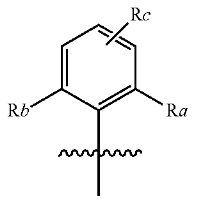

(In formula ss-1, each of Ra, Rb and Rc independently represents a hydrogen atom, an alkyl group or an aryl group, and the number of Rc is from 0 to 3).

The alkyl group represented by Ra, Rb and Rc is preferably an alkyl group having a carbon number of 1 to 30, more preferably from 1 to 20, still more preferably from 1 to 10, and examples thereof include methyl, ethyl, n-propyl, isopropyl, n-butyl, tert-butyl, n-octyl, n-nonyl, n-decyl, n-dodecyl, n-octadecyl, n-hexadecyl, cyclopropyl, cyclobutyl, cyclopentyl, cyclohexyl, cyclooctyl, 1-adamantyl and trifluoromethyl. Among these, a methyl group and an isopropyl group are preferred.

The aryl group represented by Ra, Rb and Rc is preferably an aryl group having a carbon number of 6 to 30, more preferably from 6 to 20, still more preferably from 6 to 12, and examples thereof include phenyl, o-methylphenyl, m-methylphenyl, p-methylphenyl, 2,6-xylyl, p-cumenyl, mesityl, naphthyl and anthranyl. Among these, a phenyl group, a 2,6-xylyl group and a mesityl group are preferred, and a phenyl group is more preferred.

At least one of Ra and Rb is preferably selected from an alkyl group and an aryl group; more preferably, at least one of Ra and Rb is selected from an alkyl group; still more preferably, both Ra and Rb are an alkyl group; and most preferably, both Ra and Rb are a methyl group or an isopropyl group.

The 2,6-disubstituted aryl group is preferably a 2,6-dimethylphenyl group, a 2,4,6-trimethylphenyl group, a 2,6-diisopropylphenyl group, a 2,4,6-diisopropylphenyl group, a 2,6-dimethyl-4-phenylphenyl group, a 2,6-dimethyl-4-(2,6-dimethylpyridin-4-yl)phenyl group, a 2,6-diphenylphenyl group, a 2,6-diphenyl-4-isopropylphenyl group, a 2,4,6-triphenylphenyl group, a 2,6-diisopropyl-4-(4-isopropylphenyl)phenyl group, a 2,6-diisopropyl-4-(3,5-dimethylphenyl)phenyl group, a 2,6-diisopropyl-4-(pyridin-4-yl)phenyl group or a 2,6-di-(3,5-dimethylphenyl)phenyl group, The number of Rc is preferably 0 or 1. Each Rc may be the same as or different from every other Rc.

At least one of $R_{1a}$ and $R_{1b}$ is preferably an electron-donating group; more preferably, $R_{1a}$ is an electron-donating group; and still more preferably, $R_{1a}$ is a methyl group.

The hydrocarbon substituent indicates a monovalent or divalent, chain, branched or cyclic substituent composed of only a carbon atom and a hydrogen atom.

Examples of the monovalent hydrocarbon substituent include an alkyl group having a carbon number of 1 to 20; an alkyl group having a carbon number of 1 to 20 substituted with one or more groups selected from an alkyl group having a carbon number of 1 to 20, a cycloalkyl group having a carbon number of 3 to 8 and an aryl group; a cycloalkyl group having a carbon number of 3 to 8; a cycloalkyl group having a carbon number of 3 to 8 substituted with one or more groups selected from an alkyl group having a carbon number of 1 to 20, a cycloalkyl group having a carbon number of 3 to 8 and an aryl group; an aryl group having a carbon number of 6 to 18; and an aryl group substituted with one or more groups selected from an alkyl group having a carbon number of 1 to 20, a cycloalkyl group having a carbon number of 3 to 8 and an aryl group.

Examples of the divalent hydrocarbon group include $-CH_2-$, $-CH_2CH_2-$, $-CH_2CH_2CH_2-$ and 1,2-phenylene group.

The metal in the phosphorescent metal complex for use in the present invention is preferably a metal having an atomic weight of 40 or more, which belongs to Groups 8 to 10 of the periodic table. Also, the metal is preferably a nonradioactive metal. The metal in the phosphorescent metal complex for use in the present invention is preferably any one of Re, Ru, Os, Rh, Ir, Pd, Pt, Cu and Au, more preferably Os, Ir or Pt, still more preferably Ir or Pt, and in view of high luminous efficiency, high complex stability and control of the carrier balance in the hole/electron transporting inside of the light emitting layer, most preferably Ir.

In the present invention, the metal complex composed of a ligand in the formula may be configured by a primary ligand or its tautomer and an auxiliary ligand or its tautomer, or all ligands of the metal complex may be composed of only a partial structure represented by the primary ligand or its tautomer.

If desired, the metal complex may have, as an auxiliary ligand, a ligand (sometimes referred to as a coordination compound) known as a so-called ligand to one skilled in the art and used for the formation of conventionally known metal complexes.

From the standpoint of successfully obtaining the effects described in the present invention, the complex is preferably composed of one kind or two kinds of ligands, more preferably one kind of a ligand. In view of easiness of synthesis when introducing a reactive group into the complex molecule, it is also preferred that the complex is composed of two kinds of ligands.

As for the ligand used in conventionally known metal complexes, various ligands are known, but examples thereof include ligands described in H. Yersin, *Photochemistry and Photophysics of Coordination Compounds*, Springer-Verlag (1987), and Akio Yamamoto, *Yuki Kinzoku Kagaku—Kiso to Ovo—(Organic Metal Chemistry—Basic and Application—)*, Shokabo (1982) (for example, a halogen ligand (preferably chlorine ligand), a cyano ligand, a phosphine ligand, a nitrogen-containing heteroaryl ligand (e.g., bipyridyl, phenanthroline), and a diketonate ligand (e.g., acetylacetone)). Diketones and picolinic acid derivatives are preferred.

Specific examples of the auxiliary ligand are set forth below, but the present invention is not limited thereto.

(I-1)

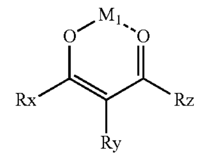

(I-2)

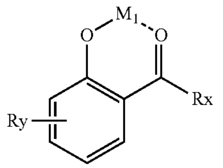

(I-3)

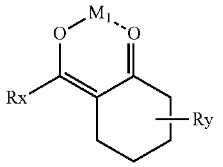

(I-4)

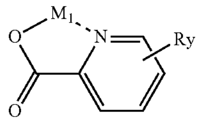

(I-5)

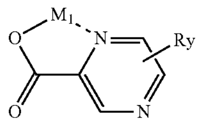

(I-6)

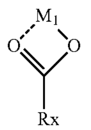

(I-7)

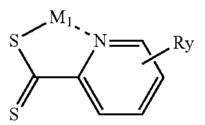

-continued (I-8)

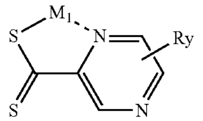

(I-9)

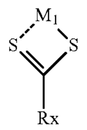

(I-10)

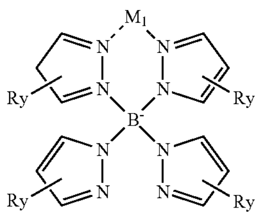

(I-11)

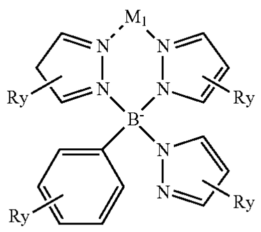

(I-12)

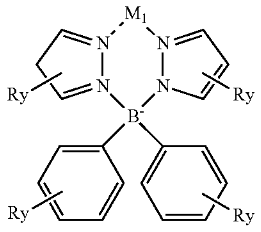

(I-13)

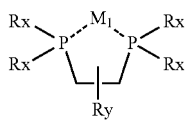

(I-14)

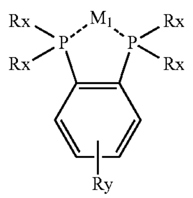

($M_1$ represents a metal atom having an atomic weight of 40 or more, and each of Rx, Ry and Rz independently represents a hydrogen atom or a substituent).

The monoanionic bidentate ligand represented by any one of formulae (A1) to (A4) is preferably a monoanionic bidentate ligand represented by formula (A1) or (A3).

The monoanionic bidentate ligand represented by formula (A1) or (A3) is preferably a monoanionic bidentate ligand represented by formula (A1-1) or (A3-1) or represented by formula (A1-2) or (A3-2).

(A1-1)

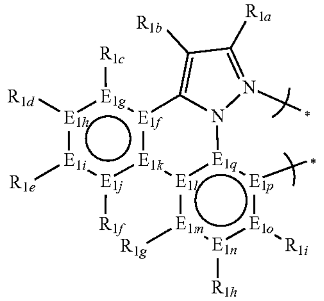

(A3-1)

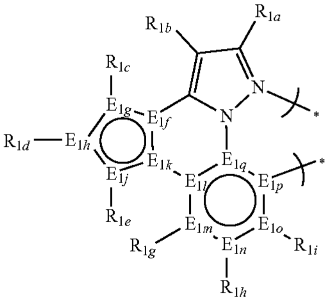

(A1-2)

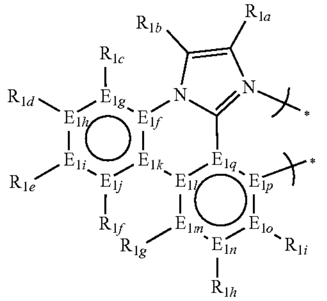

(A3-2)

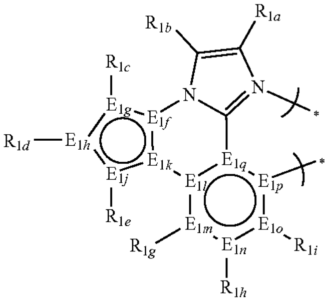

(In formulae (A1-1), (A3-1), (A1-2) and (A3-2), each of $E_{1f}$ to $E_{1q}$ independently represents a carbon atom or a heteroatom, each of $R_{1a}$ to $R_{1i}$ independently represents a hydrogen atom or a substituent, provided that at least one of $R_{1a}$ to $R_{1i}$ represents a group represented by formula (I), and each of the frameworks represented by formulae (A1-1), (A3-1), (A1-2) and (A3-2) has a structure with 18 π-electrons in total).

In formulae (A1-1), (A3-1), (A1-2) and (A3-2), the definitions of $E_{1f}$ to $E_{1q}$ and $R_{1a}$ to $R_{1i}$ are the same as those of $E_{1f}$ to $E_{1q}$ and $R_{1a}$ to $R_{1i}$ in formulate (A1) and (A3), and the preferred ranges are also the same.

The monoanionic bidentate ligand represented by formula (A1-1), (A3-1), (A1-A2) or (A3-2) is preferably a monoanionic bidentate ligand represented by formula (A1-A3) or (A3-3):

(A1-3)

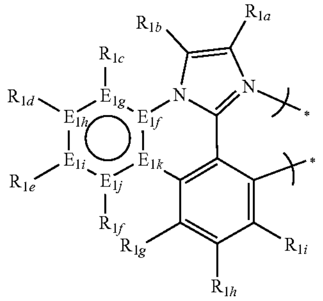

(A3-3)

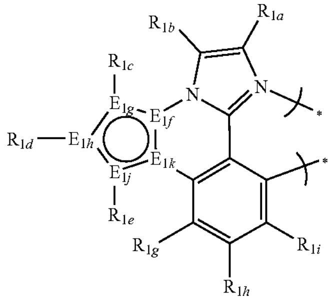

(In formulae (A1-3) and (A3-3), each of $E_{1f}$ to $E_{1k}$ independently represents a carbon atom or a heteroatom, each of $R_{1a}$ to $R_{1i}$ independently represents a hydrogen atom or a substituent, provided that at least one of $R_{1a}$ to $R_{1i}$, represents a group represented by formula (I), and each of the frameworks represented by formulae (A1-3) and (A3-3) has a structure with 18 π-electrons in total).

In formulae (A1-3) and (A3-3), the definitions of $E_{1f}$ to $E_{1q}$ and $R_{1a}$ to $R_{1i}$ are the same as those of $E_{1f}$ to $E_{1q}$ and $R_{1a}$ to $R_{1i}$ in formulae (A1-1), (A3-1), (A1-2) and (A3-2), and preferred ranges are also the same.

The phosphorescent metal complex containing a monoanionic bidentate ligand represented by formula (A1-3) or (A3-3) and a metal having an atomic weight of 40 or more is preferably an iridium complex represented by formula (A9):

(A9)

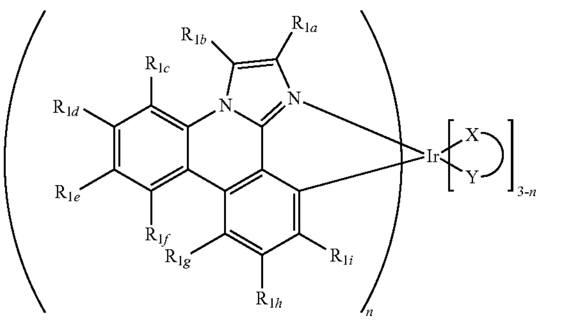

(In formula (9), each of $R_{1a}$ to $R_{1i}$ independently represents a hydrogen atom or a substituent, provided that at least one of $R_{1a}$ to $R_{1i}$ represents a group represented by formula (I), X—Y represents at least one monoanionic bidentate ligand selected from (1-1) to (1-14), and n represents an integer of 1 to 3).

In formula (A9), preferred ranges of $R_{1a}$ to $R_{1i}$ are the same as preferred ranges of $R_{1a}$ to $R_{1i}$ in formula (A1).

X—Y represents an auxiliary ligand, and n represents an integer of 1 to 3 and is preferably n=3. As for the auxiliary ligand, specifically, the same ligands as described above can be suitably used, and an acetylacetonate ligand and a substituted acetylacetonate ligand analog are preferred.

From the standpoint of easiness of synthesis, n is preferably 3, but it is also preferred in view of cost that n is 1 or 2, because the ligand can be replaced by an inexpensive auxiliary ligand.

The metal complex represented by formula (A9) is preferably a metal complex represented by formula (A10). In the formula, $R_{1c}$ is a substituent represented by formula (I).

(A10)

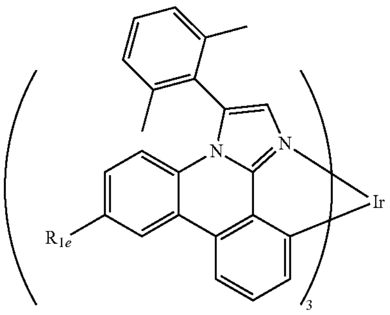

More specifically, formulae (A1) and (A3) are preferably the following structures. Among these, X-1, X-4, X-32, X-33, X-38, X-39, X-46, X-51, X-52, X-53, X-55, X-56, X-57, X-58, X-59, X-62, X-63, X-64, X-66, X-67 and X-68 are more preferred, and X-46, X-52, X-53, X-56, X-57, X-58, X-62 and X-66 are most preferred.

X-1

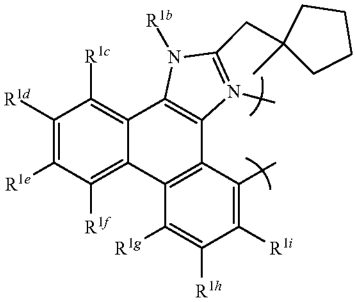

X-2

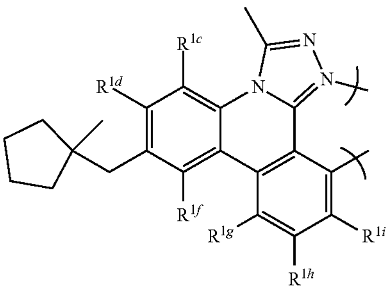

-continued

X-3

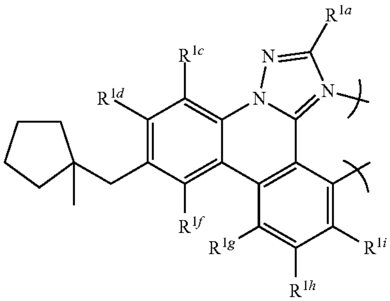

X-4

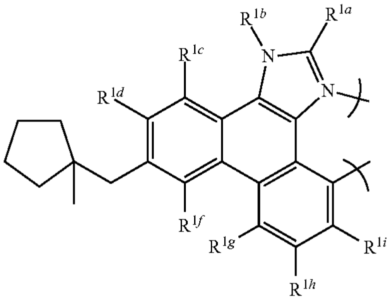

X-5

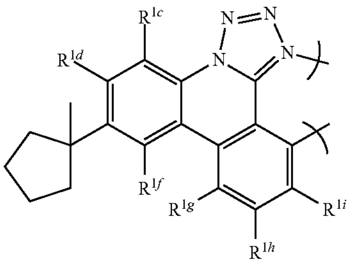

X-6

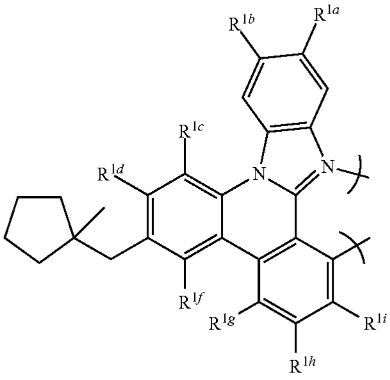

X-7

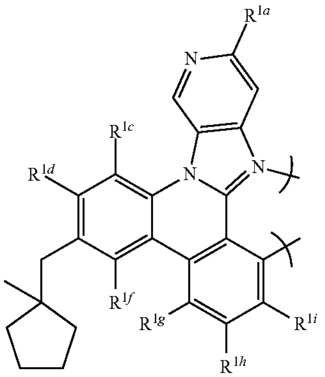

-continued
X-8
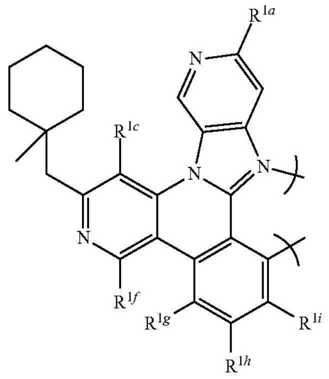
X-9
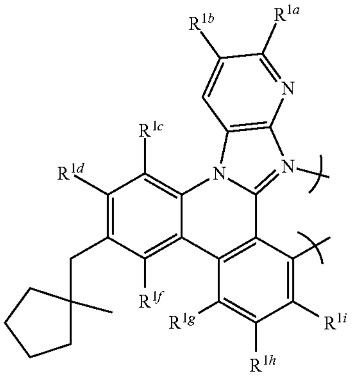
X-10
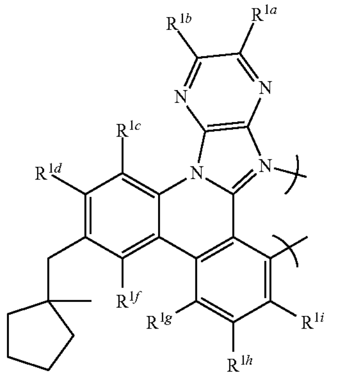
X-11
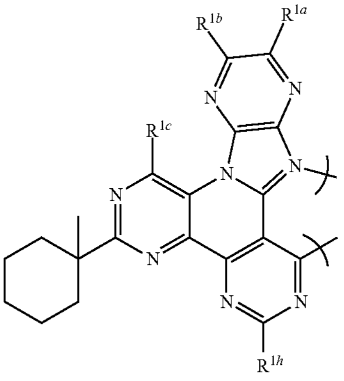
-continued
X-12
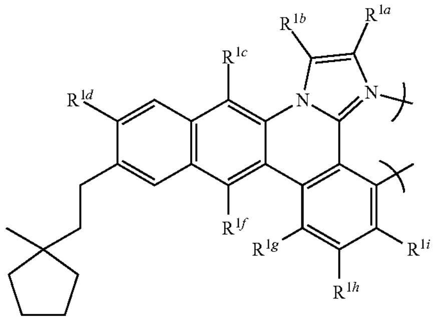
X-13
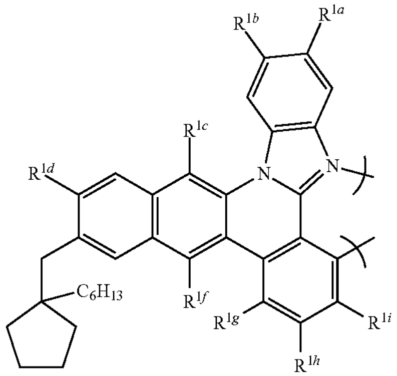
X-14
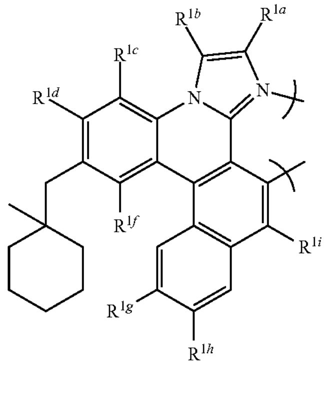
X-15
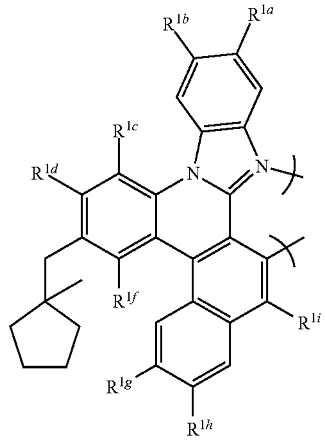

-continued
X-16
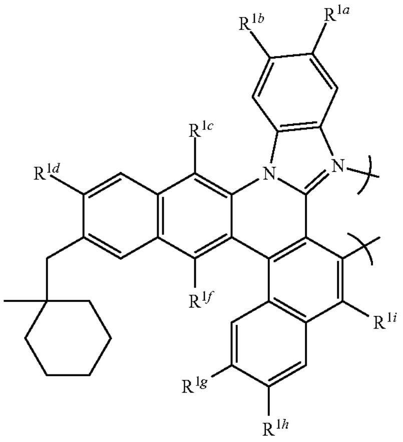
X-17
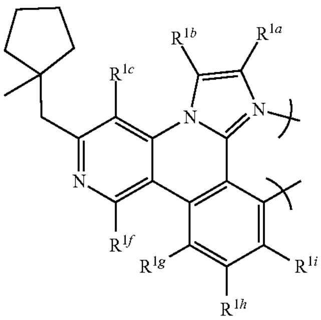
X-18
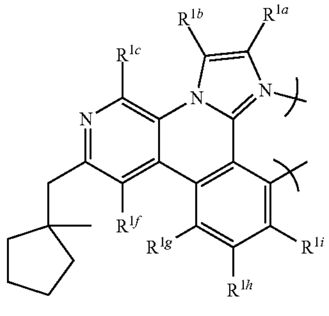
X-19
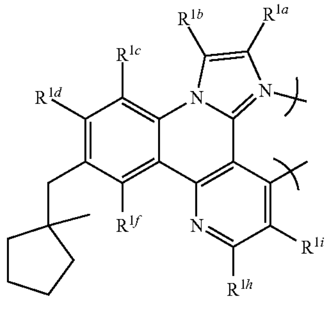
-continued
X-20
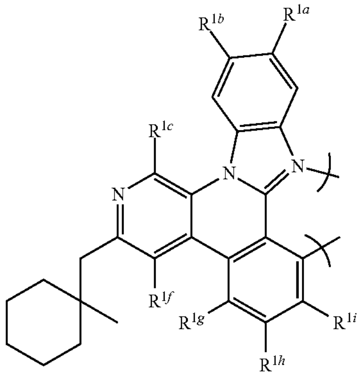
X-21
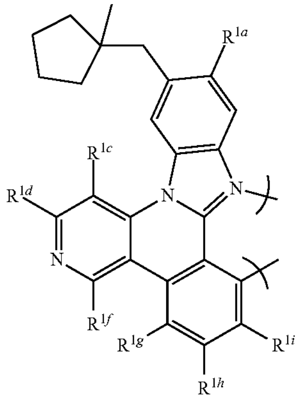
X-22
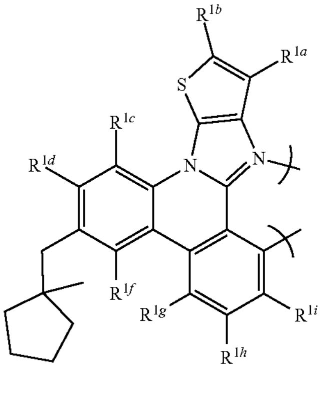
X-23
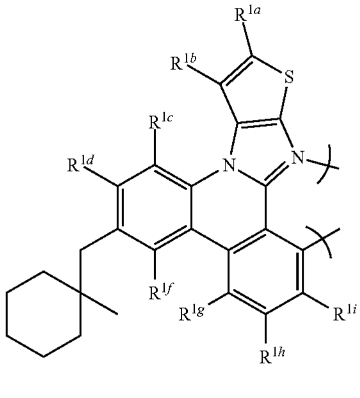

-continued
X-24
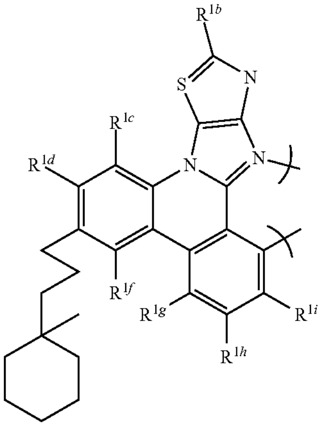
X-25
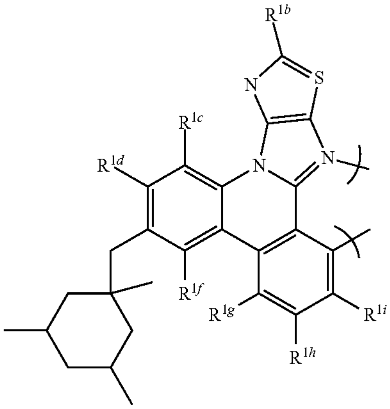
X-26
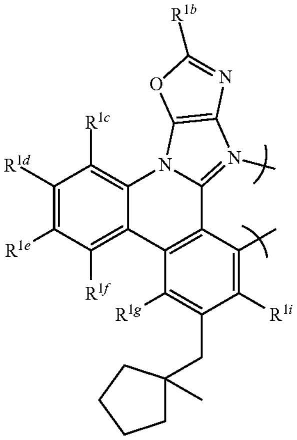
X-27
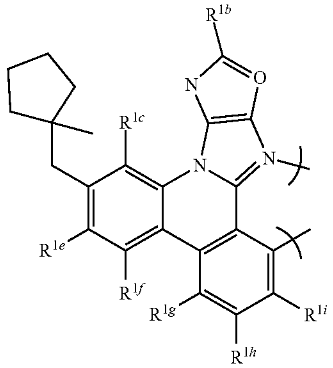
-continued
X-28
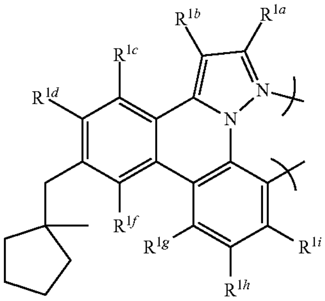
X-29
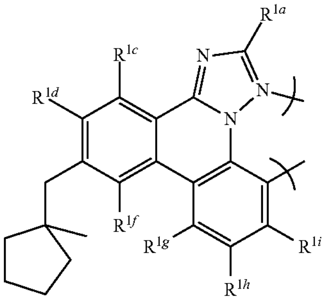
X-30
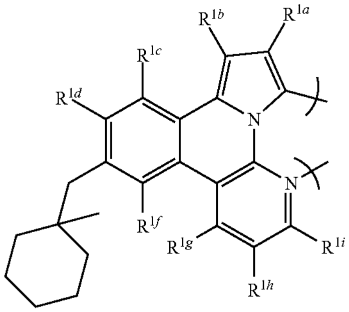
X-31
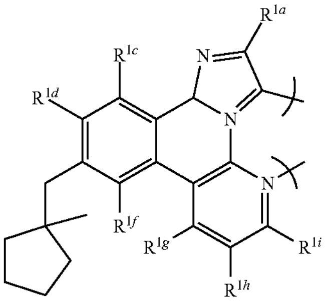
X-32
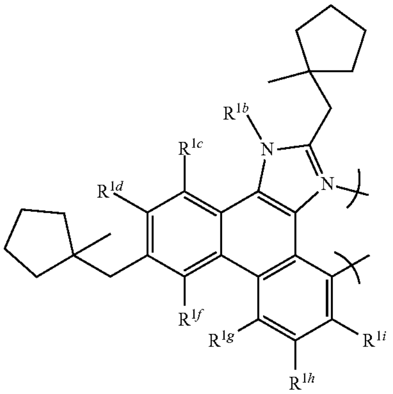

-continued
X-33
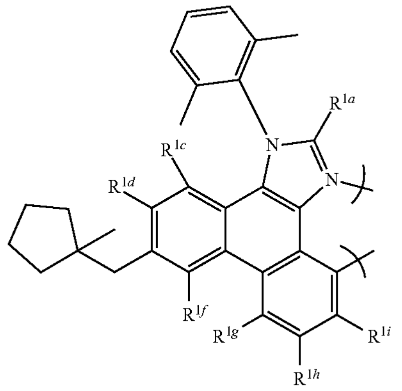
X-34
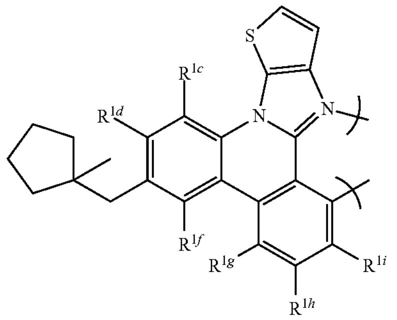
X-35
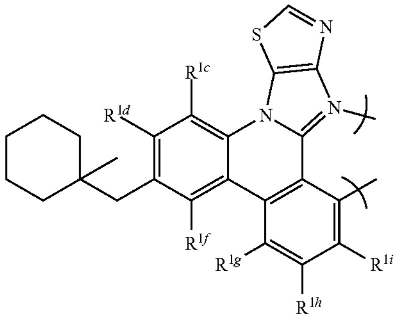
X-36
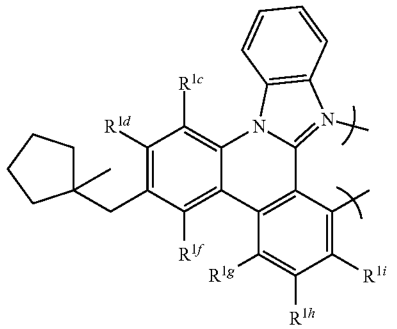
-continued
X-37
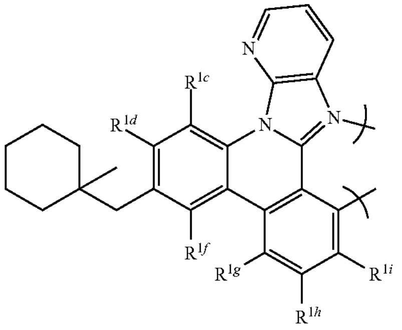
X-38
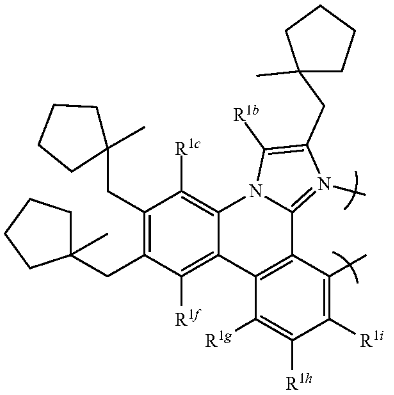
X-39
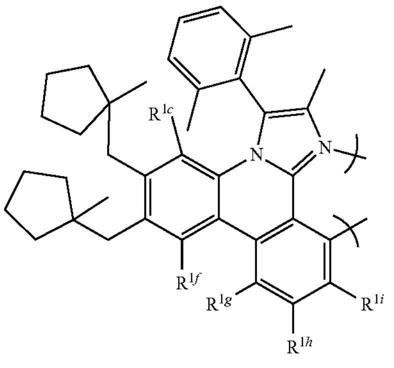
X-40
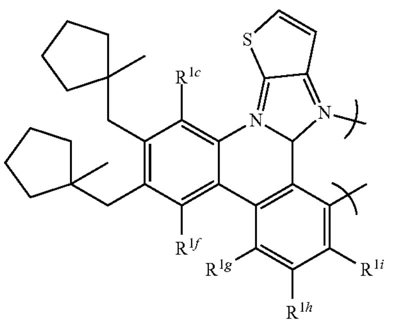

-continued
X-41
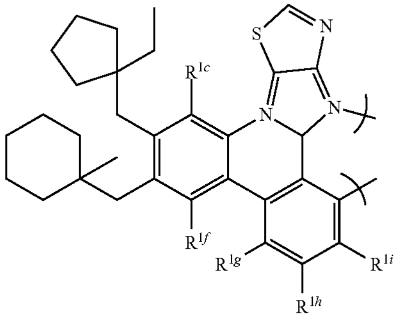
X-42
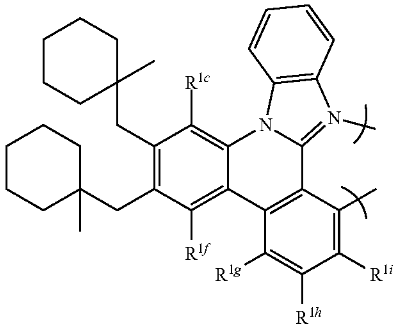
X-43
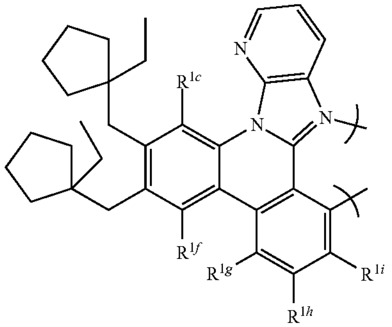
X-44
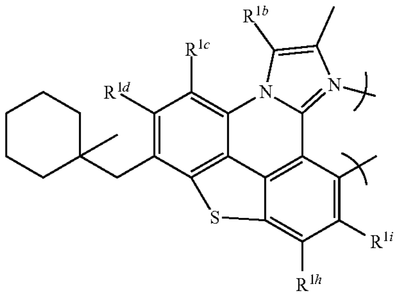
X-45
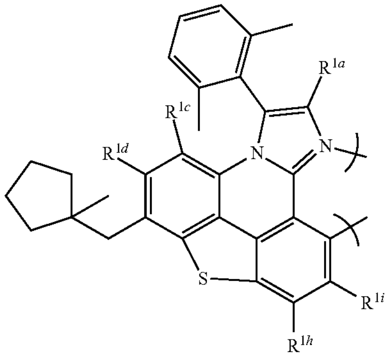
-continued
X-46
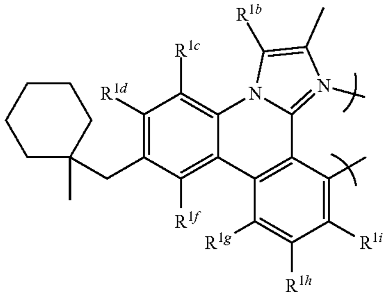
X-47
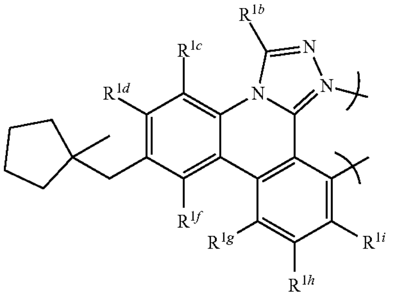
X-48
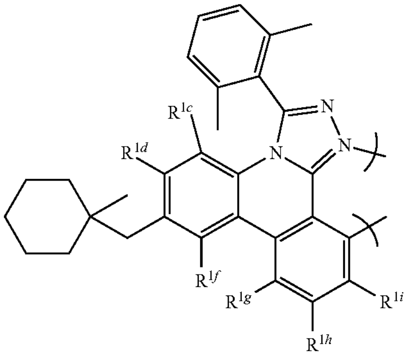
X-49
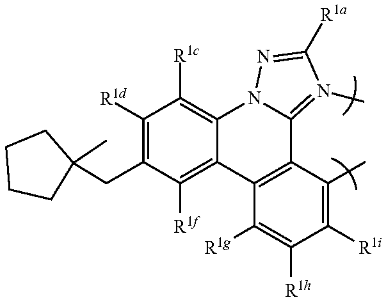
X-50
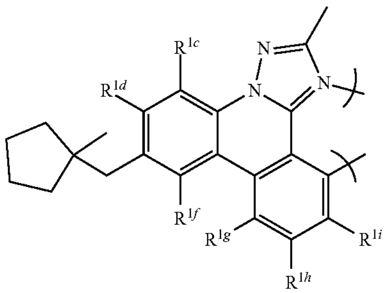

-continued
X-51
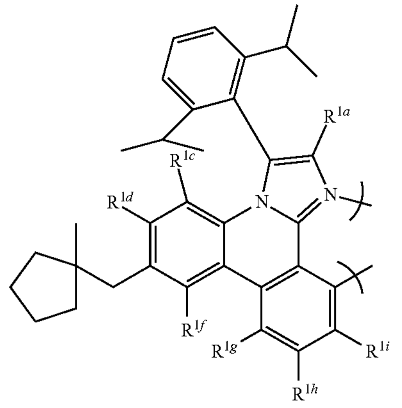
X-52
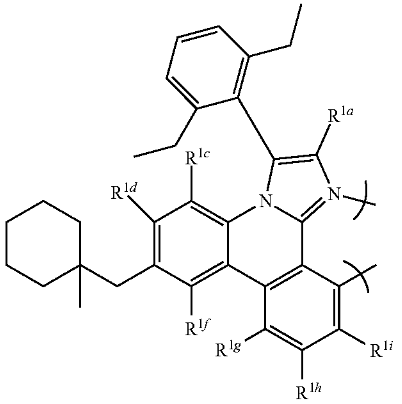
X-53
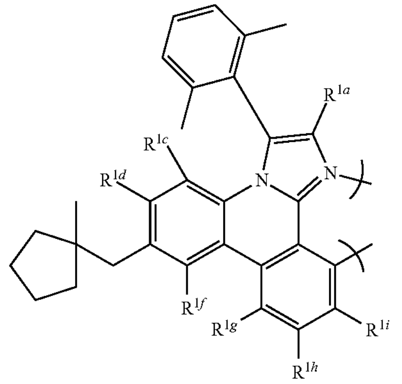
X-54
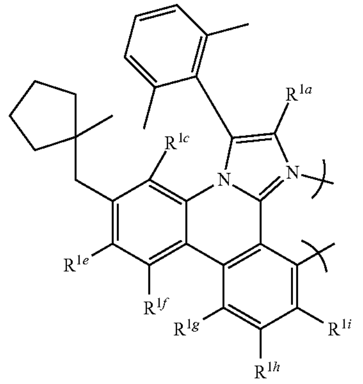
-continued
X-55
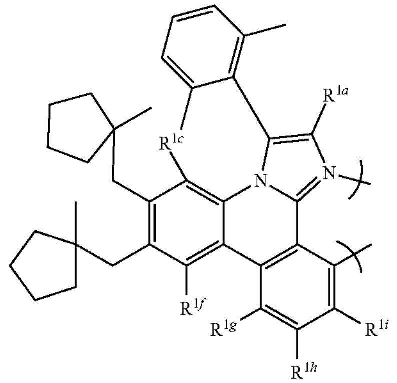
X-56
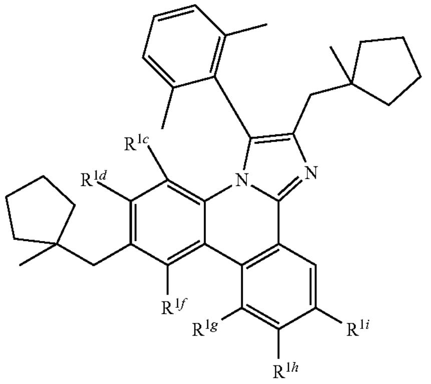
X-57
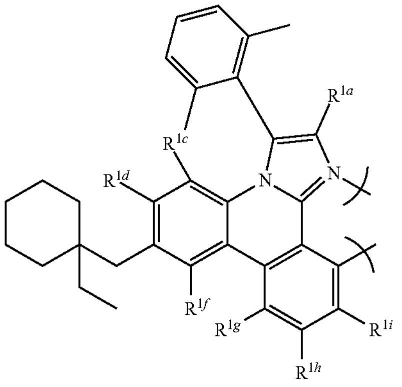
X-58
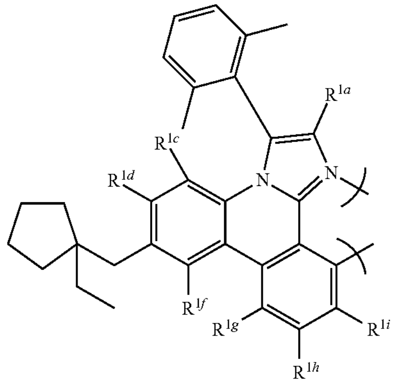

-continued
X-59
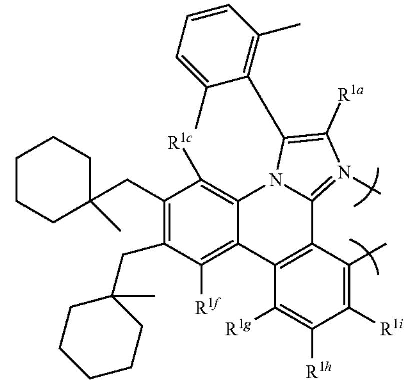
X-60
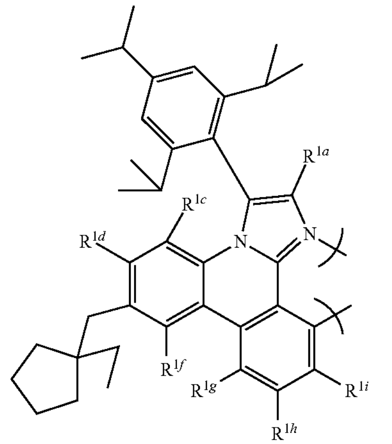
X-61
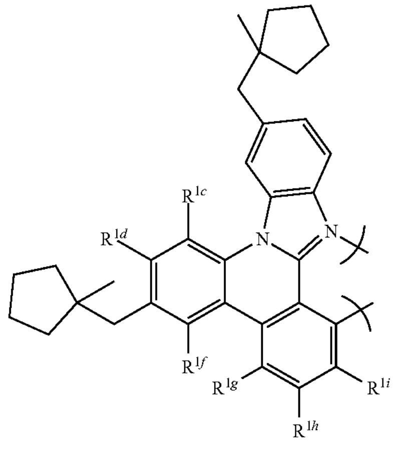
X-62
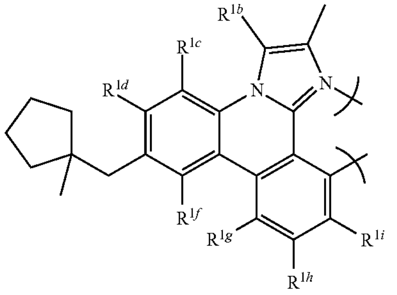
-continued
X-63
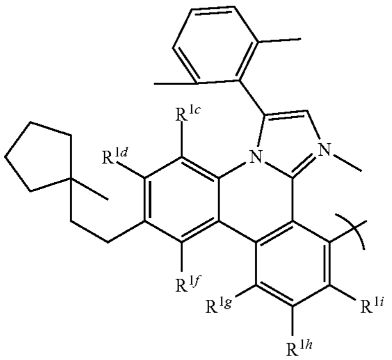
X-64
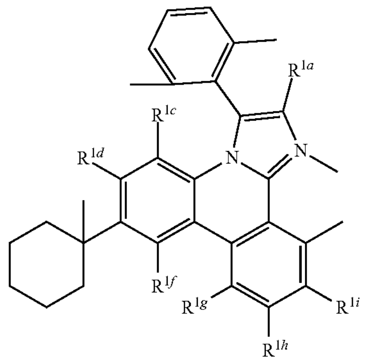
X-65
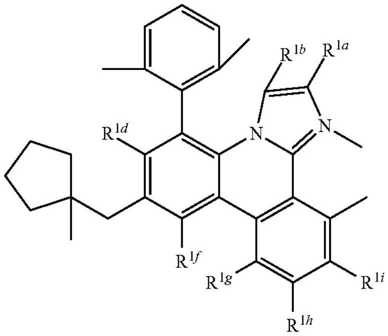
X-66
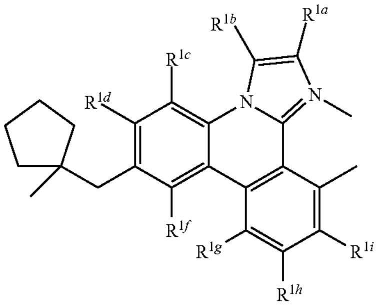

-continued

X-67

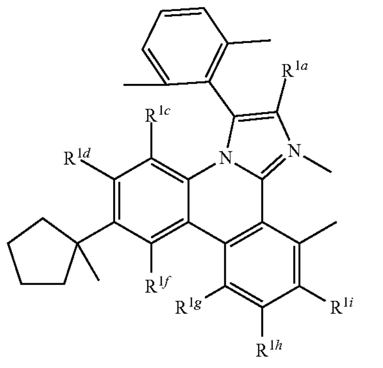

X-68

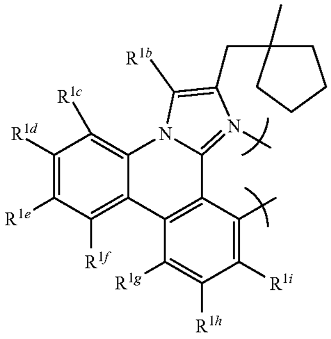

$R^{1a}$ to $R^{1i}$ have the same meanings as in formula (A1), and it is preferred that all are a hydrogen atom.

The phosphorescent metal complex containing a monoanionic bidentate ligand represented by formulae (A1) to (A4) and a metal having an atomic weight of 40 or more can be synthesized by various methods such as methods described in US2007/0190359 and US2008/0297033.

For example, a ligand or a dissociation product thereof and a metal compound are reacted with or without a solvent (for example, a halogen-based solvent, an alcohol-based solvent, an ether-based solvent, an ester-based solvent, a ketone-based solvent, a nitrile-based solvent, an amide-based solvent, a sulfone-based solvent, a sulfoxide-based solvent or water) in the presence or absence of a base (various inorganic or organic bases, for example, sodium methoxide, tert-butoxy potassium, triethylamine or potassium carbonate) at not higher than room temperature or under heating (in addition to normal heating, microwave heating is also effective), whereby the complex can be obtained. Specifically, XM-64 can be synthesized starting from 7-methyl-imidazophenanthridine according to the synthesis method described in US2007/0190359, paragraphs [0132] to [0134]. Also, XM-63 can be synthesized according to the synthesis method described in US2008/0297033, paragraphs [0281] to [0287].

In the present invention, the metal complex having a group represented by formula (I) is not limited in its use and may be contained in any layer within the organic layer. The layer into which the metal complex having a group represented by formula (I) is introduced may be any one of a light emitting layer, a hole injection layer, a hole transporting layer, an electron transporting layer, an electron injection layer, an exciton blocking layer and a charge blocking layer.

The present invention also relates to a composition containing the metal complex having a group represented by formula (I). By using a composition containing a metal complex having a saturated 5- to 8-membered ring-containing group, an organic electroluminescence device more excellent in the external quantum efficiency can be obtained.

In the present invention, in order to more reduce the change in chromaticity at high-temperature driving, the metal complex having a group represented by formula (I) is preferably incorporated into a light emitting layer.

The present invention also related to a light emitting layer containing the metal complex having a group represented by formula (I).

In the case of incorporating the metal complex having a group represented by formula (I) into a light emitting layer, the metal complex is preferably contained in an amount of 0.1 to 50 mass %, more preferably from 1 to 50 mass %, still more preferably from 2 to 40 mass %, based on the total mass of the light emitting layer.

Also, in the case of incorporating the metal complex having a group represented by formula (I) into a layer other than a light emitting layer, the metal complex is preferably contained in an amount of 0.1 to 100 mass %, more preferably from 10 to 100 mass %, still more preferably from 30 to 100 mass %.

[Organic Electroluminescence Device]

The device of the present invention is described in detail below.

The organic electroluminescence device of the present invention is an organic electroluminescence device including a substrate having thereon a pair of electrodes and at least one organic layer between the electrodes, the organic layer containing a light emitting layer, wherein any one layer of the organic layer contains a meal complex having a group represented by formula (I).

In the organic electroluminescence device of the present invention, the light emitting layer is an organic layer, and the device may have a plurality of organic layers.

In view of property of the luminescence device, at least one electrode of the anode and the cathode is preferably transparent or translucent.

FIG. 1 shows one example of the configuration of the organic electroluminescence device of the present invention. In the organic electroluminescence device 10 of the present invention shown in FIG. 1, a light emitting layer 6 is sandwiched between an anode 3 and a cathode 9 on a supporting substrate 12. More specifically, a hole injection layer 4, a hole transporting layer 5, the light emitting layer 6, a hole blocking layer 7 and an electron transporting layer 8 are stacked in this order between the anode 3 and the cathode 9.

<Configuration of Organic Layer>

The layer configuration of the organic layer is not particularly limited and may be appropriately selected according to the use and purpose of the organic electroluminescence device but is preferably formed on the transparent electrode or back plate. In this case, the organic layer is formed on the front surface or one surface of the transparent electrode or back plate.

The shape, size, thickness and the like of the organic layer are not particularly limited and may be appropriately selected according to the purpose.

Specific examples of the layer configuration include the following configurations, but the present invention is not limited thereto.

Anode/hole transporting layer/light emitting layer/electron transporting layer/cathode Anode/hole transporting layer/light emitting layer/blocking layer/electron transporting layer/cathode Anode/hole transporting layer/light emitting layer/blocking layer/electron transporting layer/electron injection layer/cathode Anode/hole injection layer/hole transporting layer/light emitting layer/blocking layer/electron transporting layer/cathode Anode/hole injection layer/hole transporting layer/light emitting layer/blocking layer/electron transporting layer/electron injection layer/cathode The device configuration, substrate, cathode and anode of an organic electroluminescence device are described in detail, for example, in JP-A-2008-270736, and the matters described therein can be applied to the present invention.

<Substrate>

The substrate used in the invention is preferably a substrate which causes neither scattering nor damping of light emitted from the organic layer. When the substrate is made from an organic material, it is preferable that the organic material has excellent heat resistance, dimensional stability, solvent resistance, electrical insulation and workability.

<Anode>

The anode is usually sufficient if it has a function as an electrode of supplying a hole to the organic layer. The shape, structure, size and the like thereof are not particularly limited, and the anode material may be appropriately selected from known electrode materials according to the use or purpose of the luminescence device. As described above, the anode is usually provided as a transparent anode.

<Cathode>

The cathode is usually sufficient if it has a function as an electrode of injecting an electron in the organic layer. The shape, structure, size and the like thereof are not particularly limited, and the cathode material may be appropriately selected from known electrode materials according to the use or purpose of the luminescence device.

As for the substrate, the anode and the cathode, the matters described in JP-A-2008-270736, paragraphs [0070] to [0089] can be applied to the present invention.

<Organic Layer>

The organic layer for use in the present invention is described below.

—Formation of Organic Layer—

In the organic electroluminescence device of the present invention, each organic layer may be suitably formed by any of a dry deposition method such as vapor deposition and sputtering, a transfer method, a printing method and the like.

(Light Emitting Layer)

<Light Emitting Material>

The light emitting material for use in the present invention is preferably a metal complex having a group represented by formula (I).

The light emitting material in the light emitting layer is generally contained in the light emitting layer, based on the mass of all compounds forming the light emitting layer, in an amount of 0.1 to 50 mass %, and in view of durability and external quantum efficiency, preferably in an amount of from 1 to 50 mass %, still more preferably from 2 to 40 mass %.

The thickness of the light emitting layer is not particularly limited but usually, the thickness is preferably from 2 to 500 nm, and in view of external quantum efficiency, more preferably from 3 to 200 nm, still more preferably from 5 to 100 nm.

In the device of the present invention, the light emitting layer may be composed of only a light emitting material or may have a mixed layer configuration of a host material and a light emitting material. The light emitting material may be either a fluorescent material or a phosphorescent material and as for the dopant, one kind of a dopant or two or more kinds of dopants may be used. The host material is preferably a charge transport material. As for the host material, one kind of a host material or two or more kinds of host materials may be used, and examples of this configuration include a configuration where an electron transporting host material and a hole transporting host material are mixed. Also, the light emitting layer may contain a material having no charge transport property and being incapable of producing luminescence.

Furthermore, the light emitting layer may be a single layer or a multilayer composed of two or more layers. In the case of a plurality of light emitting layers, the metal complex having a group represented by formula (I) may be contained in two or more light emitting layers. Also, respective light emitting layers may produce luminescence in different colors.

As regards the composition of the present invention, for example, the above-described components constituting the light emitting layer may be added to the light emitting material having a substituent represented by formula (1) of the present invention. It is also preferred to further add a compound represented by formula (VI) described later.

<Host Material>

Examples of the host material contained in the light emitting layer include a compound having a carbazole structure, a compound having an azacarbazole structure, a compound having an indole structure, a compound having an azaindole structure, a compound having a diarylamine structure, a compound having a pyridine structure, a compound having a pyrazine structure, a compound having a triazine structure, a compound having an arylsilane structure, and the materials exemplified later in the paragraphs of hole injection layer, hole transporting layer, electron injection layer and electron transporting layer. Among these, a compound having a carbazole structure and a compound having an indole structure are preferred.

Examples thereof include pyrrole, indole, carbazole (including CBP (4,4'-di(9-carbazolyl)biphenyl)), azaindole, azacarbazole, triazole, oxazole, oxadiazole, pyrazole, imidazole, thiophene, polyarylalkane, pyrazoline, pyrazolone, phenylenediamine, arylamine, amino-substituted chalcone, styrylanthracene, fluorenone, hydrazone, stilbene, silazane, aromatic tertiary amine compounds, styrylamine compounds, porphyrin compounds, polysilane compounds, poly(N-vinylcarbazole), aniline copolymers, thiophene oligomers, oligomers of conductive polymers like polythiophene, organic silanes, carbon film, pyridine, pyrimidine, triazine, anthraquinodimethane, anthrone, diphenylquinone, thiopyran dioxide, carbodiimide, fluorelenylidenemethane, distyrylpyrazine, fluoro-substituted aromatic compounds, tetracarboxylic acid anhydrides of condensed aromatic ring compounds such as naphthalene and perylene, phthalocyanine, various kinds of metal complexes, typified by metal complexes of 8-quinolinol derivatives and metal complexes whose ligands are metallo-phthalocyanines, benzoxazole or benzothiazole molecules, and derivatives of the above-recited metal complexes (e.g. those replaced with substituents or those condensed with other rings).

In view of color purity, luminous efficiency and drive durability, the lowest triplet excitation energy ($T_1$ energy) of the host material in the light emitting layer for use in the present invention is preferably higher than the $T_1$ energy of the phosphorescent material.

In the present invention, the content of the host compound is not particularly limited but in view of luminous efficiency and drive voltage, the content is preferably from 15 to 95 mass % based on the mass of all compounds forming the light emitting layer.

The thickness of the light emitting layer is not particularly limited but usually, the thickness is preferably from 1 to 500 nm, more preferably from 5 to 200 nm, still more preferably from 10 to 100 nm.

(Fluorescent Material)

Examples of a fluorescent material usable in the invention include benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, condensed aromatic compounds, perinone derivatives, oxadiazole derivatives, oxazine derivatives, aldazine derivatives, pyralidine derivatives, cyclopentadiene derivatives, bisstyrylanthracene derivatives, quinacridone derivatives, pyrrolopyridine derivatives, thiadiazolopyridine derivatives, cyclopentadiene derivatives, styrylamine derivatives, diketopyrrolopyrrole derivatives, aromatic dimethylidyne derivatives, various kinds of complexes typified by complexes of 8-quinolinol derivatives and complexes of pyrromethene derivatives, polymeric compounds such as polythiophene, polyphenylene and polyphenylenevinylene, and compounds like organic silane derivatives.

(Phosphorescent Material)

Examples of the phosphorescent material which can be used in the present invention include, other than the metal complex having a group represented by formula (I), phosphorescent compounds described in patent documents such as U.S. Pat. No. 6,303,238B1, U.S. Pat. No. 6,097,147, WO 00/57676, WO 00/70655, WO 01/08230, WO 01/39234A2, WO 01/41512A1, WO 02/02714A2, WO 02115645A1, WO 02/44189A1, WO 05/19373A2, JP-A-2001-247859, JP-A-2002-302671, JP-A-2002-117978, JP-A-2003-133074, JP-A-2002-235076, JP-A-2003-123982, JP-A-2002-170684, EP 1211257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2006-256999, JP-A-2007-19462, JP-A-2007-84635 and JP-A-2007-96259. Examples of luminescent dopants which are far preferred among those compounds include the Ir complexes, the Pt complexes, the Cu complexes, the Re complexes, the W complexes, the Rh complexes, the Ru complexes, the Pd complexes, the Os complexes, the Eu complexes, the Tb complexes, the Gd complexes, the Dy complexes and the Ce complexes. Of these complexes, Ir complexes, the Pt complexes and the Re complexes are particularly preferable, notably Ir complexes, the Pt complexes and the Re complexes each having at least one kind of coordination bond selected from metal-carbon, metal-nitrogen, metal-oxygen and metal-sulfur coordinate bonds. In terms of luminous efficiency, durability under driving, chromaticity and so on, the Ir complexes, the Pt complexes and the Re complexes each having a polydentate ligand, including a tridentate ligand or higher, are preferred over the others.

The content of the phosphorescent material in the light emitting layer is preferably from 0.1 to 50 mass %, more preferably from 0.2 to 50 mass %, still more preferably from 0.3 to 40 mass %, and most preferably from 20 to 30 mass %, based on the total mass of the light emitting layer.

The content of the phosphorescent material (the metal complex having a group represented by formula (I) and/or a phosphorescent material used in combination) which can be used in the present invention is preferably from 0.1 to 50 mass %, more preferably from 1 to 40 mass %, and most preferably from 5 to 30 mass %, based on the total mass of the light emitting layer. In particular, within the range of 5 to 30 mass %, the chromaticity of luminescence of the organic electroluminescence device is small in the dependency on the concentration of the phosphorescent material added.

The organic electroluminescence device of the present invention most preferably contains at least one kind of the compound (I) (the metal complex having a group represented by formula (I)) in an amount of 5 to 30 mass % based on the total mass of the light emitting layer.

The organic electroluminescence device preferably further contains a hydrocarbon compound, and it is more preferred to contain a hydrocarbon compound in a light emitting layer.

The hydrocarbon compound is preferably a compound represented by the following formula (VI).

By appropriately using the compound represented by formula (VI) together with the light emitting material, the interaction between material molecules can be adequately controlled to make uniform the energy gap and interaction between adjacent molecules, whereby the drive voltage can be more lowered.

Also, the compound represented by formula (VI) for use in the organic electroluminescence device is excellent in chemical stability and less causes deterioration such as decomposition of the material during driving of the device, so that the organic electroluminescence device can be prevented from reduction in the efficiency or life due to decomposition of the material.

The compound represented by formula (VI) is described below.

(VI)

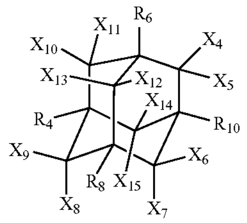

In formula (VI), each of $R_4$, $R_6$, $R_8$, $R_{10}$ and $X_4$ to $X_{15}$ independently represents a hydrogen atom, an alkyl group or an aryl group.

The alkyl group represented by each of $R_4$, $R_6$, $R_8$, $R_{10}$ and $X_4$ to $X_{15}$ in the formula (VI) may have as a substituent an adamantane structure or an aryl structure, and the number of carbon atoms in the alkyl group is preferably from 1 to 70, far preferably from 1 to 50, further preferably from 1 to 30, still further preferably from 1 to 10, especially preferably from 1 to 6. And the most preferable alkyl groups are linear alkyl groups having 2 to 6 carbon atoms.

Examples of the alkyl group represented by each of $R_4$, $R_6$, $R_8$, $R_{10}$ and $X_4$ to $X_{15}$ in the formula (VI) include an n-$C_{50}H_{101}$ group, an n-$C_{30}H_{61}$ group, 3-(3,5,7-triphenyladamantane-1-yl)propyl group (number of carbon atoms: 31), a trityl group (number of carbon atoms: 19), 3-(adamantane-1-yl)propyl group (number of carbon atoms: 13), 9-decalyl group (number of carbon atoms: 10), a benzyl group (number of carbon atoms: 7), a cyclohexyl group (number of carbon atoms: 6), a n-hexyl group (number of carbon atoms: 6), an n-pentyl group (number of carbon atoms: 5), an n-butyl group (number of carbon atoms: 4), an n-propyl group (number of carbon atoms: 3), a cyclopropyl group (number of carbon atoms: 3), an ethyl group (number of carbon atoms: 2) and a methyl group (number of carbon atoms: 1).

The aryl group represented by each of $R_4$, $R_6$, $R_8$, $R_{10}$ and $X_4$ to $X_{15}$ in the formula (VI) may have as a substituent an adamantane structure or an alkyl structure, and the number of carbon atoms the aryl group has is preferably from 6 to 30, far preferably from 6 to 20, further preferably from 6 to 15, especially preferably from 6 to 10, the most preferably is 6.

Examples of the aryl group represented by each of $R_4$, $R_6$, $R_8$, $R_{10}$ and $X_4$ to $X_{15}$ in the formula (VI) include a 1-pyrenyl group (number of carbon atoms: 16), a 9-anthracenyl group (number of carbon atoms: 14), a 1-naphthyl group (number of carbon atoms: 10), a 2-natphthyl group (number of carbon atom: 10), a p-t-butylphenyl group (number of carbon atoms: 10), a 2-m-xylyl group (number of carbon atoms: 8), a 5-m-xylyl group (number of carbon atoms: 8), an o-tolyl group (number of carbon atoms: 7), a m-tolyl group (number of carbon atoms: 7), a p-tolyl group (number of carbon atoms: 7) and a phenyl group (number of carbon atoms: 6).

Although each of $R_4$, $R_6$, $R_8$ and $R_{10}$ in the formula (VI) may be either a hydrogen atom, or an alkyl group, or an aryl group, from the viewpoint that high glass transition temperatures are preferable, it is preferable that at least one of them is an aryl group, it is far preferable that at least two of them are aryl groups, and it is particularly preferable that 3 or 4 of them are aryl groups.

Although each of $X_4$ to $X_{15}$ in the formula (VI) may represent either a hydrogen atom, or an alkyl group, or an aryl group, it is preferable that each stands for a hydrogen atom or an aryl group, especially a hydrogen atom.

The organic electroluminescence devices are made using a vacuum deposition process or a solution coating process, and therefore, in terms of vacuum deposition suitability and solubility, the molecular weight of the compounds represented by the formula (VI) in the invention is preferably 2,000 or below, far preferably 1,200 or below, especially 1,000 or below. Also, from the viewpoint of vacuum deposition suitability, the molecular weight is preferably 250 or above, far preferably 350 or above, particularly preferably 400 or above. This is because, when the compounds have too low molecular weight, their vapor pressure becomes low and change from a vapor phase to a solid phase does not occur, and it is therefore difficult for the compounds to form organic layers.

The compound represented by the formula (VI) is preferably in solid phase at room temperature (25° C.), far preferably solid phase in a range from room temperature to 40° C., especially preferably solid phase in a range from room temperature to 60° C.

In the case of using the compound which, though represented by the formula (VI), is not in solid phase at room temperature, it is possible to form a solid phase at ordinary temperatures by combining the compound with other substances.

Uses of the compound represented by the formula (VI) are not limited, and the compound may be incorporated into any of the organic layers. The layer into which the compound represented by the formula (VI) in the invention is introduced is preferably a layer selected from a light emitting layer, a hole injection layer, a hole transporting layer, an electron transporting layer, an electron injection layer, an exciton block layer and a charge blocking layer, or a combination of two or more of these layers, far preferably a layer selected from the light emitting layer, the hole injection layer, the hole transporting layer, the electron transporting layer and the electron injection layer, or a combination of two or more of these layers, especially preferably a layer selected from the light emitting layer, the hole injection layer and the hole transporting layer, or a combination of at least two of these layers, the most preferably the light emitting layer.

When the compound represented by the formula (VI) is used in an organic layer, its content is required to be limited so as not to inhibit charge transportability, and therefore it is preferable from 0.1% to 70% by mass, far preferable from 0.1% to 30% by mass, especially preferable from 0.1% to 25% by mass.

When the compound represented by the formula (VI) is used in two or more organic layers, its content in each organic layer is preferably in the range specified above.

Only one kind of a compound represented by formula (VI) may be contained in any organic layer, or a plurality of kinds of compounds represented by formula (VI) may be contained in combination in an arbitrary ratio.

Specific examples of the hydrocarbon compound are illustrated below, but the present invention is not limited thereto.

(1-1)

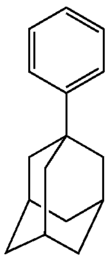

(1-2)

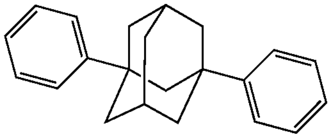

(1-3)

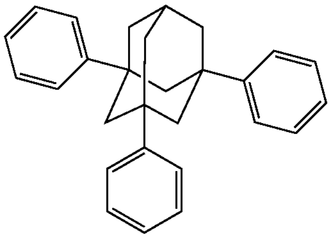

-continued
(1-4)
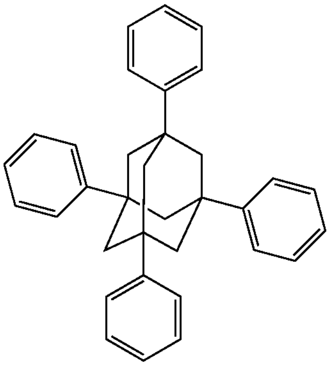
(1-5)
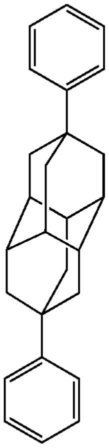
(1-6)
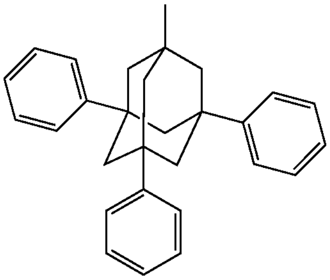
(1-7)
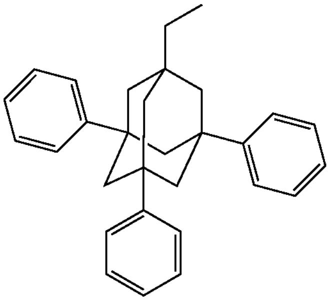
-continued
(1-8)
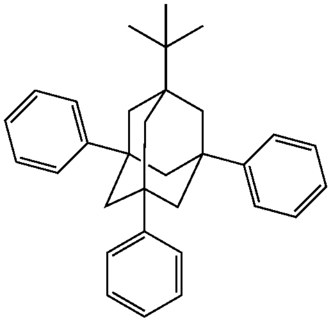
(1-9)
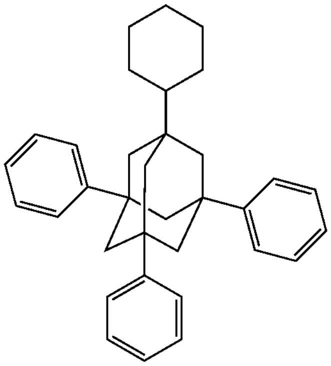
(1-10)
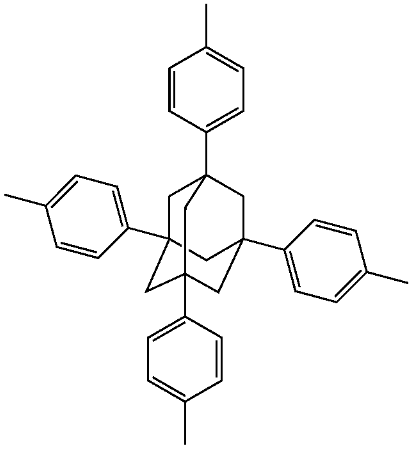
(1-11)
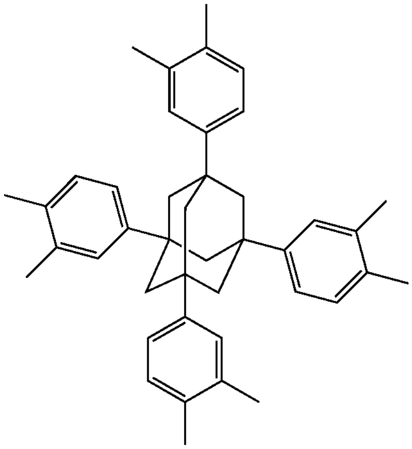

-continued
(1-12)
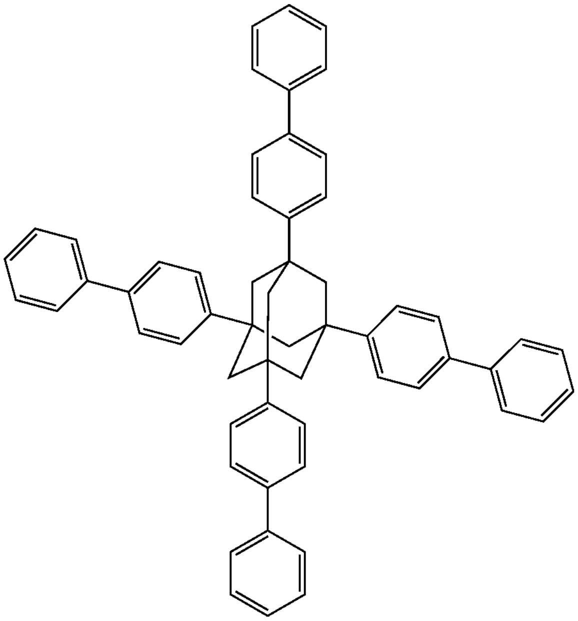
(1-13)
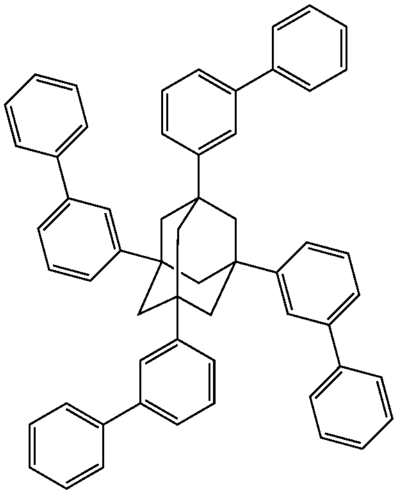
(1-14)
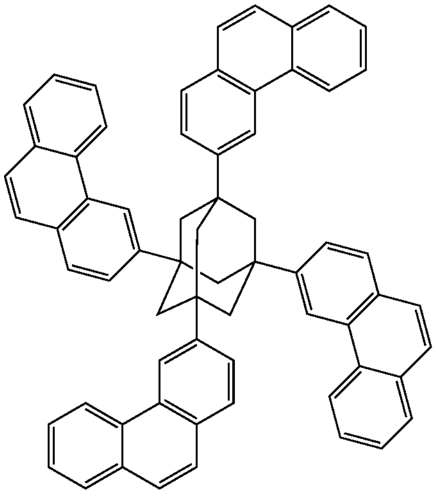
-continued
(1-15)
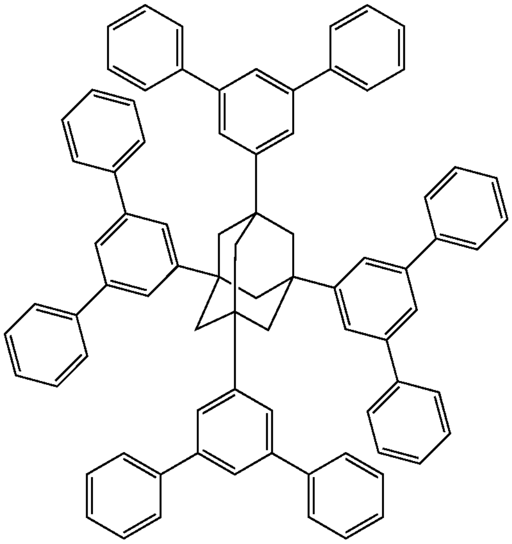
(1-16)
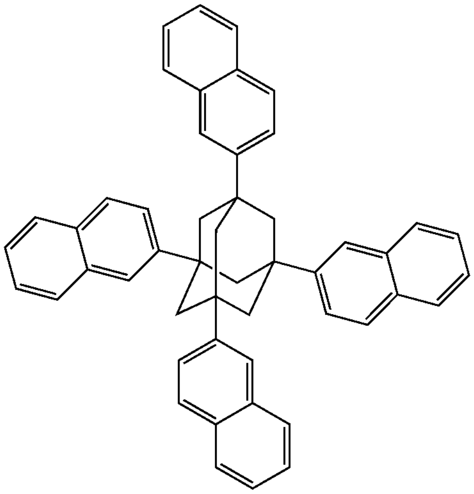
(1-17)
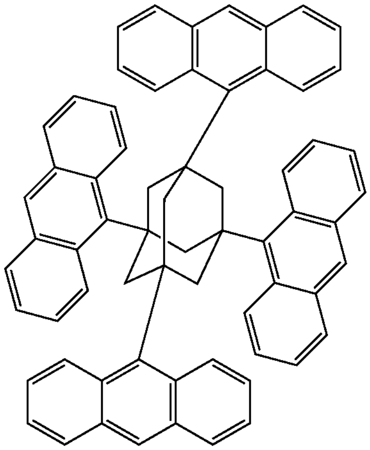

-continued
(1-18)
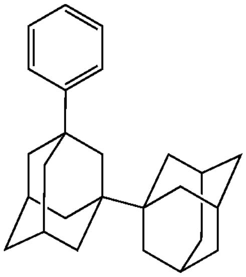
(1-19)
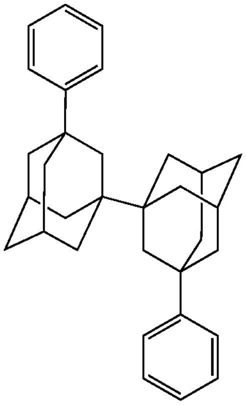
(1-20)
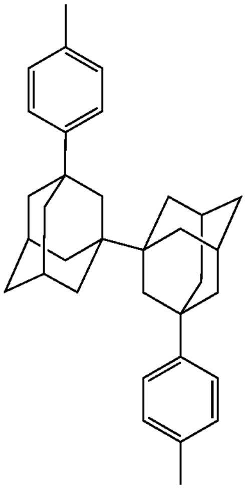
(1-21)
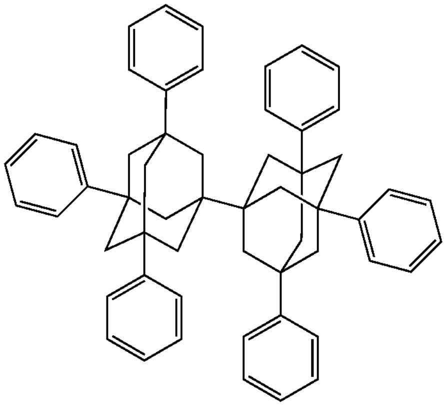
-continued
(1-22)
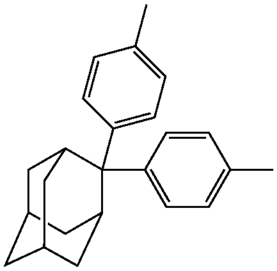
(1-23)
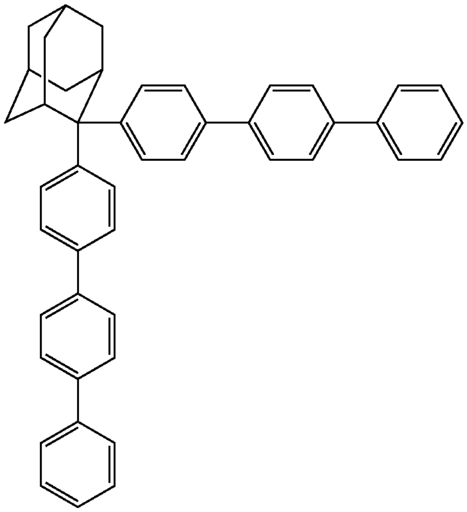
(1-24)
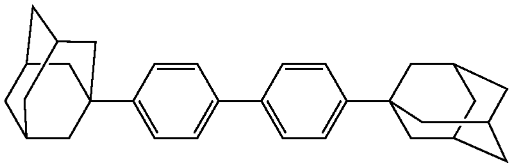
(1-25)
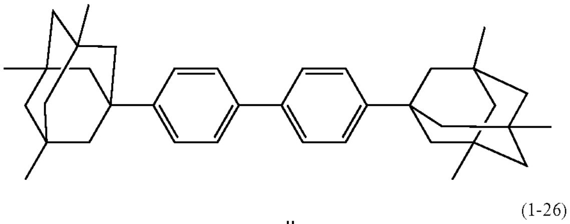
(1-26)
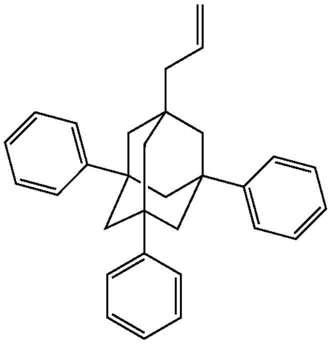

-continued
(1-27)
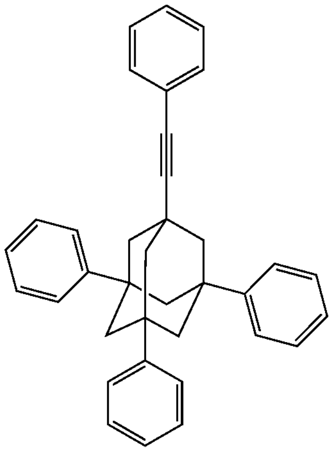
(1-28)
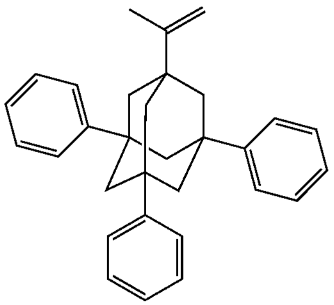
(1-29)
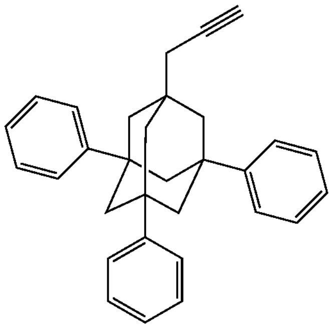
(1-30)
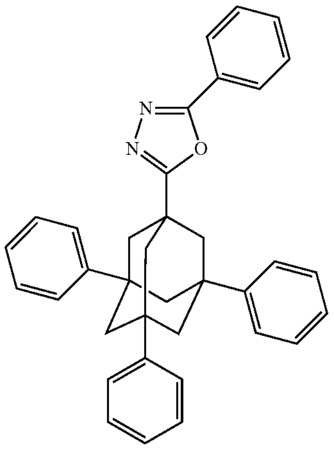
-continued
(1-31)
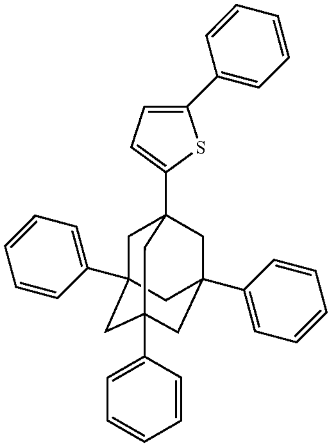
(1-32)
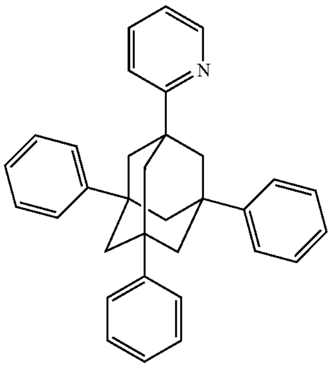
(1-33)
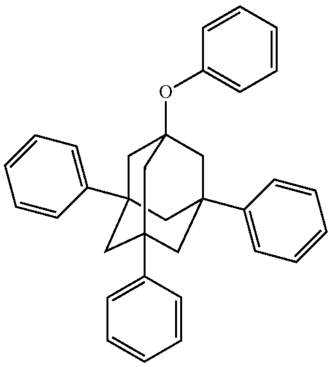
(1-34)
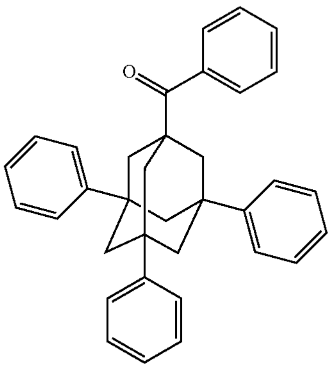

-continued
(1-35)
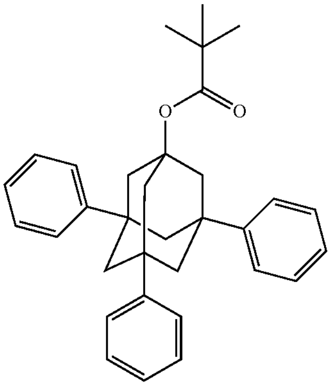
(1-36)
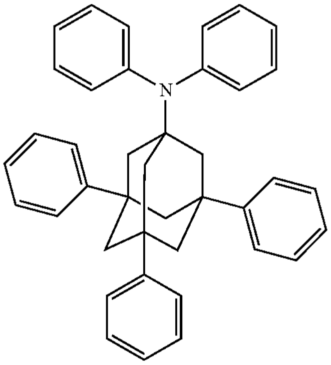
(1-37)
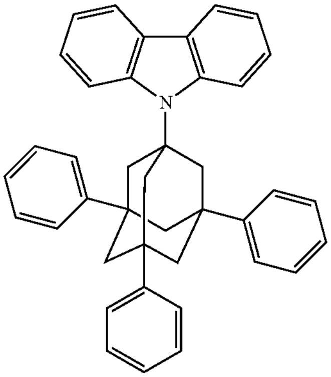
(1-38)
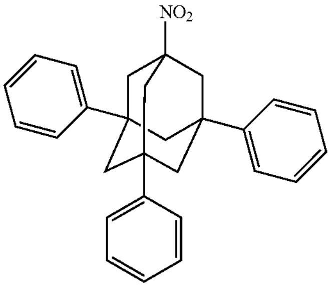
-continued
(1-39)
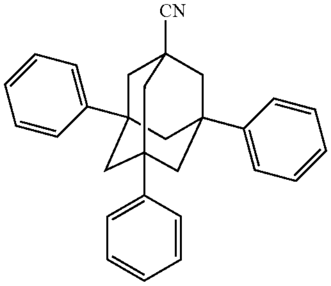
(1-40)
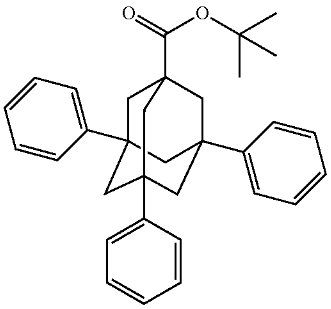
(1-41)
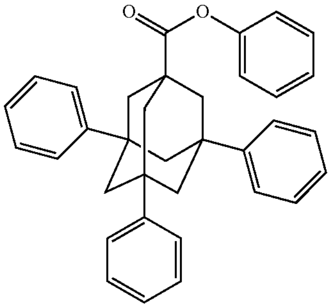
(1-42)
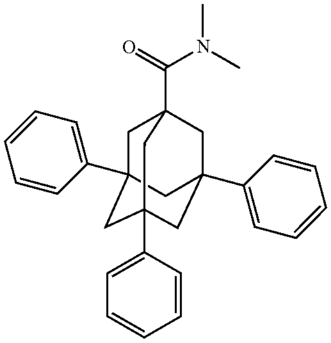
(1-43)
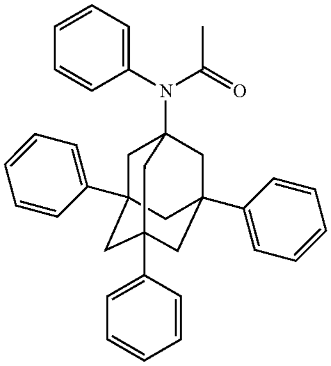

-continued (1-44)

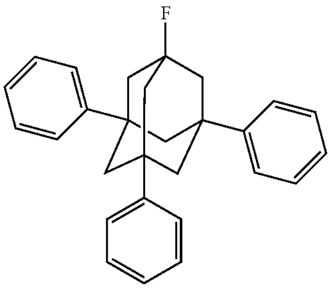

(1-45)

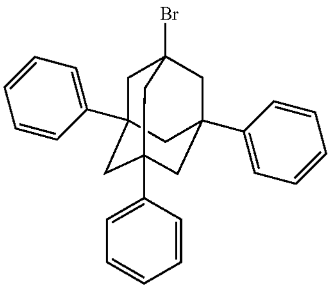

(1-46)

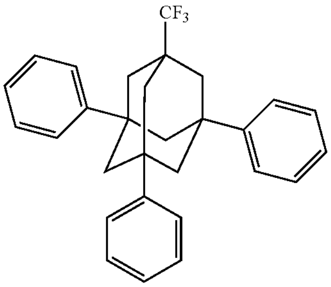

(1-47)

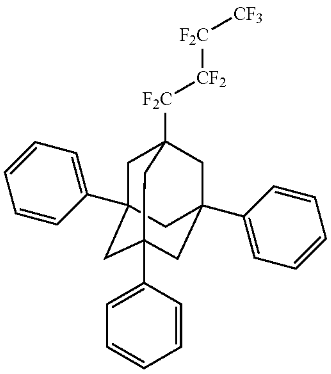

(1-48)

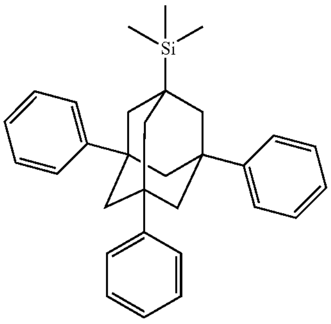

-continued (1-49)

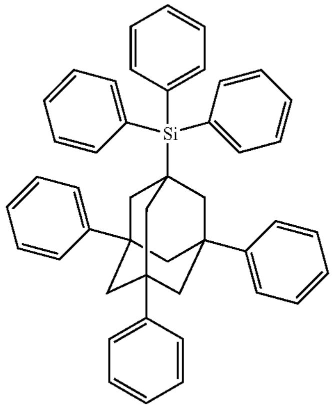

The compound represented by the formula (VI) can be synthesized by appropriately combining adamantane or haloadamantane with haloalkane or alkylmagnesium halide (Grignard reagent). For instance, it is possible to provide coupling between haloadamantane and haloalkane by use of indium (Reference 1). Alternatively, it is possible to convert haloalkane into an alkylcopper reagent and further to couple the reagent to Grignard reagent of an aromatic compound (Reference 2). Further, the coupling of haloalkane can also be performed using an appropriate arylboric acid and a palladium catalyst (Reference 3).

Reference 1: Tetrahedron Lett. 39, 9557-9558 (1998)

Reference 2: Tetrahedron Lett. 39, 2095-2096 (1998)

Reference 3: J. Am. Chem. Soc. 124, 13662-13663 (2002)

The adamantane structure having an aryl group can be synthesized by appropriately combining adamantane or haloadamantane with the corresponding arene or haloarene.

Additionally, even when defined substituents undergo changes under certain synthesis conditions in those production methods or they are unsuitable for carrying out those methods, the intended compounds can be produced with ease by adopting e.g. methods for protecting and deprotecting functional groups (T. W. Greene, Protective Groups in Organic Synthesis, John Wiley & Sons Inc. (1981)). Further, it is also possible to change the order of reaction steps, including a substituent introduction step, as appropriate, if needed.

The thickness of the light emitting layer is not particularly limited but usually, the thickness is preferably from 1 to 500 nm, more preferably from 5 to 200 nm, still more preferably from 10 to 100 nm.

—Hole Injection Layer, Hole Transporting Layer—

The hole injection layer and the hole transporting layer are a layer having a function of receiving a hole from the anode or anode side and transporting it to the cathode side.

—Electron Injection Layer, Electron Transporting Layer—

The electron injection layer and the electron transporting layer are a layer having a function of receiving an electron from the cathode or cathode side and transporting it to the anode side.

As regards the hole injection layer, hole transporting layer, electron injection layer and electron transporting layer, the matters described in JP-A-2008-270736, paragraphs [0165] to [0167] can be applied to the present invention.

—Hole Blocking Layer—

The hole blocking layer is a layer having a function of blocking the holes transported from an anode side to the light emitting layer from passing on through to the cathode side. In the invention, the hole blocking layer can be provided as an organic layer adjacent to the light emitting layer in the cathode side.

Examples of an organic compound which forms the hole blocking layer include aluminum complexes such as aluminum(III) bis(2-methyl-8-quinolinato) 4-phenylphenolate (abbreviated to BAlq), triazole derivatives, and phenanthroline derivatives such as 2,9-dimethyl-4,7-diphenyl-1,10-phenanthroline (abbreviated to BCP).

The thickness of the hole blocking layer is preferably from 1 nm to 500 nm, far preferably from 5 nm to 200 nm, further preferably from 10 nm to 100 nm.

The hole blocking layer may have either a single-layer structure made up of one or more than one material as recited above or a multiple-layer structure made up of two or more layers which are identical or different in composition.

—Electron Blocking Layer—

The electron blocking layer is a layer having a function of preventing the electrons transported from the cathode side to the light emitting layer from passing through to the anode side. In the invention, the electron blocking layer can be provided as an organic layer adjacent to the light emitting layer on the anode side.

As the examples of the compounds constituting the electron blocking layer, for instance, the hole transporting materials described above can be applied.

The thickness of the electron blocking layer is preferably from 1 nm to 500 nm, more preferably from 5 nm to 200 nm, still more preferably from 10 nm to 100 nm. The electron blocking layer may have a single layer structure composed of one or more of the above materials or may be a multilayer structure composed of two or more layers having the same composition or different compositions.

<Protective Layer>

In the present invention, the entire organic EL device may be protected by a protective layer.

As for the protective layer, the matters described in JP-A-2008-270736, paragraphs [0169] and [0170] can be applied to the present invention.

<Sealing Container>

The device of the present invention may be entirely sealed using a sealing container.

As for the sealing container, the matters described in JP-A-2008-270736, paragraph [0171] can be applied to the present invention.

(Drive)

Luminescence of the organic electroluminescence device of the present invention can be obtained by applying a DC (if desired, an AC component may be contained) voltage (generally from 2 to 15 volts) or a DC current between the anode and the cathode.

As for the driving method of the organic electroluminescence device of the present invention, the driving methods described, for example, in JP-A-2-148687, JP-A-6-301355, JP-A-5-29080, JP-A-7-134558, JP-A-8-234685, JP-A-8-241047, Japanese Patent 2784615, and U.S. Pat. Nos. 5,828,429 and 6,023,308 can be applied.

The present organic electroluminescence devices can be heightened in light extraction efficiency by utilizing various publicly-known improvements. For instance, it is possible to improve light extraction efficiency and increase external quantum efficiency by working on the substrate's surface profile (e.g. forming a pattern of microscopic asperities on the substrate's surface), or by controlling refractive indices of the substrate, the ITO layer and the organic layers, or by controlling thicknesses of the substrate, the ITO layer and the organic layers, or so on.

The luminescence device of the present invention may be in a so-called top emission system of collecting light from the anode side.

The present organic EL devices may have resonator structure. For instance, each device has on a transparent substrate a multilayer film minor made up of a plurality of laminated films that have different refractive indices, a transparent or translucent electrode, a light emitting layer and a metal electrode which are superposed on top of each other. Reflections of light produced in the light emitting layer occur repeatedly between the multilayer film minor and the metal electrode which function as reflector plates, thereby producing resonance.

In another aspect, the transparent or translucent electrode and the metal electrode function as reflector plates, respectively, on the transparent substrate, and reflections of light produced in the light emitting layer occur repeatedly between the reflector plates, thereby producing resonance.

In order to form a resonance structure, the optical distance determined from effective refractive indices of the two reflector plates, and refractive indices and thicknesses of each layers sandwiched between the two reflector plates are adjusted to have optimum values for achieving the desired resonance wavelength. The calculating formula in the first aspect case is described in JP-A-9-180883, and that in the second aspect case is described in JP-A-2004-127795.

(Use of Luminescence Device of the Present Invention)

The present luminescence devices can be used suitably for light luminous apparatus, pixels, indication devices, displays, backlights, electrophotographic devices, illumination light sources, recording light sources, exposure light sources, readout light sources, sign, billboards, interior decorations or optical communications, especially preferably for devices driven in a region of high-intensity luminescence, such as illumination apparatus and display apparatus.

Next the present light luminous apparatus is explained by reference to FIG. 2.

The present light luminous apparatus incorporates any one of the present organic electroluminescence devices.

Figure 2:
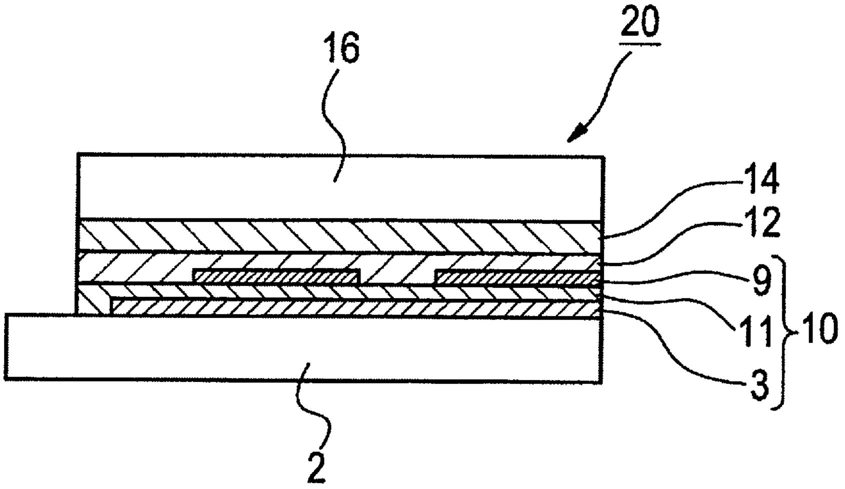
FIG. 2 is a schematic view showing one example of the light emission apparatus according to the present invention.

FIG. 2 is a cross-sectional diagram schematically showing one example of the present light luminous apparatus.

The light luminous apparatus 20 in FIG. 2 includes a transparent substrate 2 (supporting substrate), an organic electroluminescence device 10, a sealing enclosure 16 and so on.

The organic electroluminescence device 10 is formed by stacking on the substrate 2 an anode 3 (first electrode), an organic layer 11 and a cathode 9 (second electrode) in the order of mention. In addition, a protective layer 12 is superposed on the cathode 9, and on the protective layer 12 a sealing enclosure 16 is further provided via an adhesive layer 14. Incidentally, part of each of the electrodes 3 and 9, a diaphragm and an insulating layer are omitted in FIG. 2.

Herein, a light cure adhesive such as epoxy resin, or a thermosetting adhesive can be used for the adhesive layer 14. Alternatively, a thermosetting adhesive sheet may be used as the adhesive layer 14.

The present light emission apparatus has no particular restrictions as to its uses, and specifically, it can be utilized e.g. as not only illumination apparatus but also display apparatus of a television set, a personal computer, a mobile phone, an electronic paper or the like.

The illumination apparatus according to an embodiment of the present invention is described below by referring to FIG. 3.

Figure 3:
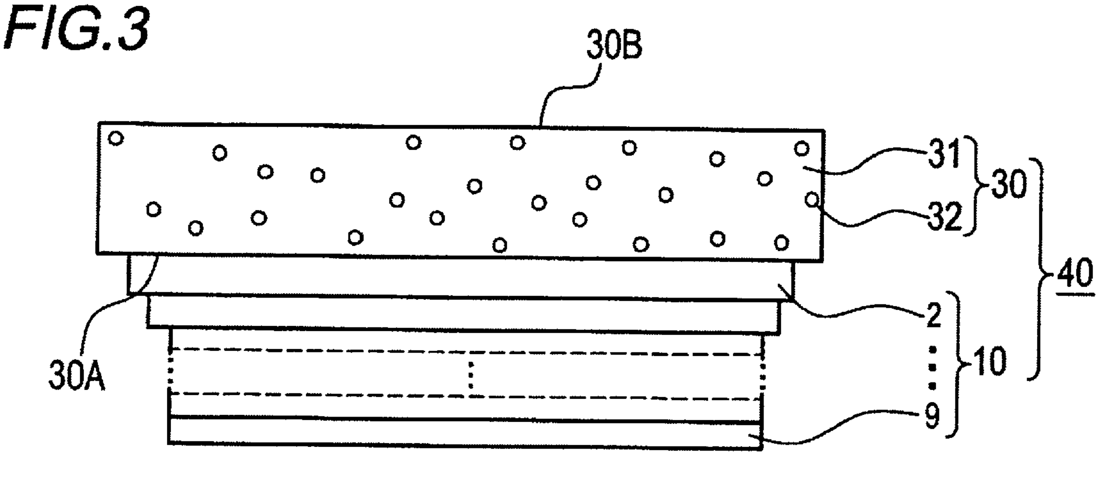
FIG. 3 is a schematic view showing one example of the illumination apparatus according to the present invention.

The illumination apparatus 40 according to an embodiment of the present invention contains, as shown in FIG. 3, the above-described organic electroluminescence device 10 and a light scattering member 30. More specifically, the illumination apparatus 40 is configured such that the substrate 2 of the organic electroluminescence device 10 and the light scattering member 30 are in contact with each other.

The light scattering member 30 is not particularly limited as long as it can scatter light, but in FIG. 3, a member obtained by dispersing fine particles 32 in a transparent substrate 31 is used. Suitable examples of the transparent substrate 31 include a glass substrate, and suitable examples of the fine particle 31 include a transparent resin fine particle. As the glass substrate and the transparent resin fine particle, a known product can be used for both. In such an illumination apparatus 40, when light emitted from the organic electroluminescence device 10 is incident on the light incident surface 30A of the scattering member 30, the incident light is scattered by the light scattering member and the scattered light is output as illuminating light from the light output surface 30B.

EXAMPLES

The present invention is described in greater detail below by referring to Examples, but the embodiment of the present invention is not limited thereto.

[Synthesis of Compound 2]

Compound 2 was synthesized according to the following scheme.

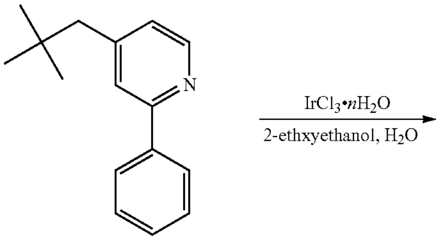

Ligand 1

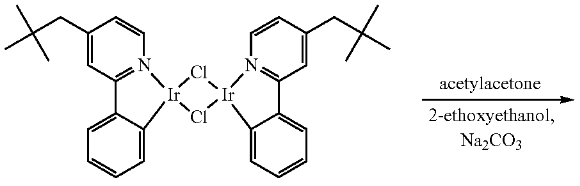

Chlorine Linked Complex 2

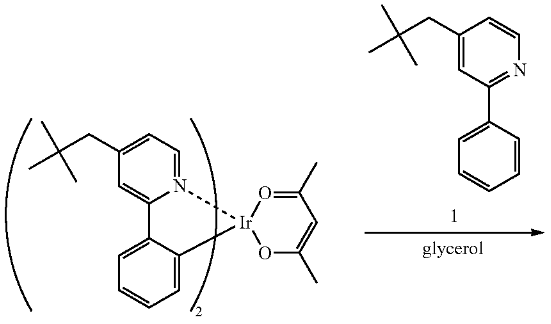

acac Complex 3

-continued

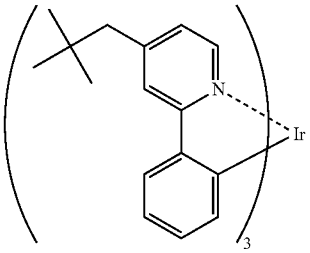

Compound 2

In a nitrogen atmosphere, 2.1 equivalents of Ligand 1 and 1 equivalent of iridium chloride n-hydrate were reacted in a mixed solvent of 2-ethoxyethanol/$H_2O$ (=3:1) by refluxing at the boiling point for 5 hours to obtain Chlorine Linked Complex 2. In 2-ethoxyethanol, Chlorine Linked Complex 2 and 3 equivalents of acetylacetone were refluxed at the boiling point for 3 hours in the co-presence of sodium carbonate to obtain acac Complex 3. Subsequently, acac Complex 3 and 1.5 equivalents of Ligand 1 were reacted in glycerol at 200° C., whereby the objective Compound 2 was synthesized.

[Synthesis of Compound 157]

Compound 157 was synthesized according to the following scheme.

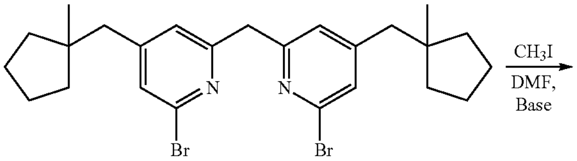

(A)

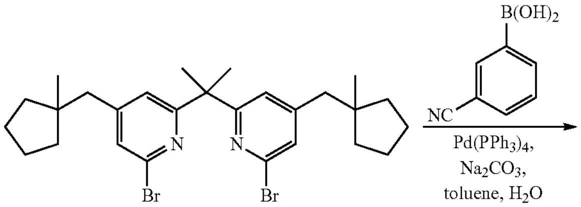

(B)

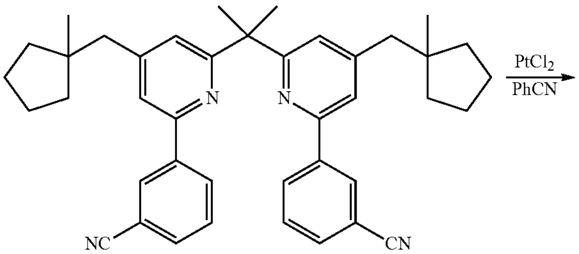

(C)

-continued

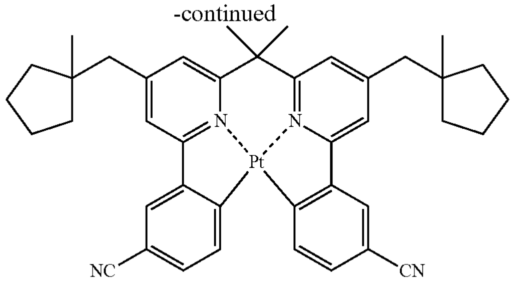

Compound 157

From 1 to 1.2 equivalents of a base such as lithium diisopropylamide, potassium tert-butoxide and sodium hydride was added to an N,N-dimethylformamide solution of Compound (A) at 0° C. to room temperature, and the reaction was allowed to proceed at 0° C. to room temperature for about 30 minutes. Thereto, from 1.5 to 4 equivalents of methyl iodide was added and after monomethylation through reaction at room temperature for about 30 minutes, from 1 to 1.2 equivalents of the base described above and excess methyl iodide were again reacted under the same conditions to obtain Dimethyl Substitution (B) in a yield of 70 to 99%.

In the process of obtaining Compound (C) from Compound (B), Compound (B) as well as from 2 to 3 equivalents of sodium carbonate and from 0.05 to 0.2 equivalents of tetrakis(triphenylphosphine)palladium(0) were dissolved in a toluene/ethanol/water mixed solvent or a 1,2-dimethoxyethane/water mixed solvent, and the solution was heated to a temperature of 70° C. to heat-refluxing temperature and stirred for 2 to 24 hours, whereby Compound (C) was synthesized.

In the process of obtaining Compound 157 from Compound (C), Compound (C) and from 1 to 1.5 equivalents of platinum chloride were dissolved in benzonitrile, and the solution was heated to a temperature of 130° C. to heat-refluxing temperature (boiling point of benzonitrile: 191° C.) and stirred for 30 minutes to 4 hours, whereby the compound was synthesized. Compound 157 was purified by recrystallization using chloroform or ethyl acetate, silica gel column chromatography, sublimation purification or the like.

Incidentally, metal complexes represented by formulae (A1) to (A4) were also synthesized by various techniques, for example, the methods described in U.S. Patent Application Publication 2007/0190359 and U.S. Patent Application Publication 2008/0297033. Furthermore, 11 and 12 can be synthesized using the synthesis method described in JP-A-2009-102533, page 189, paragraphs 288 to 302.

A-1

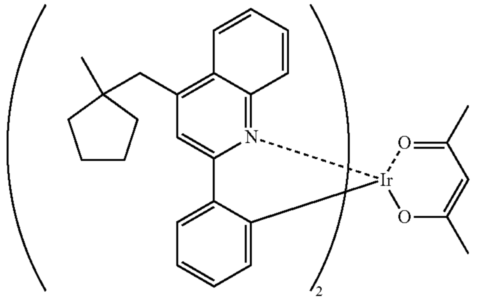

-continued

A-2

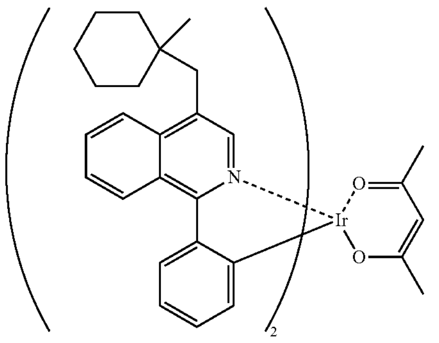

A-3

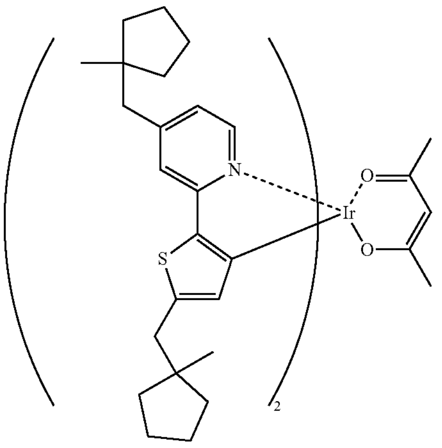

A-4

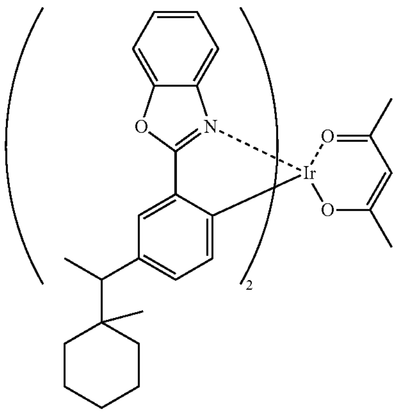

A-5

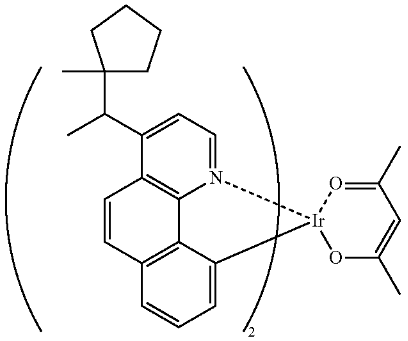

-continued
B-1
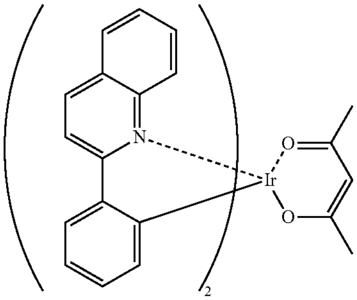
B-2
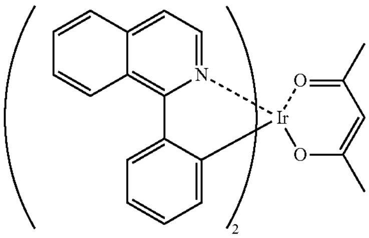
B-3
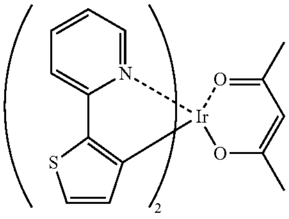
B-4
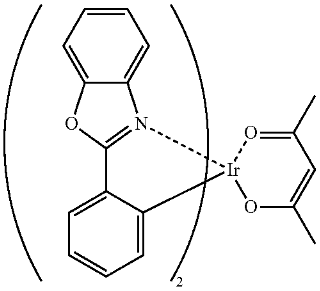
B-5
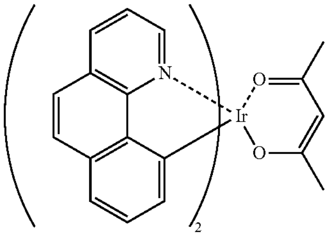
H-1
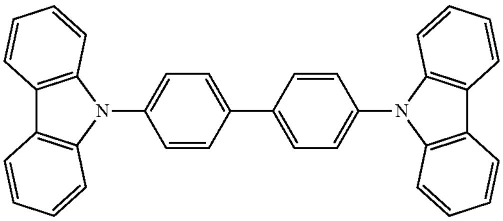
-continued
H-2
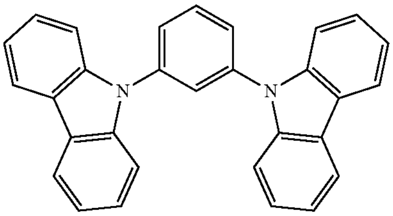
H-3
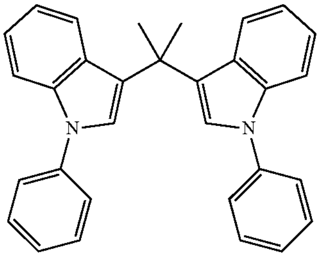
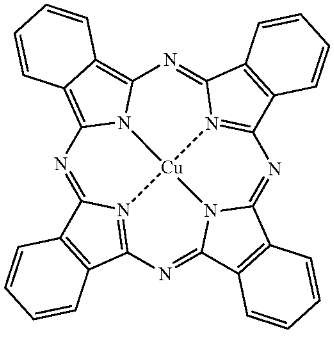
Copper Phthalocyanine
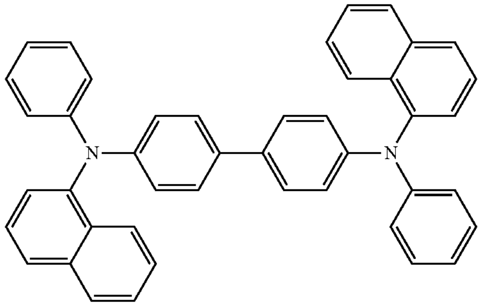
NPD
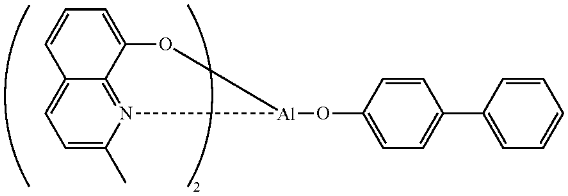
BAlq
Example 1
Example 1-1
A 0.5 mm-thickness 2.5 cm-square glass substrate having thereon ITO film (produced by GEOMATEC Corporation, surface resistance: 10 Ω/sq.) was placed in a cleaning vessel and subjected to ultrasonic cleaning in 2-propanol and then to a UV-ozone treatment for 30 minutes. On this transparent anode (ITO film), the following organic layers (organic compound layers) were sequentially deposited by the vacuum deposition method.

Unless otherwise indicated, the vapor deposition rate in Examples of the present invention is 0.2 nm/sec. The vapor deposition rate was measured using a crystal oscillator. In the following, the film thickness is a value as measured also by using a crystal oscillator.

After placing the cleaned ITO substrate in a vapor deposition apparatus, copper phthalocyanine was deposited to a thickness of 10 nm (first layer), and NPD (N,N'-di-α-naphthyl-N,N'-diphenyl)-benzidine) was deposited thereon to a thickness of 40 nm (second layer). Furthermore, H-1 and Compound A-1 of the present invention in a ratio of 95:5 (by mass) were deposited thereon to a thickness of 30 nm (third layer/light emitting layer), and BAlq [aluminum bis-(2-methyl-8-quinolinato)-4-phenylphenolate] was deposited thereon to a thickness of 40 nm (fourth layer). Thereafter, lithium fluoride was deposited thereon to a thickness of 3 nm, and aluminum was further deposited to a thickness of 60 nm. The obtained laminate was placed in an argon gas-purged glove box without exposing to the atmosphere and then encapsulated using a stainless steel-made sealing can and an ultraviolet curable adhesive (XNR5516HV, produced by Nagase-Ciba Ltd.) to produce the organic EL device of Example 1-1. A DC voltage was applied to the organic EL device to produce luminescence by using Source Measure Unit Model 2400 manufactured by Toyo Corp., as a result, luminescence derived from Compound A-1 of the present invention was obtained.

Examples 1-2 to 1-5 and Comparative Examples 1-1 to 1-5

The devices of Examples 1-2 to 1-5 and Comparative Examples 1-1 to 1-5 were produced in the same manner as in Example 1-1 except for changing the materials used in Example 1-1 to the materials shown in Table 1. A DC voltage was applied to the organic EL device to produce luminescence by using Source Measure Unit Model 2400 manufactured by Toyo Corp., as a result, luminescence derived from respective light emitting materials was obtained.

(Measurement of Drive Voltage)

Each of the organic electroluminescence devices of Examples 1-1 to 1-5 and Comparative Examples 1-1 to 1-5 was set in an emission spectrum-measuring system (ELS1500) manufactured by Shimadzu Corporation, and the applied voltage at a luminance of 100 cd/$m^2$ was measured.

(Evaluation of Drive Durability)

Each of the organic electroluminescence devices of Examples 1-1 to 1-5 and Comparative Examples 1-1 to 1-5 was set in OLED Test System Model ST-D manufactured by Tokyo System Development Co., Ltd. and driven under the conditions of a constant-current mode and an initial luminance of 1,000 cd/$m^2$, and the half-luminance time was measured.

(Evaluation of External Quantum Efficiency)

With respect to the organic electroluminescence devices of Examples 1-1 to 1-5 and Comparative Examples 1-1 to 1-5, a DC voltage was applied to the EL device to produce luminescence by using Source Measure Unit Model 2400 manufactured by Toyo Corp., and the external quantum efficiency (%) was calculated from the frontal luminance at 100 cd/$m^2$, (Evaluation of Chromaticity)

A DC voltage was applied to obtain a luminance of 1,000 cd/$m^2$, and the emission spectrum was measured by an emission spectrum-measuring system (ELS1500) manufactured by Shimadzu Corporation to calculate the chromaticity (CIE chromaticity).

TABLE 1

| | Light Emitting Layer | | Drive | External Quantum | Half-Luminance Time at | | Chromaticity after |
|---|---|---|---|---|---|---|---|
| | Light Emitting Material | Host Material | Voltage at 100 cd/$m^2$ (V) | Efficiency at 100 cd/$m^2$ (%) | 1000 cd/$m^2$ (relative value) | Initial Chromaticity | Decrease to Half Luminance |
| Comparative Example 1-1 | B-1 | H-1 | 7.6 | 13.8 | 100 | (0.61, 0.38) | (0.65, 0.33) |
| Comparative Example 1-2 | B-2 | H-1 | 8.4 | 14.0 | 106 | (0.65, 0.32) | (0.68, 0.29) |
| Comparative Example 1-3 | B-3 | H-1 | 7.3 | 11.6 | 76 | (0.50, 0.49) | (0.53, 0.45) |
| Comparative Example 1-4 | B-4 | H-1 | 7.1 | 10.1 | 56 | (0.39, 0.56) | (0.46, 0.50) |
| Comparative Example 1-5 | B-5 | H-1 | 7.3 | 14.6 | 82 | (0.41, 0.57) | (0.44, 0.52) |
| Example 1-1 | A-1 | H-1 | 7.4 | 14.4 | 125 | (0.60, 0.36) | (0.61, 0.36) |
| Example 1-2 | A-2 | H-1 | 8.2 | 14.9 | 136 | (0.66, 0.33) | (0.65, 0.32) |
| Example 1-3 | A-3 | H-1 | 7.2 | 12.7 | 87 | (0.51, 0.49) | (0.51, 0.48) |
| Example 1-4 | A-4 | H-1 | 7.0 | 10.9 | 71 | (0.40, 0.56) | (0.42, 0.55) |
| Example 1-5 | A-5 | H-1 | 7.2 | 15.1 | 91 | (0.42, 0.56) | (0.42, 0.56) |

It is seen that in Examples 1-1 to 1-5, the compound of the present invention is used as the light emitting material and therefore, the device exhibits high efficiency and a long half-luminance time and is excellent in terms of durability as compared with Comparative Examples 1-1 to 1-5. Also, the chromaticity shift is less caused at the device deterioration and the voltage is low.

Example 2

Example 2-1

A-6

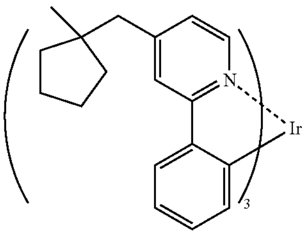

A-7

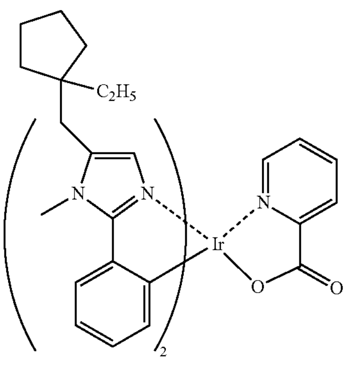

A-8

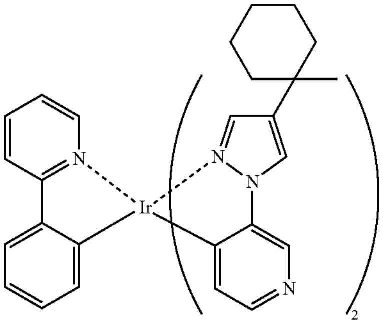

A-9

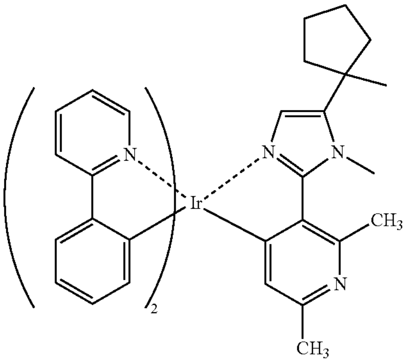

-continued

B-6

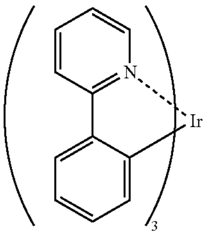

B-7

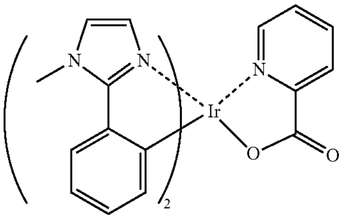

B-8

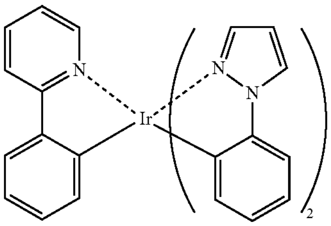

B-9

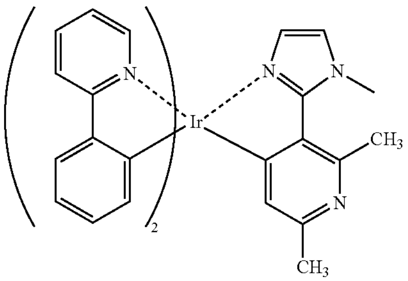

The organic EL device of Example 2-1 was produced in the same manner as in Example 1-1 except that in Example 1-1, the film of the third layer (light emitting layer) was deposited (film thickness: 50 nm) by changing the compositional ratio to H-1 and A-6 of 93:7 (by mass) from H-1 and A-1 of 95:5 (by mass). A DC voltage was applied to the organic EL device to produce luminescence by using Source Measure Unit Model 2400 manufactured by Toyo Corp., as a result, luminescence derived from A-6 was obtained.

Examples 2-2 to 2-4 and Comparative Examples 2-1 to 2-4

The devices of Examples 2-2 to 2-4 and Comparative Examples 2-1 to 2-4 were produced in the same manner as in Example 2-1 except for changing the materials used in Example 2-1 to the materials shown in Table 2. A DC voltage was applied to the organic EL device to produce luminescence by using Source Measure Unit Model 2400 manufactured by Toyo Corp., as a result, luminescence derived from respective light emitting materials was obtained.

TABLE 2

| | Light Emitting Layer | | Drive | External Quantum | Half-Luminance Time at | | Chromaticity after |
|---|---|---|---|---|---|---|---|
| | Light Emitting Material | Host Material | Voltage at 100 cd/$m^2$ (V) | Efficiency at 100 cd/$m^2$ (%) | 1000 cd/$m^2$ (relative value) | Initial Chromaticity | Decrease to Half Luminance |
| Comparative Example 2-1 | B-6 | H-1 | 8.1 | 13.3 | 100 | (0.29, 0.64) | (0.32, 0.60) |
| Comparative Example 2-2 | B-7 | H-1 | 7.9 | 13.8 | 43 | (0.25, 0.62) | (0.33, 0.58) |
| Comparative Example 2-3 | B-8 | H-1 | 8.5 | 11.8 | 66 | (0.27, 0.61) | (0.30, 0.66) |
| Comparative Example 2-4 | B-9 | H-1 | 7.8 | 12.3 | 83 | (0.28, 0.62) | (0.33, 0.64) |
| Example 2-1 | A-6 | H-1 | 7.9 | 14.1 | 125 | (0.28, 0.65) | (0.29, 0.64) |
| Example 2-2 | A-7 | H-1 | 7.7 | 14.6 | 63 | (0.24, 0.62) | (0.25, 0.60) |
| Example 2-3 | A-8 | H-1 | 8.4 | 12.3 | 79 | (0.26, 0.60) | (0.26, 0.62) |
| Comparative Example 2-4 | A-9 | H-1 | 7.7 | 12.6 | 89 | (0.28, 0.63) | (0.30, 0.64) |

It is seen that in Examples 2-1 to 2-4, the compound of the present invention is used as the light emitting material and therefore, the device exhibits high efficiency and a long half-luminance time and is excellent in terms of durability as compared with Comparative Examples 2-1 to 2-4. Also, the chromaticity shift is less caused at the device deterioration and the voltage is low.

Example 3

Example 3-1

A-10

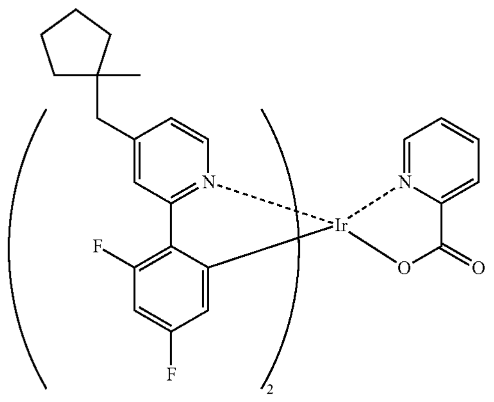

A-11

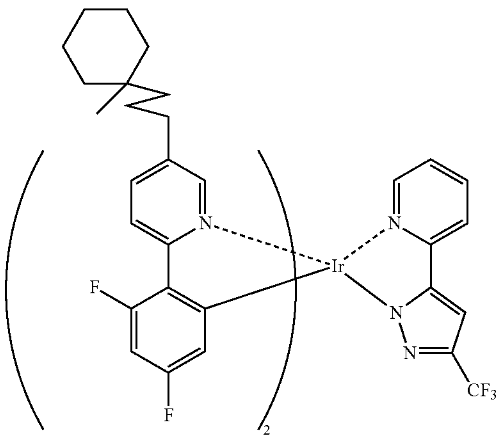

A-12

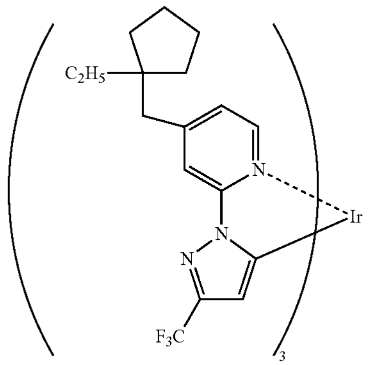

A-13

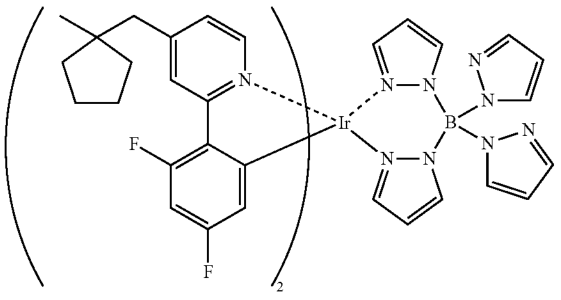

-continued
A-14
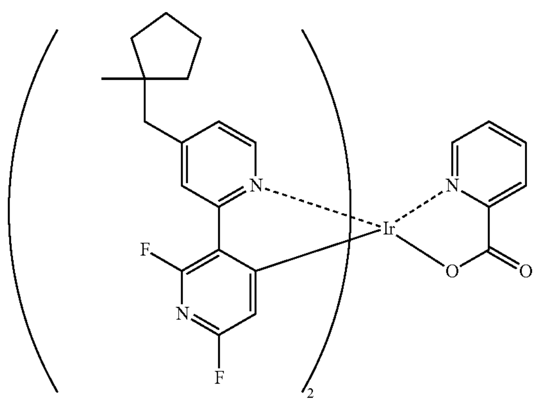
A-15
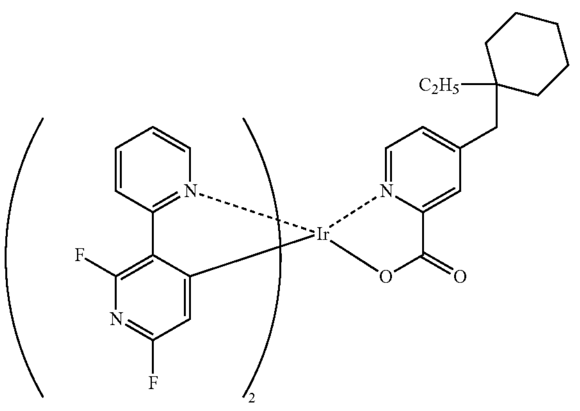
A-35
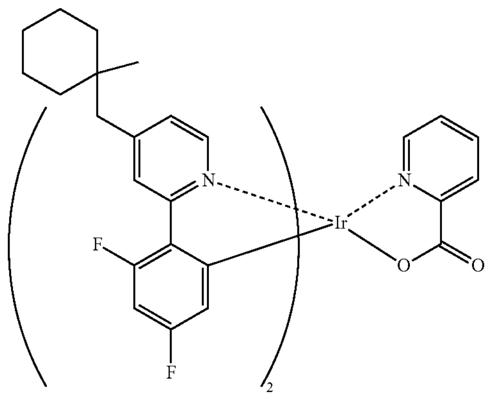
A-36
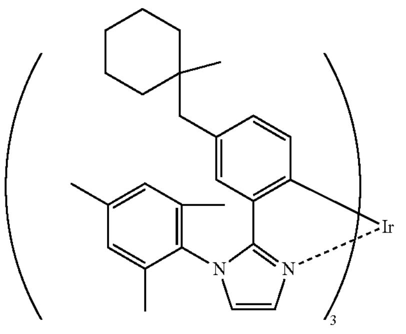
A-37
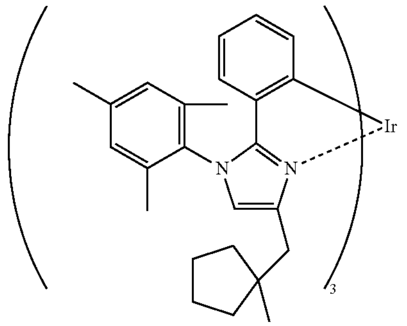
B-10
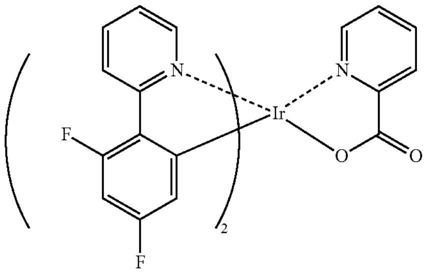
B-11
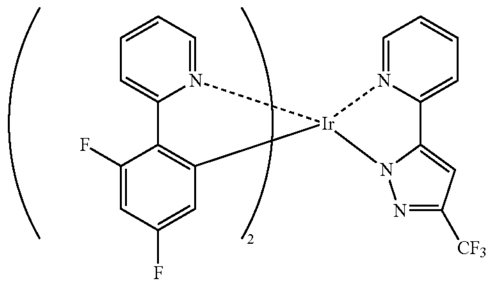
B-12
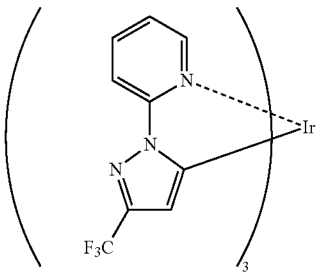

-continued

B-13

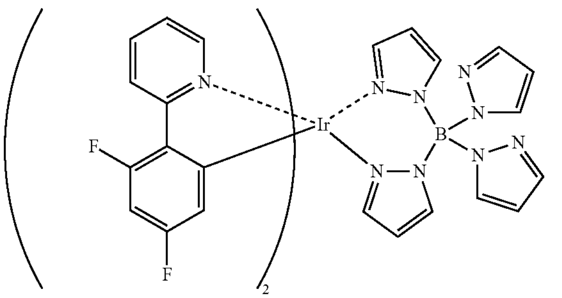

B-14

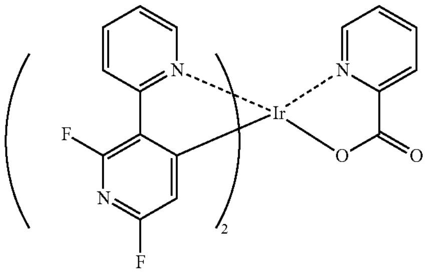

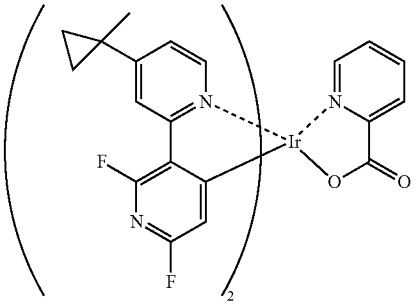

C-10

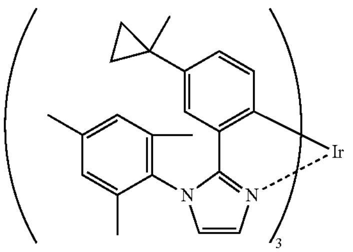

C-36

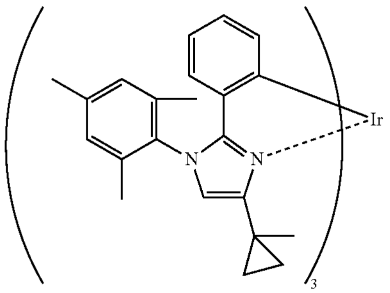

C-37

(Compounds 33, 38 and 42 described in JP-A-2008-210941)

The organic EL device of Example 3-1 was produced in the same manner as in Example 1-1 except that in Example 1-1, the film of the third layer (light emitting layer) was deposited (film thickness: 50 nm) by changing the compositional ratio to H-2 and A-10 of 93:7 (by mass) from H-1 and A-1 of 95:5 (by mass). A DC voltage was applied to the organic EL device to produce luminescence by using Source Measure Unit Model 2400 manufactured by Toyo Corp., as a result, luminescence derived from A-10 was obtained.

Examples 3-2 to 3-9 and Comparative Examples 3-1 to 3-8

The devices of Examples 3-2 to 3-9 and Comparative Examples 3-1 to 3-8 were produced in the same manner as in Example 3-1 except for changing the materials used in Example 3-1 to the materials shown in Table 3. A DC voltage was applied to the organic EL device to produce luminescence by using Source Measure Unit Model 2400 manufactured by Toyo Corp., as a result, luminescence derived from respective light emitting materials was obtained.

TABLE 3

| | Light Emitting Layer | | Drive | External Quantum | Half-Luminance Time at | | Chromaticity after |
|---|---|---|---|---|---|---|---|
| | Light Emitting Material | Host Material | Voltage at 100 cd/m$^2$ (V) | Efficiency at 100 cd/m$^2$ (%) | 1000 cd/m$^2$ (relative value) | Initial Chromaticity | Decrease to Half Luminance |
| Comparative Example 3-1 | B-10 | H-2 | 8.1 | 9.2 | 100 | (0.17, 0.32) | (0.19, 0.39) |
| Comparative Example 3-2 | B-11 | H-3 | 8.8 | 7.8 | 43 | (0.17, 0.29) | (0.21, 0.35) |

TABLE 3-continued

| | Light Emitting Layer | | Drive | External Quantum | Half-Luminance Time at | | Chromaticity after |
|---|---|---|---|---|---|---|---|
| | Light Emitting Material | Host Material | Voltage at 100 cd/$m^2$ (V) | Efficiency at 100 cd/$m^2$ (%) | 1000 cd/$m^2$ (relative value) | Initial Chromaticity | Decrease to Half Luminance |
| Comparative Example 3-3 | B-12 | H-3 | 10.4 | 3.6 | 16 | (0.17, 0.26) | (0.20, 0.35) |
| Comparative Example 3-4 | B-13 | H-2 | 7.9 | 8.7 | 83 | (0.17, 0.28) | (0.22, 0.35) |
| Comparative Example 3-5 | B-14 | H-2 | 8.3 | 9.5 | 71 | (0.17, 0.22) | (0.21, 0.30) |
| Comparative Example 3-6 | C-10 | H-2 | 8.3 | 8.8 | 49 | (0.17,0.33) | (0.21,0.41) |
| Comparative Example 3-7 | C-36 | H-2 | 8.5 | 6.8 | 21 | (0.17, 0.29) | (0.21, 0.36) |
| Comparative Example 3-8 | C-37 | H-2 | 8.6 | 6.9 | 22 | (0.17, 0.29) | (0.21, 0.36) |
| Example 3-1 | A-10 | H-2 | 8.0 | 9.7 | 110 | (0.18, 0.33) | (0.18, 0.36) |
| Example 3-2 | A-11 | H-3 | 8.7 | 8.4 | 53 | (0.18, 0.30) | (0.19, 0.32) |
| Example 3-3 | A-12 | H-3 | 10.0 | 4.2 | 25 | (0.18, 0.28) | (0.18, 0.30) |
| Example 3-4 | A-13 | H-2 | 7.6 | 9.4 | 94 | (0.17, 0.28) | (0.19, 0.31) |
| Example 3-5 | A-14 | H-2 | 7.8 | 9.9 | 103 | (0.17, 0.23) | (0.18, 0.25) |
| Example 3-6 | A-15 | H-2 | 8.1 | 9.8 | 89 | (0.17, 0.23) | (0.17, 0.24) |
| Example 3-7 | A-35 | H-2 | 7.8 | 9.0 | 108 | (0.17, 0.33) | (0.19, 0.35) |
| Example 3-8 | A-36 | H-2 | 7.9 | 7.1 | 36 | (0.17, 0.29) | (0.18, 0.31) |
| Example 3-9 | A-37 | H-2 | 7.9 | 7.2 | 37 | (0.17, 0.29) | (0.18, 0.31) |

It is seen that in Examples 3-1 to 3-6, the compound of the present invention is used as the light emitting material and therefore, the device exhibits high efficiency and a long half-luminance time and is excellent in terms of durability as compared with Comparative Examples 3-1 to 3-5. Also, the chromaticity shift is less caused at the device deterioration and the voltage is low. Furthermore, in Examples 3-6 to 3-9 using A-15, A-35, A-36 and A-37 of the present invention, the device is excellent in terms of durability (the half-luminance time is long), chromaticity shift at device deterioration, and low voltage as compared with Comparative Examples 3-6 to 3-8 using corresponding Compounds C-10, C-36 and C-37 described in JP-A-2008-210941.

Example 4

Example 4-1

A-16

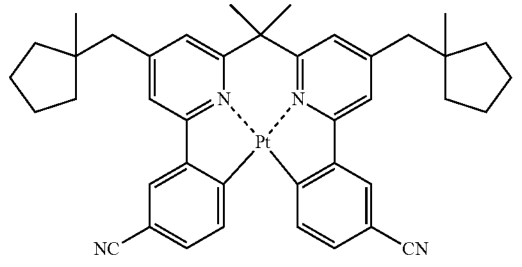

-continued

A-17

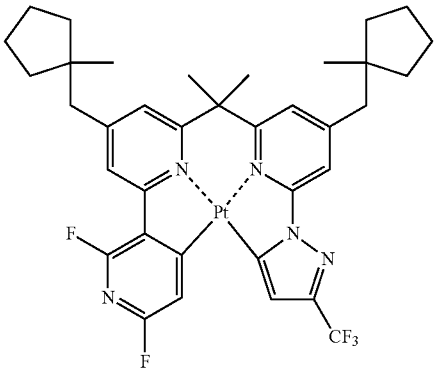

A-18

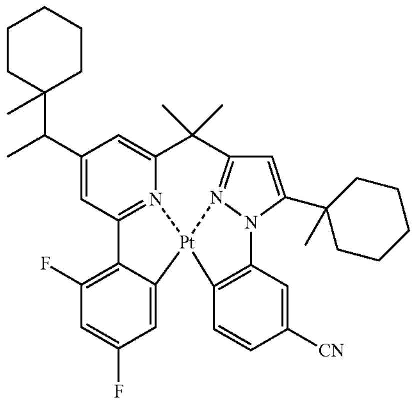

-continued
A-19
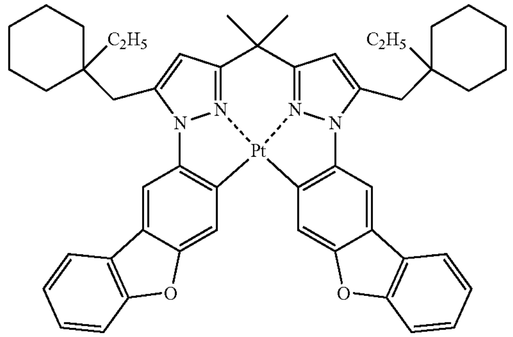
A-20
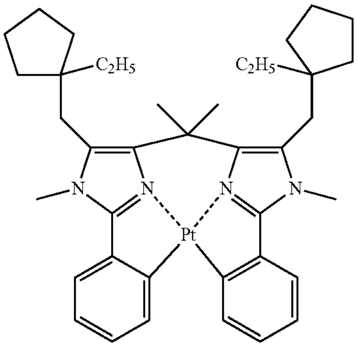
A-21
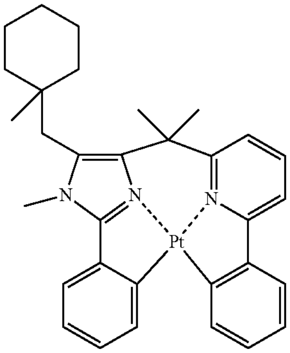
A-22
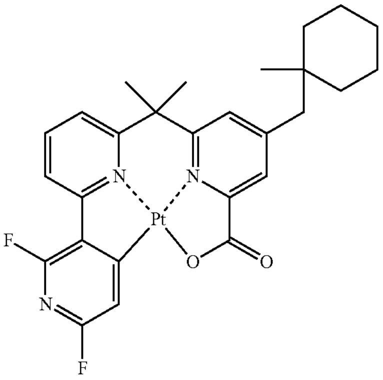
-continued
A-23
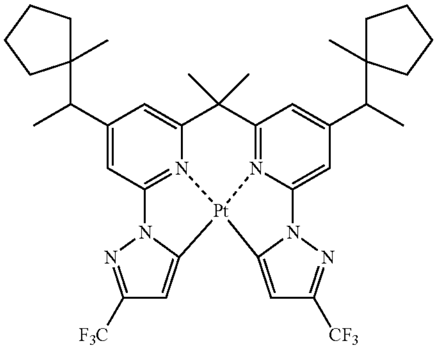
A-24
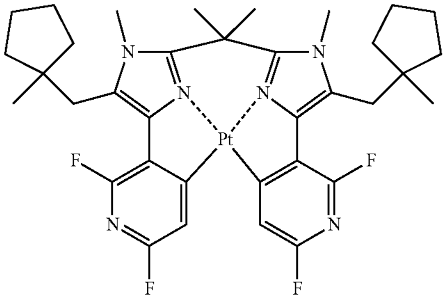
B-16
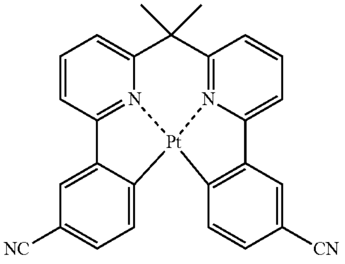
B-17
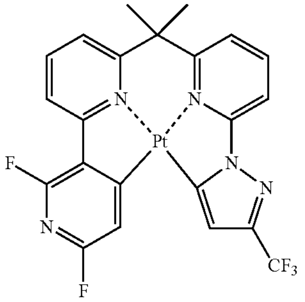
B-18
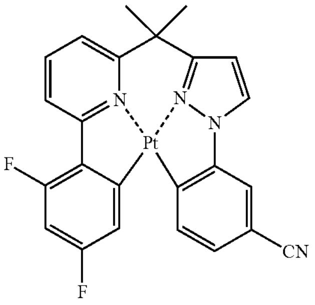

-continued

B-19

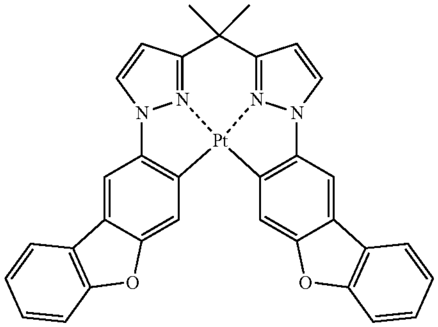

B-20

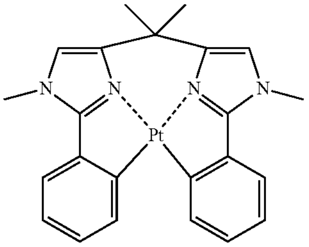

B-21

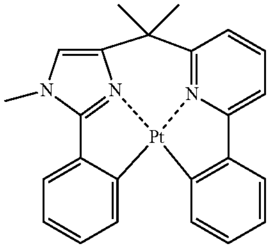

B-22

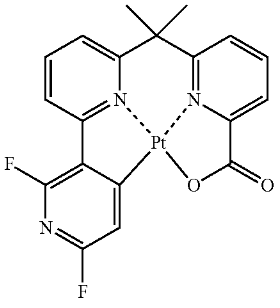

-continued

B-23

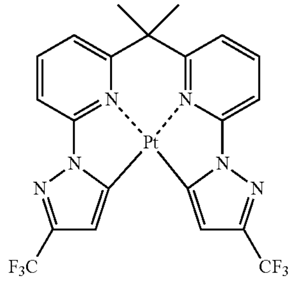

B-24

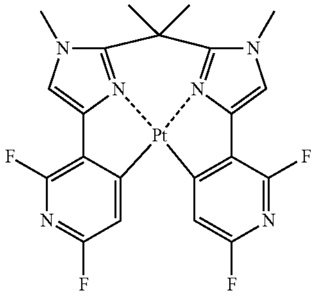

The organic EL device of Example 4-1 was produced in the same manner as in Example 1-1 except that in Example 1-1, the film of the third layer (light emitting layer) was deposited (film thickness: 50 nm) by changing the compositional ratio to H-2 and A-16 of 95:5 (by mass) from H-1 and A-1 of 95:5 (by mass). A DC voltage was applied to the organic EL device to produce luminescence by using Source Measure Unit Model 2400 manufactured by Toyo Corp., as a result, luminescence derived from A-14 was obtained.

Examples 4-2 to 4-9 and Comparative Examples 4-1 to 4-9

The devices of Examples 4-2 to 4-9 and Comparative Examples 4-1 to 4-9 were produced in the same manner as in Example 4-1 except for changing the materials used in Example 4-1 to the materials shown in Table 4. A DC voltage was applied to the organic EL device to produce luminescence by using Source Measure Unit Model 2400 manufactured by Toyo Corp., as a result, luminescence derived from respective light emitting materials was obtained.

TABLE 4

| | Light Emitting Layer | | Drive | External Quantum | Half-Luminance Time at | | Chromaticity after |
|---|---|---|---|---|---|---|---|
| | Light Emitting Material | Host Material | Voltage at 100 cd/m$^2$ (V) | Efficiency at 100 cd/m$^2$ (%) | 1000 cd/m$^2$ (relative value) | Initial Chromaticity | Decrease to Half Luminance |
| Comparative Example 4-1 | B-16 | H-2 | 8.6 | 9.9 | 100 | (0.29, 0.63) | (0.34, 0.63) |
| Comparative Example 4-2 | B-17 | H-3 | 9.8 | 7.9 | 59 | (0.17, 0.29) | (0.24, 0.35) |
| Comparative Example 4-3 | B-18 | H-3 | 9.4 | 8.5 | 57 | (0.17, 0.29) | (0.23, 0.35) |
| Comparative Example 4-4 | B-19 | H-2 | 9.9 | 7.7 | 52 | (0.20, 0.29) | (0.26, 0.35) |
| Comparative Example 4-5 | B-20 | H-2 | 8.9 | 8.2 | 55 | (0.21, 0.30) | (0.26, 0.34) |
| Comparative Example 4-6 | B-21 | H-2 | 9.0 | 7.1 | 44 | (0.24, 0.66) | (0.29, 0.60) |

TABLE 4-continued

| | Light Emitting Layer | | Drive | External Quantum | Half-Luminance Time at | | Chromaticity after |
|---|---|---|---|---|---|---|---|
| | Light Emitting Material | Host Material | Voltage at 100 cd/m$^2$ (V) | Efficiency at 100 cd/m$^2$ (%) | 1000 cd/m$^2$ (relative value) | Initial Chromaticity | Decrease to Half Luminance |
| Comparative Example 4-7 | B-22 | H-2 | 9.6 | 7.2 | 58 | (0.23, 0.37) | (0.27, 0.42) |
| Comparative Example 4-8 | B-23 | H-2 | 9.9 | 6.8 | 28 | (0.16, 0.24) | (0.22, 0.30) |
| Comparative Example 4-9 | B-24 | H-3 | 8.9 | 7.8 | 46 | (0.20, 0.30) | (0.26, 0.35) |
| Example 4-1 | A-16 | H-2 | 7.9 | 11.3 | 118 | (0.29, 0.60) | (0.29, 0.61) |
| Example 4-2 | A-17 | H-3 | 8.9 | 8.0 | 77 | (0.16, 0.28) | (0.19, 0.31) |
| Example 4-3 | A-18 | H-3 | 9.3 | 9.2 | 69 | (0.18, 0.30) | (0.18, 0.32) |
| Example 4-4 | A-19 | H-2 | 7.6 | 9.2 | 61 | (0.21, 0.30) | (0.22, 0.31) |
| Example 4-5 | A-20 | H-2 | 8.2 | 9.7 | 66 | (0.22, 0.30) | (0.23, 0.33) |
| Example 4-6 | A-21 | H-2 | 8.1 | 9.7 | 55 | (0.24, 0.65) | (0.25, 0.63) |
| Example 4-7 | A-22 | H-2 | 9.0 | 8.1 | 70 | (0.23, 0.36) | (0.25, 0.38) |
| Example 4-8 | A-23 | H-2 | 9.5 | 7.4 | 38 | (0.16, 0.24) | (0.18, 0.26) |
| Example 4-9 | A-24 | H-3 | 8.4 | 8.3 | 56 | (0.19, 0.29) | (0.21, 0.32) |

It is seen that in Examples 4-1 to 4-9, the compound of the present invention is used as the light emitting material and therefore, the device exhibits high efficiency and a long half-luminance time and is excellent in terms of durability as compared with Comparative Examples 4-1 to 4-9. Also, the chromaticity shift is less caused at the device deterioration and the voltage is low.

Example 5

Example 5-1

A 0.5 mm-thick 2.5 cm-square glass substrate having thereon ITO film (produced by GEOMATEC Corporation, surface resistance: 10 Ω/sq.) was placed in a cleaning vessel and subjected to ultrasonic cleaning in 2-propanol and then to a UV-ozone treatment for 30 minutes. On this substrate, a solution obtained by diluting poly(3,4-ethylenedioxythiophene)-polystyrene sulfonate (PEDOT/PSS) to 70% with pure water was coated by means of a spin coater to provide a hole transporting layer of 50 nm in thickness, and a methylene chloride solution having dissolved therein H-1 and A-1 in a ratio of 98/2 (by mass) was further coated by means of a spin coater to obtain a light emitting layer of 30 nm in thickness. Thereafter, BAlq [aluminum bis-(2-methyl-8-quinolinato)-4-phenylphenolate] was deposited thereon to a thickness of 40 nm (fourth layer). On this organic compound layer, lithium fluoride of 0.5 nm as a cathode buffer layer and aluminum of 150 nm as a cathode were deposited in a vapor deposition apparatus. The obtained laminate was placed in an argon gas-purged glove box without exposing to the atmosphere and then encapsulated using a stainless steel-made sealing can and an ultraviolet curable adhesive (XNR5516HV, produced by Nagase-Ciba Ltd.) to produce the organic EL device of Example 5-1. A DC voltage was applied to the organic EL device to produce luminescence by using Source Measure Unit Model 2400 manufactured by Toyo Corp., as a result, luminescence derived from Compound A-1 of the present invention was obtained.

Examples 5-2 to 5-3 and Comparative Examples 5-1 to 5-3

The devices of Examples 5-2 to 5-3 and Comparative Examples 5-1 to 5-3 were produced in the same manner as in Example 5-1 except for changing the materials used in Example 5-1 to the materials shown in Table 5. A DC voltage was applied to the organic EL device to produce luminescence by using Source Measure Unit Model 2400 manufactured by Toyo Corp., as a result, luminescence derived from respective light emitting materials was obtained.

TABLE 5

| | Light Emitting Layer | | Drive | External Quantum | Half-Luminance Time at | | Chromaticity after |
|---|---|---|---|---|---|---|---|
| | Light Emitting Material | Host Material | Voltage at 100 cd/m$^2$ (V) | Efficiency at 100 cd/m$^2$ (%) | 1000 cd/m$^2$ (relative value) | Initial Chromoaticity | Decrease to Half Luminance |
| Comparative Example 5-1 | B-1 | H-1 | 11.2 | 8.3 | 100 | (0.61, 0.38) | (0.66, 0.31) |
| Comparative Example 5-2 | B-3 | H-1 | 11.8 | 6.7 | 66 | (0.49, 0.49) | (0.53, 0.45) |
| Comparative Example 5-3 | B-5 | H-1 | 11.1 | 9.2 | 62 | (0.41, 0.57) | (0.44, 0.52) |
| Example 5-1 | A-1 | H-1 | 10.5 | 9.0 | 128 | (0.60, 0.37) | (0.61, 0.35) |
| Example 5-2 | A-3 | H-1 | 10.4 | 7.8 | 85 | (0.51, 0.49) | (0.52, 0.47) |
| Example 5-3 | A-5 | H-1 | 10.2 | 10.4 | 87 | (0.42, 0.56) | (0.41, 0.55) |

It is seen that in Examples 5-1 to 5-3, the compound of the present invention is used as the light emitting material and therefore, the device exhibits high efficiency and a long half-luminance time and is excellent in terms of durability as compared with Comparative Examples 5-1 to 5-3. Also, the chromaticity shift is less caused at the device deterioration and the voltage is low.

Example 6

Example 6-1

The organic EL device of Example 6-1 was produced in the same manner as in Example 5-1 except that in Example 5-1, the solution of the third layer (light emitting layer) was coated (film thickness: 50 nm) by changing the compositional ratio to H-1 and A-6 of 96:4 (by mass) from H-1 and A-1 of 98:2 (by mass). A DC voltage was applied to the organic EL device to produce luminescence by using Source Measure Unit Model 2400 manufactured by Toyo Corp., as a result, luminescence derived from A-6 was obtained.

Example 6-2 and Comparative Examples 6-1 and 6-2

The devices of Example 6-2 and Comparative Examples 6-1 and 6-2 were produced in the same manner as in Example 6-1 except for changing the materials used in Example 6-1 to the materials shown in Table 6. A DC voltage was applied to the organic EL device to produce luminescence by using Source Measure Unit Model 2400 manufactured by Toyo Corp., as a result, luminescence derived from respective light emitting materials was obtained.

TABLE 6

| | Light Emitting Layer | | Drive | External Quantum | Half-Luminance Time at | | Chromaticity after |
|---|---|---|---|---|---|---|---|
| | Light Emitting Material | Host Material | Voltage at 100 cd/$m^2$ (V) | Efficiency at 100 cd/$m^2$ (%) | 1000 cd/$m^2$ (relative value) | Initial Chromaticity | Decrease to Half Luminance |
| Comparative Example 6-1 | B-6 | H-1 | 11.6 | 8.3 | 100 | (0.29, 0.64) | (0.33, 0.59) |
| Comparative Example 6-2 | B-8 | H-1 | 11.9 | 6.8 | 71 | (0.27, 0.61) | (0.32, 0.68) |
| Example 6-1 | A-6 | H-1 | 10.7 | 9.0 | 115 | (0.27, 0.65) | (0.29, 0.64) |
| Example 6-2 | A-8 | H-1 | 11.2 | 7.5 | 80 | (0.26, 0.60) | (0.28, 0.64) |

It is seen that in Examples 6-1 and 6-2, the compound of the present invention is used as the light emitting material and therefore, the device exhibits high efficiency and a long half-luminance time and is excellent in terms of durability as compared with Comparative Examples 6-1 and 6-2. Also, the chromaticity shift is less caused at the device deterioration and the voltage is low.

Example 7

Example 7-1

H-4

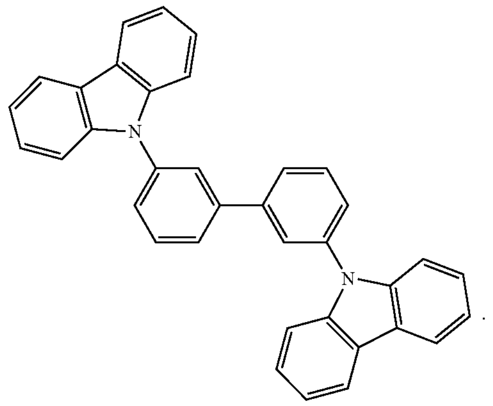

The organic EL device of Example 7-1 was produced in the same manner as in Example 5-1 except that in Example 5-1, the solution of the third layer (light emitting layer) was coated (film thickness: 50 nm) by changing the compositional ratio to H-4 and A-10 of 96:4 (by mass) from H-1 and A-1 of 98:2 (by mass). A DC voltage was applied to the organic EL device to produce luminescence by using Source Measure Unit Model 2400 manufactured by Toyo Corp., as a result, luminescence derived from A-6 was obtained.

Example 7-2 and Comparative Examples 7-1 and 7-2

The devices of Example 7-2 and Comparative Examples 7-1 and 7-2 were produced in the same manner as in Example 7-1 except for changing the materials used in Example 7-1 to the materials shown in Table 7. A DC voltage was applied to the organic EL device to produce luminescence by using Source Measure Unit Model 2400 manufactured by Toyo Corp., as a result, luminescence derived from respective light emitting materials was obtained.

TABLE 7

| | Light Emitting Layer | | Drive | External Quantum | Half-Luminance Time at | | Chromaticity after |
|---|---|---|---|---|---|---|---|
| | Light Emitting Material | Host Material | Voltage at 100 cd/m$^2$ (V) | Efficiency at 100 cd/m$^2$ (%) | 1000 cd/m$^2$ (relative value) | Initial Chromaticity | Decrease to Half Luminance |
| Comparative Example 7-1 | B-10 | H-4 | 14.1 | 5.8 | 100 | (0.17, 0.32) | (0.20, 0.40) |
| Comparative Example 7-2 | B-14 | H-4 | 13.9 | 6.1 | 75 | (0.17, 0.22) | (0.21, 0.30) |
| Example 7-1 | A-10 | H-4 | 13.6 | 6.7 | 113 | (0.18, 0.33) | (0.19, 0.34) |
| Example 7-2 | A-14 | H-4 | 13.4 | 6.9 | 94 | (0.17, 0.22) | (0.18, 0.24) |

It is seen that in Examples 7-1 and 7-2, the compound of the present invention is used as the light emitting material and therefore, the device exhibits high efficiency and a long half-luminance time and is excellent in terms of durability as compared with Comparative Examples 7-1 and 7-2. Also, the chromaticity shift is less caused at the device deterioration and the voltage is low.

Example 8

Example 8-1

The organic EL device of Example 8-1 was produced in the same manner as in Example 5-1 except that in Example 5-1, the solution of the third layer (light emitting layer) was coated (film thickness: 50 nm) by changing the compositional ratio to H-4 and A-16 of 96:4 (by mass) from H-1 and A-1 of 98:2 (by mass). A DC voltage was applied to the organic EL device to produce luminescence by using Source Measure Unit Model 2400 manufactured by Toyo Corp., as a result, luminescence derived from A-16 was obtained.

Examples 8-2 to 8-5 and Comparative Examples 8-1 to 8-5

The devices of Examples 8-2 to 8-5 and Comparative Examples 8-1 to 8-5 were produced in the same manner as in Example 8-1 except for changing the materials used in Example 8-1 to the materials shown in Table 8. A DC voltage was applied to the organic EL device to produce luminescence by using Source Measure Unit Model 2400 manufactured by Toyo Corp., as a result, luminescence derived from respective light emitting materials was obtained.

TABLE 8

| | Light Emitting Layer | | Drive | External Quantum | Half-Luminance Time at | | Chromaticity after |
|---|---|---|---|---|---|---|---|
| | Light Emitting Material | Host Material | Voltage at 100 cd/$m^2$ (V) | Efficiency at 100 cd/$m^2$ (%) | 1000 cd/$m^2$ (relative value) | Initial Chromoaticity | Decrease to Half Luminance |
| Comparative Example 8-1 | B-15 | H-4 | 13.3 | 6.1 | 100 | (0.29, 0.63) | (0.31, 0.63) |
| Comparative Example 8-2 | B-16 | H-4 | 14.5 | 4.7 | 64 | (0.18, 0.30) | (0.20, 0.34) |
| Comparative Example 8-3 | B-17 | H-4 | 14.1 | 5.7 | 61 | (0.18, 0.30) | (0.20, 0.33) |
| Comparative Example 8-4 | B-20 | H-4 | 13.8 | 5.3 | 47 | (0.24, 0.66) | (0.27, 0.62) |
| Comparative Example 8-5 | B-22 | H-4 | 15.5 | 4.3 | 32 | (0.16, 0.24) | (0.23, 0.32) |
| Example 8-1 | A-15 | H-4 | 12.7 | 6.9 | 116 | (0.29, 0.60) | (0.30, 0.62) |
| Example 8-2 | A-16 | H-4 | 13.6 | 5.6 | 79 | (0.17, 0.29) | (0.19, 0.32) |
| Example 8-3 | A-17 | H-4 | 13.7 | 6.6 | 73 | (0.19, 0.30) | (0.20, 0.32) |
| Example 8-4 | A-20 | H-4 | 13.0 | 6.3 | 56 | (0.24, 0.65) | (0.26, 0.64) |
| Example 8-5 | A-22 | H-4 | 14.9 | 5.0 | 43 | (0.16, 0.24) | (0.19, 0.27) |

It is seen that in Examples 8-1 to 8-5, the compound of the present invention is used as the light emitting material and therefore, the device exhibits high efficiency and a long half-luminance time and is excellent in terms of durability as compared with Comparative Examples 8-1 to 8-5. Also, the chromaticity shift is less caused at the device deterioration and the voltage is low.

Example 9

Example 9-1

A-6

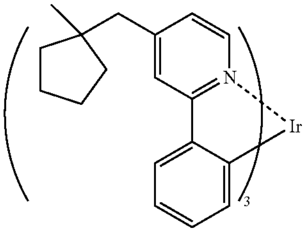

A-25

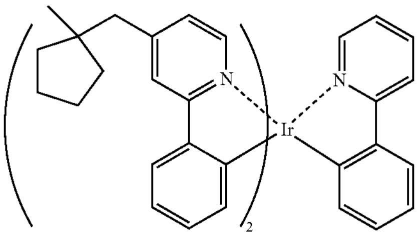

A-26

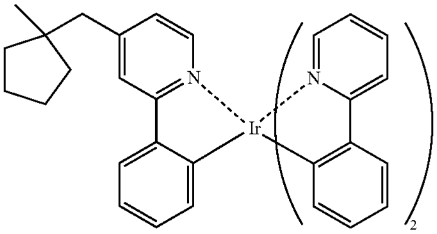

A-27

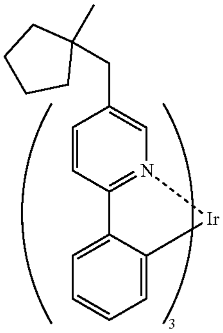

-continued

A-28

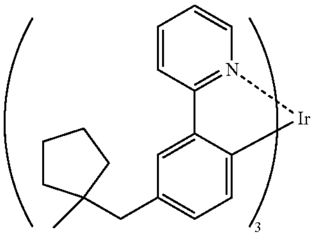

A-29

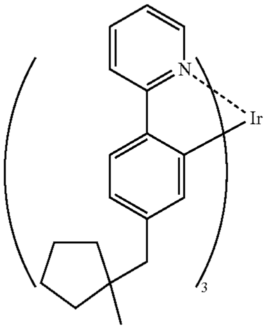

B-6

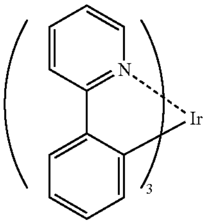

The organic EL device of Example 9-1 was produced in the same manner as in Example 1-1 except that in Example 1-1, the film of the third layer (light emitting layer) was deposited (film thickness: 50 nm) by changing the compositional ratio to H-1 and A-6 of 93:7 (by mass) from H-1 and A-1 of 98:2 (by mass). A DC voltage was applied to the organic EL device to produce luminescence by using Source Measure Unit Model 2400 manufactured by Toyo Corp., as a result, luminescence derived from A-6 was obtained.

Examples 9-2 to 9-6 and Comparative Example 9-1

The devices of Examples 9-2 to 9-6 and Comparative Example 9-1 were produced in the same manner as in Example 9-1 except for changing the materials used in Example 9-1 to the materials shown in Table 9. A DC voltage was applied to the organic EL device to produce luminescence by using Source Measure Unit Model 2400 manufactured by Toyo Corp., as a result, luminescence derived from respective light emitting materials was obtained.

TABLE 9

| | Light Emitting Layer | | Drive | External Quantum | Half-Luminance Time at | | Chromaticity after |
|---|---|---|---|---|---|---|---|
| | Light Emitting Material | Host Material | Voltage at 100 cd/m$^2$ (V) | Efficiency at 100 cd/m$^2$ (%) | 1000 cd/m$^2$ (relative value) | Initial Chromoaticity | Decrease to Half Luminance |
| Comparative Example 9-1 | B-6 | H-1 | 8.1 | 13.3 | 100 | (0.29, 0.64) | (0.32, 0.60) |
| Example 9-1 | A-6 | H-1 | 7.9 | 14.1 | 125 | (0.28, 0.65) | (0.29, 0.64) |
| Example 9-2 | A-25 | H-1 | 7.8 | 14.0 | 121 | (0.29, 0.64) | (0.30, 0.63) |
| Example 9-3 | A-26 | H-1 | 7.7 | 13.8 | 109 | (0.29, 0.64) | (0.31, 0.62) |
| Example 9-4 | A-27 | H-1 | 8.0 | 13.8 | 119 | (0.30, 0.62) | (0.31, 0.63) |
| Example 9-5 | A-28 | H-1 | 7.9 | 14.0 | 121 | (0.31, 0.63) | (0.31, 0.62) |
| Example 9-6 | A-29 | H-1 | 7.9 | 13.9 | 119 | (0.29, 0.64) | (0.30, 0.63) |

It is seen that in Examples 9-1 to 9-6, the compound of the present invention is used as the light emitting material and therefore, although the degree of effect differs according to the number of partial structures and the substitution position, the device exhibits high efficiency and a long half-luminance time and is excellent in terms of durability as compared with Comparative Example 9-1. Also, the chromaticity shift is less caused at the device deterioration and the voltage is low.

Example 10

Example 10-1

A-14

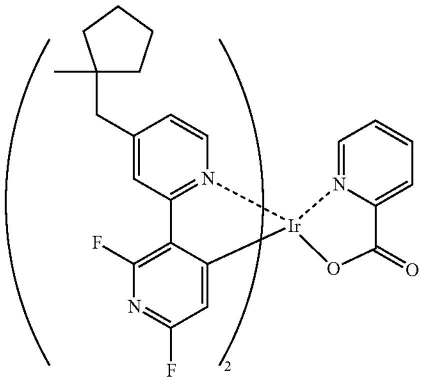

A-30

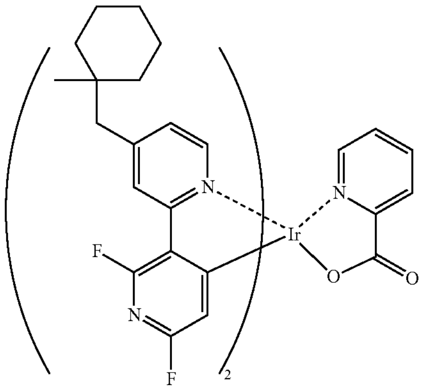

-continued

A-31

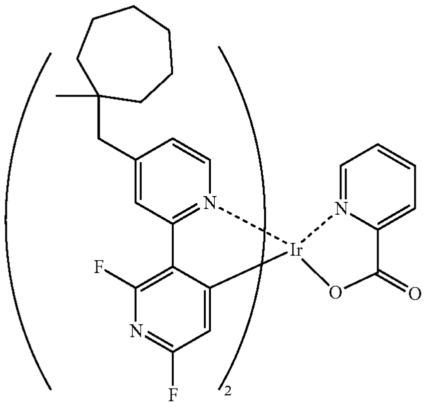

A-32

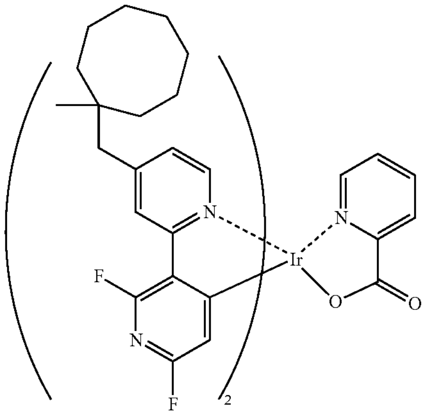

B-14

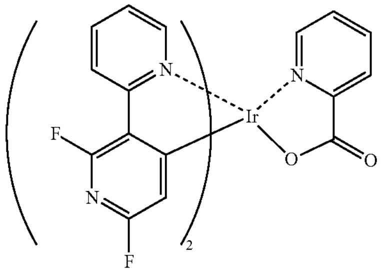

The organic EL device of Example 10-1 was produced in the same manner as in Example 1-1 except that in Example 1-1, the film of the third layer (light emitting layer) was deposited (film thickness: 50 nm) by changing the compositional ratio to H-2 and A-14 of 90:10 (by mass) from H-1 and A-1 of 95:5 (by mass). A DC voltage was applied to the organic EL device to produce luminescence by using Source Measure Unit Model 2400 manufactured by Toyo Corp., as a result, luminescence derived from A-14 was obtained.

Examples 10-2 to 10-4 and Comparative Example 10-1

The devices of Examples 10-2 to 10-4 and Comparative Example 10-1 were produced in the same manner as in Example 10-1 except for changing the materials used in Example 10-1 to the materials shown in Table 10. A DC voltage was applied to the organic EL device to produce luminescence by using Source Measure Unit Model 2400 manufactured by Toyo Corp., as a result, luminescence derived from respective light emitting materials was obtained.

TABLE 10

| | Light Emitting Layer | | Drive | External Quantum | Half-Luminance Time at | | Chromaticity after |
|---|---|---|---|---|---|---|---|
| | Light Emitting Material | Host Material | Voltage at 100 cd/m$^2$ (V) | Efficiency at 100 cd/m$^2$ (%) | 1000 cd/m$^2$ (relative value) | Initial Chromoaticity | Decrease to Half Luminance |
| Comparative Example 10-1 | B-14 | H-2 | 8.3 | 9.5 | 100 | (0.17, 0.22) | (0.21, 0.30) |
| Example 10-1 | A-14 | H-2 | 7.8 | 10.2 | 143 | (0.17, 0.23) | (0.18, 0.24) |
| Example 10-2 | A-30 | H-2 | 7.9 | 10.1 | 145 | (0.17, 0.22) | (0.17, 0.23) |
| Example 10-3 | A-31 | H-2 | 8.1 | 9.7 | 127 | (0.17, 0.23) | (0.19, 0.26) |
| Example 10-4 | A-32 | H-2 | 8.1 | 9.7 | 125 | (0.17, 0.23) | (0.19, 0.26) |

It is seen that in Examples 10-1 to 10-4, the compound of the present invention is used as the light emitting material and therefore, although the degree of effect differs according to the number of partial structures and the substitution position, the device exhibits high efficiency and a long half-luminance time and is excellent in terms of durability as compared with Comparative Example 10-1. Also, the chromaticity shift is less caused at the device deterioration and the voltage is low.

Example 11

Example 11-1

A-17

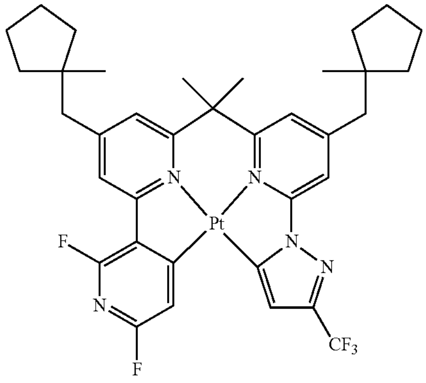

-continued

A-33

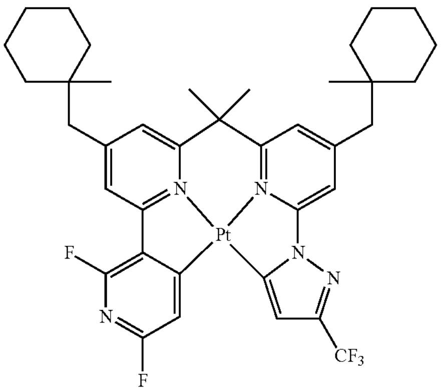

A-34

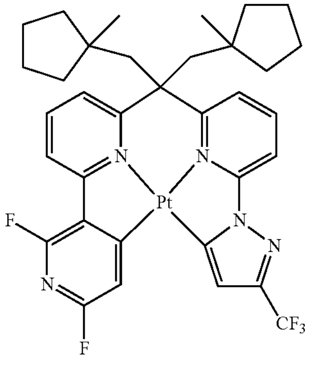

-continued

B-17

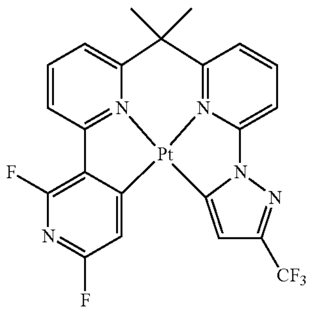

The organic EL device of Example 11-1 was produced in the same manner as in Example 1-1 except that in Example 1-1, the film of the third layer (light emitting layer) was deposited (film thickness: 50 nm) by changing the compositional ratio to H-2 and A-17 of 90:10 (by mass) from H-1 and A-1 of 95:5 (by mass). A DC voltage was applied to the organic EL device to produce luminescence by using Source Measure Unit Model 2400 manufactured by Toyo Corp., as a result, luminescence derived from A-17 was obtained.

Examples 11-2 and 11-3 and Comparative Example 11-1

The devices of Examples 11-2 and 11-3 and Comparative Example 11-1 were produced in the same manner as in Example 11-1 except for changing the materials used in Example 11-1 to the materials shown in Table 11. A DC voltage was applied to the organic EL device to produce luminescence by using Source Measure Unit Model 2400 manufactured by Toyo Corp., as a result, luminescence derived from respective light emitting materials was obtained.

TABLE 11

| | Light Emitting Layer | | Drive | External Quantum | Half-Luminance Time at | | Chromaticity after |
|---|---|---|---|---|---|---|---|
| | Light Emitting Material | Host Material | Voltage at 100 cd/m$^2$ (V) | Efficiency at 100 cd/m$^2$ (%) | 1000 cd/m$^2$ (relative value) | Initial Chromoaticity | Decrease to Half Luminance |
| Comparative Example 11-1 | B-17 | H-3 | 9.8 | 7.9 | 100 | (0.17, 0.29) | (0.24, 0.35) |
| Example 11-1 | A-17 | H-3 | 8.8 | 8.6 | 126 | (0.16, 0.28) | (0.20, 0.33) |
| Example 11-2 | A-33 | H-3 | 9.0 | 8.5 | 121 | (0.16, 0.28) | (0.20, 0.32) |
| Example 11-3 | A-34 | H-3 | 8.9 | 8.6 | 125 | (0.16, 0.29) | (0.20, 0.32) |

It is seen that in Examples 11-1 to 11-3, the compound of the present invention is used as the light emitting material and therefore, the device exhibits high efficiency and a long half-luminance time and is excellent in terms of durability as compared with Comparative Example 11-1. Also, the chromaticity shift is less caused at the device deterioration and the voltage is low.

Example 12

Example 12-1

A 100 μm-thick 2.5 cm-square glass substrate having thereon indium tin oxide (ITO) film (produced by GEOMATEC Corporation, surface resistance: 10 Ω/sq.) was placed in a cleaning vessel and subjected to ultrasonic cleaning in 2-propanol and then to a UV-ozone treatment for 30 minutes. On this transparent anode (ITO film), the following organic compound layers were sequentially deposited by the vacuum deposition method.

First layer: CuPc (copper phthalocyanine), thickness: 120 nm

Second layer: NPD (N,N'-di-α-naphthyl-N,N'-diphenyl)-benzidine, thickness: 7 nm

Third layer: CBP (4,4'-di(9-carbazoyl)biphenyl), thickness: 3 nm

Fourth layer (light emitting layer): dopant (9 mass %), mCBP (91 mass %), thickness: 30 nm Fifth layer: first electron transporting material (Balq), thickness: 30 nm On this layer, lithium fluoride of 1 nm and metal aluminum of 100 nm were deposited in this order to form a cathode.

The obtained laminate was placed in an argon gas-purged glove box without exposing to the atmosphere and then encapsulated using a stainless steel-made sealing can and an ultraviolet curable adhesive (XNR5516HV, produced by Nagase-Ciba Ltd.) to obtain the organic EL device of Example 12-1.

Examples 12-2 to 12-16 and Comparative Examples 12-1 to 12-13

The devices of Examples 12-2 to 12-16 and Comparative Examples 12-1 to 12-13 were produced in the same manner as in Example 12-1 except for changing the light emitting material of the device as shown in Table 12 below.

(Performance Evaluation of Organic Electroluminescence Device)

A DC voltage was applied to the organic EL device to produce luminescence by using Source Measure Unit Model 2400 manufactured by Toyo Corp., as a result, luminescence derived from the light emitting material used was obtained. The results are shown together in Table 12.

ref1

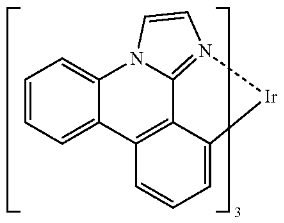

-continued
ref2
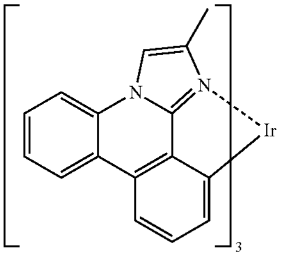
ref3
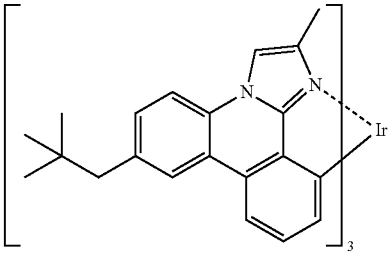
ref4
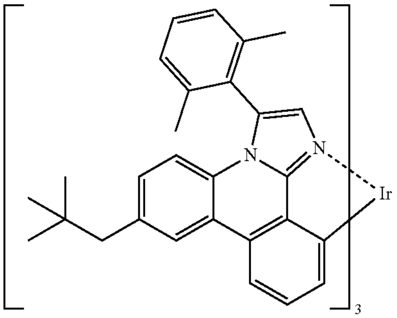
ref5
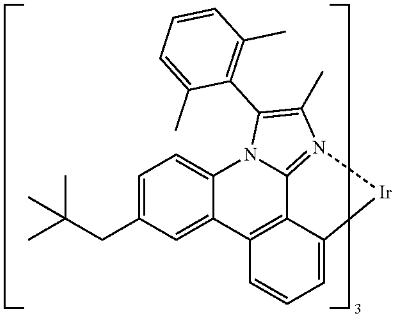
ref6
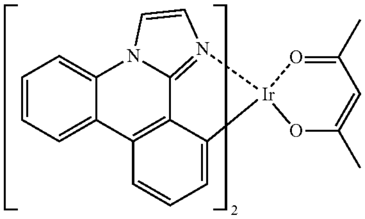
I-1
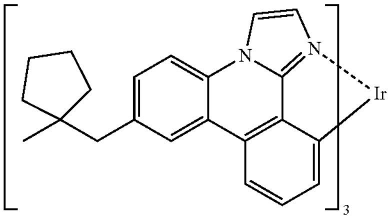
-continued
I-2
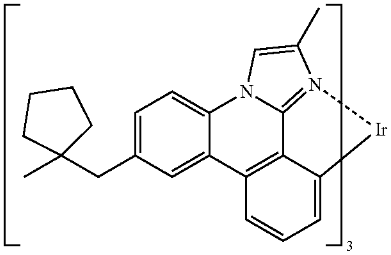
I-3
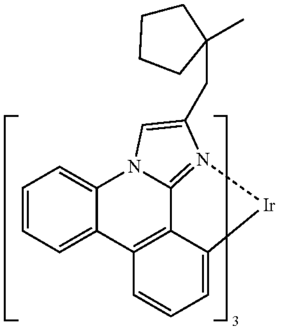
I-4
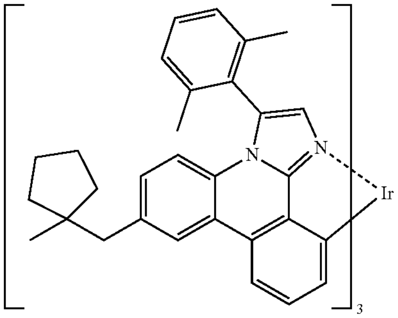
I-5
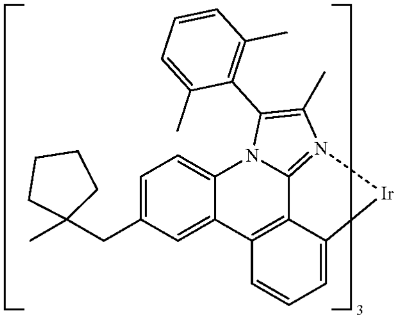
I-6
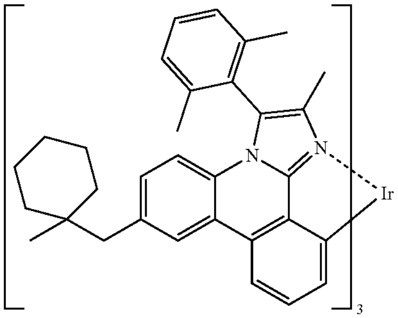

I-7
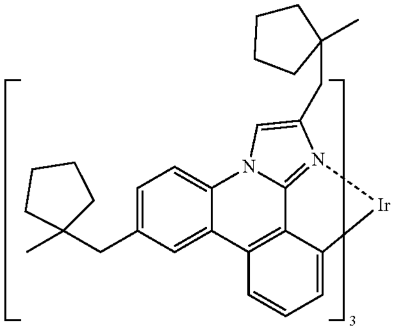
I-8
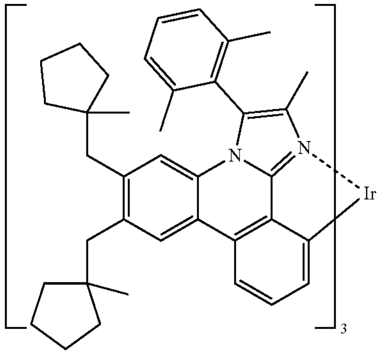
I-9
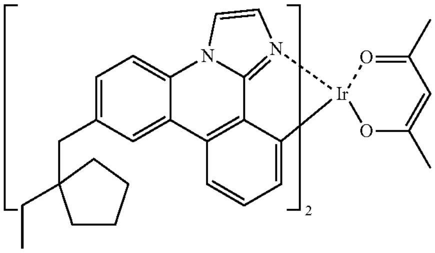
ref7
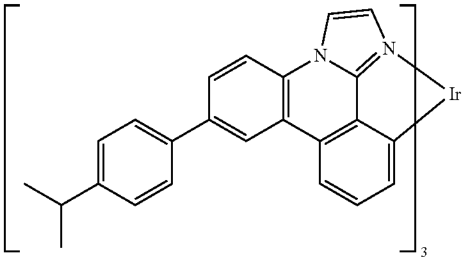
ref8
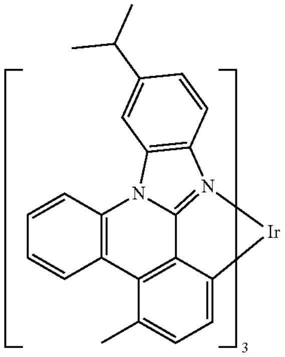
ref9
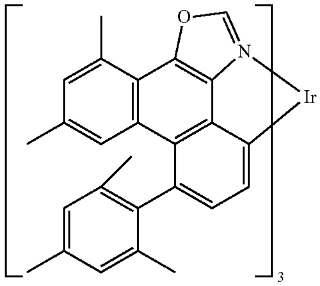
ref10
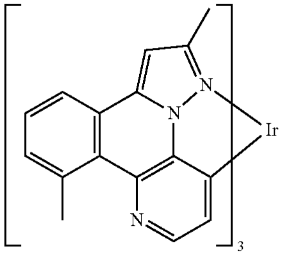
ref11
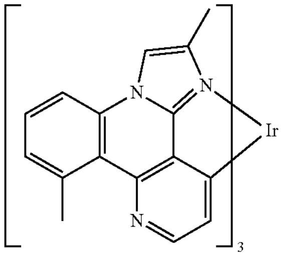
ref12
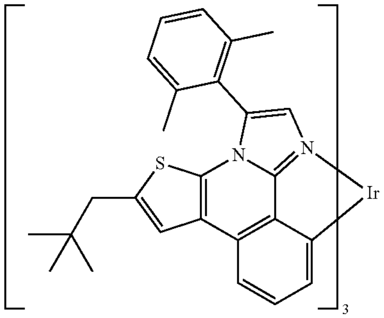
ref13
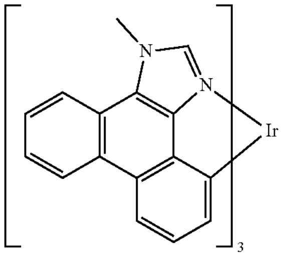

-continued
I-10
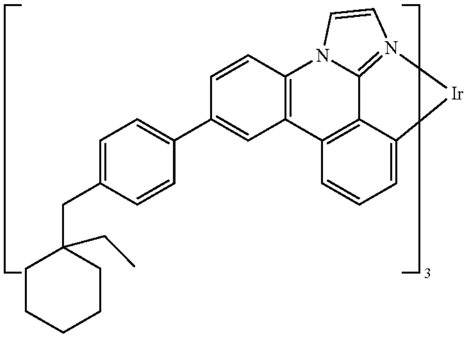
I-11
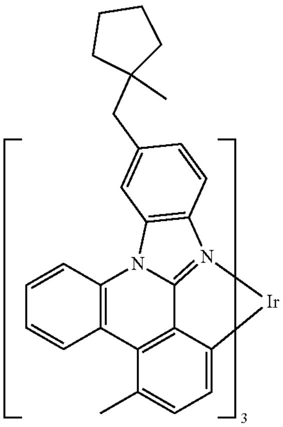
I-12
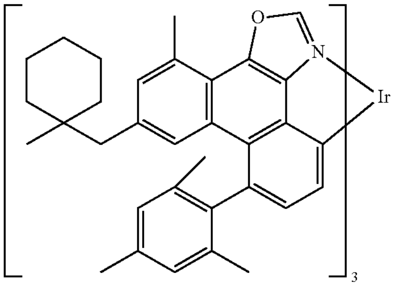
I-13
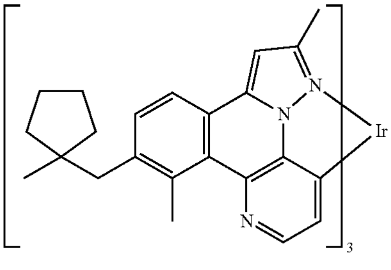
I-14
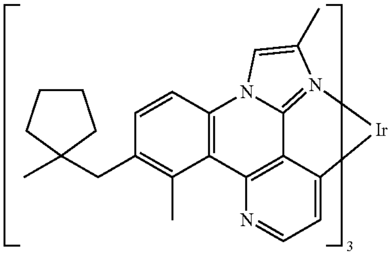
-continued
I-15
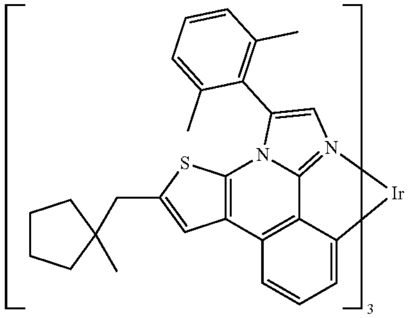
I-16
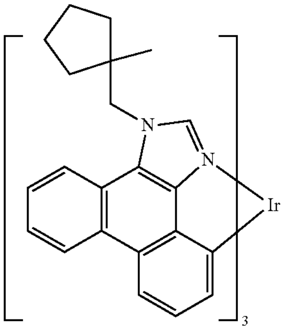
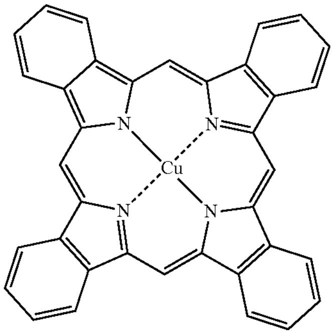
CuPc
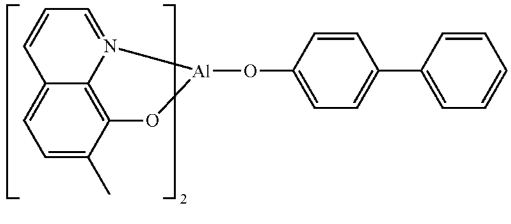
BAlq
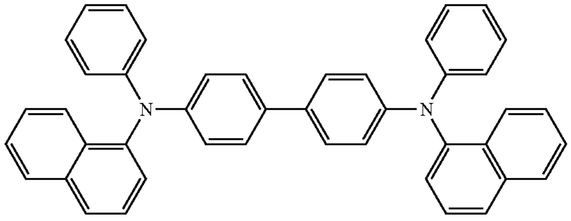
NPD -continued

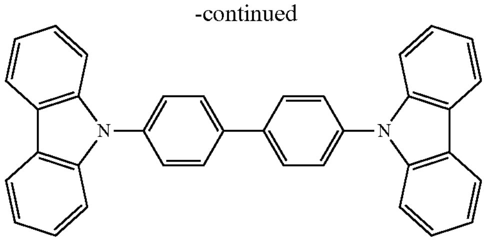

CBP

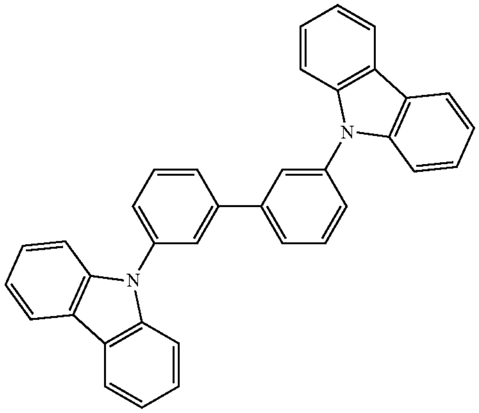

mCBP

TABLE 12

| | Light Emitting Material | Drive Voltage at 100 cd/$m^2$ (V) | External Quantum Efficiency at 100 cd/$m^2$ (%) | Half-Luminance Time at 1000 cd/$m^2$ (relative value) | Initial Chromoaticity | Chromaticity after Decrease to Half Luminance |
|---|---|---|---|---|---|---|
| Comparative Example 12-1 | ref 1 | 9.2 | 3.1 | 100 | (0.17, 0.29) | (0.23, 0.37) |
| Example 12-1 | I-1 | 9.0 | 5.1 | 115 | (0.17, 0.28) | (0.20, 0.35) |
| Comparative Example 12-2 | ref 2 | 9.3 | 8.8 | 85 | (0.17, 0.29) | (0.23, 0.37) |
| Comparative Example 12-3 | ref 3 | 9.6 | 7.0 | 120 | (0.17, 0.28) | (0.21, 0.36) |
| Example 12-2 | I-2 | 9.2 | 9.9 | 135 | (0.17, 0.28) | (0.19, 0.32) |
| Example 12-3 | I-3 | 9.3 | 9.8 | 125 | (0.17, 0.30) | (0.20, 0.33) |
| Comparative Example 12-4 | ref 4 | 9.5 | 6.6 | 128 | (0.17, 0.29) | (0.22, 0.35) |
| Example 12-4 | I-4 | 9.2 | 7.2 | 143 | (0.17, 0.29) | (0.20, 0.32) |
| Comparative Example 12-5 | ref 5 | 9.5 | 7.0 | 122 | (0.17, 0.30) | (0.23, 0.34) |
| Example 12-5 | I-5 | 9.0 | 7.8 | 139 | (0.17, 0.29) | (0.20, 0.32) |
| Example 12-6 | I-6 | 9.0 | 7.7 | 138 | (0.17, 0.29) | (0.20, 0.33) |
| Example 12-7 | I-7 | 9.2 | 7.6 | 135 | (0.17, 0.30) | (0.19, 0.32) |
| Example 12-8 | I-8 | 9.2 | 7.6 | 137 | (0.17, 0.30) | (0.19, 0.31) |
| Comparative Example 12-6 | ref 6 | 9.0 | 8.0 | 88 | (0.17, 0.30) | (0.23, 0.39) |
| Example 12-9 | I-9 | 8.8 | 8.8 | 105 | (0.18, 0.31) | (0.22, 0.36) |
| Comparative Example 12-7 | ref 7 | 9.3 | 6.1 | 95 | (0.21, 0.34) | (0.26, 0.39) |
| Example 12-10 | I-10 | 9.0 | 6.7 | 107 | (0.21, 0.33) | (0.25, 0.35) |
| Comparative Example 12-8 | ref 8 | 9.4 | 6.0 | 92 | (0.24, 0.36) | (0.28, 0.42) |
| Example 12-11 | I-11 | 9.2 | 6.9 | 106 | (0.23, 0.35) | (0.26, 0.39) |
| Comparative Example 12-9 | ref 9 | 9.5 | 5.8 | 60 | (0.26, 0.54) | (0.29, 0.59) |
| Example 12-12 | I-12 | 9.3 | 6.5 | 70 | (0.26, 0.54) | (0.27, 0.56) |
| Comparative Example 12-10 | ref 10 | 9.3 | 6.1 | 130 | (0.19, 0.28) | (0.24, 0.33) |
| Example 12-13 | I-13 | 9.1 | 6.7 | 142 | (0.19, 0.28) | (0.21, 0.30) |
| Comparative Example 12-11 | ref 11 | 9.2 | 6.7 | 135 | (0.19, 0.28) | (0.25, 0.32) |

TABLE 12-continued

| | Light Emitting Material | Drive Voltage at 100 cd/m$^2$ (V) | External Quantum Efficiency at 100 cd/m$^2$ (%) | Half-Luminance Time at 1000 cd/m$^2$ (relative value) | Initial Chromoaticity | Chromaticity after Decrease to Half Luminance |
|---|---|---|---|---|---|---|
| Example 12-14 | I-14 | 9.0 | 7.5 | 147 | (0.18, 0.28) | (0.20, 0.31) |
| Comparative Example 12-12 | ref 12 | 9.5 | 6.6 | 75 | (0.21, 0.34) | (0.25, 0.38) |
| Example 12-15 | I-15 | 9.2 | 7.3 | 88 | (0.20, 0.34) | (0.23, 0.36) |
| Comparative Example 12-13 | ref-13 | 9.2 | 7.0 | 90 | (0.17, 0.30) | (0.24, 0.36) |
| Example 12-16 | I-16 | 9.0 | 7.8 | 105 | (0.17, 0.29) | (0.20, 0.32) |

It is seen that in Examples 12-1 to 12-16, the compound of the present invention is used as the light emitting material and therefore, both high efficiency and a long half-luminance time are satisfied and the device is excellent in terms of durability as compared with Comparative Examples 12-1 to 12-13 using corresponding compounds described in U.S. Patent Application Publication 2008-297033. Also, the chromaticity shift is less caused at the device deterioration and the voltage is low.

INDUSTRIAL APPLICABILITY

According to the present invention, an organic electroluminescence device having high luminous efficiency (for example, external quantum efficiency), high durability and a long life of the device and causing little chromaticity shift after device deterioration can be provided.

This application is based on Japanese patent application No. 2009-201150 filed on Aug. 31, 2009, the entire content of which is hereby incorporated by reference, the same as if set forth at length.

REFERENCE SIGNS LIST

2 Substrate
3 Anode
4 Hole injection layer
5 Hole transporting layer
6 Light emitting layer
7 Hole blocking layer
8 Electron transporting layer
9 Cathode
10 Organic electroluminescence device (organic EL device)
11 Organic layer
12 Protective layer
14 Adhesive layer
16 Sealing container
20 Light emission apparatus
30 Light scattering member
30A Light incident surface
30B Light output surface
32 Fine particle
40 Illumination apparatus

The invention claimed is:

1. A metal complex represented by formula (2), a metal complex represented by formula (14), or a phosphorescent metal complex containing a monoanionic bidentate ligand represented by the formulae (A1) to (A4) and a metal having an atomic weight of 40 or more, having a group represented by the following formula (I):

(I)

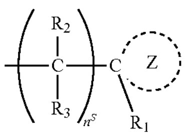

wherein $R_1$ represents an alkyl group;
each of $R_2$ and $R_3$ independently represents a hydrogen atom or an alkyl group;
$n^s$ represents an integer of 0 to 6; and
Z represents a saturated 5- to 8-membered ring;

(2)

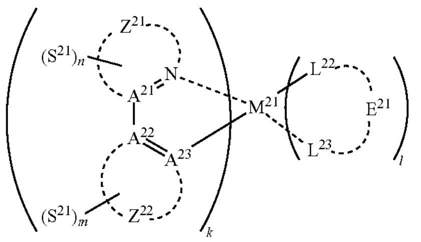

wherein $M^{21}$ represents a metal belonging to Groups 8 to 11 in the periodic table of elements;
each of $A^{21}$ to $A^{23}$ independently represents a nitrogen atom or a carbon atom;
$Z^{21}$ comprises an aromatic nitrogen-containing heterocyclic ring which may be substituted and which may form a condensed ring with other rings;
$Z^{22}$ represents an aromatic heterocyclic ring or an aromatic hydrocarbon ring which may be substituted and which may form a condensed ring with other rings;
$L^{22}$ and $L^{23}$ together with $E^{21}$ form a bidentate ligand which may be substituted; provided that if $L^{22}$-$E^{21}$-$L^{23}$ represents phenylpyridine, then $L^{22}$-$E^{21}$-$L^{23}$ is not further substituted with two alkenyl groups joined to form a ring;
k represents an integer of 1 to 3;
l represents an integer of 0 to 2;
k+l is 2 or 3;
each of $S^{21}$ and $S^{22}$ independently represents a group represented by formula (I);
each of n and m represents an integer of 0 to 4; wherein when n is 1-4, $S^{21}$ is bonded to a carbon atom of $Z^{21}$
n+m is an integer of 1 to 4; and
each $S^{21}$ or $S^{22}$ may be the same as or different from every other $S^{21}$ or $S^{22}$;

with the proviso that when $Z^{21}$ represents an imidazole ring, $n_s$ represents an integer of 1 to 6; and with the proviso that $Z^{21}$ does not represent pyrazole; and $Z^{21}$ does not represent a pyridine ring having additional rings fused thereto;

(14)

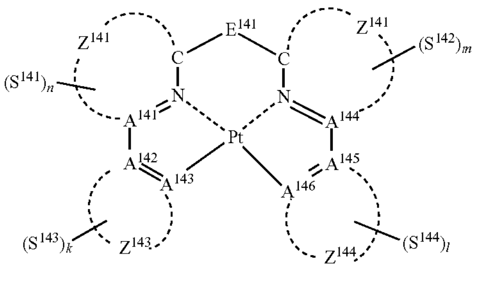

wherein each of $A^{141}$ to $A^{146}$ represents a nitrogen atom or a carbon atom;

$Z^{141}$ and $Z^{142}$ each independently represent an aromatic nitrogen-containing heterocyclic ring which may be substituted and which may form a condensed ring with other rings;

$Z^{143}$ and $Z^{144}$ each independently represent an aromatic heterocyclic ring or an aromatic hydrocarbon ring which may be substituted and which may form a condensed ring with other rings;

$E^{141}$ represents a divalent linking group;

$S^{141}$ to $S^{144}$ each independently represent the group represented by formula (I);

n, m, k and l represents an integer of 0 to 4;

n+m+k+l is an integer of 1 to 4; and each $S^{141}$, $S^{142}$, $S^{143}$, or $S^{144}$ may be the same as or different from every other $S^{141}$, $S^{142}$, $S^{143}$ or $S^{144}$;

with the proviso that when the metal complex is represented by formula (14), then $n^s$ is 1-6;

(A1)

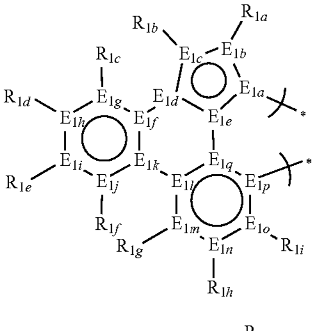

(A2)

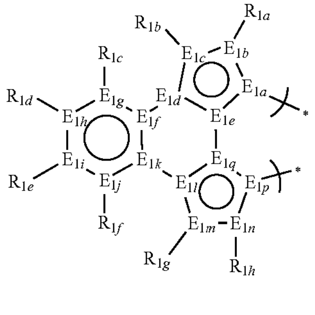

-continued (A3)

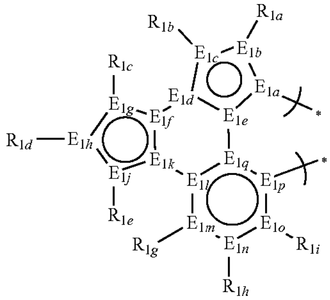

(A4)

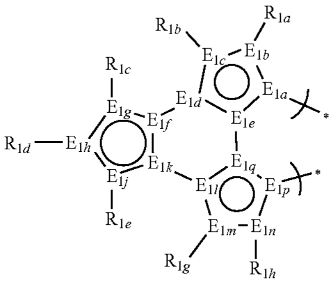

wherein each of $E_{1a}$ to $E_{1q}$ independently represents a carbon atom or a heteroatom;

each of $R_{1a}$ to $R_{1i}$ independently represents a hydrogen atom or a substituent, provided that at least one of $R_{1a}$ to $R_{1i}$ represents a group represented by formula (I);

two of $R_{1a}$ to $R_{1i}$ may combine with each other to form a saturated or unsaturated, aromatic or non-aromatic ring; and each of the frameworks represented by formulae (A1) to (A4) has a structure with 18 π-electrons in total;

with the proviso that when the metal complex is a phosphorescent metal complex containing a monoanionic bidentate ligand represented by the formulae (A1), (A2), (A3), or (A4), then $n^s$ is 1-6.

2. The metal complex as claimed in claim 1, wherein in formula (I), $n^s$ represents an integer of 1 to 3.

3. The metal complex as claimed in claim 1 wherein in formula (I), $n^s$ is 1.

4. The metal complex as claimed in claim 1, wherein in formula (I), each of $R_2$ and $R_3$ represents a hydrogen atom.

5. The metal complex as claimed in claim 1, wherein in formula (I), Z represents a cyclopentyl group or a cyclohexyl group.

6. The metal complex as claimed in claim 1, wherein the metal complex represented by formula (2) is a metal complex represented by the following formula (3):

(3)

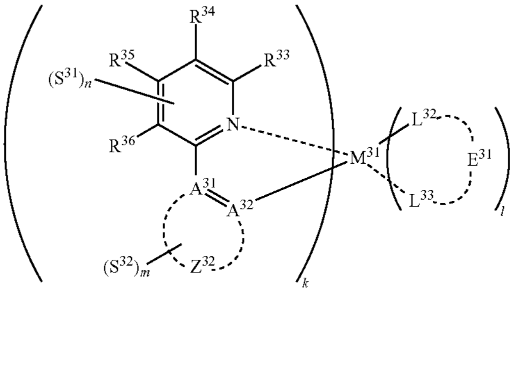

wherein $M^{31}$ represents a metal belonging to Groups 8 to 11 in the periodic table of elements;

each of $A^{31}$ and $A^{32}$ independently represents a nitrogen atom or a carbon atom;

each of $R^{33}$ to $R^{36}$ independently represents a hydrogen atom or a substituent;

$Z^{32}$ represents an aromatic heterocyclic ring or an aromatic hydrocarbon ring which may form a condensed ring with other rings;

$L^{32}$ and $L^{33}$ together with $E^{31}$ form a bidentate ligand which may be further substituted;

k represents an integer of 1 to 3;

l represents an integer of 0 to 2;

k+l is 2 or 3;

each of $S^{31}$ and $S^{32}$ independently represents a group represented by formula (I);

each of n and m represents an integer of 0 to 4;

n+m is an integer of 1 to 4; and each $S^{31}$ or $S^{32}$ may be the same as or different from every other $S^{31}$ or $S^{32}$.

7. The metal complex as claimed in claim 1, wherein the metal complex represented by formula (2) is represented by the following formula (4):

(4)

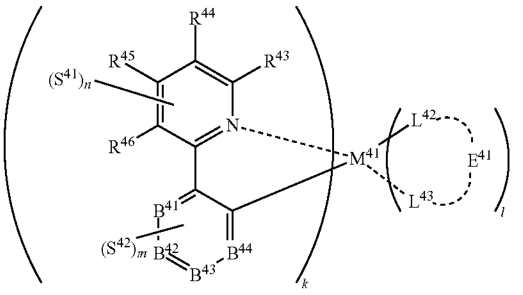

wherein $M^{41}$ represents a metal belonging to Groups 8 to 11 in the periodic table of elements;

each of $R^{43}$ to $R^{46}$ independently represents a hydrogen atom or a substituent;

each of $B^{41}$ to $B^{44}$ independently represents a nitrogen atom or C—$R^{47}$, $R^{47}$ represents a hydrogen atom or a substituent which may join together to form a condensed ring;

each $R^{47}$ may be the same as or different from every other $R^{47}$;

adjacent groups $R^{43}$, $R^{44}$, $R^{45}$, $R^{46}$, and $R^{47}$ may join together to form a condensed ring;

$L^{42}$ and $L^{43}$ together with $E^{41}$ form a bidentate ligand which may be substituted;

k represents an integer of 1 to 3;

l represents an integer of 0 to 2;

k+l is 2 or 3;

each of $S^{41}$ and $S^{42}$ independently represents a group represented by formula (I);

each of n and m represents an integer of 0 to 4;

n+m is an integer of 1 to 4; and each $S^{41}$ or $S^{42}$ may be the same as or different from every other $S^{41}$ or $S^{42}$.

8. The metal complex as claimed in claim 7, wherein the metal complex represented by formula (4) is represented by the following formula (5):

(5)

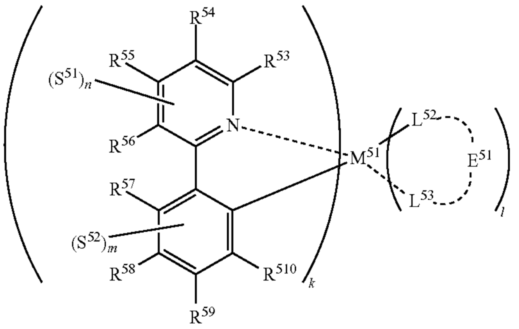

wherein $M^{51}$ represents a metal belonging to Groups 8 to 11 in the periodic table of elements;

each of $R^{53}$ to $R^{59}$ and $R^{510}$ independently represents a hydrogen atom or a substituent;

adjacent $R^{57}$ to $R^{59}$ and $R^{510}$ may join together to form a condensed ring;

$L^{52}$ and $L^{53}$ together with $E^{51}$ form a bidentate ligand which may be substituted;

k represents an integer of 1 to 3;

l represents an integer of 0 to 2;

k+l is 2 or 3;

each of $S^{51}$ and $S^{52}$ independently represents a group represented by formula (I);

each of n and m represents an integer of 0 to 4;

n+m is an integer of 1 to 4; and each $S^{51}$ or $S^{52}$ may be the same as or different from every other $S^{51}$ or $S^{52}$.

9. The metal complex as claimed in claim 1, wherein the metal complex represented by formula (2) is represented by the following formula (7):

(7)

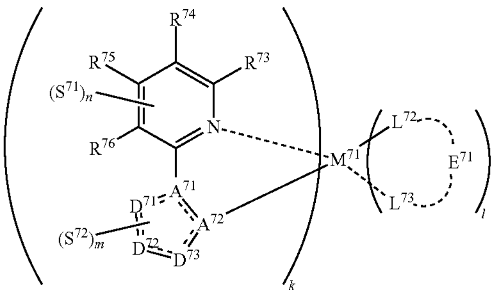

wherein $M^{71}$ represents a metal belonging to Groups 8 to 11 in the periodic table of elements;

each of $R^{73}$ to $R^{76}$ independently represents a hydrogen atom or a substituent;

each of $A^{71}$ and $A^{72}$ independently represents a nitrogen atom or a carbon atom;

each of $D^{71}$ to $D^{73}$ independently represents an atom selected from carbon, nitrogen, oxygen, sulfur and silicon;

the bond between atoms in the 5-membered ring formed by $D^{71}$ to $D^{73}$, $A^{71}$ and $A^{72}$ represents a single bond or a double bond;

each of $D^{71}$ to $D^{73}$ when these can be further substituted may be substituted; adjacent substituents may join together to form a condensed ring;

$L^{72}$ and $L^{73}$ together with $E^{71}$ form a bidentate ligand which may be substituted;

k represents an integer of 1 to 3;

l represents an integer of 0 to 2;

k+l is 2 or 3;

each of $S^{71}$ and $S^{72}$ independently represents a group represented by formula (I);

each of n and m represents an integer of 0 to 4;

n+m is an integer of 1 to 4; and each $S^{71}$ or $S^{72}$ may be the same as or different from every other $S^{71}$ or $S^{72}$.

10. The metal complex as claimed in claim 1, wherein the metal complex represented by formula (2) is represented by the following formula (9):

(9)

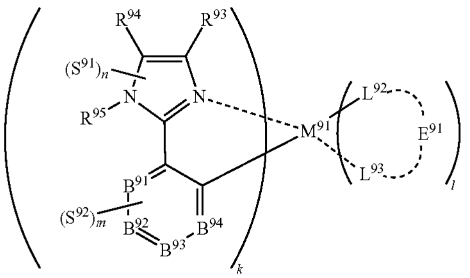

wherein $M^{91}$ represents a metal belonging to Groups 8 to 11 in the periodic table of elements;

each of $R^{93}$ and $R^{94}$ independently represents a hydrogen atom or a substituent;

$R^{95}$ represents a hydrogen atom or a substituent;

each of $B^{91}$ to $B^{94}$ independently represents a nitrogen atom or C—$R^{96}$, $R^{96}$ represents a hydrogen atom or a substituent, each $R^{96}$ may be the same as or different from every other $R^{96}$;

adjacent groups $R^{93}$, $R^{94}$, $R^{95}$, and $R^{96}$ may join together to form a condensed ring;

$L^{92}$ and $L^{93}$ together with $E^{91}$ form a bidentate ligand which may be substituted;

k represents an integer of 1 to 3;

l represents an integer of 0 to 2;

k+l is 2 or 3;

each of $S^{91}$ and $S^{92}$ independently represents a group represented by formula (I);

each of n and m represents an integer of 0 to 4;

n+m is an integer of 1 to 4; and each $S^{91}$ or $S^{92}$ may be the same as or different from every other $S^{91}$ or $S^{92}$.

11. The metal complex as claimed in claim 1, wherein the metal complex represented by formula (14) is represented by the following formula (15):

(15)

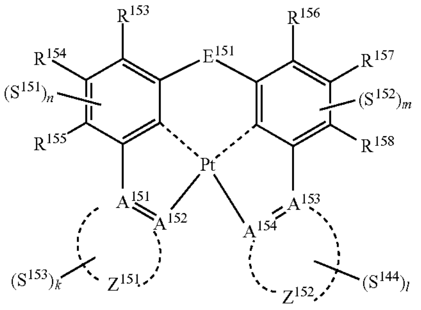

wherein each of $A^{151}$ to $A^{154}$ independently represents a nitrogen atom or a carbon atom;

each $R^{153}$ to $R^{158}$ independently represents a hydrogen atom or a substituent; adjacent groups $R^{153}$ to $R^{158}$ may join together to form a condensed ring;

each of $Z^{151}$ and $Z^{152}$ independently represents an aromatic heterocyclic ring or an aromatic hydrocarbon ring which may be substituted and which may form a condensed ring with other rings;

each of $S^{151}$ to $S^{154}$ independently represents a group represented by formula (I);

each of n, m, k, and l represents an integer of 0 to 4;

n+m+k+l is an integer of 1 to 4; and each $S^{151}$, $S^{152}$, $S^{153}$, or $S^{154}$ may be the same as or different from every other $S^{151}$, $S^{152}$, $S^{153}$ or $S^{154}$.

12. The metal complex as claimed in claim 1, wherein the metal complex represented by formula (14) is represented by the following formula (18):

(18)

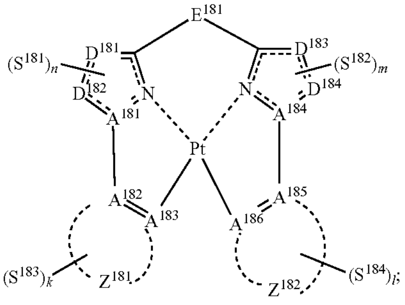

wherein each of $A^{181}$ to $A^{186}$ independently represents a nitrogen atom or a carbon atom;

each of $D^{181}$ to $D^{184}$ independently represents an atom selected from carbon, nitrogen, oxygen, sulfur, and silicon;

the bond between atoms in the 5-membered ring formed by $D^{181}$, $D^{182}$, $A^{181}$, the nitrogen atom and the carbon atom or by $D^{183}$, $D^{184}$, $A^{184}$, the nitrogen atom and the carbon atom represents a single bond or a double bond;

each of $D^{181}$ to $D^{184}$ when these can be further substituted may be substituted; adjacent substituents may join together to form a condensed ring;

each of $Z^{181}$ and $Z^{182}$ independently represents an aromatic heterocyclic ring or an aromatic hydrocarbon ring which may be substituted and which may form a condensed ring with other rings;

$E^{181}$ represents a divalent linking group;

each of $S^{181}$ to $S^{184}$ independently represents a group represented by formula (I);

each of n, m, k and l represents an integer of 0 to 4;

n+m+k+l is an integer of 1 to 4; and each $S^{181}$, $S^{182}$, $S^{183}$ or $S^{184}$ may be the same as or different from every other $S^{181}$, $S^{182}$, $S^{183}$ or $S^{184}$.

13. The metal complex as claimed in claim 1, wherein the monoanionic bidentate ligand represented by the formulae (A1) or (A3) is represented by the following formulae (A1-1), (A3-1), (A1-2), or (A3-2):

(A1-1)

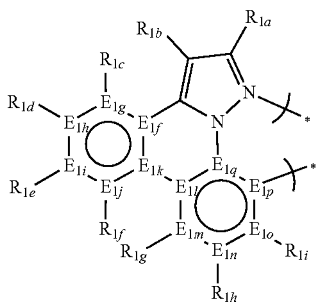

(A3-1)

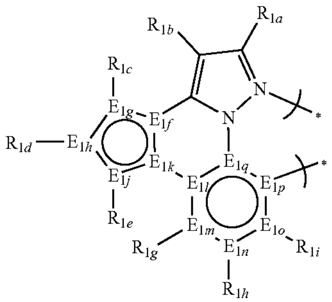

(A1-2)

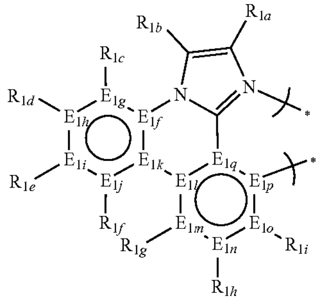

(A3-2)

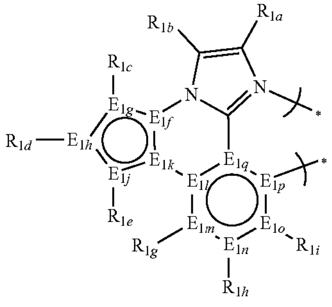

wherein each of $E_{1f}$ to $E_{1q}$ independently represents a carbon atom or a heteroatom;

each of $R_{1a}$ to $R_{1i}$ independently represents a hydrogen atom or a substituent, provided that at least one of $R_{1a}$ to $R_{1i}$ represents a group represented by formula (I);

two of $R_{1a}$ to $R_{1i}$ may combine with each other to form a saturated or unsaturated, aromatic or non-aromatic ring; and each of the frameworks represented by formulae (A1-1), (A3-1), (A1-2) and (A3-2) has a structure with 18π-electrons in total.

14. The metal complex as claimed in claim 1, wherein the group represented by formula (I) is selected from the group consisting of a1 to a31:

a1

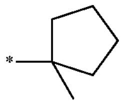

a2

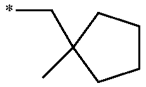

a3

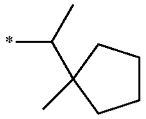

a4

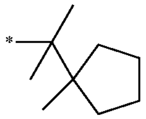

a5

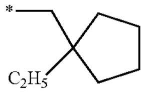

a6

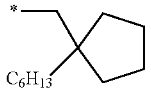

a7

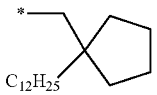

a8

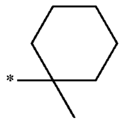

a9

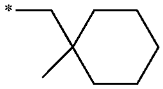

a10

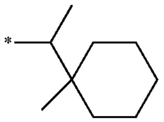

a11

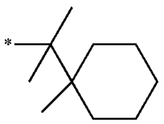

-continued a12

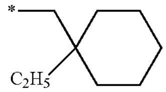

a13

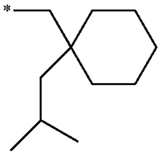

a14

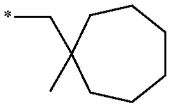

a15

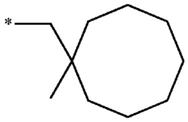

a16

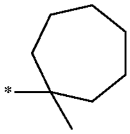

a17

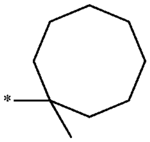

a18

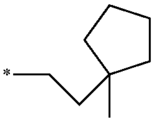

a19

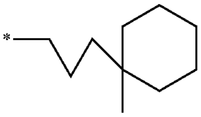

a20

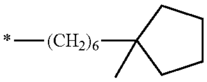

a21

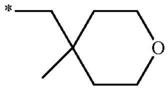

a22

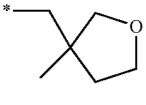

a23

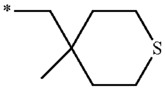

a24

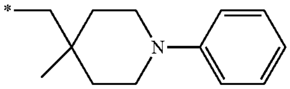

-continued a25

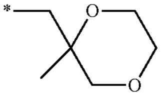

a26

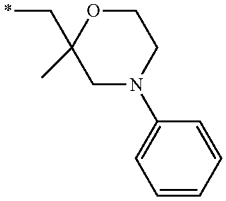

a27

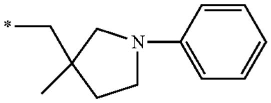

a28

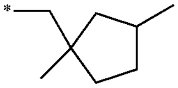

a29

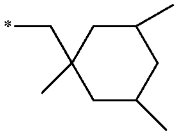

a30

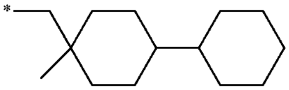

a31

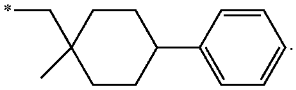

15. An organic electroluminescence device comprising:

a pair of electrodes; and at least one organic layer between the pair of electrodes, the organic layer containing a light emitting layer, wherein any one layer of the at least one organic layer contains a metal complex represented by formula (2), a metal complex represented by formula (14), or a phosphorescent metal complex containing a monoanionic bidentate ligand represented by the formulae (A1) to (A4) and a metal having an atomic weight of 40 or more, having a group represented by the following formula (I):

(I)

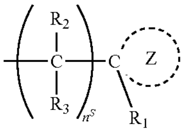

wherein $R_1$ represents an alkyl group;

each of $R_2$ and $R_3$ independently represents a hydrogen atom or an alkyl group;

$n^S$ represents an integer of 0 to 6; and

Z represents a saturated 5- to 8-membered ring;

(2)

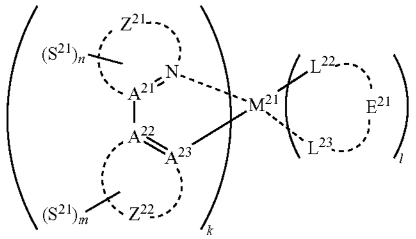

wherein $M^{21}$ represents a metal belonging to Groups 8 to 11 in the periodic table of elements;

each of $A^{21}$ to $A^{23}$ independently represents a nitrogen atom or a carbon atom;

$Z^{21}$ comprises an aromatic nitrogen-containing heterocyclic ring which may be substituted and which may form a condensed ring with other rings;

$Z^{22}$ represents an aromatic heterocyclic ring or an aromatic hydrocarbon ring which may be substituted and which may form a condensed ring with other rings;

$L^{22}$ and $L^{23}$ together with $E^{21}$ form a bidentate ligand which may be substituted; provided that if $L^{22}$-$E^{21}$-$L^{23}$ represents phenylpyridine, then $L^{22}$-$E^{21}$-$L^{23}$ is not further substituted with two alkenyl groups joined to form a ring;

k represents an integer of 1 to 3;

l represents an integer of 0 to 2;

k+l is 2 or 3;

each of $S^{21}$ and $S^{22}$ independently represents a group represented by formula (I);

each of n and m represents an integer of 0 to 4; wherein when n is 1-4, $S^{21}$ is bonded to a carbon atom of $Z^{21}$ n+m is an integer of 1 to 4; and each $S^{21}$ or $S^{22}$ may be the same as or different from every other $S^{21}$ or $S^{22}$;

with the proviso that when $Z^{21}$ represents an imidazole ring, $n^s$ represents an integer of 1 to 6; and with the proviso that $Z^{21}$ does not represent pyrazole; and $Z^{21}$ does not represent a pyridine ring having additional rings fused thereto;

(14)

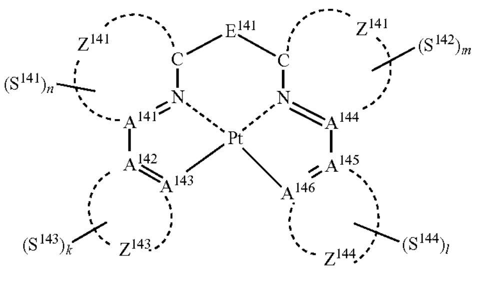

wherein each of $A^{141}$ to $A^{146}$ represents a nitrogen atom or a carbon atom;

$Z^{141}$ and $Z^{142}$ each independently represent an aromatic nitrogen-containing heterocyclic ring which may be substituted and which may form a condensed ring with other rings;

$Z^{143}$ and $Z^{144}$ each independently represent an aromatic heterocyclic ring or an aromatic hydrocarbon ring which may be substituted and which may form a condensed ring with other rings;

$E^{141}$ represents a divalent linking group;

$S^{141}$ to $S^{144}$ each independently represent the group represented by formula (I);

n, m, k and l represents an integer of 0 to 4;

n+m+k+l is an integer of 1 to 4; and each $S^{141}$, $S^{142}$, $S^{143}$, or $S^{144}$ may be the same as or different from every other $S^{141}$, $S^{142}$, $S^{143}$ or $S^{144}$;

with the proviso that when the metal complex is represented by formula (14), then $n^s$ is 1-6;

(A1)

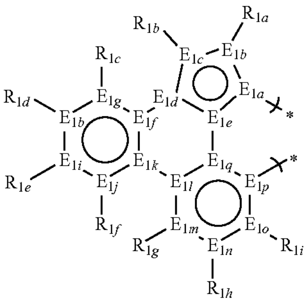

(A2)

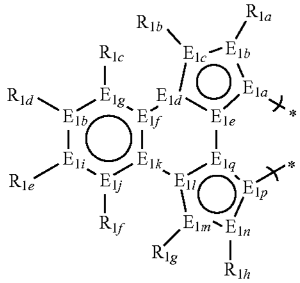

(A3)

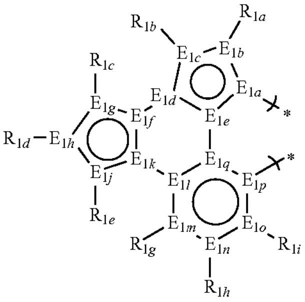

(A4)

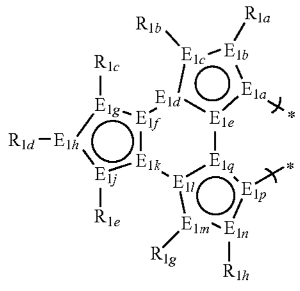

wherein each of $E_{1a}$ to $E_{1q}$ independently represents a carbon atom or a heteroatom;

each of $R_{1a}$ to $R_{1i}$ independently represents a hydrogen atom or a substituent, provided that at least one of $R_{1a}$ to $R_{1i}$ represents a group represented by formula (I);

two of $R_{1a}$ to $R_{1i}$ may combine with each other to form a saturated or unsaturated, aromatic or non-aromatic ring; and each of the frameworks represented by formulae (A1) to (A4) has a structure with 18 π-electrons in total;

with the proviso that when the metal complex is a phosphorescent metal complex containing a monoanionic bidentate ligand represented by the formulae (A1), (A2), (A3), or (A4), then $n^{s}$ is 1-6.

16. The organic electroluminescence device as claimed in claim 15, wherein the any one layer of the at least one organic layer containing the metal complex represented by formula (2), the metal complex represented by formula (14), or the phosphorescent metal complex containing the monoanionic bidentate ligand represented by the formulae (A1) to (A4) and a metal having an atomic weight of 40 or more, having a group represented by formula (I), is the light-emitting layer.

17. A light emission apparatus comprising the organic electroluminescence device as claimed in claim 15.

18. A display apparatus comprising the organic electroluminescence device as claimed in claim 15.

19. An illumination apparatus comprising the organic electroluminescence device as claimed in claim 15.

* * * * *

UNITED STATES PATENT AND TRADEMARK OFFICE
CERTIFICATE OF CORRECTION

PATENT NO. : 11,832,508 B2
APPLICATION NO. : 16/535491
DATED : November 28, 2023
INVENTOR(S) : Hiroo Takizawa, Saki Takada and Eiji Fukuzaki It is certified that error appears in the above-identified patent and that said Letters Patent is hereby corrected as shown below:

In the Specification

The structure on Column 66, Line 11-Line 25 should read as follows:

-- 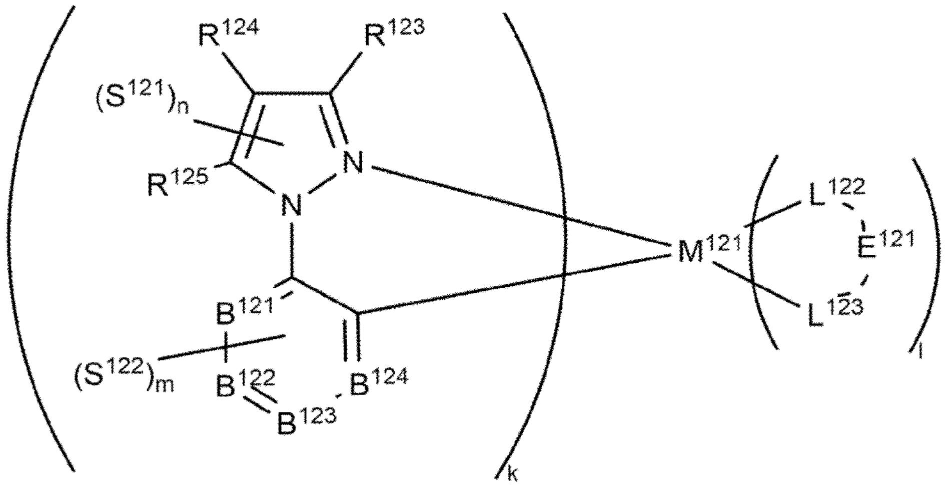 (12) --

Signed and Sealed this
Fourth Day of March, 2025

Coke Morgan Stewart
*Acting Director of the United States Patent and Trademark Office*

In the Claims
The structure on Column 223, Line 6-Line 19 should read as follows:
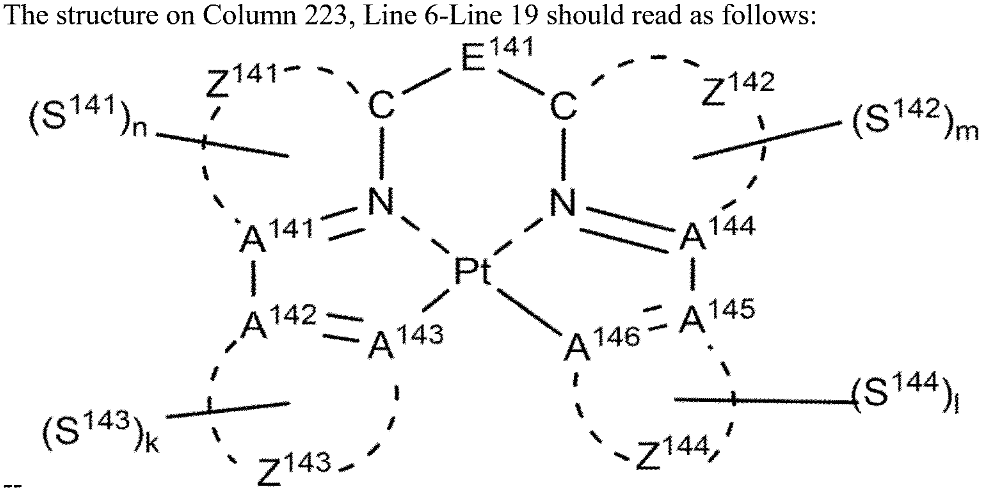
(14)
-- --
The structure on Column 228, Line 1-Line 14 should read as follows:
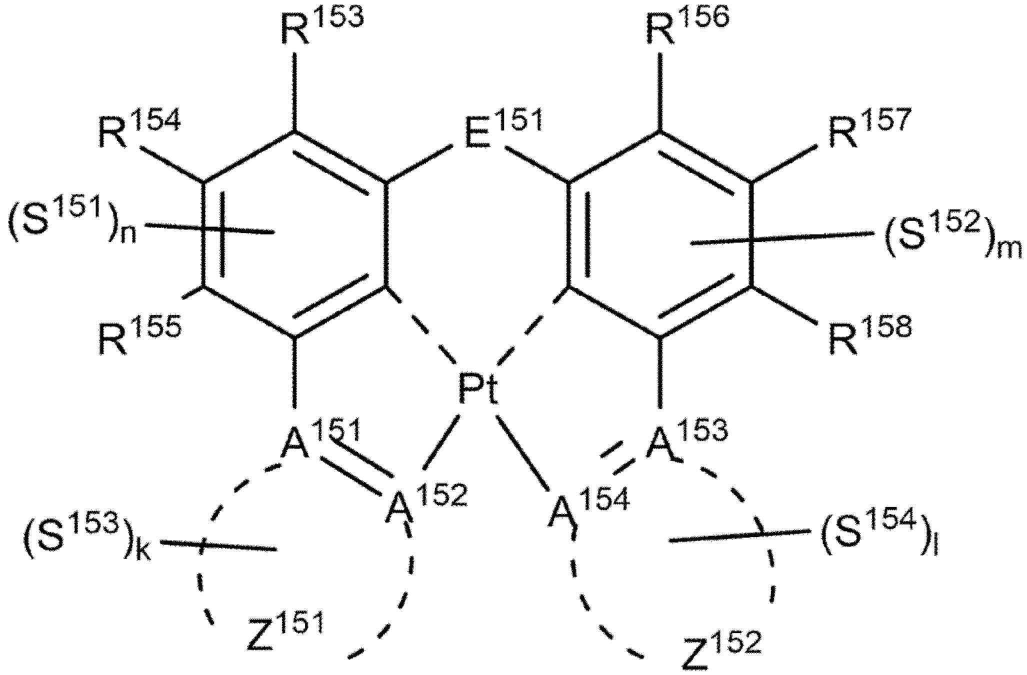
(15)
-- --

The structure on Column 233, Line 1-Line 11 should read as follows:
--
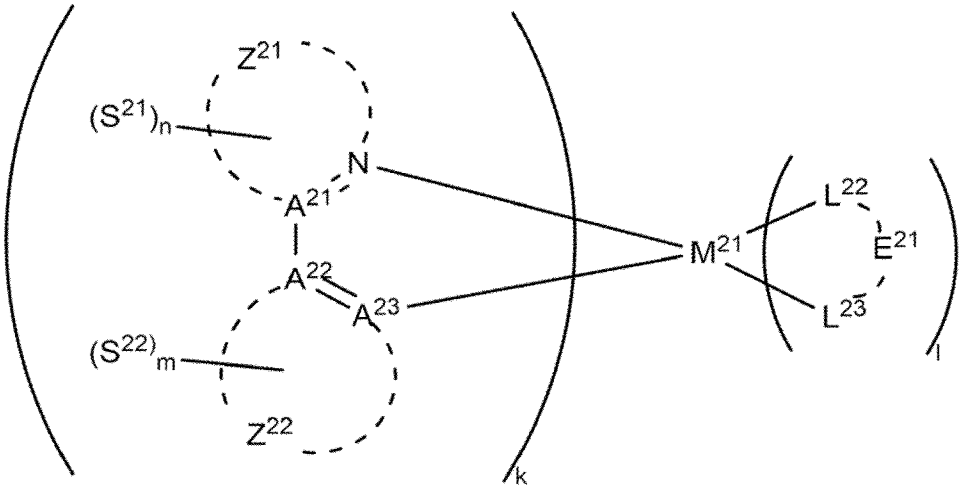
(2)
--
The structure on Column 233, Line 44-Line 56 should read as follows:
--
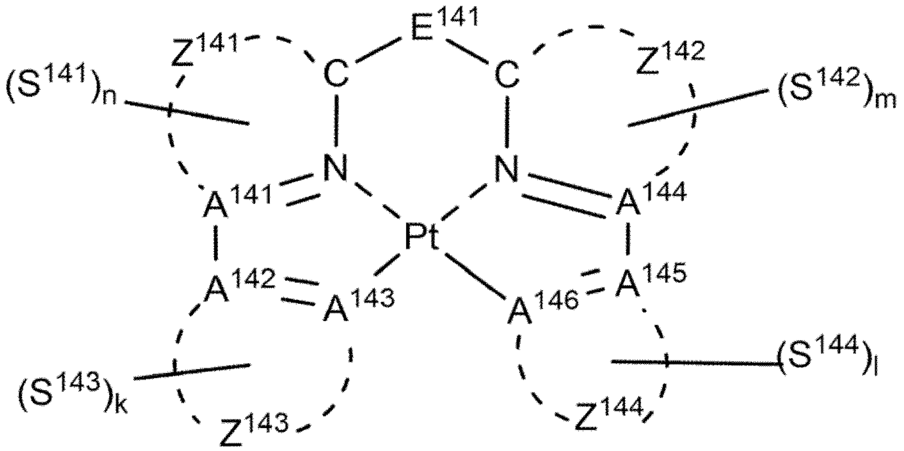
(14)
--